US008017838B2

(12) United States Patent
Damude et al.

(10) Patent No.: US 8,017,838 B2
(45) Date of Patent: Sep. 13, 2011

(54) MUTANT DELTA-8 DESATURASE GENES ENGINEERED BY TARGETED MUTAGENSIS AND THEIR USE IN MAKING POLYUNSATURATED FATTY ACIDS

(75) Inventors: Howard G. Damude, Hockessin, DE (US); Hongxian He, Drexel Hill, PA (US); Der-ing Liao, Wilmington, DE (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 826 days.

(21) Appl. No.: 11/951,697

(22) Filed: Dec. 6, 2007

(65) Prior Publication Data

US 2009/0176003 A1 Jul. 9, 2009

Related U.S. Application Data

(60) Provisional application No. 60/868,953, filed on Dec. 7, 2006.

(51) Int. Cl.
*C12N 15/82* (2006.01)
*A01H 5/00* (2006.01)

(52) U.S. Cl. ........................................ 800/298; 800/281

(58) Field of Classification Search ........................ None
See application file for complete search history.

(56) References Cited

U.S. PATENT DOCUMENTS

| | | | |
|---|---|---|---|
| 6,825,017 | B1 | 11/2004 | Browse et al. |
| 2005/0273885 | A1 | 12/2005 | Singh et al. |
| 2005/0287652 | A1 | 12/2005 | Damude et al. |
| 2006/0051847 | A1 | 3/2006 | Gunnarsson et al. |
| 2006/0090221 | A1 | 4/2006 | Browse et al. |
| 2006/0246556 | A1 | 11/2006 | Napier et al. |

FOREIGN PATENT DOCUMENTS

| | | | |
|---|---|---|---|
| WO | WO 00/34439 | A1 | 6/2000 |
| WO | WO 2004/057001 | A2 | 7/2004 |
| WO | WO2004057001 | A2 * | 7/2004 |
| WO | WO 2005/012316 | A1 | 1/2005 |
| WO | WO 2005/083093 | A1 | 4/2005 |
| WO | WO 2005/103253 | A1 | 11/2005 |
| WO | WO 2006/012325 | A1 | 2/2006 |
| WO | WO 2006/012326 | A1 | 2/2006 |
| WO | WO2007/127381 | | 11/2007 |

OTHER PUBLICATIONS

U.S. Appl. No. 60/795,810, filed Apr. 28, 2006, Howard Glenn Damude et. al.
U.S. Appl. No. 10/840,478, filed Dec. 16, 2006, Stephen K. Picatoaggio et. al.
U.S. Appl. No. 10/840,579, filed Jun. 23, 2005, Stephen K. Picataggio et. al.
U.S. Appl. No. 10/840,325, filed Feb. 24, 2005, Narendra S. Yadav et. al.
U.S. Appl. No. 10/869,630, filed Jan. 20, 2005, Stephen K. Picataggio et. al.
U.S. Appl. No. 10/882,760, filed Jul. 20, 2006, Narendra S. Yadav et. al.
U.S. Appl. No. 10/985,254, filed Jun. 16, 2005, Narendra S. Yadav et. al.
U.S. Appl. No. 10/985,691, filed Sep. 29, 2005, Narendra S. Yadav et. al.
U.S. Appl. No. 10/987,548, filed Jun. 16, 2005, Dana M. Walters Pollak et. al.
U.S. Appl. No. 11/024,545, filed May 4, 2006, Zhixiong Xue et. al.
U.S. Appl. No. 11/024,544, filed May 4, 2006, Narendra S. Yadav et. al.
U.S. Appl. No. 11/166,993, filed Dec. 29, 2005, Howard Glenn Damude et. al.
U.S. Appl. No. 11/183,664, Jan. 26, 2006, Stephen K. Picataggio et. al.
U.S. Appl. No. 11/185,301, filed May 4, 2006, Zhixiong Xue et. al.
U.S. Appl. No. 11/190,750, May 4, 2006, Stephen K. Picataggio et. al.
U.S. Appl. No. 11/198,975, filed Aug. 8, 2005, Quinn Qun Zhu et. al.
U.S. Appl. No. 11/225,354, filed Mar. 16, 2006, Zhixiong Xue et. al.
U.S. Appl. No. 11/251,466, May 4, 2006, Howard Glenn Damude et. al.
U.S. Appl. No. 11/254,173, filed May 4, 2006, Daniel Joseph Macool et. al.
U.S. Appl. No. 11/253,882, filed Apr. 19, 2007, Daniel Joseph Macool et. al.
U.S. Appl. No. 11/264,784, filed May 4, 2006, Howard Glenn Damude et. al.
U.S. Appl. No. 11/264,737, filed May 25, 2006, Howard Glenn Damude et. al.
U.S. Appl. No. 11/265,761, filed Jun. 1, 2006, Howard Glenn Damude et. al.
U.S. Appl. No. 60/739,989, filed Nov. 23, 2005, Howard Glenn Damude et. al.
U.S. Appl. No. 60/793,575, filed Apr. 20, 2006, Zhixong Xue et. al.
U.S. Appl. No. 60/796,637, filed May 1, 2006, Narendra S. Yadav et. al.
U.S. Appl. No. 60/801,172, filed May 17, 2006, Howard Glenn Damude et. al.
U.S. Appl. No. 60/801,119, filed May 17, 2006, Howard Glenn Damude et. al.
U.S. Appl. No. 10/776,311, filed Sep. 2, 2004, Edgar Benjamin Cahoon et. al.
U.S. Appl. No. 10/776,889, filed Feb. 11, 2004, Anthony J. Kinney et. al.
J. Dyerberg et. al., Fatty Acid Composition of the Plasma Lipids in Greenland Eskimos, Amer. J. Clin. Nutr., 1975, vol. 28:958-966.

(Continued)

*Primary Examiner* — Elizabeth McElwain

(57) ABSTRACT

The present invention relates to mutant delta-8 desaturase genes, which have the ability to convert eicosadienoic acid [20:2 omega-6, EDA] to dihomo-γ-linolenic acid [20:3, DGLA] and/or eicosatrienoic acid [20:3 omega-3, ETrA] to eicosatetraenoic acid [20:3 omega-3, ETA]. Isolated nucleic acid fragments and recombinant constructs comprising such fragments encoding delta-8 desaturase along with methods of making long-chain polyunsaturated fatty acids (PUFAs) using these mutant delta-8 desaturases in plants and oleaginous yeast are disclosed.

6 Claims, 19 Drawing Sheets

OTHER PUBLICATIONS

J. Dyerberg et. al., Eicosapentaenoic Acid and Prevention of Thrombosis and atherosclerosis, Lancet., 1978, vol. 2:117-119.

H. Shimokawa, Beneficial Effects of Eicosapentaenoic Acid on Enodothelial Vasodilator Functions in Animals And Humans, World Rev. Nutr. Diet, 2001, vol. 88:100-108.

C. Schacky et. al., 3 Fatty Acids—From Eskimos to Clinical Cardiology—What Took Us So Long? World Rev. Nutr. Diet, 2001, vol. 88:90-99.

Wallis et. al., The Desatturase of Euglena Gracilis: An Alternate Pathway for Synthesis of 20-Carbon Polyunsaturated Fatty Acids, Arch. Biochem. and Biophys., 1999, vol. 365:307-316.

Sayanova et. al., The Alternative Pathway C20 8-Desaturase From The Non-Photosynthetic Organism Acanthamoeba Castellanii is an Atypical Cytochrome B5-Fusion Desaturas, FEBS Lett., 2006, vol. 580:1946-1952.

National Center for Biotechnology information General Identifier No. 1706221, Accession No. P40312, Feb. 1, 1995, G. Truan et al., Cloning and characterization of a yeast cytochrome b5-encoding gene which suppresses ketoconazole hypersensitivity in a NADPH-P-450 reductase-deficient strain.

National Center for Biotechnology information General Identifier No. 20137715, Accession No. 094391, Mar. 5, 2002, V. Wood et al., The genome sequence of Schizosaccharomyces pombe.

National Center for Biotechnology information General Identifier No. 68130365, Accession No. CAJ09677, Nov. 9, 2007, A. C. Ivens et al., The genome of the kinetoplastid parasite.

National Center for Biotechnology information General Identifier No. 11559824, Accession No. AAG38104, Dec. 6, 2000, L. Ming-Chun et al., Cloning and sequencing analysis of delta6-fatty acid desaturase gene from Mortierella isabellina.

Linda G. Otten et al., Directed evolution : selecting today's biocatalysts, Biomolecular Engineering, vol. 22, pp. 1-9, 2005.

* cited by examiner

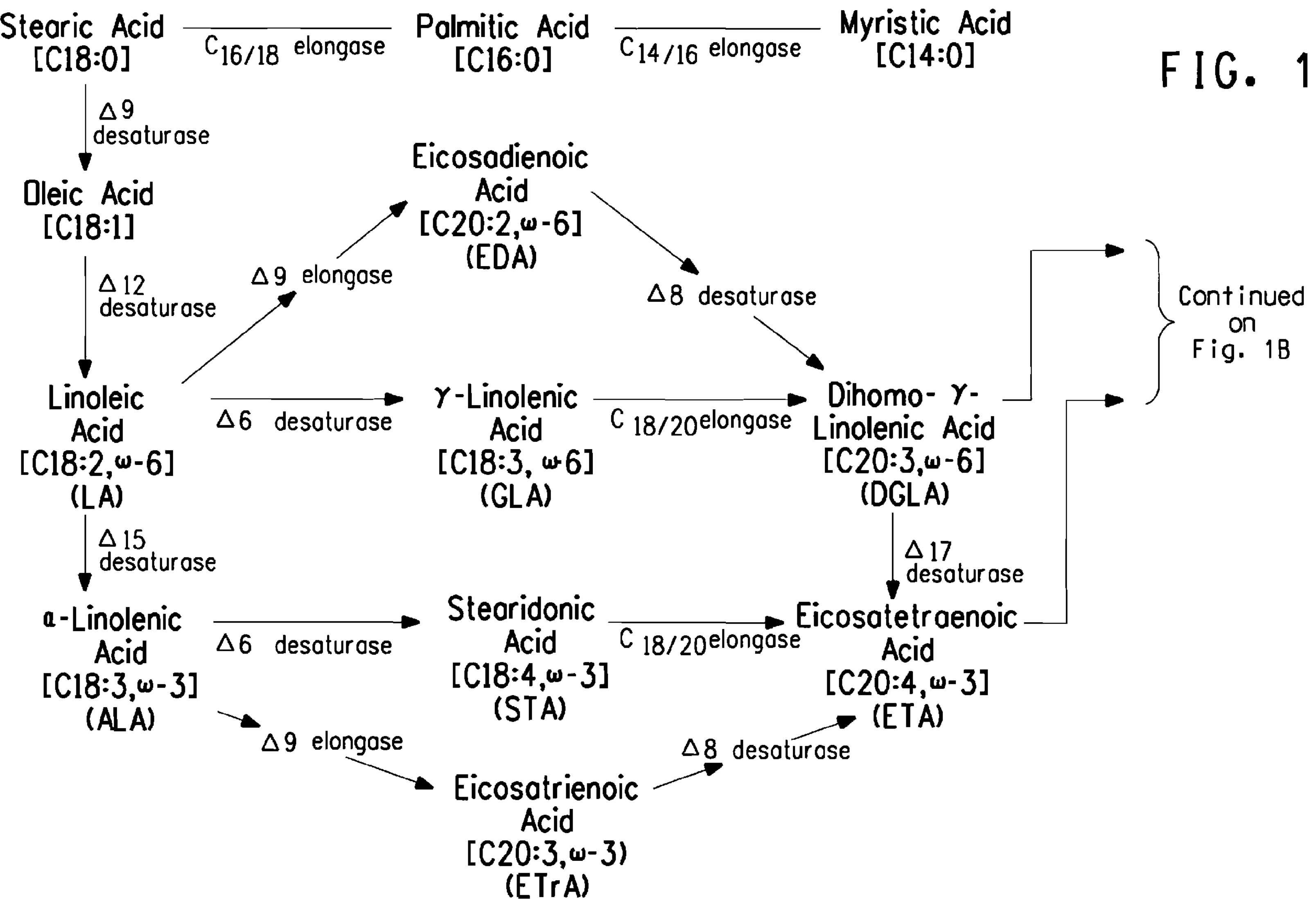

FIG. 1A
Stearic Acid [C18:0]
C16/18 elongase
Palmitic Acid [C16:0]
C14/16 elongase
Myristic Acid [C14:0]
Δ9 desaturase
Oleic Acid [C18:1]
Δ12 desaturase
Eicosadienoic Acid [C20:2,ω-6] (EDA)
Δ9 elongase
Δ8 desaturase
Linoleic Acid [C18:2,ω-6] (LA)
Δ6 desaturase
γ-Linolenic Acid [C18:3, ω6] (GLA)
C 18/20elongase
Dihomo-γ-Linolenic Acid [C20:3,ω-6] (DGLA)
Continued on Fig. 1B
Δ15 desaturase
Δ17 desaturase
α-Linolenic Acid [C18:3,ω-3] (ALA)
Δ6 desaturase
Stearidonic Acid [C18:4,ω-3] (STA)
C 18/20elongase
Eicosatetraenoic Acid [C20:4,ω-3] (ETA)
Δ9 elongase
Δ8 desaturase
Eicosatrienoic Acid [C20:3,ω-3) (ETrA)

FIG. 3 A

```
                          10         20         30         40         50
  1  -------------MVKSKRQALP--------------LTIDGTTYDVSAWV  SEQ ID NO 10.pro
  1  -------------MVFELTPPYKYHS----SLPKCVIRIDDNWYDCTSWR  SEQ ID NO 15.pro
  1  MSSDVGATVPHFYTRAELADIHQDVL-DKKPEARKLIVVENKVYDITDFV  SEQ ID NO 13.pro
  1  MAAAPSVRT---FTRAEILNAEALNEGKKDAEAPFLMIIDNKVYDVREFV  SEQ ID NO 16.pro
  1  MSTSDRQSV---FTLKELELINQKHR-DGDKSAMKFIIIDRKVYDVTEFL  SEQ ID NO 14.pro

                          60         70         80         90        100
 25  NFHPGGAEIIENYQGRDATDAFMVMHSQEAFDKLKRMPKINPS------S  SEQ ID NO 10.pro
 34  NSHPGGAQMCDEFHGKDATDAFYSLHSKEAIQKLKRMKALPLK-------  SEQ ID NO 15.pro
 50  FDHPGGERVLLTQEGRDATDVFHEMHPPSAYELLANCYVGDCEPKLPIDS  SEQ ID NO 13.pro
 48  PDHPGGS-VILTHVGKDGTDVFDTFHPEAAWETLANFYVGDID-------  SEQ ID NO 16.pro
 47  EDHPGGAQVLLTHVGKDASDVFHAMHPESAYEILNNYFVGDVK------D  SEQ ID NO 14.pro

                         110        120        130        140        150
 69  ELPPQAAVNEAQEDFRKLREELIATGMFDA-SPLWYSYKISTTLGLGVLG  SEQ ID NO 10.pro
 77  --EGDEPRDQVSLNFEKLLQQLRSEGWFERRWIIDFARNIMPVIVLCVVG  SEQ ID NO 15.pro
100  TDKKALNSAAFAQEIRDLRDKLEKQGYFDA-STGFYIYKVSTTLLVCIVG  SEQ ID NO 13.pro
 90  ESDRAIKNDDFAAEVRKLRTLFQSLGYYDS-SKAYYAFKVSFNLCIWGLS  SEQ ID NO 16.pro
 91  AHVKETPSAQFASEMRQLRDQLKKEGYFHS-SKAYYVYKVLSTLALCAAG  SEQ ID NO 14.pro

                         160        170        180        190        200
118  YFLMVQY-----QMYFIGAVLLGMHYQQMGWLSHDICHHQTFKNRNWNNL  SEQ ID NO 10.pro
125  TYLSYSR-------PFLATILIGLGMQQGGWLAHDFTHARGKFAR----F  SEQ ID NO 15.pro
149  LAILKAWGRESTLAVFIAASLVGLFWQQCGWLAHDYAHYQVIKDPNVNNL  SEQ ID NO 13.pro
139  TFIVAKWGQTSTLANVLSAALLGLFWQQCGWLAHDFLHHQVFQDRFWGDL  SEQ ID NO 16.pro
140  LTLLYAYGHTSTLAVVASAIIVGIFWQQCGWLAHDFGHHQCFEDRSWNDV  SEQ ID NO 14.pro

                         210        220        230        240        250
163  VGLVFGNGLQGFSVTWWKDRHNAHHSATNVQGHDPDIDNLPLLAWSEDDV  SEQ ID NO 10.pro
164  LANACGGMINAFSVEWWSNKHNSHHIFVNRKGMDADIHNEPALFLWVPDV  SEQ ID NO 15.pro
199  FLVTFGNLVQGFSLSWWKNKHNTHHASTNVSGEDPDIDTAPILLWDEFAV  SEQ ID NO 13.pro
189  FGAFLGGVCQGFSSSWWKDKHNTHHAAPNVHGEDPDIDTHPLLTWSEHAL  SEQ ID NO 16.pro
190  LVVFLGNFCQGFSLSWWKNKHNTHHASTNVHGHDPDIDTAPVLLWDEYAS  SEQ ID NO 14.pro
```

FIG. 3 B

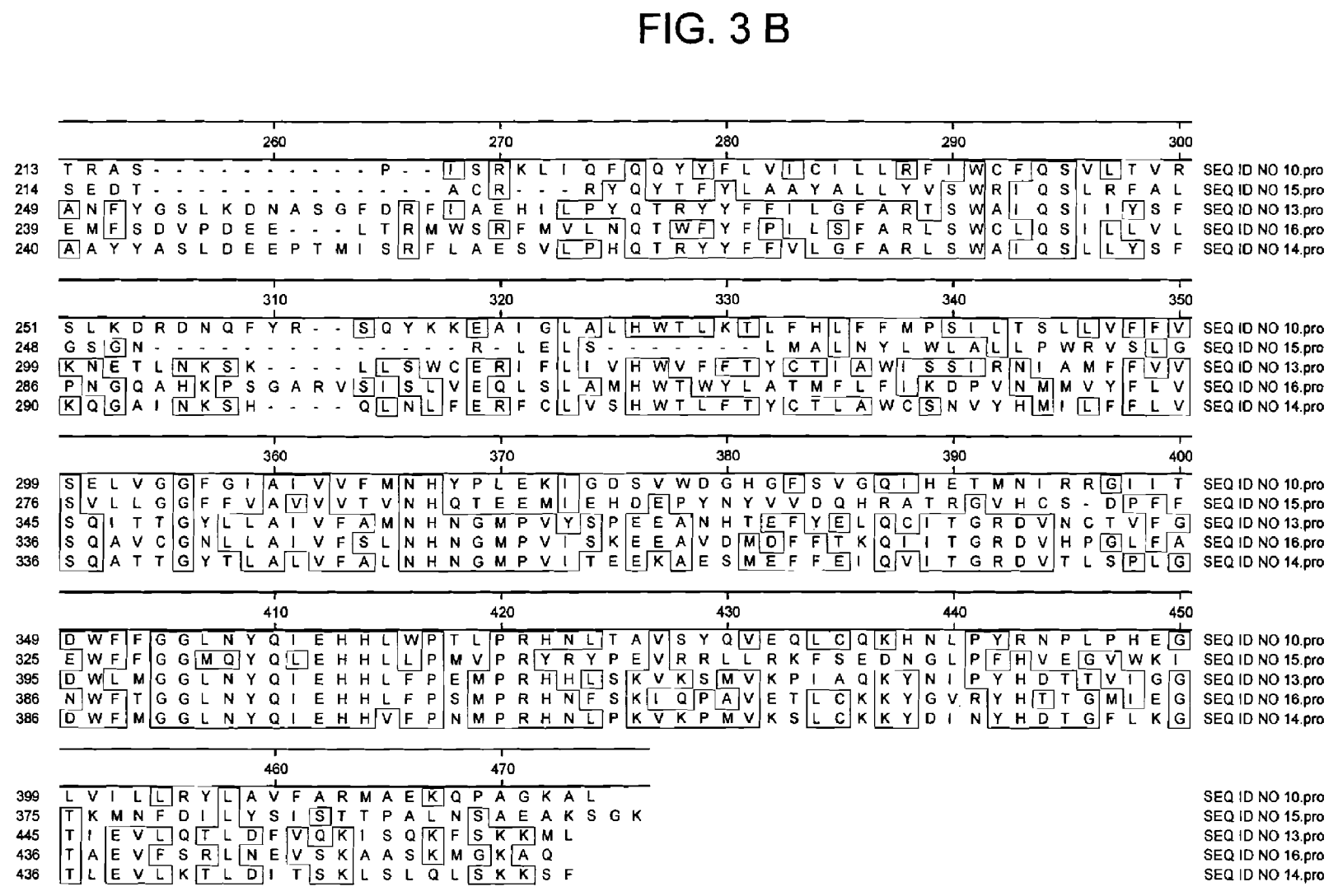

```
                                   260                 270                 280                 290                 300
213  T R A S - - - - - - - - - - P - - I S R K L I Q F Q Q Y Y F L V I C I L L R F I W C F Q S V L T V R   SEQ ID NO 10.pro
214  S E D T - - - - - - - - - - - - - A C R - - - R Y Q Y T F Y L A A Y A L L Y V S W R I Q S L R F A L   SEQ ID NO 15.pro
249  A N F Y G S L K D N A S G F D R F I A E H I L P Y Q T R Y Y F F I L G F A R T S W A I Q S I I Y S F   SEQ ID NO 13.pro
239  E M F S D V P D E E - - - L T R M W S R F M V L N Q T W F Y F P I L S F A R L S W C L Q S I L L V L   SEQ ID NO 16.pro
240  A A Y Y A S L D E E P T M I S R F L A E S V L P H Q T R Y Y F F V L G F A R L S W A I Q S L L Y S F   SEQ ID NO 14.pro

                                   310                 320                 330                 340                 350
251  S L K D R D N Q F Y R - - S Q Y K K E A I G L A L H W T L K T L F H L F F M P S I L T S L L V F F V   SEQ ID NO 10.pro
248  G S G N - - - - - - - - - - - - - - R - L E L S - - - - - - - L M A L N Y L W L A L L P W R V S L G   SEQ ID NO 15.pro
299  K N E T L N K S K - - - - L L S W C E R I F L I V H W V F F T Y C T I A W I S S I R N I A M F F V V   SEQ ID NO 13.pro
286  P N G Q A H K P S G A R V S I S L V E Q L S L A M H W T W Y L A T M F L F I K D P V N M M V Y F L V   SEQ ID NO 16.pro
290  K Q G A I N K S H - - - - Q L N L F E R F C L V S H W T L F T Y C T L A W C S N V Y H M I L F F L V   SEQ ID NO 14.pro

                                   360                 370                 380                 390                 400
299  S E L V G G F G I A I V V F M N H Y P L E K I G D S V W D G H G F S V G Q I H E T M N I R R G I I T   SEQ ID NO 10.pro
276  S V L L G G F F V A V V V T V N H Q T E E M I E H D E P Y N Y V V D Q H R A T R G V H C S - D P F F   SEQ ID NO 15.pro
345  S Q I T T G Y L L A I V F A M N H N G M P V Y S P E E A N H T E F Y E L Q C I T G R D V N C T V F G   SEQ ID NO 13.pro
336  S Q A V C G N L L A I V F S L N H N G M P V I S K E E A V D M D F F T K Q I I T G R D V H P G L F A   SEQ ID NO 16.pro
336  S Q A T T G Y T L A L V F A L N H N G M P V I T E E K A E S M E F F E I Q V I T G R D V T L S P L G   SEQ ID NO 14.pro

                                   410                 420                 430                 440                 450
349  D W F F G G L N Y Q I E H H L W P T L P R H N L T A V S Y Q V E Q L C Q K H N L P Y R N P L P H E G   SEQ ID NO 10.pro
325  E W F F G G M Q Y Q L E H H L L P M V P R Y R Y P E V R R L L R K F S E D N G L P F H V E G V W K I   SEQ ID NO 15.pro
395  D W L M G G L N Y Q I E H H L F P E M P R H H L S K V K S M V K P I A Q K Y N I P Y H D T T V I G G   SEQ ID NO 13.pro
386  N W F T G G L N Y Q I E H H L F P S M P R H N F S K I Q P A V E T L C K K Y G V R Y H T T G M I E G   SEQ ID NO 16.pro
386  D W F M G G L N Y Q I E H H V F P N M P R H N L P K V K P M V K S L C K K Y D I N Y H D T G F L K G   SEQ ID NO 14.pro

                                   460                 470
399  L V I L L R Y L A V F A R M A E K Q P A G K A L                                                      SEQ ID NO 10.pro
375  T K M N F D I L Y S I S T T P A L N S A E A K S G K                                                  SEQ ID NO 15.pro
445  T I E V L Q T L D F V Q K I S Q K F S K K M L                                                        SEQ ID NO 13.pro
436  T A E V F S R L N E V S K A A S K M G K A Q                                                          SEQ ID NO 16.pro
436  T L E V L K T L D I T S K L S L Q L S K K S F                                                        SEQ ID NO 14.pro
```

FIG. 4

```
                10        20        30        40        50
 1  ------------MVKSKRQALPLTIDGTTYDVSAWVNFHPGGAEIIENYQG  SEQ ID NO 10.pro
 1  -MPKVYSYQEVAEHNGPENFWIIIDDKVYDVSQFKDEHPGGDEIIMDLGG  SEQ ID NO 178.pro
 1  MSVKYFEPEEIVEHNNSKDMYMVINGKVYDVSNFADDHPGGLDIMLDYAG  SEQ ID NO 179.pro

                60        70        80        90       100
40  RDATDAFMVMHSQEAFDKLKRMPKINPSSELPPQAAVNEAQEDFRKLREE  SEQ ID NO 10.pro
50  QDATESFVDIGHSDEALRLLKGLYIG---------DVDKTSER---VSVE  SEQ ID NO 178.pro
51  QDATKAYQDIGHSIAADELLEEMYIG---------DLKPGTEER-LKELK  SEQ ID NO 179.pro

               110       120       130       140       150
90  LIATGMFDASPLWYSYKISTTLGLGVLGYFLMVQYQMYFIGAVLLGMHYQ  SEQ ID NO 10.pro
88  KVSTSENQSKGSGTLVVILAILMLGVAYYLLNE                   SEQ ID NO 178.pro
91  KPRSFDNDTPPLPLLIALIVLPAIAVIVFVKLNK                  SEQ ID NO 179.pro
```

FIG. 10 A

```
                10        20        30        40        50
  1  MVKSKRQALPLTIDGTTYDVSAWVNFHPGGAEIIENYQGRDATDAFMVMH  SEQ_ID_NO_10
  1  MVKASRQALPLVIDGKVYDVSAWVNFHPGGAEIIENYQGRDATDAFMVMH  SEQ_ID_NO_4
  1  MVKASRQALPLVIDGKVYDVSAWVNFHPGGAEIIENYQGRDATDAFMVMH  SEQ_ID_NO_6
  1  MVKASRQALPLVIDGKVYDVSAWVNFHPGGAEIIENYQGRDATDAFMVMH  SEQ_ID_NO_8

                60        70        80        90       100
 51  SQEAFDKLKRMPKINPSSELPPQAAVNEAQEDFRKLREELIATGMFDASP  SEQ_ID_NO_10
 51  SQEAFDKLKRMPKINQASELPPQAAVNEAQEDFRKLREELIATGMFDASP  SEQ_ID_NO_4
 51  SQEGYDKLKRMPKINQASELPPQAAVNEAQEDFRKLREELIATGMFDASP  SEQ_ID_NO_6
 51  SQEGYDKLKRMPKINQASELPPQAAVNEAQEDFRKLREELIATGMFDASP  SEQ_ID_NO_8

               110       120       130       140       150
101  LWYSYKISTTLGLGVLGYFLMVQYQMYFIGAVLLGMHYQQMGWLSHDICH  SEQ_ID_NO_10
101  LWYSYKILTTLGLGVLAFFMLVQYHLYFIGALVLGMHYQQMGWLSHDICH  SEQ_ID_NO_4
101  LWYSYKILTTLGLGVLAFFMLVQYHLYFIGALVLGMHYQQMGWLSHDICH  SEQ_ID_NO_6
101  LWYSYKILTTLGLGVLAFFMLVQYHLYFIGAVLLGMHYQQMGWLSHDICH  SEQ_ID_NO_8

               160       170       180       190       200
151  HQTFKNRNWNNLVGLVFGNGLQGFSVTWWKDRHNAHHSATNVQGHDPDID  SEQ_ID_NO_10
151  HQTFKNRNWNNVLGLVFGNGLQGFSVTWWKDRHNAHHSATNVQGHDPDID  SEQ_ID_NO_4
151  HQTFKNRNWNNVLGLVFGNAVQGFSVTWWKDRHNAHHSATNVQGHDPDID  SEQ_ID_NO_6
151  HQTFKNRNWNNVLGLVFGNAVQGFSVTWWKDRHNAHHSATNVQGHDPDID  SEQ_ID_NO_8

               210       220       230       240       250
201  NLPLLAWSEDDVTRASPISRKLIQFQQYYFLVICILLRFIWCFQSVLTVR  SEQ_ID_NO_10
201  NLPLLAWSEDDVTRASPISRKLIQFQQYYFLVICILLRFIWCFQSVLTVR  SEQ_ID_NO_4
201  NLPLLAWSEDDVTRASPISRKLIQFQQYYFLVICILLRFIWCFQSVLTVR  SEQ_ID_NO_6
201  NLPLLAWSEDDVTRASPISRKLIQFQQYYFLVICILLRFIWCFQSVLTVR  SEQ_ID_NO_8
```

FIG. 10 B

```
                                   260                                     270                                     280                                     290                                     300
251 S L K D R D N Q F Y R S Q Y K K E A I G L A L H W T L K T L F H L F F M P S I L T S L L V F F V S E  SEQ_ID_NO_10
251 S L K D R D N Q F Y R S Q Y K K E A I G L A L H W T L K T L F H L F F M P S I L T S M L V F F V S E  SEQ_ID_NO_4
251 S L K D R D N Q F Y R S Q Y K K E A I G L A L H W T L K T L F H L F F M P S I L T S M L V F F V S E  SEQ_ID_NO_6
251 S L K D R D N Q F Y R S Q Y K K E A I G L A L H W T L K L T F H L F F M P S I L T S M L V F F V S E  SEQ_ID_NO_8

                                   310                                     320                                     330                                     340                                     350
301 L V G G F G I A I V V F M N H Y P L E K I G D S V W D G H G F S V G Q I H E T M N I R R G I I T D W  SEQ_ID_NO_10
301 L V G G F G I A I V V F M N H Y P L E K I G D S V W D G H G F S V G Q I H E T M N I R R G I I T D W  SEQ_ID_NO_4
301 L V G G F G I A I V V F M N H Y P L E K I G D S V W D G H G F S V G Q I H E T M N I R R G I I T D W  SEQ_ID_NO_6
301 L V G G F G I A I V V F M N H Y P L E K I G D S V W D G H G F S V G Q I H E T M N I R R G V L S D W  SEQ_ID_NO_8

                                   360                                     370                                     380                                     390                                     400
351 F F G G L N Y Q I E H H L W P T L P R H N L T A V S Y Q V E Q L C Q K H N L P Y R N P L P H E G L V  SEQ_ID_NO_10
351 F F G G L N Y Q I E H H L W P T L P R H N L T A V S Y Q V E Q L C Q K H N L P Y R N P L P H E G L V  SEQ_ID_NO_4
351 F F G G L N Y Q I E H H L W P T L P R H N L T A V S Y Q V E Q L C Q K H N L P Y R N P L P H E G L V  SEQ_ID_NO_6
351 F F G G L N Y Q I E H H L W P T L P R H N L T A V S Y Q V E Q L C Q K H N L P Y R N P L P H E G L V  SEQ_ID_NO_8

                                   410                                     420
401 I L L R Y L A V F A R M A E K Q P A G K A L  SEQ_ID_NO_10
401 I L L R Y L S Q F A R M A E K Q P G A K A Q  SEQ_ID_NO_4
401 I L L R Y L S Q F A R M A E K Q P G A K A Q  SEQ_ID_NO_6
401 I L L R Y L S Q F A R M A E K Q P G A K A Q  SEQ_ID_NO_8
```

| Event | Fatty acid composition (wt.%) | | | | | | | | | | C20 % delta-8 desat | EDA % delta-8 desat | ERA % delta-8 desat | Ratio (EDA/ERA) % desat |
|---|---|---|---|---|---|---|---|---|---|---|---|---|---|---|
| | 16:0 | 18:0 | 18:1 | LA | GLA | ALA | EDA | DGLA | ERA | ETA | | | | |
| 2063-1-4-1 | 19.8 | 5.1 | 14.4 | 23.5 | 0.0 | 8.3 | 8.0 | 15.4 | 1.1 | 4.4 | 68.4 | 65.8 | 79.8 | 0.8 |
| 2063-1-4-2 | 19.9 | 5.6 | 19.2 | 22.3 | 0.2 | 8.5 | 6.5 | 12.9 | 0.8 | 4.0 | 69.7 | 66.4 | 83.1 | 0.8 |
| 2063-1-4-3 | 20.4 | 5.1 | 16.8 | 23.0 | 0.0 | 9.2 | 6.8 | 13.5 | 1.0 | 4.3 | 69.7 | 66.6 | 81.7 | 0.8 |
| 2063-1-4-4 | 22.2 | 6.3 | 19.8 | 21.0 | 0.2 | 8.0 | 6.2 | 11.7 | 1.0 | 3.8 | 68.1 | 65.3 | 78.5 | 0.8 |
| 2063-1-4-5 | 20.6 | 5.8 | 19.9 | 21.5 | 0.0 | 8.3 | 6.9 | 12.3 | 0.8 | 4.0 | 68.1 | 64.1 | 84.1 | 0.8 |
| 2063-1-4-6 | 18.7 | 5.3 | 15.8 | 23.7 | 0.2 | 9.8 | 7.4 | 13.2 | 1.1 | 4.7 | 67.8 | 64.1 | 80.7 | 0.8 |
| 2063-2-5-1 | 16.7 | 4.2 | 12.8 | 30.3 | 0.1 | 12.1 | 8.1 | 10.1 | 1.2 | 4.5 | 61.2 | 55.5 | 79.3 | 0.7 |
| 2063-2-5-2 | 18.4 | 4.0 | 10.4 | 39.5 | 0.0 | 22.7 | 1.5 | 2.1 | 0.2 | 1.0 | 63.8 | 58.0 | 80.6 | 0.7 |
| 2063-2-5-3 | 18.1 | 5.4 | 16.5 | 29.1 | 0.1 | 12.3 | 5.8 | 8.3 | 0.9 | 3.5 | 64.1 | 59.0 | 80.5 | 0.7 |
| 2063-2-5-4 | 17.2 | 4.1 | 11.0 | 43.1 | 0.0 | 23.9 | 0.3 | 0.4 | 0.0 | 0.2 | 62.1 | 53.9 | 100.0 | 0.5 |
| 2063-2-5-5 | 18.7 | 3.9 | 11.9 | 31.6 | 0.1 | 18.6 | 4.5 | 6.6 | 0.8 | 3.3 | 64.9 | 59.2 | 80.1 | 0.7 |
| 2063-2-5-6 | 17.9 | 4.0 | 13.2 | 31.4 | 0.2 | 15.7 | 5.3 | 8.0 | 0.8 | 3.5 | 65.4 | 60.2 | 81.4 | 0.7 |
| 2063-3-3-1 | 20.4 | 4.3 | 8.8 | 27.7 | 0.0 | 14.7 | 7.0 | 11.2 | 1.2 | 4.7 | 65.9 | 61.4 | 79.9 | 0.8 |
| 2063-3-3-2 | 21.6 | 5.2 | 15.7 | 26.1 | 0.0 | 14.2 | 4.9 | 8.0 | 0.9 | 3.5 | 66.5 | 62.0 | 79.2 | 0.8 |
| 2063-3-3-3 | 19.8 | 4.0 | 7.7 | 27.0 | 0.0 | 13.4 | 7.5 | 13.4 | 1.5 | 5.7 | 68.0 | 64.1 | 79.4 | 0.8 |
| 2063-3-3-4 | 20.0 | 3.9 | 9.0 | 27.0 | 0.0 | 13.0 | 7.0 | 13.3 | 1.2 | 5.7 | 69.8 | 65.5 | 82.2 | 0.8 |
| 2063-3-3-5 | 21.1 | 4.5 | 8.3 | 26.7 | 0.0 | 13.7 | 6.8 | 12.5 | 1.3 | 5.2 | 68.7 | 64.9 | 80.1 | 0.8 |
| 2063-3-3-6 | 20.3 | 4.8 | 9.4 | 28.1 | 0.0 | 15.8 | 6.0 | 9.9 | 1.4 | 4.4 | 65.9 | 62.1 | 76.5 | 0.8 |
| 2063-3-5-1 | 18.2 | 3.8 | 11.3 | 25.9 | 0.0 | 11.2 | 9.3 | 14.4 | 1.1 | 4.7 | 64.6 | 60.8 | 80.4 | 0.8 |
| 2063-3-5-2 | 20.3 | 5.3 | 18.7 | 23.7 | 0.0 | 9.7 | 6.6 | 11.0 | 0.9 | 3.7 | 66.2 | 62.5 | 80.8 | 0.8 |
| 2063-3-5-3 | 21.3 | 5.0 | 15.7 | 24.6 | 0.0 | 9.6 | 7.5 | 11.6 | 0.8 | 3.9 | 65.1 | 60.7 | 83.3 | 0.7 |
| 2063-3-5-4 | 19.8 | 4.4 | 11.8 | 26.1 | 0.0 | 10.5 | 9.1 | 13.1 | 1.1 | 4.0 | 62.6 | 59.0 | 78.1 | 0.8 |
| 2063-3-5-5 | 20.7 | 5.2 | 15.0 | 25.3 | 0.0 | 13.2 | 6.0 | 9.9 | 0.9 | 3.9 | 66.6 | 62.3 | 80.5 | 0.8 |
| 2063-3-5-6 | 21.6 | 5.2 | 13.7 | 24.0 | 0.0 | 9.7 | 8.2 | 12.2 | 1.2 | 4.1 | 63.4 | 59.8 | 77.7 | 0.8 |
| 2063-3-7-1 | 17.9 | 4.4 | 16.4 | 27.9 | 0.0 | 9.8 | 7.9 | 11.1 | 1.1 | 3.5 | 61.8 | 58.4 | 76.2 | 0.8 |
| 2063-3-7-2 | 18.2 | 4.0 | 10.6 | 29.1 | 0.0 | 11.9 | 7.9 | 12.9 | 1.3 | 4.2 | 65.1 | 62.1 | 76.7 | 0.8 |
| 2063-3-7-3 | 17.9 | 3.6 | 11.0 | 29.4 | 0.0 | 12.7 | 7.6 | 12.6 | 1.0 | 4.3 | 66.4 | 62.4 | 81.7 | 0.8 |
| 2063-3-7-4 | 17.9 | 3.7 | 9.4 | 30.4 | 0.2 | 13.9 | 6.8 | 12.5 | 1.0 | 4.2 | 68.2 | 64.7 | 80.8 | 0.8 |
| 2063-3-7-5 | 19.0 | 4.3 | 10.9 | 27.9 | 0.0 | 13.4 | 7.5 | 11.0 | 1.9 | 4.1 | 61.6 | 59.4 | 68.5 | 0.9 |
| 2063-3-7-6 | 18.3 | 4.4 | 14.8 | 29.3 | 0.0 | 10.4 | 7.9 | 10.9 | 0.9 | 3.1 | 61.3 | 57.7 | 78.0 | 0.7 |

FIG. 14

MUTANT DELTA-8 DESATURASE GENES ENGINEERED BY TARGETED MUTAGENSIS AND THEIR USE IN MAKING POLYUNSATURATED FATTY ACIDS

This application claims the benefit of U.S. Provisional Application No. 60/868,953, filed Dec. 7, 2006, the entire contents of which are herein incorporated by reference.

FIELD OF THE INVENTION

This invention is in the field of biotechnology. More specifically, this invention pertains to the creation of nucleic acid fragments encoding mutant delta-8 fatty acid desaturase enzymes and the use of these desaturases in making long-chain polyunsaturated fatty acids (PUFAs).

BACKGROUND OF THE INVENTION

The importance of PUFAs is undisputed. For example, certain PUFAs are important biological components of healthy cells and are considered "essential" fatty acids that cannot be synthesized de novo in mammals and instead must be obtained either in the diet or derived by further desaturation and elongation of linoleic acid (LA; 18:2 omega-6) or α-linolenic acid (ALA; 18:3 omega-3). Additionally PUFAs are constituents of plasma membranes of cells, where they may be found in such forms as phospholipids or triacylglycerols. PUFAs are necessary for proper development (particularly in the developing infant brain) and for tissue formation and repair and are precursors to several biologically active eicosanoids of importance in mammals (e.g., prostacyclins, eicosanoids, leukotrienes, prostaglandins). Studies have shown that a high intake of long-chain omega-3 PUFAs produces cardiovascular protective effects (Dyerberg, J. et al., *Amer. J. Clin. Nutr.* 28:958-966 (1975); Dyerberg, J. et al., *Lancet.* 2(8081):117-119 (1978); Shimokawa, H., *World Rev. Nutr. Diet* 88:100-108 (2001); von Schacky, C. and Dyerberg, J., *World Rev. Nutr. Diet* 88:90-99 (2001)). The literature reports wide-ranging health benefits conferred by administration of omega-3 and/or omega-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts can be substantially altered to produce various long-chain omega-3/omega-6 PUFAs. For example, production of arachidonic acid (ARA; 20:4 omega-6), eicosapentaenoic acid (EPA; 20:5 omega-3) and docosahexaenoic acid (DHA; 22:6 omega-3) all require expression of either the delta-9 elongase/delta-8 desaturase pathway or the delta-6 desaturase/delta-6 elongase pathway. The delta-9 elongase/delta-8 desaturase pathway is present for example in euglenoid species and is characterized by the production of eicosadienoic acid (EDA; 20:2 omega-6] and/or eicosatrienoic acid (ETrA; 20:3 omega-3). (FIG. 1). The delta-6 desaturase/delta-6 elongase pathway is predominantly found in algae, mosses, fungi, nematodes and humans and is characterized by the production of γ-linoleic acid (GLA; 18:3 omega-6) and/or stearidonic acid (STA; 18:4 omega-3) (FIG. 1).

For some applications the delta-9 elongase/delta-8 desaturase pathway is favored. However, delta-8 desaturase enzymes are not well known in the art leaving the construction of a recombinant delta-9 elongase/delta-8 desaturase pathway with limited options. The few delta-8 desaturase enzymes identified thus far have the ability to convert both EDA to dihomo-γ-linolenic acid (DGLA; 20:3) and ETrA to eicosatetraenoic acid (ETA; 20:4) (wherein ARA are EPA are subsequently synthesized from DGLA and ETA, respectively, following reaction with a delta-5 desaturase, while DHA synthesis requires subsequent expression of an additional $C_{20/22}$ elongase and a delta-4 desaturase).

Several delta-8 desaturase enzymes are known and have been partially characterized (see for example delta-8 desaturases from *Euglena gracilis* Wallis et al., *Arch. Biochem. and Biophys.* 365(2):307-316 (1999); WO 2000/34439; U.S. Pat. No. 6,825,017; WO 2004/057001; WO 2006/012325; WO 2006/012326). Additionally WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Furthermore, commonly owned and co-pending U.S. Provisional Application No. 60/795,810 filed Apr. 28, 2006, discloses amino acid and nucleic acid sequences for a delta-8 desaturase enzyme from *Pavlova lutheri* (CCMP459).

A need remains therefore for additional delta-8 desaturase enzymes to be used in recombinant pathways for the production of PUFAs. Applicants have solved the stated need by developing a synthetically engineered mutant *Euglena gracilis* delta-8 desaturase.

SUMMARY OF THE INVENTION

The invention concerns an isolated polynucleotide comprising:

(a) a nucleotide sequence encoding a mutant polypeptide having delta-8 desaturase activity wherein the mutant polypeptide has an amino acid sequence as set forth in SEQ ID NO:2 and further wherein SEQ ID NO:2 is not identical to SEQ ID NO:10; or, (b) a complement of the nucleotide sequence of part (a), wherein the complement and the nucleotide sequence consist of the same number of nucleotides and are 100% complementary.

In a second embodiment, the invention concerns an isolated polynucleotide of Claim 1 wherein the nucleotide sequence comprises SEQ ID NO:1 and wherein SEQ ID NO:1 is not identical to SEQ ID NO:9.

In a third embodiment, the invention comprises an isolated polynucleotide comprising:

(a) a nucleotide sequence encoding a mutant polypeptide having delta-8 desaturase activity wherein the mutant polypeptide has an amino acid sequence as set forth in SEQ ID NO:198 and further wherein SEQ ID NO:198 is not identical to SEQ ID NO:10; or, (b) a complement of the nucleotide sequence of part (a), wherein the complement and the nucleotide sequence consist of the same number of nucleotides and are 100% complementary.

In a fourth embodiment, the invention concerns an isolated polynucleotide of Claim 3 wherein the nucleotide sequence comprises SEQ ID NO:197 and wherein SEQ ID NO:197 is not identical to SEQ ID NO:9.

In a fifth embodiment, the invention concerns a recombinant construct comprising any of the polynucleotides of the invention operably linked to at least one regulatory sequence.

In a sixth embodiment, the invention concerns a cell comprising in its genome the recombinant DNA construct of the invention.

In a seventh embodiment, the invention concerns a method for producing a transgenic plant, comprising transforming a plant cell with at least one polynucleotide of the invention and regenerating a transgenic plant from the transformed plant cell. A preferred plant is soybean.

In an eighth embodiment, the invention concerns a transgenic seed comprising the recombinant construct of the invention.

In a ninth embodiment, a method for making a long-chain polyunsaturated fatty acid in a plant cell comprising:

(a) transforming a cell with the recombinant construct of the invention; and (b) selecting those transformed cells that make long-chain polyunsaturated fatty acids. Preferably, the plant cell is a soybean cell.

In a tenth embodiment, the invention concerns a method for producing at least one polyunsaturated fatty acid in a soybean cell comprising:

(a) transforming a soybean cell with a first recombinant construct comprising an isolated polynucleotide encoding at least one mutant delta-8 desaturase polypeptide, operably linked to at least one regulatory sequence and at least one additional recombinant construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating a soybean plant from the transformed soybean cell of step (a); and (c) selecting those seeds obtained from the plants of step (b) having an altered level of polyunsaturated fatty acids when compared to the level in seeds obtained from a nontransformed soybean plant.

In an eleventh embodiment, the invention concerns an oilseed plant comprising:

(a) a first recombinant construct comprising an isolated polynucleotide encoding at least one mutant delta-8 desaturase polypeptide, operably linked to at least one regulatory sequence; and (b) at least one additional recombinant construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, $C_{14/16}$ elongase, a $C_{16/18}$ elongase, a $C_{18/20}$ elongase and a $C_{20/22}$ elongase.

Also of interest are transgenic seeds obtained from such oilseed plants and oil obtained from these seeds.

In a twelfth embodiment, the invention concerns food or feed which incorporates oil of the invention.

In a thirteenth embodiment, the invention concerns food or feed comprising an ingredient derived from the processing of the seeds of the invention.

In a fourteenth embodiment, the invention concerns progeny plants obtained from obtained from a plant made by the method of the invention or an oilseed plant of the invention.

Biological Deposits

The following plasmid has been deposited with the American Type Culture Collection (ATCC), 10801 University Boulevard, Manassas, Va. 20110-2209, and bears the following designation, Accession Number and date of deposit (Table 1).

TABLE 1

| ATCC Deposits | | |
|---|---|---|
| Plasmid | Accession Number | Date of Deposit |
| pKR72 | PTA-6019 | May 28, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 3 shows an alignment of EgD8S (SEQ ID NO:10), a delta-6 desaturase of *Amylomyces rouxii* (SEQ ID NO:13), a delta-6 desaturase of *Rhizopus orizae* (SEQ ID NO:14), a delta-8 fatty acid desaturase-like protein of *Leishmania major* (GenBank Accession No. CAJ09677; SEQ ID NO:15), and a delta-6 desaturase of *Mortierella isabellina* (GenBank Accession No. AAG38104; SEQ ID NO:16). The method of alignment used corresponds to the "Clustal W method of alignment".

FIG. 4 shows an alignment of EgD8S (SEQ ID NO:10), the cytochrome $b_5$ of *Saccharomyces cerevisiae* (GenBank Accession No. P40312; SEQ ID NO:178) and a probable cytochrome $b_5$ 1 of *Schizosaccharomyces pombe* (GenBank Accession No. O94391; SEQ ID NO:179). The method of alignment used corresponds to the "Clustal W method of alignment".

Figure 5A:
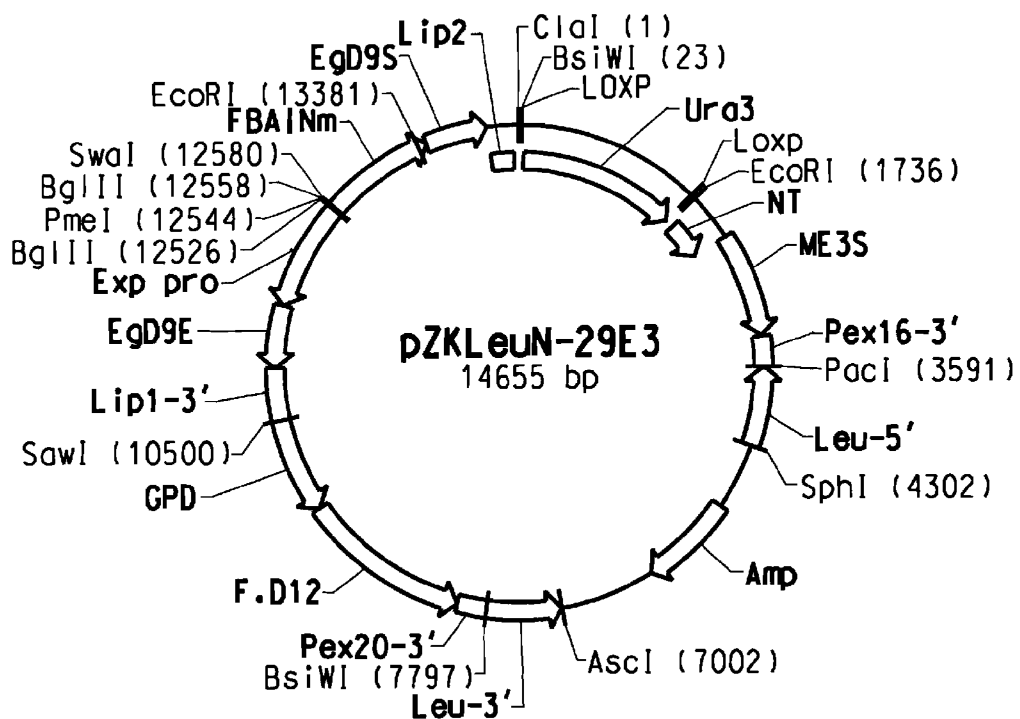
Figure 5B:
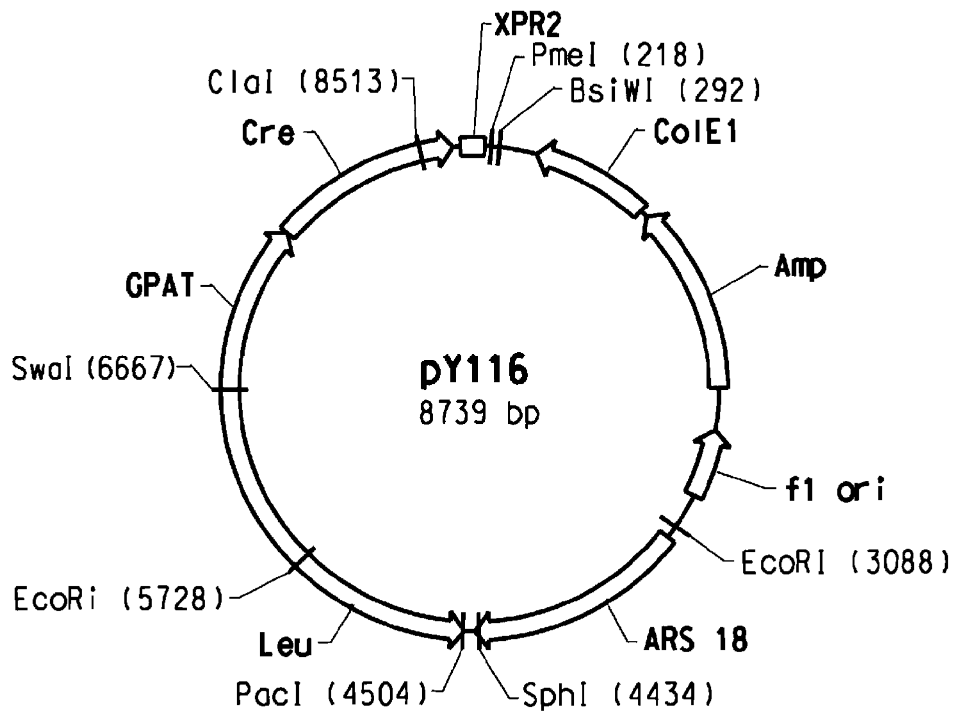

FIG. 5 provides plasmid maps for the following: (A) pZKLeuN-29E3; and, (B) pY116.

FIG. 6 provides plasmid maps for the following: (A) pKUNFmkF2; (B) pDMW287F; (C) pDMW214; and, (D) pFmD8S.

Figure 7:
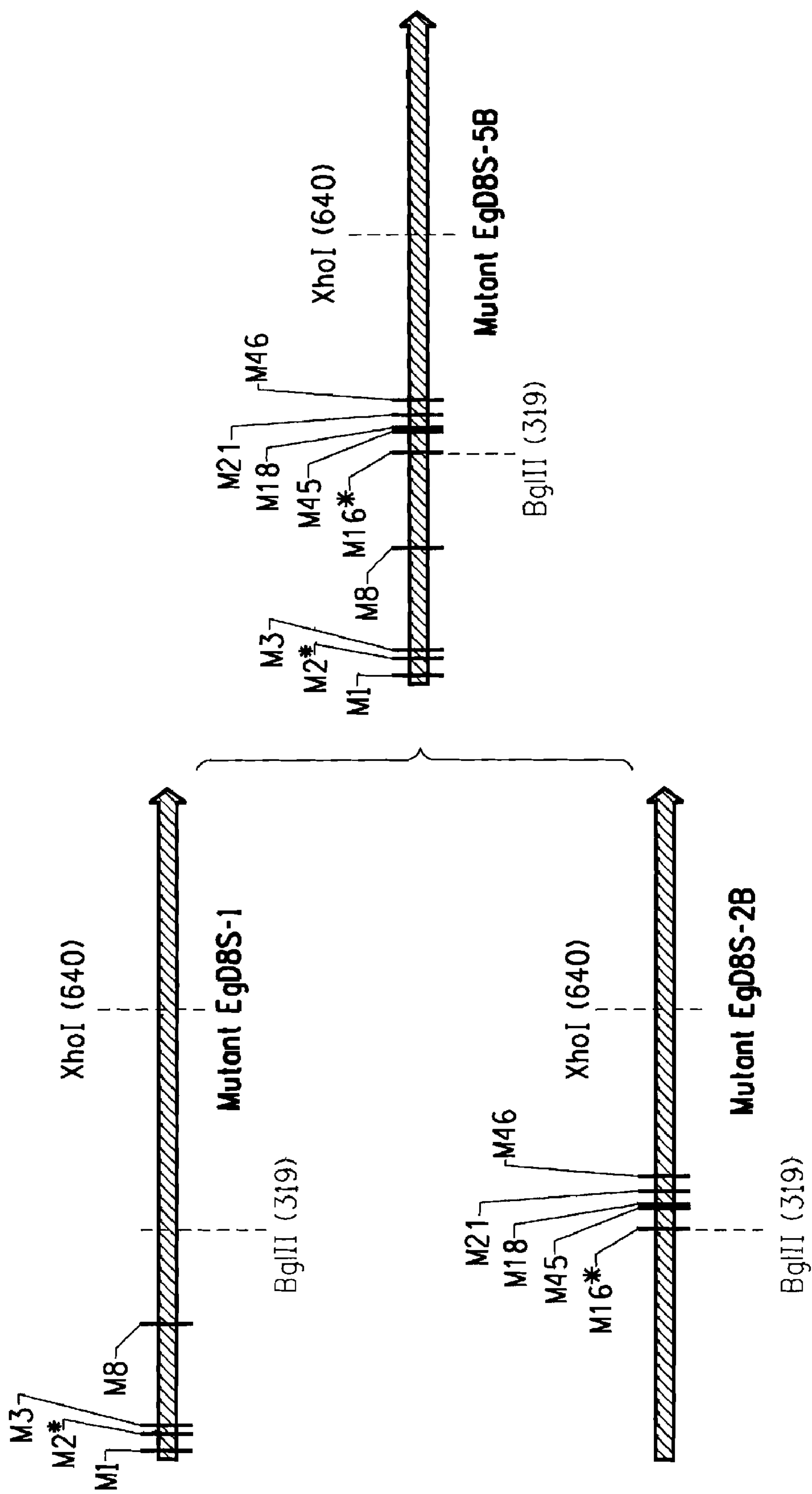

FIG. 7 diagrams the synthesis of the Mutant EgD8S-5B, by ligation of fragments from Mutant EgD8S-1 and Mutant EgD8S-2B.

Figure 8A:
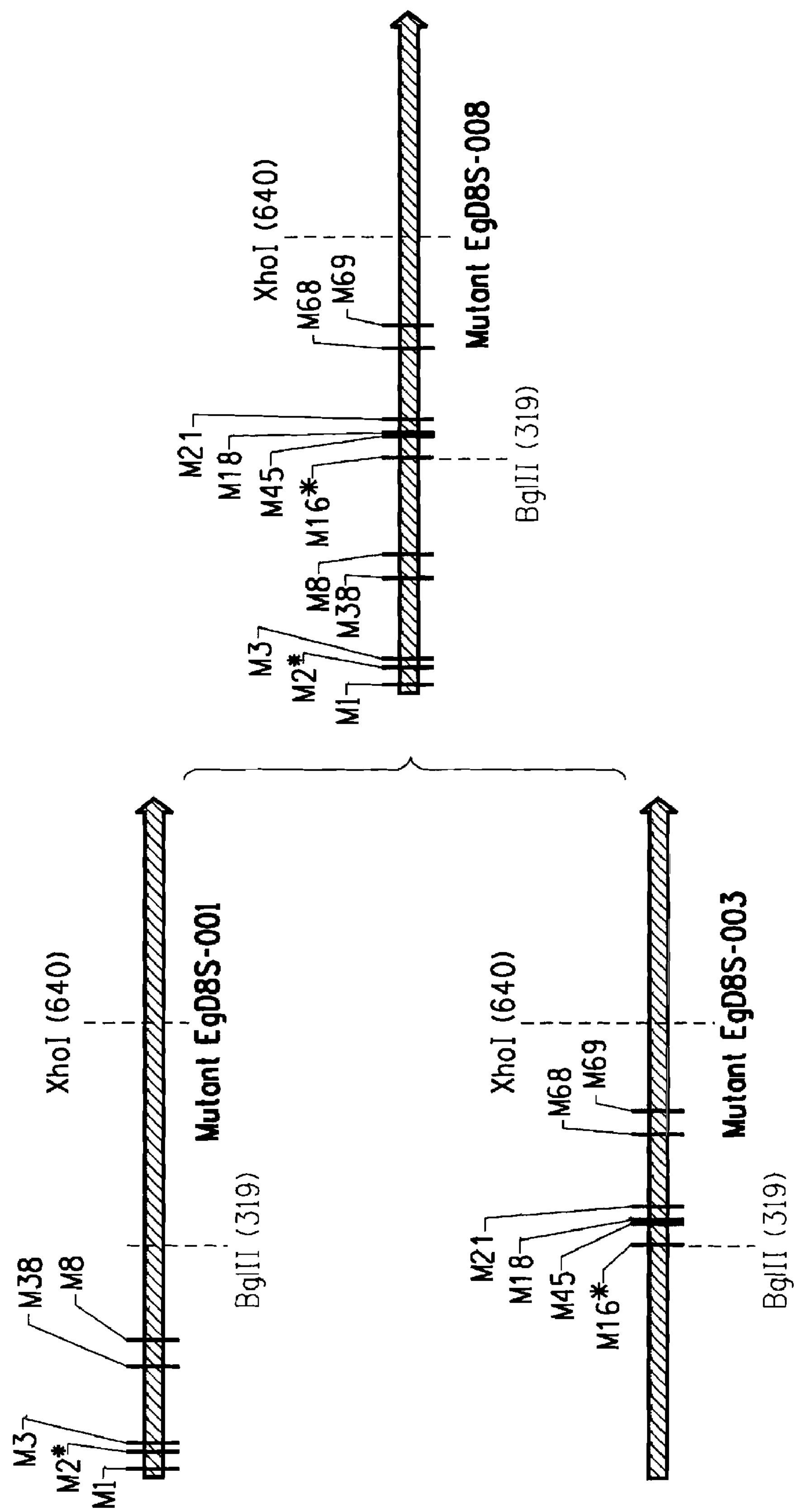

FIG. 8A diagrams the synthesis of Mutant EgD8S-008, by ligation of fragments from Mutant EgD8S-001 and Mutant EgD8S-003. Similarly, FIG. 8B diagrams the synthesis of Mutant EgD8S-009, by ligation of fragments from Mutant EgD8S-001 and Mutant EgD8S-004.

Figure 9A:
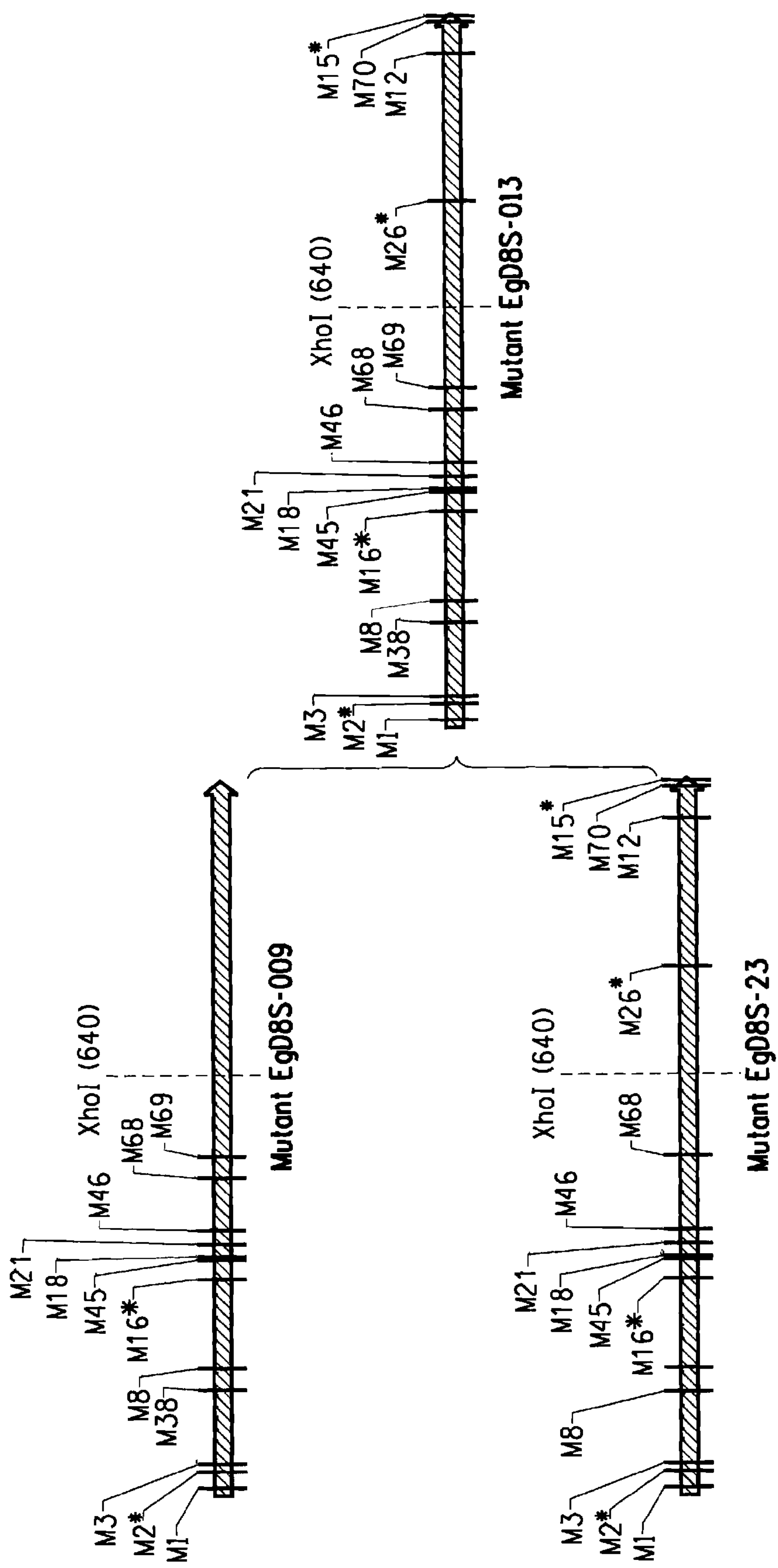

FIG. 9A diagrams the synthesis of Mutant EgD8S-013, by ligation of fragments from Mutant EgD8S-009 and Mutant EgD8S-23. Similarly, FIG. 9B diagrams the synthesis of Mutant EgD8S-015, by ligation of fragments from Mutant EgD8S-008 and Mutant EgD8S-28.

FIG. 10 shows an alignment of EgD8S (SEQ ID NO:10), Mutant EgD8S-23 (SEQ ID NO:4), Mutant EgD8S-013 (SEQ ID NO:6) and Mutant EgD8S-015 (SEQ ID NO:8). The method of alignment used corresponds to the "Clustal W method of alignment".

FIG. 11 provides plasmid maps for the following: (A) pKo2UFm8; and, (B) pKO2UF8289.

Figure 12:
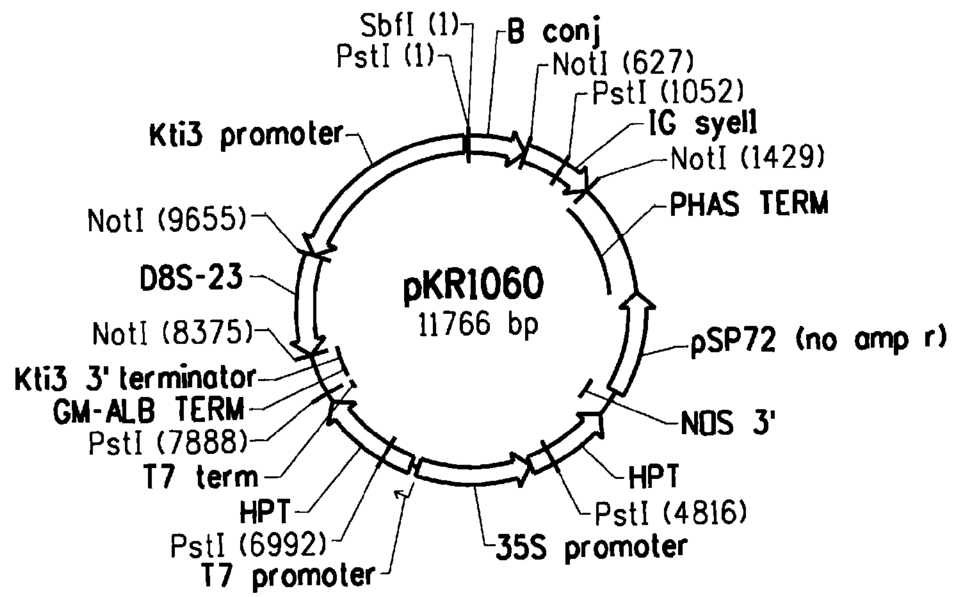

FIG. 12 provides a plasmid map for pKR1060.

Figure 13:
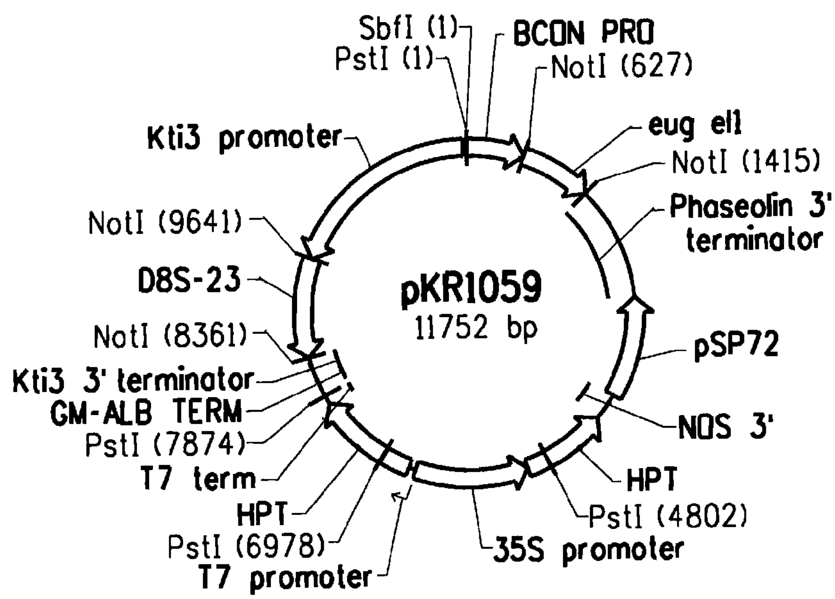

FIG. 13 provides a plasmid map for pKR1059.

FIG. 14 shows the lipid profiles of somatic soybean embryos expressing EgD8S-23 and the *Euglena gracilis* delta-9 elongase for the top 5 events (see example 17).

The sequence descriptions summarize the Sequences Listing provided herewith. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2): 345-373 (1984). The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs:1-17, 19-23,165 and 172-177 are ORFs encoding genes or proteins (or portions thereof) or plasmids, as identified in Table 2.

TABLE 2

Summary Of Nucleic Acid And Protein SEQ ID Numbers

| Description and Abbreviation | Nucleic acid SEQ ID NO. | Protein SEQ ID NO. |
|---|---|---|
| Synthetic mutant delta-8 desaturase, derived from *Euglena gracilis* ("EgD8S-consensus") optionally comprising M1, M2, M3, M8, M12, M15, M16, M18, M21, M26, M38, M45, M46, M51, M63, M68, M69 and M70 mutation sites | 1 (1272 bp) | 2 (422 AA) |
| Synthetic mutant delta-8 desaturase, derived from *Euglena gracilis* ("EgD8S-consensus") optionally comprising M1, M2, M3, M6, M8, M12, M14, M15, M16, M18, M19, M21, M22, M26, M38, M39, M40, M41, M45, M46, M49, M50, M51, M53, M54, M58, M63, M68, M69 and M70 mutation sites | 197 (1272 bp) | 198 (422 AA) |
| Synthetic mutant delta-8 desaturase, derived from *Euglena gracilis* ("Mutant EgD8S-23") | 3 (1272 bp) | 4 (422 AA) |
| Synthetic mutant delta-8 desaturase, derived from *Euglena gracilis* ("Mutant EgD8S-013") | 5 (1272 bp) | 6 (422 AA) |
| Synthetic mutant delta-8 desaturase, derived from *Euglena gracilis* ("Mutant EgD8S-015") | 7 (1272 bp) | 8 (422 AA) |
| Synthetic delta-8 desaturase, derived from Euglena gracilis, codon-optimized for expression in *Yarrowia lipolytica* ("EgD8S") | 9 (1272 bp) | 10 (422 AA) |
| *Euglena gracilis* delta-8 desaturase (full-length gene is nucleotides 4-1269 (Stop)) ("EgD8") | 11 (1271 bp) | 12 (421 AA) |
| *Amylomyces rouxii* delta-6 desaturase (GenBank Accession No. AAR27297) | — | 13 (467 AA) |
| *Rhizopus orizae* delta-6 desaturase (GenBank Accession No. AAS93682) | — | 14 (445 AA) |
| *Leishmania major* delta-8 fatty acid desaturase-like protein (GenBank Accession No. CAJ09677) | — | 15 (382 AA) |
| *Mortierella isabellina* delta-6 desaturase (GenBank Accession No. AAG38104) | — | 16 (439 AA) |
| *Saccharomyces cerevisiae* cytochrome $b_5$ (GenBank Accession No. P40312) | — | 178 (120 AA) |
| *Schizosaccharomyces pombe* probable cytochrome $b_5$ 1 (GenBank Accession No. O94391) | — | 179 (124 AA) |
| Plasmid pZKLeuN-29E3 | 17 (14,655 bp) | — |
| Synthetic $C_{16/18}$ elongase gene derived from *Mortierella alpina* ELO3, codon-optimized for expression in *Yarrowia lipolytica* | 19 (828 bp) | — |

TABLE 2-continued

Summary Of Nucleic Acid And Protein SEQ ID Numbers

| Description and Abbreviation | Nucleic acid SEQ ID NO. | Protein SEQ ID NO. |
|---|---|---|
| Plasmid pFmD8S | 20 (8,910 bp) | — |
| Plasmid pKUNFmkF2 | 21 (7,145 bp) | — |
| Plasmid pDMW287F | 22 (5,473 bp) | — |
| Plasmid pDMW214 | 23 (9,513 bp) | — |
| Plasmid pKO2UFkF2 | 165 (8,560 bp) | — |
| *Isochrysis galbana* delta-9 elongase (GenBank Accession No. AF390174) | 172 (1064 bp) | 173 (263 AA) |
| Synthetic delta-9 elongase gene derived from *Isochrysis galbana*, codon-optimized for expression in *Yarrowia lipolytica* | 174 (792 bp) | 173 (263 AA) |
| *Euglena gracilis* delta-9 elongase | 175 (777 bp) | 176 (258 AA) |
| Synthetic delta-9 elongase gene derived from *Euglena gracilis*, codon-optimized for expression in *Yarrowia lipolytica* | 177 (777 bp) | 176 (258 AA) |
| Plasmid pY116 | 180 (8739 bp) | — |
| Plasmid pKO2UF8289 | 181 (15,304 bp) | — |
| Synthetic mutant delta-8 desaturase, derived from *Euglena gracilis* ("modified Mutant EgD8S-23"), comprising a 5' Not1 site | 182 (1288 bp) | — |
| Plasmid pKR457 | 183 (5252 bp) | — |
| Plasmid pKR1058 | 184 (6532 bp) | — |
| Plasmid pKR607 | 185 (7887 bp) | — |
| Plasmid pKR1060 | 186 (11,766 bp) | — |
| Plasmid pKR906 | 189 (4311 bp) | — |
| Plasmid pKR72 | 190 (7085 bp) | — |
| Plasmid pKR1010 | 191 (7873 bp) | — |
| Plasmid pKR1059 | 192 (11752 bp) | — |
| *Euglena gracilis* delta-9 elongase - 5' sequence of the cDNA insert from clone eeg1c.pk001.n5.f. | 194 (757 bp) | — |
| *Euglena gracilis* delta-9 elongase - 3' sequence of the cDNA insert from clone eeg1c.pk001.n5.f. | 195 (774 bp) | — |
| *Euglena gracilis* delta-9 elongase - sequence aligned from SEQ ID NO: 1 and SEQ ID NO: 2 (full cDNA sequence excluding polyA tail) | 196 (1201 bp) | — |

SEQ ID NO:18 corresponds to a LoxP recombination site that is recognized by a Cre recombinase enzyme.

SEQ ID NOs:24-164 correspond to 70 pairs of nucleotide primers (i.e., 1A, 1B, 2A, 2B, 3A, 3B, etc. up to 69A, 69B, 70A and 70B, respectively), used to create specific targeted mutations at mutation sites M1, M2, M3, etc. up to M70.

SEQ ID NOs:166-171 correspond to His-rich motifs that are featured in membrane-bound fatty acid desaturases belonging to a super-family of membrane di-iron proteins.

SEQ ID NOs:187 and 188 correspond to primers oEugEL1-1 and oEugEL1-2, respectively, used to amplify a *Euglena gracilis* delta-9 elongase.

SEQ ID NO:193 is the M13F universal primer.

DETAILED DESCRIPTION OF THE INVENTION

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

All patents, patent applications, and publications cited herein are incorporated by reference in their entirety. This specifically includes the following commonly owned and copending applications: U.S. patent application Ser. No. 10/840,478, No. 10/840,579 and No. 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,254 and No. 10/985,691 (filed Nov. 10, 2004), U.S. patent application Ser. No. 10/987,548 (filed Nov. 12, 2004), U.S. patent application Ser. No. 11/024,545 and No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/251,466 (filed Oct. 14, 2005), U.S. patent application Ser. No. 11/254,173 and No. 11/253,882 (filed Oct. 19, 2005), U.S. patent application Ser. No. 11/264,784 and No. 11/264,737 (filed Nov. 1, 2005), U.S. patent application Ser. No. 11/265,761 (filed Nov. 2, 2005), U.S. Patent Application No. 60/739,989 (filed Nov. 23, 2005), U.S. Patent Application No. 60/793,575 (filed Apr. 20, 2006), U.S. Patent Application No. 60/795,810 (filed Apr. 28, 2006), U.S. Patent Application No. 60/796,637 (filed May 1, 2006) and U.S. patent application Ser. No. 60/801,172 and No. 60/801,119 (filed May 17, 2006).

Additionally, commonly owned U.S. patent application Ser. No. 10/776,311, (published Aug. 26, 2004) relating to the production of PUFAs in plants, and U.S. patent application Ser. No. 10/776,889 (published Aug. 26, 2004) relating to annexin promoters and their use in expression of transgenes in plants, are incorporated by reference in their entirety.

The present invention provides mutant delta-8 desaturase enzymes and genes encoding the same, that may be used for the manipulation of biochemical pathways for the production of healthful PUFAs.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. PUFAs may also be used as anti-inflammatory or cholesterol lowering agents as components of pharmaceutical or veterinary compositions.

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (omega-6 or n-6) versus "omega-3 fatty acids" (omega-3 or n-3) are provided in WO2004/101757.

Fatty acids are described herein by a simple notation system of "X:Y", wherein X is the number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c). Unless otherwise specified, 18:1, 18:2 and 18:3 refer to oleic, LA and ALA fatty acids. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 3. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids and their precursors, the abbreviations that will be used throughout the specification, and each compounds' chemical name.

TABLE 3

Nomenclature Of Polyunsaturated Fatty Acids And Precursors

| Common Name | Abbreviation | Chemical Name | Shorthand Notation |
|---|---|---|---|
| myristic | — | tetradecanoic | 14:0 |
| palmitic | PA | hexadecanoic | 16:0 |
| palmitoleic | — | 9-hexadecenoic | 16:1 |
| stearic | — | octadecanoic | 18:0 |
| oleic | — | cis-9-octadecenoic | 18:1 |
| linoleic | LA | cis-9,12-octadecadienoic | 18:2 omega-6 |
| gamma-linolenic | GLA | cis-6,9,12-octadecatrienoic | 18:3 omega-6 |
| eicosadienoic | EDA | cis-11,14-eicosadienoic | 20:2 omega-6 |
| dihomo-gamma-linolenic | DGLA | cis-8,11,14-eicosatrienoic | 20:3 omega-6 |
| sciadonic | SCI | cis-5,11,14-eicosatrienoic | 20:3b omega-6 |
| arachidonic | ARA | cis-5,8,11,14-eicosatetraenoic | 20:4 omega-6 |
| alpha-linolenic | ALA | cis-9,12,15-octadecatrienoic | 18:3 omega-3 |
| stearidonic | STA | cis-6,9,12,15-octadecatetraenoic | 18:4 omega-3 |
| eicosatrienoic | ETrA or ERA | cis-11,14,17-eicosatrienoic | 20:3 omega-3 |
| eicosa-tetraenoic | ETA | cis-8,11,14,17-eicosatetraenoic | 20:4 omega-3 |
| juniperonic | JUP | cis-5,11,14,17-eicosatrienoic | 20:4b omega-3 |
| eicosa-pentaenoic | EPA | cis-5,8,11,14,17-eicosapentaenoic | 20:5 omega-3 |
| docosa-pentaenoic | DPA | cis-7,10,13,16,19-docosapentaenoic | 22:5 omega-3 |
| docosa-hexaenoic | DHA | cis-4,7,10,13,16,19-docosahexaenoic | 22:6 omega-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a $C_{14/16}$ elongase, a delta-9 elongase, a $C_{16/18}$ elongase, a $C_{18/20}$ elongase and/or a $C_{20/22}$ elongase.

Figure 1B:
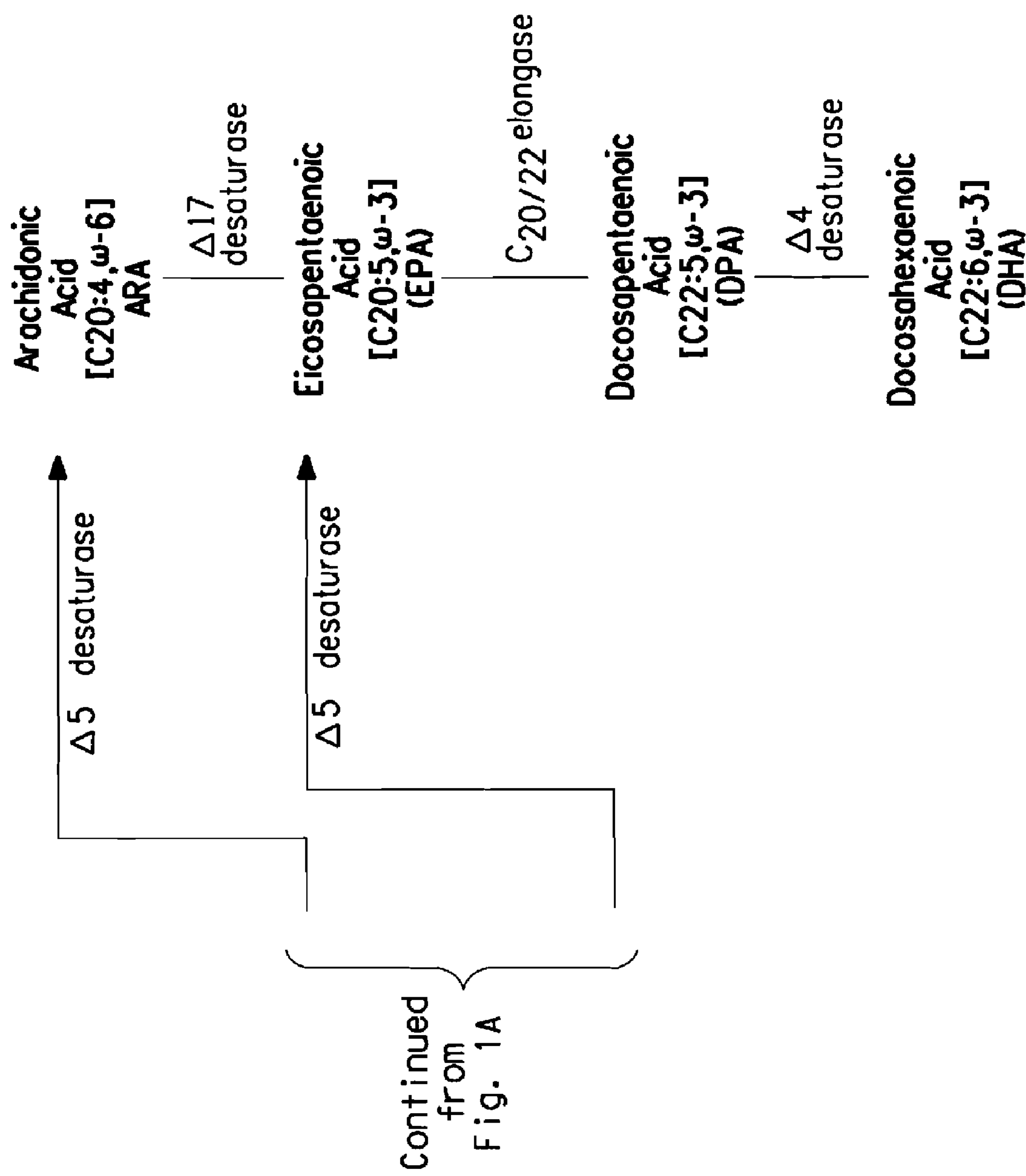
FIG. 1 is a representative PUFA biosynthetic pathway.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode some or all of the following enzymes: delta-12 desaturase, delta-6 desaturase, $C_{18/20}$ elongase, $C_{20/22}$ elongase, delta-5 desaturase, delta-17 desaturase, delta-15 desaturase, delta-9 desaturase, delta-8 desaturase, a delta-9 elongase and delta-4 desaturase. A representative pathway is illustrated in FIG. 1, providing for the conversion of oleic acid through various intermediates to DHA, which demonstrates how both omega-3 and omega-6 fatty acids may be produced from a common source. The pathway is naturally divided into two portions where one portion will generate omega-3 fatty acids and the other portion, only omega-6 fatty acids. That portion that only generates omega-3 fatty acids will be referred to herein as the omega-3 fatty acid biosynthetic pathway, whereas that portion that generates only omega-6 fatty acids will be referred to herein as the omega-6 fatty acid biosynthetic pathway.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-8 desaturases that will desaturate a fatty acid between the $8^{th}$ and $9^{th}$ carbon atom numbered from the carboxyl-terminal end of the molecule and that can, for example, catalyze the conversion of EDA to DGLA and/or ETrA to ETA. Other desaturases include: (1) delta-5 desaturases that catalyze the conversion of DGLA to ARA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitate to palmitoleic acid (16:1) and/or stearate to oleic acid (18:1). In the art, delta-15 and delta-17 desaturases are also occasionally referred to as "omega-3 desaturases", "w-3 desaturases", and/or "omega-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "EgD8" refers to a delta-8 desaturase enzyme (SEQ ID NO:12) isolated from *Euglena gracilis*, encoded by SEQ ID NO:11 herein. EgD8 is 100% identical and functionally equivalent to "Eg5", as described in WO 2006/012325 and WO 2006/012326 (US2005-0287652-A1).

Similarly, the term "EgD8S" refers to a synthetic delta-8 desaturase derived from *Euglena gracilis* that is codon-optimized for expression in *Yarrowia lipolytica* herein (i.e., SEQ ID NOs:9 and 10). EgD8S is 100% identical and functionally equivalent to "D8SF", as described in WO 2006/012325 and WO 2006/012326.

The term "mutant EgD8S" refers to a delta-8 desaturase of the present invention that has at least one mutation with respect to the synthetic delta-8 desaturase derived from *Euglena gracilis* that is codon-optimized for expression in *Yarrowia lipolytica* (i.e., EgD8S). Although "mutations" may include any deletions, insertions and point mutations (or combinations thereof), preferred embodiments of the mutant EgD8S are set forth in SEQ ID NO:2, wherein: (i) SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to the synthetic codon-optimized sequence of EgD8S (i.e., SEQ ID NO:10); and (ii) SEQ ID NO:2 is not 100% identical to SEQ ID NO:10. In more preferred embodiments, the mutant EgD8S has at least about 10-18 mutations with respect to the synthetic codon-optimized sequence of EgD8S, more preferably at least about 19-25 mutations, and most preferably at least about 26-33 mutations with respect to synthetic codon-optimized sequence of EgD8S (i.e., SEQ ID NO:10). In still another embodiment, the delta-8 desaturase activity of the mutant EgD8S is at least about functionally equivalent to the delta-8 desaturase activity of the synthetic codon-optimized EgD8S (SEQ ID NO:10).

A mutant EgD8S is "at least about functionally equivalent" to EgD8S when enzymatic activity and specific selectivity of the mutant EgD8S sequence are comparable to that of EgD8S, despite differing polypeptide sequences. Thus, a functionally equivalent mutant EgD8S sequence will possess delta-8 desaturase activity that is not substantially reduced with respect to that of EgD8S when the "conversion efficiency" of each enzyme is compared (i.e., a mutant EgD8S will have at least about 50%, preferably at least about 75%, more preferably at least about 85%, and most preferably at least about 95% of the enzymatic activity of EgD8S). In more preferred embodiments, the mutant EgD8S will have increased enzymatic activity and specific selectivity when compared to that of EgD8S (i.e., at least about 105%, more preferably at least about 115% and most preferably at least about 125% of the enzymatic activity of EgD8S).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase system" refers to a suite of four enzymes that are responsible for elongation of a fatty acid carbon chain to produce a fatty acid that is 2 carbons longer than the fatty acid substrate that the elongase system acts upon. More specifically, the process of elongation occurs in association with fatty acid synthase, whereby CoA is the acyl carrier (Lassner et al., *The Plant Cell*, 8:281-292 (1996)). In the first step, which has been found to be both substrate-specific and also rate-limiting, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, a delta-9 elongase is able to catalyze the conversion of LA and ALA to EDA and ETrA, respectively (e.g., WO 2002/077213). It is important to note that some elongases have broad specificity and thus a single enzyme may be capable of catalyzing several elongase reactions (e.g., thereby acting as both a $C_{16/18}$ elongase and a $C_{18/20}$ elongase).

The term "delta-9 elongase/delta-8 desaturase pathway" refers to a biosynthetic pathway for production of long-chain PUFAs, said pathway minimally comprising a delta-9 elongase and a delta-8 desaturase and thereby enabling biosynthesis of DGLA and/or ETA from LA and ALA, respectively. This pathway may be advantageous in some embodiments, as the biosynthesis of GLA and/or STA is excluded.

The term "amino acid" will refer to the basic chemical structural unit of a protein or polypeptide. The amino acids are identified by either the one-letter code or the three-letter codes for amino acids, in conformity with the IUPAC-IYUB standards described in *Nucleic Acids Research*, 13:3021-3030 (1985) and in the *Biochemical Journal*, 219 (2):345-373 (1984), which are herein incorporated by reference.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but do not affect the structural and functional properties of the encoded, folded protein) are common. For the purposes of the present invention, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: His [H], Arg [R], Lys [K];
4. Large aliphatic, nonpolar residues: Met [M], Leu [L], Ile [I], Val [V] (Cys [C]); and
5. Large aromatic residues: Phe [F], Tyr [Y], Trp [W].

Thus, Ala, a slightly hydrophobic amino acid, may be substituted by another less hydrophobic residue (e.g., Gly). Similarly, changes which result in substitution of one negatively charged residue for another (e.g., Asp for Glu) or one positively charged residue for another (e.g., Lys for Arg) can also be expected to produce a functionally equivalent product. As such, conservative amino acid substitutions generally maintain: 1.) the structure of the polypeptide backbone in the area of the substitution; 2.) the charge or hydrophobicity of the molecule at the target site; or 3.) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1.) a hydrophilic residue is substituted for/by a hydrophobic residue (e.g., Ser or Thr for/by Leu, Ile, Val); 2.) a Cys or Pro is substituted for/by any other residue; 3.) a residue having an electropositive side chain is substituted for/by an electronegative residue (e.g., Lys, Arg or His for/by Asp or Glu); or, 4.) a residue having a bulky side chain is substituted for/by one not having a side chain (e.g., Phe for/by Gly). Sometimes, non-conservative amino acid substitutions between two of the five groups will not affect the activity of the encoded protein.

The terms "polynucleotide", "polynucleotide sequence", "nucleic acid sequence", "nucleic acid fragment" and "isolated nucleic acid fragment" are used interchangeably herein. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2$^{nd}$ ed., Cold Spring Harbor Laboratory Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding one or more particular delta-8 desaturase proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the invention herein also includes isolated nucleic acid fragments that are complementary to the complete sequences as reported in the accompanying Sequence Listing, as well as those substantially similar nucleic acid sequences.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant delta-8 desaturase polypeptides as set forth in SEQ ID NOs:2, and 12. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ, that plant is heterozygous at that locus.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. The promoter sequence may consist of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants,* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.,* 3:225-236 (1995)).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. The use of different 3' non-coding sequences is exemplified by Ingelbrecht, I. L., et al. (*Plant Cell,* 1:671-680 (1989)).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to a RNA transcript that is complementary to all or part of a target primary transcript or mRNA, and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain strains or lines displaying the desired expression level and pattern. Such screening may be accomplished by Southern analysis of DNA blots (Southern, *J. Mol. Biol.,* 98:503 (1975)), Northern analysis of mRNA expression (Kroczek, *J. Chromatogr. Biomed. Appl.,* 618 (1-2):133-145 (1993)), Western and/or Elisa analyses of protein expression, phenotypic analysis or GC analysis of the PUFA products, among others.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be, but are not limited to, intracellular localization signals.

"Transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Thus, the nucleic acid molecule used for transformation may be a plasmid that replicates autonomously, for example, or, it may integrate into the genome of the host organism. Host organisms containing the transformed nucleic acid fragments are referred to as "transgenic" or "recombinant" or "transformed" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.,* 16:651-659 (1998); Gura, *Nature,* 404:804-808 (2000)). The overall efficiency of this phenomenon is low, and the extent of the RNA reduction is widely variable. Subsequent work has described the use of "hairpin" structures that incorporate all, or part, of a mRNA encoding sequence in a complementary orientation that results in a potential "stem-loop" structure for the expressed RNA (WO 99/53050; WO 02/00904). This increases the frequency of co-suppression in the recovered transgenic plants. Another variation describes the use of plant viral sequences to direct the suppression, or "silencing", of proximal mRNA encoding sequences (WO 98/36083). Both of these co-suppressing phenomena have not been elucidated mechanistically, although genetic evidence has begun to unravel this complex situation (Elmayan et al., *Plant Cell,* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). Generally, the cellular oil or TAG content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)).

The term "oleaginous yeast" refers to those microorganisms classified as yeasts that can make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs.

The "Clustal V method of alignment" corresponds to the alignment method labeled Clustal V (described by Higgins and Sharp, *CABIOS*. 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). Sequence alignments and percent identity calculations may be performed using the MegAlign™ program. Multiple alignment of the sequences is performed using the Clustal method of alignment (Higgins and Sharp, *CABIOS,* 5:151153 (1989); Higgins, D. G. et al., *Comput. Appl. Biosci.,* 8:189-191 (1992)) with default parameters (GAP PENALTY=10, GAP LENGTH PENALTY=10), unless otherwise specified. Default parameters for pairwise alignments and calculation of percent identity of protein sequences using the Clustal V method are: KTUPLE 1, GAP PENALTY=3, WINDOW=5 and DIAGONALS SAVED=5. After alignment of the sequences using the Clustal program, it is possible to obtain a "percent identity" by viewing the "sequence distances" table in the same program.

The "Clustal W method of alignment" corresponds to the alignment method labeled Clustal W (described by Thompson et al., *Nucleic Acids Res.* 22:4673-4680 (1994)) and found in the MegAlign™ v5.07 program of the LASERGENE bioinformatics computing suite (DNASTAR Inc., Madison, Wis.). Default parameters for multiple alignments and calculation of percent identity of protein sequences are GAP PENALTY=10, GAP LENGTH PENALTY=0.2, DELAY DIVERGENCE SEQS (%)=30, DNA TRANSITION WEIGHT=0.50, protein weight matrix=Gonnet series and DNA weight matrix=IUB, unless otherwise specified. Default parameters for pairwise alignments and calculation of percent identity of protein sequences are GAP PENALTY=10, GAP LENGTH PENALTY=0.1, protein weight matrix=Gonnet 250 and DNA weight matrix=IUB, unless otherwise specified.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: (1) the GCG suite of programs (Wisconsin Package Version 9.0, Genetics Computer Group (GCG), Madison, Wis.); (2) BLASTP, BLASTN, BLASTX (Altschul et al., *J. Mol. Biol.,* 215:403-410 (1990)); (3) DNASTAR (DNASTAR Inc., Madison, Wis.); (4) Sequencher (Gene Codes Corporation, Ann Arbor, Mich.); and (5) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Suitable nucleic acid fragments (isolated polynucleotides of the present invention) encode polypeptides that are at least about 85% identical to the amino acid sequences reported herein. More preferred nucleic acid fragments encode amino acid sequences that are at least about 90% identical to the amino acid sequences reported herein while most preferred are nucleic acid fragments that encode amino acid sequences that are at least about 95% identical. It is well understood by one skilled in the art that many levels of sequence identity are useful in identifying polypeptides from other species, wherein such polypeptides have the same or similar function or activity; although preferred ranges are described above, any integer percentage from 85% to 100% is useful for the purposes herein.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

Standard recombinant DNA and molecular cloning techniques used herein are well known in the art and are described more fully in Sambrook, J., Fritsch, E. F. and Maniatis, T., *Molecular Cloning: A Laboratory Manual,* 2nd ed., Cold Spring Harbor Laboratory Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

An Overview Biosynthesis of Omega Fatty Acids and Triacylglycerols

The metabolic process wherein oleic acid is converted to omega-3/omega-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific omega-3/omega-6 fatty acid.

Specifically, all pathways require the initial conversion of oleic acid to LA, the first of the omega-6 fatty acids, by a delta-12 desaturase. Then, using the "delta-9 elongase/delta-8 desaturase pathway", omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be expressed in a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell (see WO 2004/101757).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired omega-3/omega-6 fatty acid, as well as various upstream intermediary PUFAs. Thus, consideration of each enzyme's conversion efficiency is also an important variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Once fatty acids are synthesized within an organism (including saturated and unsaturated fatty acids and short-chain and long-chain fatty acids), they may be incorporated into triacylglycerides (TAGs). TAGs (the primary storage unit for fatty acids, including PUFAs) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of an acyltransferase to form TAG.

Sequence Identification of a *Euglena qracilis* Delta-8 Desaturase

Commonly owned WO 2006/012325 and WO 2006/012326 disclose a *Euglena gracilis* delta-8 desaturase able ability to desaturate EDA and EtrA (identified therein as "Eg5 and assigned SEQ ID NO:2). In the present application, the *Euglena gracilis* delta-8 desaturase described as "EgD8" (SEQ ID NOs:11 and 12 herein) is 100% identical and equivalent to the nucleotide and amino acid sequences of Eg5.

As is well known in the art, codon-optimization can be a useful means to further optimize the expression of an enzyme in an alternate host, since use of host-preferred codons can substantially enhance the expression of the foreign gene encoding the polypeptide. As such, a synthetic delta-8 desaturase derived from *Euglena gracilis* and codon-optimized for expression in *Yarrowia lipolytica* was also disclosed in WO 2006/012325 and WO 2006/012326 as SEQ ID NOs:112 and 113 (designated therein as "D8SF"). Specifically, 207 bp (16.4%) of the 1263 bp coding region were modified, corresponding to codon-optimization of 192 codons. Additionally, "D8SF" had one additional valine amino acid inserted between amino acid residues 1 and 2 of the wildtype Eg5; thus, the total length of the codon-optimized desaturase is 422 amino acids. Expression of the codon-optimized gene (i.e., "D8SF") in *Y. lipolytica* demonstrated more efficient desaturation of EDA to DGLA and/or ETrA to ETA than the wild-type gene (i.e., Eg5). In the present application, the synthetic delta-8 desaturase derived from *Euglena gracilis* and codon-optimized for expression in *Y. lipolytica* described as "EgD8S" (SEQ ID NOs:9 and 10 herein) is 100% identical and equivalent to the nucleotide and amino acid sequences of D8SF.

Engineering Targeted Mutations within the Synthetic Delta-8 Desaturase, Derived from *Euglena gracilis* and Codon-Optimized for Expression in *Yarrowia lipolytica*

Methods for synthesizing sequences and bringing sequences together are well established in the literature. Many techniques are commonly employed in the literature to obtain mutations of naturally occurring desaturase genes (wherein such mutations may include deletions, insertions and point mutations, or combinations thereof). This would permit production of a polypeptide having desaturase activity, respectively, in vivo with more desirable physical and kinetic parameters for function in the host cell such as a longer half-life or a higher rate of production of a desired PUFA. Or, if desired, the regions of a polypeptide of interest (i.e., a desaturase) important for enzymatic activity can be determined through routine mutagenesis, expression of the resulting mutant polypeptides and determination of their activities. All such mutant proteins and nucleotide sequences encoding them that are derived from the wildtype (i.e., SEQ ID NOs:11 and 12) and synthetic codon-optimized (SEQ ID NOs:9 and 10) delta-8 desaturase described supra are within the scope of the present invention.

More specifically in the invention herein, mutant sequences encoding delta-8 desaturases were synthetically engineered, by making targeted mutations within the known, functional *Euglena gracilis* delta-8 desaturase that was codon-optimized for expression in *Yarrowia lipolytica* (i.e., "EgD8S", as set forth in SEQ ID NOs:9 and 10). The effect of each mutation on the delta-8 desaturase activity of the resulting mutant EgD8S was screened. Although not to be construed as limiting to the invention herein, a mutant EgD8S enzyme (SEQ ID NO:2) was ultimately created comprising at least one amino acid mutation (and up to about 33 amino acid mutations) with respect to the synthetic codon-optimized EgD8S and having functionally equivalent delta-8 desaturase activity, using the methodology described below.

Creation of a Topological Model and Identification of Suitable Amino Acid Sites for Mutation General characteristics of delta-8 desaturases, based on desaturase evolution, are well-described by P. Sperling et al. (*Prostaglandins Leukot. Essent. Fatty Acids,* 68:73-95 (2003)). Along with delta-6, delta-5 and delta-4 desaturases, delta-8 desaturases are known as long-chain PUFA "front-end" desaturases (wherein desaturation occurs between a pre-existing double bond and the carboxyl terminus of the fatty acid's acyl group, as opposed to methyl-directed desaturation). These desaturases are characterized by three histidine boxes [$H(X)_{3-4}H$ (SEQ ID NOs:166 and 167), $H(X)_{2-3}HH$ (SEQ ID NOs:168 and 169) and $H/Q(X)_{2-3}HH$ (SEQ ID NOs:170 and 171)] and are members of the cytochrome $b_5$ fusion superfamily, since they possess a fused cytochrome $b_5$ domain at their N-terminus which serves as an electron donor. The cytochrome $b_5$ domain also contains an absolutely conserved heme-binding motif (i.e., "HPGG") which has been shown to be necessary for enzyme activity (J. A. Napier, et al., *Prostaglandins Leukot. Essent. Fatty Acids,* 68:135-143 (2003); P. Sperling, et al., supra). Finally, although the crystal structure of a "front-end" desaturase is not yet available, hydropathy plots reveal 4-6 membrane spanning helices that account for nearly 30% of the amino acid sequence of these proteins.

Figure 2:
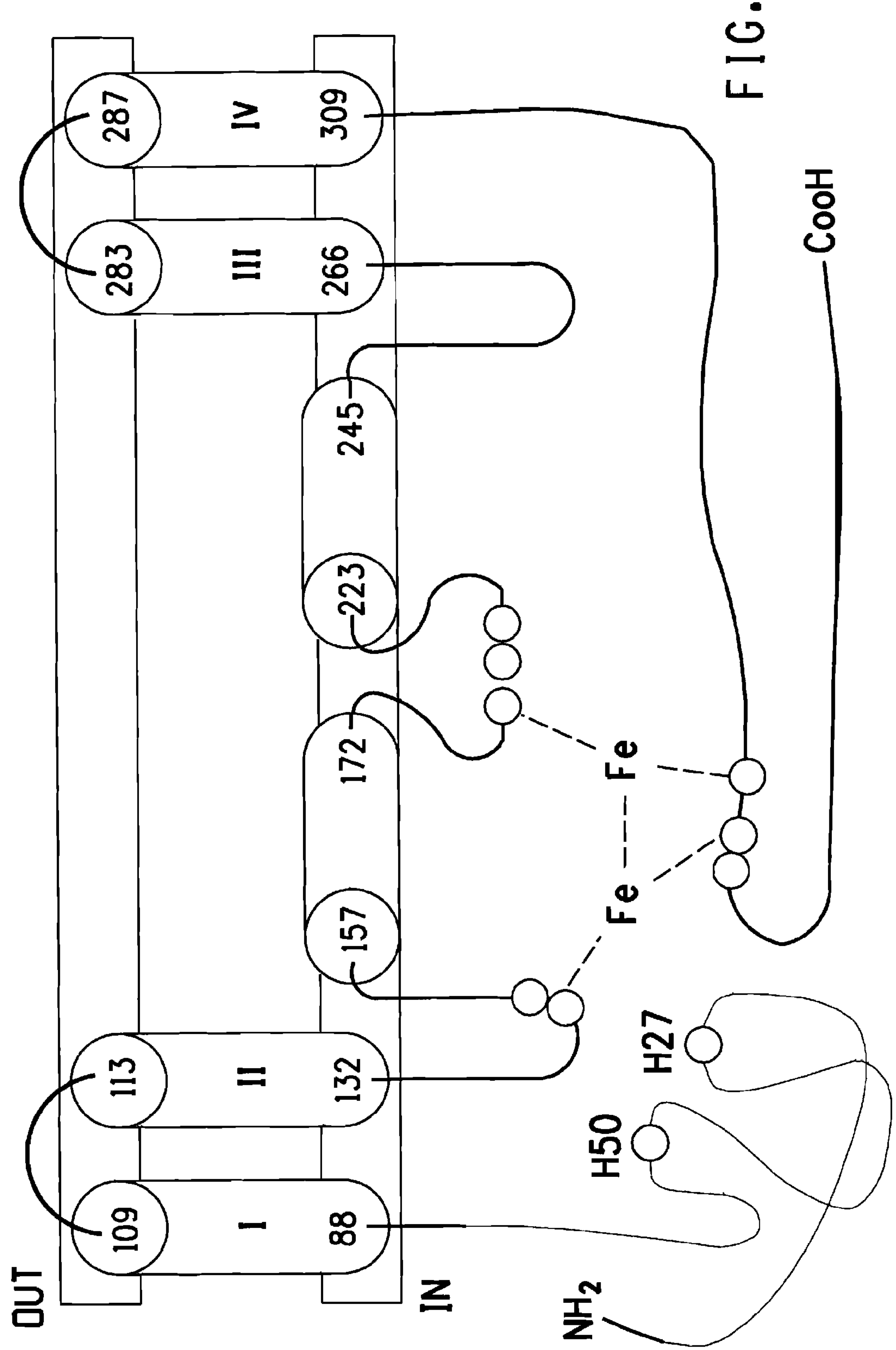
FIG. 2 shows a topological model of EgD8S.

Based on the generalizations above, the protein sequence of EgD8S (SEQ ID NO:10) was specifically analyzed to enable creation of a topological model (FIG. 2). As expected, EgD8S contained two domains: an N-terminal cytochrome $b_5$ domain (located between amino acid residues 5 to 71 of SEQ ID NO:10) and a C-terminal desaturase domain (located between amino acid residues 79 to 406 of SEQ ID NO:10). Four membrane-spanning helices were identified at amino acid residues 88-109, 113-132, 266-283 and 287-309 of SEQ ID NO:10 (labeled as regions I, II, III and IV on FIG. 2), with both the N- and C-termini located on the cytoplasmic side of the membrane. Two additional hydrophobic regions were located at amino acid residues 157-172 and 223-245. Finally, the three histidine boxes were located between amino acid residues 146-150, 183-187 and 358-362, and the conserved heme-binding motif ("HPGG") was located at amino acid residues 27-30.

Using the topological model, alignment of EgD8S with other front-end desaturases and alignment of EgD8S's cytochrome $b_5$ domain with other cytochrome $b_5$ genes, 70 sites within EgD8S were subsequently selected as possibly suitable for mutagenesis (criteria for selection are described in detail in Example 2). These sites corresponded to 126 individual amino acid mutations (i.e., 57.9% conserved amino acid substitutions and 42.1% non-conserved amino acid substitutions), as detailed in Table 7 of Example 2.

Site-Directed Mutagenesis for Creation of EgD8S Mutants

Although a variety of approaches may be used for mutagenesis of a delta-8 desaturase enzyme, based on the strategies herein it was desirable to create specific point mutations within EgD8S using oligonucleotide-mediated site-directed mutagenesis. Furthermore, although numerous site-directed mutagenesis protocols exist (e.g., Ishii, T. M., et al., *Methods Enzymol.,* 293:53-71 (1998); Ling M. M. and B. H. Robinson, *Anal. Biochem.,* 254:157-178 (1997); Braman J. (ed.) *In Vitro Mutagenesis Protocols.* $2^{nd}$ Ed., Humania: Totowa, N.J. (2002); Kunkel T. A., et al., *Methods Enzymol.,* 154:367-382 (1987); Sawano A. and Miyawaki, A. *Nucleic Acids Res.,* 28:e78 (2000)), the QuikChange® site-directed mutagenesis kit (Stratagene, La Jolla, Calif.) was selected for use based on its facile implementation and high efficiency. Specifically, the kit requires no specialized vectors, unique restriction sites, or multiple transformations and allows site-specific mutation in virtually any double-stranded plasmid. The basic procedure utilizes a supercoiled double-stranded DNA vector with an insert of interest and two synthetic oligonucleotide primers containing the desired mutation. The oligonucleotide primers, each complementary to opposite strands of the vector, are extended during temperature cycling by a DNA polymerase. Incorporation of the oligonucleotide primers generates a mutated plasmid containing staggered nicks. Following temperature cycling, the product is treated with Dpn I endonuclease (specific for methylated and hemi-methylated DNA) as a means to digest the parental DNA template and to select for newly synthesized mutant DNA. The nicked vector DNA containing the desired mutations is then transformed and propagated in an *Escherichia coli* host.

Using the techniques described above, the feasibility of engineering a synthetic EgD8S (having multiple point mutations with respect to EgD8S but maintaining functional equivalence with respect to the enzyme's delta-8 desaturase activity) was then tested. Specifically, selected individual point mutations were introduced by site-directed mutagenesis into EgD8S (within a plasmid construct comprising a chimeric FBAINm::EgD8S::XPR gene), transformed into *E. coli*, and then screened for delta-8 desaturase activity based on GC analyses.

The skilled person will be able to envision additional screens for the selection of genes encoding proteins having delta-8 desaturase activity. For example, desaturase activity may be demonstrated by assays in which a preparation containing an enzyme is incubated with a suitable form of substrate fatty acid and analyzed for conversion of this substrate to the predicted fatty acid product. Alternatively, a DNA sequence proposed to encode a desaturase protein may be incorporated into a suitable vector construct and thereby expressed in cells of a type that do not normally have an ability to desaturate a particular fatty acid substrate. Activity of the desaturase enzyme encoded by the DNA sequence can then be demonstrated by supplying a suitable form of substrate fatty acid to cells transformed with a vector containing the desaturase-encoding DNA sequence and to suitable control cells (e.g., transformed with the empty vector alone). In such an experiment, detection of the predicted fatty acid product in cells containing the desaturase-encoding DNA sequence and not in control cells establishes the desaturase activity.

Results from the experiment described above resulted in the identification of some mutations that resulted in completely non-functional mutant delta-8 desaturases having 0% delta-8 desaturase activity (e.g., simultaneous mutation of 48V to F and 49M to L or simultaneous mutation of 304G to F and 305F to G). Despite this, ~75% of the individual mutations tested did not significantly diminish the mutant enzyme's delta-8 desaturase activity as compared to the delta-8 desaturase activity of EgD8S. More specifically, the following mutations were identified as preferred mutations, wherein delta-8 desaturase activity was functionally equivalent (i.e., 100%) or greater than that of EgD8S (i.e., SEQ ID NO:10):

TABLE 4

Initial Preferred Mutations Within EgD8S

| Mutation Site | Sequence Mutations With Respect to EgD8S (SEQ ID NO: 10) | % Activity* |
|---|---|---|
| M3 | 16T to K, 17T to V | 100% |
| M8 | 66P to Q, 67S to A | 100% |
| M12 | 407A to S, 408V to Q | 100% |
| M14 | 416Q to V, 417P to Y | 100% |
| M16 | 108S to L | 100% |
| M19 | 122V to S | 100% |
| M38 | 54A to G, 55F to Y | 100% |
| M39 | 64I to L, 65N to D | 100% |
| M40 | 69E to D, 70L to V | 100% |
| M41 | 75A to G, 76V to L | 100% |
| M45 | 117G to A, 118Y to F | 100% |
| M46 | 132V to L, 133L to V | 100% |
| M49 | 297F to V, 298V to L | 100% |
| M50 | 309I to V, 310V to I | 100% |
| M51 | 347I to L, 348T to S | 100% |
| M51B | 346I to V, 347I to L, 348T to S | 100% |
| M53 | 9L to V | 100% |
| M54 | 19D to E, 20V to I | 100% |
| M58 | 65N to Q | 100% |
| M63 | 279T to L, 280L to T | 100% |
| M68 | 162L to V, 163V to L | 100% |
| M69 | 170G to A, 171L to V | 100% |
| M70 | 418A to G, 419G to A | 100% |
| M2 | 12T to V | 110% |
| M22 | 127Y to Q | 110% |
| M26 | 293L to M | 110% |
| M6 | 59K to L | 110% |
| M1 | 4S to A, 5K to S | 115% |
| M21 | 125Q to H, 126M to L | 120% |
| M15 | 422L to Q | 125% |

*"% Activity" refers to the delta-8 desaturase activity of each mutant EgD8S with respect to the delta-8 desaturase activity of EgD8S, as set forth as SEQ ID N0: 10.

It will be appreciated by one of skill in the art that the useful mutant delta-8 desaturases of the present invention are not limited to the 30 mutation combinations described above. For example, although the mutation site described as M3 includes two specific amino acid mutations (i.e., 16T to K and 17T to V), one skilled in the art will expect that a single mutation of either 16T to K or 17T to V will have utility in the design of a mutant delta-8 desaturase whose delta-8 desaturase activity is at least about functionally equivalent to the delta-8 desaturase activity of the synthetic codon-optimized EgD8S. Thus, in actuality, Table 4 presents 52 single amino acid mutations that are useful for the purposes herein, in the design of a mutant delta-8 desaturase having delta-8 desaturase activity that is at least about functionally equivalent to the delta-8 desaturase activity of SEQ ID NO:10.

Based on the results above, experimental work was continued in an effort to "stack" appropriate individual amino acid mutations within the synthetic codon-optimized EgD8S sequence. This resulted in creation of a mutant delta-8 desaturase as set forth in SEQ ID NO:2 having "n" amino acid mutations, wherein "n" is any integer from 1 to 33 inclusive (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33), and having delta-8 desaturase activity comparable to that of EgD8S. Specifically, SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to the synthetic codon-optimized sequence of EgD8S (i.e., SEQ ID NO:10); wherein SEQ ID NO:2 is not 100% identical to SEQ ID NO:10; and wherein the mutant EgD8S is at least about functionally equivalent to EgD8S (SEQ ID NO:10). It will be appreciated by the skilled person that each of the above mutations can be used in any combination with one another. And, all such mutant proteins and nucleotide sequences encoding them that are derived from EgD8 and/or EgD8S as described herein are within the scope of the present invention.

In more preferred embodiments, the mutant EgD8S has at least about 10-18 conservative and non-conservative amino acid substitutions (i.e., mutations) with respect to the synthetic codon-optimized sequence of EgD8S, more preferably at least about 19-25 conservative and non-conservative amino acid substitutions, and most preferably at least about 26-33 conservative and non-conservative amino acid substitutions with respect to the synthetic codon-optimized sequence of EgD8S (i.e., SEQ ID NO:10). Thus, for example, in one preferred embodiment mutant EgD8S-23 (SEQ ID NO:4) comprises the following 24 amino acid mutations with respect to the synthetic codon-optimized EgD8S sequence set forth as SEQ ID NO:10: 4S to A, 5K to S, 12T to V, 16T to K, 17T to V, 66P to Q, 67S to A, 108S to L, 117G to A, 118Y to F, 120L to M, 121M to L, 125Q to H, 126M to L, 132V to L, 133L to V, 162L to V, 163V to L, 293L to M, 407A to S, 408V to Q, 418A to G, 419G to A and 422L to Q. Pairwise alignment of the mutant EgD8S-23 amino acid sequence to the synthetic codon-optimized sequence of SEQ ID NO:10 using default parameters of Vector NTI®'s AlignX program (Invitrogen Corporation, Carlsbad, Calif.) revealed 94.3% sequence identity and 97.9% consensus between the two proteins over a length of 422 amino acids.

In another preferred embodiment, mutant EgD8S-013 (SEQ ID NO:6) comprises the following 28 amino acid mutations with respect to the synthetic codon-optimized EgD8S sequence set forth as SEQ ID NO:10: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 293L to M, 407A to S, 408V to Q, 418A to G, 419G to A and 422L to Q. Pairwise alignment of the mutant EgD8S-013 amino acid sequence to the synthetic codon-optimized sequence of SEQ ID NO:10 using default parameters of Vector NTI®'s AlignX program revealed 93.4% sequence identity and 97.9% consensus between the two proteins over a length of 422 amino acids.

In another preferred embodiment, mutant EgD8S-015 (SEQ ID NO:8) comprises the following 31 amino acid mutations with respect to the synthetic codon-optimized EgD8S sequence set forth as SEQ ID NO:10: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 162L to V, 163V to L, 170G to A, 171L to V, 293L to M, 279T to L, 280L to T, 346I to V, 347I to L, 348T to S, 407A to S, 408V to Q, 418A to G, 419G to A and 422L to Q. Pairwise alignment of the mutant EgD8S-015 amino acid sequence to the synthetic codon-optimized sequence of SEQ ID NO:10 using default parameters of Vector NTI®'s AlignX program revealed 92.7% sequence identity and 97.4% consensus between the two proteins over a length of 422 amino acids.

Thus, in one embodiment, the present invention concerns an isolated polynucleotide comprising:

(a) a nucleotide sequence encoding a mutant polypeptide having delta-8 desaturase activity, wherein the mutant polypeptide has an amino acid sequence as set forth in SEQ ID NO:2, wherein:
  (i) SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to the synthetic codon-optimized sequence of EgD8S (i.e., SEQ ID NO:10); and,
  (ii) SEQ ID NO:2 is not identical to SEQ ID NO:10; or,
(b) a complement of the nucleotide sequence, wherein the complement and the nucleotide sequence consist of the same number of nucleotides and are 100% complementary.

In further preferred embodiments, the delta-8 desaturase activity of SEQ ID NO:2, as described above, is at least about functionally equivalent to the delta-8 desaturase activity of SEQ ID NO:10.

Alternate Means of Mutagenesis for Creation of EgD8S Mutants

As is well known to one of skill in the art, in vitro mutagenesis and selection or error prone PCR (Leung et al., *Techniques,* 1:11-15 (1989); Zhou et al., *Nucleic Acids Res.,* 19:6052-6052 (1991); Spee et al., *Nucleic Acids Res.,* 21:777-778 (1993); Melnikov et al., *Nucleic Acids Res.,* 27(4):1056-1062 (Feb. 15, 1999)) could also be employed as a means to obtain mutations of naturally occurring desaturase genes, such as EgD8 or EgD8S, wherein the mutations may include deletions, insertions and point mutations, or combinations thereof. The principal advantage of error-prone PCR is that all mutations introduced by this method will be within the desired desaturase gene, and any change may be easily controlled by changing the PCR conditions. Alternatively, in vivo mutagenesis may be employed using commercially available materials such as the *E. coli* XL1-Red strain and *Epicurian coli* XL1-Red mutator strain from Stratagene (La Jolla, Calif.; Greener and Callahan, *Strategies,* 7:32-34 (1994)). This strain is deficient in three of the primary DNA repair pathways (mutS, mutD and mutT), resulting in a mutation rate 5000-fold higher than that of wild-type. In vivo mutagenesis does not depend on ligation efficiency (as with error-prone PCR); however, a mutation may occur at any region of the vector and the mutation rates are generally much lower.

In other embodiments, it is contemplated that a mutant delta-8 desaturase enzyme with altered or enhanced delta-8 desaturase activity may be constructed using the method of "gene shuffling" (U.S. Pat. No. 5,605,793; U.S. Pat. No. 5,811,238; U.S. Pat. No. 5,830,721; and U.S. Pat. No. 5,837,458). The method of gene shuffling is particularly attractive due to its facile implementation and high rate of mutagenesis. The process of gene shuffling involves the restriction of a gene of interest into fragments of specific size in the presence of additional populations of DNA regions of both similarity to (or difference to) the gene of interest. This pool of fragments will then denature and reanneal to create a mutated gene. The mutated gene is then screened for altered activity.

Delta-8 desaturase sequences (i.e., wildtype, synthetic, codon-optimized or mutant) may be mutated and screened for altered or enhanced delta-8 desaturase activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Maniatis, supra). In addition to the full-length sequences, populations of fragments that are hybridizable to all or portions of the sequence may be added. Similarly, a population of fragments that are not hybridizable to the wildtype sequence may also be added. Typically, these additional fragment populations are added in about a 10- to 20-fold excess by weight as compared to the total nucleic acid. Generally this process will allow generation of about 100 to 1000 different specific nucleic acid fragments in the mixture. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid, wherein the temperature is preferably from about 80° C. to about 100° C. The nucleic acid fragments may be reannealed by cooling, wherein the temperature is preferably from about 20° C. to about 75° C. Renaturation can be accelerated by the addition of polyethylene glycol ("PEG") or salt, wherein the salt concentration is preferably from about 0 mM to about 200 mM. The annealed nucleic acid fragments are next incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, and more preferably the sequence is repeated from 10 to 40 times. The resulting nucleic acid is a larger double-stranded polynucleotide of from about 50 bp to about 100 kB and may be screened for expression and altered delta-8 desaturase activity by standard cloning and expression protocols (Maniatis, supra).

Irrespective of the method of mutagenesis, it is contemplated that a mutant delta-8 desaturase having delta-8 desaturase activity at least about functionally equivalent to that of EgD8 (SEQ ID NO:12) or EgD8S (SEQ ID NO:10) may be evolved as set forth in SEQ ID NO:2, wherein: (i) SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to the synthetic codon-optimized sequence of EgD8S (i.e., SEQ ID NO:10); and, (ii) SEQ ID NO:2 is not 100% identical to SEQ ID NO:10. Furthermore, it will be appreciated that the invention encompasses not only the specific mutations described above, but also those that allow for the substitution of chemically equivalent amino acids. So, for example, where a substitution of an amino acid with the aliphatic, nonpolar amino acid alanine is made, it will be expected that the same site may be substituted with the chemically equivalent amino acid serine.

In other embodiments, any of the delta-8 desaturase nucleic acid fragments described herein may be used for creation of new and improved fatty acid desaturases by domain swapping, wherein a functional domain from any of the delta-8 desaturase nucleic acid fragments is exchanged with a functional domain in an alternate desaturase gene to thereby result in a novel protein.

Identification and Isolation of Homologs

Any of the instant desaturase sequences (i.e., those mutants derived from EgD8 or EgD8S) or portions thereof may be used to search for delta-8 desaturase homologs in the same or other bacterial, algal, fungal, Oomycete or plant species using sequence analysis software. In general, such computer software matches similar sequences by assigning degrees of homology to various substitutions, deletions and other modifications.

Alternatively, any of the instant desaturase sequences or portions thereof may also be employed as hybridization reagents for the identification of delta-8 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia, Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-8 desaturase nucleic acid fragments described herein (or any homologs identified thereof) may be used to isolate genes encoding homologous proteins from the same or other bacterial, algal, fungal, Oomycete or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA,* 82:1074 (1985); or strand displacement amplification (SDA), Walker, et al., *Proc. Natl. Acad. Sci. USA,* 89:392 (1992)]; and 3.) methods of library construction and screening by complementation.

For example, genes encoding similar proteins or polypeptides to the delta-8 desaturases described herein could be isolated directly by using all or a portion of the instant nucleic acid fragments as DNA hybridization probes to screen libraries from e.g., any desired marine euglenoid, yeast or fungus using methodology well known to those skilled in the art (wherein those organisms producing EDA or ETrA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA,* 86:5673 (1989); Loh et al., *Science,* 243:217 (1989)).

Methods for Production of Various Omega-3 and/or Omega-6 Fatty Acids

It is expected that introduction of chimeric genes encoding the delta-8 desaturases described herein, under the control of the appropriate promoters will result in increased production of DGLA and/or ETA in the transformed host organism, respectively. As such, the present invention encompasses a method for the direct production of PUFAs comprising exposing a fatty acid substrate (i.e., EDA or ETrA) to the desaturase enzymes described herein (i.e., those mutants derived from EgD8 or EgD8S, or homologs thereof), such that the substrate is converted to the desired fatty acid product (i.e., DGLA and/or ETA).

More specifically, it is an object of the present invention to provide a method for the production of DGLA in a host cell (e.g., oleaginous yeast, soybean), wherein the host cell comprises:

a.) a recombinant construct encoding a delta-8 desaturase polypeptide as set forth in SEQ ID NO:2 wherein SEQ ID NO:2 is not 100% identical to SEQ ID NO:10; and, b.) a source of EDA;

wherein the host cell is grown under conditions such that the delta-8 desaturase is expressed and the EDA is converted to DGLA, and wherein the DGLA is optionally recovered.

The person of skill in the art will recognize that the broad substrate range of the delta-8 desaturase may additionally allow for the use of the enzyme for the conversion of ETrA to ETA. Accordingly the invention provides a method for the production of ETA, wherein the host cell comprises:

a.) a recombinant construct encoding a delta-8 desaturase polypeptide as set forth in SEQ ID NO:2 wherein SEQ ID NO:2 is not 100% identical to SEQ ID NO:10; and, b.) a source of ETrA;

wherein the host cell is grown under conditions such that the delta-8 desaturase is expressed and the ETrA is converted to ETA, and wherein the ETA is optionally recovered.

Alternatively, each delta-8 desaturase gene and its corresponding enzyme product described herein can be used indirectly for the production of omega-3 fatty acids (see WO 2004/101757). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-8 desaturases described herein (i.e., those mutants derived from EgD8 or EgD8S, or homologs thereof) may be expressed in conjunction with additional genes encoding enzymes of the PUFA biosynthetic pathway (e.g., delta-6 desaturases, $C_{18/20}$ elongases, delta-17 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/omega-6 fatty acids (e.g., ARA, EPA, DPA and DHA). In preferred embodiments, the delta-8 desaturases of the present invention will minimally be expressed in conjunction with a delta-9 elongase (e.g., a delta-9 elongase as set forth in SEQ ID NO:173 or SEQ ID NO:176). However, the particular genes included within a particular expression cassette will depend on the host cell (and its PUFA profile and/or desaturase/elongase profile), the availability of substrate and the desired end product(s).

Plant Expression Systems, Cassettes & Vectors, and Transformation

In one embodiment, this invention concerns a recombinant construct comprising any one of the delta-8 desaturase polynucleotides of the invention operably linked to at least one regulatory sequence suitable for expression in a plant. A promoter is a DNA sequence that directs the cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-8 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the α-prime subunit of β-conglycinin promoter, the Kunitz trypsin inhibitor 3 promoter, the annexin promoter, the Gly1 promoter, the β subunit of β-conglycinin promoter, the P34/Gly Bd m 30K promoter, the albumin promoter, the Leg A1 promoter and the Leg A2 promoter.

The annexin, or P34, promoter is described in WO 2004/071178 (published Aug. 26, 2004). The level of activity of the annexin promoter is comparable to that of many known strong promoters, such as: (1) the CaMV 35S promoter (Atanassova et al., *Plant Mol. Biol.,* 37:275-285 (1998); Battraw and Hall, *Plant Mol. Biol.,* 15:527-538 (1990); Holtorf et al., *Plant Mol. Biol.,* 29:637-646 (1995); Jefferson et al., *EMBO J.,* 6:3901-3907 (1987); Wilmink et al., *Plant Mol. Biol.,* 28:949-955 (1995)); (2) the *Arabidopsis* oleosin promoters (Plant et al., *Plant Mol. Biol.,* 25:193-205 (1994); Li, Texas A&M University Ph.D. dissertation, pp. 107-128 (1997)); (3) the *Arabidopsis* ubiquitin extension protein promoters (Callis et al., *J. Biol. Chem.,* 265(21):12486-93 (1990)); (4) a tomato ubiquitin gene promoter (Rollfinke et al., *Gene,* 211(2):267-76 (1998)); (5) a soybean heat shock protein promoter (Schoffl et al., *Mol. Gen. Genet.,* 217 (2-3):246-53 (1989)); and, (6) a maize H3 histone gene promoter (Atanassova et al., *Plant Mol. Biol.,* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.,* 10:112-122 (1989); Ellerstrom et al., *Plant Mol. Biol.,* 32:1019-1027 (1996); Keddie et al., *Plant Mol. Biol.,* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-8 desaturase coding sequence, the promoter is then operably linked in a sense orientation using conventional means well known to those skilled in the art.

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with a recombinant construct of the invention and selecting those cells transformed with the recombinant construct, wherein said recombinant construct comprises a nucleotide sequence encoding a mutant polypeptide having delta-8 desaturase activity, wherein the amino acid sequence of the mutant polypeptide is set forth in SEQ ID NO:2, and wherein SEQ ID NO:2 is not identical to SEQ ID NO:10.

Also of interest is a method for producing a transformed plant comprising transforming a plant cell with the mutant delta-8 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al., *Plant Cell Rep.,* 15:653-657 (1996); McKently et al., *Plant Cell Rep.,* 14:699-703 (1995)); papaya (Ling, K. et al., *Bio/technology,* 9:752-758 (1991)); and pea (Grant et al., *Plant Cell Rep.,* 15:254-258 (1995)). For a review of other commonly used methods of plant transformation see Newell, C. A. (*Mol. Biotechnol.,* 16:53-65 (2000)). One of these methods of transformation uses *Agrobacterium rhizogenes* (Tepfler, M. and Casse-Delbart, F., *Microbiol. Sci.,* 4:24-28 (1987)). Transformation of soybeans using direct delivery of DNA has been published using PEG fusion (WO 92/17598), electroporation (Chowrira, G. M. et al., *Mol. Biotechnol.,* 3:17-23 (1995); Christou, P. et al., *Proc. Natl. Acad. Sci. Sci. USA,* 84:3962-3966 (1987)), microinjection, or particle bombardment (McCabe, D. E. et al., *Bio/Technology,* 6:923 (1988); Christou et al., *Plant Physiol.,* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

In one embodiment this invention concerns an oilseed plant comprising:

a) a first recombinant DNA construct comprising an isolated polynucleotide encoding a mutant polypeptide having delta-8 desaturase activity, operably linked to at least one regulatory sequence; and, b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

Such additional desaturases are discussed in U.S. Pat. No. 6,075,183, No. 5,968,809, No. 6,136,574, No. 5,972,664, No. 6,051,754, No. 6,410,288 and WO 98/46763, WO 98/46764, WO 00/12720 and WO 00/40705.

The choice of combination of cassettes used depends in part on the PUFA profile and/or desaturase/alongase profile of the oilseed plant cells to be transformed and the long-chain PUFA(s) which is to be expressed.

In another aspect, this invention concerns a method for making long-chain PUFAs in a plant cell comprising:

(a) transforming a cell with a recombinant construct of the invention; and, (b) selecting those transformed cells that make long-chain PUFAs.

In still another aspect, this invention concerns a method for producing at least one PUFA in a soybean cell comprising:

(a) transforming a soybean cell with a first recombinant DNA construct comprising:

(i) an isolated polynucleotide encoding a mutant polypeptide having delta-8 desaturase activity, operably linked to at least one regulatory sequence; and, (ii) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase;

(b) regenerating a soybean plant from the transformed cell of step (a); and, (c) selecting those seeds obtained from the plants of step (b) having an altered level of PUFAs when compared to the level in seeds obtained from a nontransformed soybean plant.

In particularly preferred embodiments, the at least one additional recombinant DNA construct encodes a polypeptide having delta-9 elongase activity, e.g., the delta-9 elongase isolated and/or derived from *Isochrysis galbana* (GenBank Accession No. AF390174) and set forth in SEQ ID NOs:172-174 or the delta-9 elongase isolated and/or derived from *Euglena gracilis* and set forth in SEQ ID NOs:175-177.

Microbial Expression Systems, Cassettes & Vectors, and Transformation

The delta-8 desaturase genes and gene products described herein (i.e., those mutants derived from EgD8 or EgD8S, or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-8 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and 6.) the codon usage within the cloned gene, such that its frequency approaches the frequency of preferred codon usage of the host cell. Each of these types of modifications are encompassed in the present invention, as means to further optimize expression of the mutant delta-8 desaturases described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.,* 48(2): 232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in WO2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura-phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-8 desaturases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes of the present invention have been isolated for expression in an oleaginous yeast (and in particular *Yarrowia lipolytica*). It is contemplated that because transcription, translation and the protein biosynthetic apparatus is highly conserved, any bacteria, yeast, algae, oomycete and/or fungus will be a suitable microbial host for expression of the present nucleic acid fragments.

Preferred microbial hosts are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida* lipolytica).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (WO 2006/055322), No. 11/265,761 (WO 2006/052870) and No. 11/264,737 (WO 2006/052871), respectively.

Other preferred microbial hosts include oleaginous bacteria, algae, Oomycetes and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-8 desaturase genes under the control of inducible or regulated promoters could yield a transformant organism capable of synthesizing increased quantities of EDA. The method of transformation of *M. alpina* is described by Mackenzie et al. (*Appl. Environ. Microbiol.,* 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either DGLA or ETA, respectively, comprising:

a) providing an oleaginous yeast comprising:
   - (i) a nucleotide sequence encoding a mutant polypeptide having delta-8 desaturase activity, wherein the mutant polypeptide has an amino acid sequence as set forth in SEQ ID NO:2 and wherein SEQ ID NO:2 is not identical to SEQ ID NO:10; and,
   - (ii) a source of desaturase substrate consisting of either EDA or ETrA, respectively; and, b) growing the yeast of step (a) in the presence of a suitable fermentable carbon source wherein the gene encoding the delta-8 desaturase polypeptide is expressed and EDA is converted to DGLA or ETrA is converted to ETA, respectively; and, c) optionally recovering the DGLA or ETA, respectively, of step (b). Substrate feeding may be required.

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the delta-8 desaturase described herein.

Specifically, in one embodiment this invention concerns an oleaginous yeast comprising:

a) a first recombinant DNA construct comprising an isolated polynucleotide encoding a mutant delta-8 desaturase polypeptide, operably linked to at least one regulatory sequence; and, b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having delta-9 elongase activity, e.g., the delta-9 elongase isolated and/or derived from *Isochrysis galbana* (GenBank Accession No. AF390174) and set forth in SEQ ID NOs:172-174 or the delta-9 elongase isolated and/or derived from *Euglena gracilis* and set forth in SEQ ID NOs:175-177.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-8 desaturase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and the most economical yield of the preferred PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time and method of cell harvest. Microorganisms of interest (i.e., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12 (5/6): 463-491 (1992)). A brief review of downstream processing is also available by A. Singh and O. Ward (*Adv. Appl. Microbiol.,* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of WO 2004/101757 for additional details.

Methods of isolating seed oils are well known in the art (Young et al., Processing of Fats and Oils, In *The Lipid Handbook*, Gunstone et al., eds., Chapter 5, pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in the Table below.

TABLE 5

Generalized Steps For Soybean Oil And Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |

TABLE 5-continued

| Generalized Steps For Soybean Oil And Byproduct Production | | |
|---|---|---|
| Process Step | Process | Impurities Removed and/or By-Products Obtained |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., anti-sticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionery fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which, in turn, alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids described herein will be suitable for use in a variety of food and feed products including, but not limited to: food analogs, meat products, cereal products, snack foods, baked foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oil may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to: imitation milk and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking, i.e., to dry or harden by subjecting to heat. Examples of a baked good product include, but are not limited to: bread, cakes, doughnuts, bars, pastas, bread crumbs, baked snacks, mini-biscuits, mini-crackers, mini-cookies and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form. For example, there can be mentioned non-carbonated drinks; fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enternal nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ [Mead Johnson & Company] and Similac Advance™ [Ross Products Division, Abbott Laboratories]) Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example: chewing gums, confections and frostings, gelatins and puddings, hard and soft candies, jams and jellies, white granulated sugar, sugar substitutes, sweet sauces, toppings and syrups, and dry-blended powder mixes.

Health Food Products and Pharmaceuticals

A health food product is any food product that imparts a health benefit and includes functional foods, medical foods, medical nutritionals and dietary supplements. Additionally, plant/seed oils, altered seeds and microbial oils of the invention may be used in standard pharmaceutical compositions. For example, the oils of the invention could readily be incorporated into the any of the above mentioned food products, to thereby produce, e.g., a functional or medical food. More concentrated formulations comprising PUFAs include capsules, powders tablets, softgels, gelcaps, liquid concentrates and emulsions which can be used as a dietary supplement in humans or animals other than humans.

Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited herein, it is expected that the oils of the invention can be used within pet food products, ruminant and poultry food products and aquacultural food products. Pet food products are those products intended to be fed to a pet [e.g., a dog, cat, bird, reptile, rodent]; these products can include the cereal and health food products above, as well as meat and meat byproducts, soy protein products and grass and hay products (e.g., alfalfa, timothy, oat or brome grass, vegetables). Ruminant and poultry food products are those wherein the product is intended to be fed to e.g., turkeys, chickens, cattle and swine. As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms, animals and/or plants in fresh or marine waters.

DESCRIPTION OF PREFERRED EMBODIMENTS

One object of the present invention is the synthesis of suitable delta-8 desaturases that will enable expression of the delta-9 elongase/delta-8 desaturase pathway in plants and oleaginous yeast.

In commonly owned WO 2006/012325 and WO 2006/012326 (US2005-0287652) applicants describe the isolation of a delta-8 desaturase from *Euglena gracilis* ("Eg5"), and the enzyme's functional characterization upon expression in *Saccharomyces cerevisiae*. The wildtype Eg5 sequence was additionally codon-optimized for expression in *Yarrowia lipolytica*, resulting in the synthesis of a synthetic, functional codon-optimized delta-8 desaturase designated as "D8SF". Upon co-expression of D8SF with a codon-optimized delta-9 elongase (derived from *Isochrysis galbana* (GenBank Accession No. 390174) in *Yarrowia lipolytica,* 6.4% DGLA (with no co-synthesis of GLA) was demonstrated (Example 16 in WO 2006/012325 and WO 2006/012326 (US2005-0287652-A1)).

In the present Application, the synthetic codon-optimized delta-8 desaturase designated as "D8SF" (and designated herein as EgD8S") was subjected to targeted mutations. Ultimately, a mutant EgD8S enzyme (SEQ ID NO:2) was created comprising at least one amino acid mutation (and up to about 33 amino acid mutations) with respect to the synthetic codon-optimized EgD8S, wherein: (i) the at least one mutation is selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to the synthetic codon-optimized sequence set forth in SEQ ID NO:10; (ii) SEQ ID NO:2 is not identical to SEQ ID NO:10; and, (iii) SEQ ID NO:2 is at least about functionally equivalent to SEQ ID NO:10.

Given the teaching of the present application the skilled person will recognize the commercial utility of the recombinant genes of the present invention encoding delta-8 desaturases, to enable production of a variety of omega-3 and/or omega-6 PUFAs via expression of a heterologous delta-9 elongase/delta-8 desaturase pathway.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

General molecular cloning was performed according to standard methods (Sambrook et al., supra). Oligonucleotides were synthesized by Sigma-Genosys (Spring, Tex.). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNAStar Inc., Madison, Wis.). Alternatively, manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "hr" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s). Parts and percentages are by weight and degrees are Celsius.

Transformation and Cultivation of *Yarrowia lipolytica*

*Yarrowia lipolytica* strains ATCC #20362, #76982 and #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol. Biotechnol.,* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil or leucine were added as appropriate to a final concentration of 0.01% (thereby producing "MMU" or "MMLeu" selection media, respectively, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G., and Nishida I., *Arch. Biochem. Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Development of a Topological Model for EgD8S

BLASTP analysis showed that EgD8S contained two domains: an N-terminal cytochrome $b_5$ domain (located between amino acid residues 5 to 71 of SEQ ID NO:10) and a C-terminal desaturase domain (located between amino acid residues 79 to 406 of SEQ ID NO:10). In order to mutate the amino acid sequence of EgD8S without negatively affecting the delta-8 desaturase activity, a topological model (FIG. 2) was developed based on the logic and analyses below.

First, the TMHMM program ("Prediction of transmembrane helices in proteins"; TMHMM Server v. 2.0, Center for Biological Sequence Analysis, BioCentrum-DTU, Technical University of Denmark, DK-2800 Lyngby, Denmark) predicted that EgD8S had four membrane-spanning helices (amino acid residues 113-132, 223-245, 266-283 and 287-309), with both the N- and C-termini located on the cytoplasmic side of the membrane.

The membrane-bound fatty acid desaturases belong to a super-family of membrane di-iron proteins that feature three His-rich motifs: $HX_{(3-4)}H$ (SEQ ID NOs:166 and 167), $HX_{(2-3)}HH$ (SEQ ID NOs:168 and 169) and $(H/Q)X_{(2-3)}HH$ (SEQ ID NOs:170 and 171). These His-rich residues have been predicted to be located in the cytoplasmic face of the membrane and have been shown to be important for enzyme activity (Shanklin, J. et al., *Biochemistry,* 33:12787-12794 (1994); Shanklin, J., and Cahoon, E. B., *Annu. Rev. Plant Physiol. Plant Mol. Biol.,* 49:611-641 (1998)). Within SEQ ID NO:10, these three histidine boxes were located between amino acid residues 146-150, 183-187 and 358-362; two additional His residues are located at amino acid residues 27 and 50. Each of these His residues are depicted on FIG. 2 with a small round circle.

If the model predicted by TMHMM (supra) were accepted without alteration, the first two His-rich regions (i.e., the regions spanning between amino acid residues 146-150 and 183-187) would be located in the periplasmic space, thus preventing their participation in the iron-active site.

The conflict noted above was resolved when hydropathy plot analysis (Kyte, J., and Doolittle, R., *J. Mol. Biol.,* 157: 105-132 (1982)) predicted one more hydrophobic region located between amino acid residues 88-109 that immediately preceded the first predicted transmembrane segment (i.e., residues 113-132). Since the N-terminal cytochrome-$b_5$ domain is located in the cytoplasmic space, it was predicted that the hydrophobic region (i.e., residues 88-109) should be the first membrane-spanning segment (i.e., region I, as shown in FIG. 2), while the predicted transmembrane segment corresponding to residues 113-132 was designated as the second membrane-spanning segment (i.e., region II, as shown in FIG. 2). As a result, the transmembrane segment found between residues 223-245 that was originally predicted by TMHMM to span through the membrane was instead predicted to lie in the cytoplasmic face, such that the first two His-rich motifs (i.e., the regions spanning between amino acid residues 146-150 and 183-187) could be adjusted to be within the cytoplasmic side.

Finally, the hydropathy plot analysis also predicted another hydrophobic region (i.e., residues 157-172) between the first two His-rich motifs. Because the substrate for the desaturase is highly hydrophobic, it was expected to most likely partition into the lipid bilayer of the cytoplasmic membrane. This suggested that the desaturase active site assembled from the His-rich motifs might be at (or very near) the membrane surface. Thus, it was hypothesized that both hydrophobic regions (i.e., residues 157-172 and residues 223-245) lie near the membrane surface to ensure that the active site sits close the membrane.

The last two membrane-spanning helices predicted by TMHMM (i.e., residues 266-283 and 287-309) are included within the final topological model shown in FIG. 2 as region III and region IV.

Thus, the topological model depicted in FIG. 2 includes four transmembrane regions labeled as regions I, II, III and IV, which correspond to amino acid residues 88-109, 113-132, 266-283 and 287-309, respectively. Two additional hydrophobic regions are located at amino acid residues 157-172 and 223-245. Finally, "IN" corresponds with the cytoplasmic space, while "OUT" corresponds with the periplasmic space.

Example 2

Strategies to Select Amino Acid Residues for Mutation

Close homologs to the EgD8S sequence were determined by conducting BLAST (Basic Local Alignment Search Tool; Altschul, S. F., et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). Specifically, EgD8S (SEQ ID NO:10) was compared for similarity to all publicly available protein sequences contained in the "nr" database, using the BLASTP algorithm (Altschul et al., *J. Mol. Biol.* 215:403-410 (1990)) provided by the NCBI.

Ignoring all hits to any delta-8 desaturase isolated from *Euglena gracilis*, the BLASTP searches showed that EgD8S was most homologous to the following proteins:

TABLE 6

Homologous Proteins To EgD8S, Based On BLASTP Analysis

| GenBank Accession No. | Protein | Organism | % Identity | % Similarity | E-Value |
|---|---|---|---|---|---|
| CAE65324 | hypothetical protein CBG10258 | *Caenorhabditis briggsae* | 38 | 56 | 1E−65 |
| AAR27297 | delta-6 desaturase | *Amylomyces rouxii* | 35 | 52 | 3E−65 |
| AAS93682 | delta-6 desaturase | *Rhizopus orizae* | 32 | 53 | 4E−64 |

* "% Identity" is defined as the percentage of amino acids that are identical between the two proteins.
** "% Similarity" is defined as the percentage of amino acids that are identical or conserved between the two proteins.

***"E-Value" (Expectation Value) estimates the statistical significance of the match, specifying the number of matches, with a given score, that are expected in a search of a database of this size absolutely by chance.

In order to select the amino acid residues that could be mutated within EgD8S without affecting the delta-8 desaturase activity, a set of criteria were developed to identify preferred targets for mutation, as outlined below.

1. Preferred amino acid residue targets of the EgD8S desaturase domain (located between amino acid residues 79 to 406 of SEQ ID NO:10) are not conserved, when compared to the delta-6 desaturase of *A. rouxii* (supra; "ArD6"; SEQ ID NO:13), the delta-6 desaturase of *R. orizae* (supra; "RoD6"; SEQ ID NO:14) and representatives of other desaturases such as the delta-8 fatty acid desaturase-like protein of *Leishmania major* (GenBank Accession No. CAJ09677; "LmD8L"; SEQ ID NO:15), and the delta-6 desaturase of *Mortierella isabellina* (GenBank Accession No. AAG38104; "MiD6"; SEQ ID NO:16). An alignment of these proteins is shown in FIG. 3, using the method of Clustal W (slow, accurate, Gonnet option; Thompson et al., *Nucleic Acids Res.,* 22:4673-4680 (1994)) of the MegAlign™ program of DNASTAR software. It was hypothesized that changes in the non-conserved regions among these 5 different desaturases should not affect the delta-8 desaturase activity of EgD8S.

2. Preferred amino acid residue targets of the cytochrome $b_5$ domain of EgD8S (located between amino acids 5 to 71 of SEQ ID NO:10) are not conserved, when compared to the cytochrome $b_5$ genes of *Saccharomyces cerevisiae* (GenBank Accession No. P40312; "SCb5"; SEQ ID NO:178) and *Schizosaccharomyces pombe* (GenBank Accession No. O94391; SPb5; SEQ ID NO:179). An alignment of the N-terminal portion of EgD8S (i.e., amino acid residues 1-136 of SEQ ID NO:10) with SCb5 and SPb5 is shown in FIG. 4, using the method of Clustal W (supra) of the MegAlign™ program of DNASTAR software. It was hypothesized that changes in the non-conserved region among these 3 different proteins should not affect the electron transport function of the cytochrome $b_5$ domain of EgD8S and thus not affect the delta-8 desaturase activity.

3. Preferred amino acid residue targets are on the transmembrane helices close to the endoplasmic reticulum (ER) side of the membrane or exposed to the ER lumen.

4. Preferred amino acid residue targets are close to the N-terminal or C-terminal ends of the EgD8S enzyme, since non-conserved residues in these regions may tolerate more mutations.

Based on the above criteria, a set of 70 target mutation sites (comprising one, two or three amino acid residues) within EgD8S (i.e., SEQ ID NO:10) were selected for mutation as described below in Table 7. Of the individual 126 amino acid residue mutations, 53 (i.e., 42.1%) were identified as "non-conservative amino acid substitutions" while 73 (i.e., 57.9%) were identified as "conservative amino acid substitutions".

TABLE 7

Selected Amino Acid Residues Suitable For Targeted Mutation

| Mutation Site | Sequence Mutations Within SEQ ID NO: 10 |
|---|---|
| M1 | 4S to A, 5K to S |
| M2 | 12T to V |
| M3 | 16T to K, 17T to V |
| M4 | 25N to D, 26F to E |
| M5 | 31A to D, 32E to S |
| M6 | 59K to L |
| M7 | 61M to A, 62P to V |
| M8 | 66P to Q, 67S to A |
| M9 | 72P to Q, 73Q to P |
| M10 | 79A to Q, 80Q to A |
| M11 | 87R to A, 88E to I |
| M12 | 407A to S, 408V to Q |
| M13 | 412M to S, 413A to Q |
| M14 | 416Q to V, 417P to Y |
| M15 | 422L to Q |
| M16 | 108S to L |
| M17 | 110T to A |
| M18 | 120L to M, 121M to L |
| M19 | 122V to S |
| M20 | 123Q to Y, 124Y to Q |
| M21 | 125Q to H, 126M to L |
| M22 | 127Y to Q |
| M23 | 288S to N |
| M24 | 289I to P, 290L to M |
| M25 | 291T to V, 292S to V |
| M26 | 293L to M |
| M27 | 296F to T |
| M28 | 298V to S |
| M29 | 392N to T, 393P to T |
| M30 | 394L to G, 395P to M |
| M31 | 7Q to L, 8A to S |
| M32 | 10P to W, 11L to Q |
| M33 | 21S to F, 22A to S |
| M34 | 46F to S, 47M to L |
| M35 | 48V to F, 49M to L |
| M36 | 37Y to F, 38Q to N |
| M37 | 51S to T, 52Q to N |
| M38 | 54A to G, 55F to Y |
| M39 | 64I to L, 65N to D |
| M40 | 69E to D, 70L to V |
| M41 | 75A to G, 76V to L |
| M42 | 89E to D, 90L to I |
| M43 | 97D to E, 98A to V |
| M44 | 110T to S, 111L to V |
| M45 | 117G to A, 118Y to F |
| M46 | 132V to L, 133L to V |
| M47 | 198D to E, 199I to L |
| M48 | 231L to V, 232V to L |
| M49 | 297F to V, 298V to L |
| M50 | 309I to V, 310V to I |
| M51A | 347I to L, 348T to S |
| M51B | 346I to V, 347I to L, 348T to S |
| M52 | 400V to I, 401I to V |
| M53 | 9L to V |
| M54 | 19D to E, 20V to I |
| M55 | 33I to L |
| M56 | 45A to G, 46F to Y |
| M57 | 57K to R, 58L to I |
| M58 | 65N to Q |
| M59 | 73Q to N, 74A to G |

TABLE 7-continued

Selected Amino Acid Residues Suitable For Targeted Mutation

| Mutation Site | Sequence Mutations Within SEQ ID NO: 10 |
|---|---|
| M60 | 96F to Y |
| M61 | 239F to I, 240I to F |
| M62 | 271L to M, 272A to S |
| M63 | 279T to L, 280L to T |
| M64 | 130G to A, 131A to G |
| M65 | 304G to F, 305F to G |
| M66 | 229F to Y, 230Y to F |
| M67 | 291T to S, 292S to L |
| M68 | 162L to V, 163V to L |
| M69 | 170G to A, 171L to V |
| M70 | 418A to G, 419G to A |

Example 3

Generation of *Yarrowia lipolytica* Strains Y4001 and Y4001U to Produce about 17% EDA of Total Lipids The present Example describes the construction of strains Y4001 and Y4001U, derived from *Yarrowia lipolytica* ATCC #20362, and each capable of producing 17% EDA (C20:2) relative to the total lipids. Both strains were engineered to test functional expression of EgD8S and mutations thereof. Thus, it was necessary to construct host strains capable of producing the delta-8 desaturase substrate, EDA.

The development of strain Y4001*l* U, having a Leu- and Ura-phenotype, required the construction of strain Y2224 (a FOA resistant mutant from an autonomous mutation of the Ura3 gene of wildtype *Yarrowia* strain ATCC #20362) and strain Y4001.

Generation of Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Generation of Strain Y4001 to Produce 17% EDA of Total Lipids

Strain Y4001 was created via integration of construct pZKLeuN-29E3 (FIG. 5A; comprising four chimeric genes [a delta-12 desaturase, a $C_{16/18}$ elongase and two delta-9 elongases]) into the Leu2 loci of Y2224 strain to thereby enable production of EDA.

Construct pZKLeuN-29E3 contained the following components:

TABLE 8

Description of Plasmid pZKLeuN-29E3 (SEQ ID NO: 17)

| RE Sites And Nucleotides Within SEQ ID NO: 17 | Description Of Fragment And Chimeric Gene Components |
|---|---|
| BsiW I/Asc I 7797-7002 | 795 bp 3' part of *Yarrowia* Leu2 gene (GenBank Accession No. AF260230) |
| Sph I/Pac I (4302-3591) | 703 bp 5' part of *Yarrowia* Leu2 gene (GenBank Accession No. AF260230) |
| Swa I/BsiW I (10500-7797) | GPD::F.D12::Pex20, comprising:<br>GPD: *Yarrowia lipolytica* GPD promoter (WO 2005/003310)<br>F.D12: *Fusarium moniliforme* delta-12 desaturase gene (WO 2005/047485)<br>Pex20: Pex20 terminator sequence from Yarrowia Pex20 gene (GenBank Accession No. AF054613) |
| Bgl II/Swa I (12526-10500) | Exp pro::EgD9E::Lip1, comprising:<br>Exp pro: *Yarrowia lipolytica* export protein (EXP1) promoter (WO 2006/052870 and U.S. Patent Application No. 11/265761)<br>EgD9E: codon-optimized delta-9 elongase gene (SEQ ID NO: 177), derived from *Euglena gracilis* (SEQ ID NOs: 175 and 176; U.S. Patent Application No. 60/739989; see also Example 16 herein)<br>Lip1: Lip1 terminator sequence from *Yarrowia* Lip1 gene (GenBank Accession No. Z50020) |
| Pme I/Cla I (12544-1) | FBAINm::EgD9S::Lip2, comprising:<br>FBAINm: *Yarrowia lipolytica* FBAINm promoter (WO 2005/049805)<br>EgD9S: codon-optimized delta-9 elongase gene (SEQ ID NO: 177; supra)<br>Lip2: Lip2 terminator sequence from *Yarrowia* Lip2 gene (GenBank Accession No. AJ012632) |
| Cla I/EcoR I (1-1736) | LoxP::Ura3::LoxP, comprising:<br>LoxP sequence (SEQ ID NO: 18)<br>*Yarrowia* Ura3 gene (GenBank Accession No. AJ306421)<br>LoxP sequence (SEQ ID NO: 18) |
| EcoR I/Pac I (1736-3591) | NT::ME3S::Pex16, comprising:<br>NT: *Yarrowia lipolytica* YAT1 promoter (Patent Publication US 2006/0094102-A1)<br>ME3S: codon-optimized $C_{16/18}$ elongase gene (SEQ ID NO: 19), derived from *M. alpina* (see U.S. Patent Application No. 11/253882 and also WO 2006/052870)<br>Pex16: Pex16 terminator sequence of *Yarrowia* Pex 16 gene (GenBank Accession No. U75433) |

Plasmid pZKLeuN-29E3 was digested with Asc I/Sph I, and then used for transformation of *Y. lipolytica* strain Y2224 (i.e., ATCC #20362 Ura3−) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu-strains. Single colonies of Leu-strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu-strains produced about 12 to 16.9% EDA of total lipids. There were 3 strains (i.e., strains #11, #30 and #34) that produced about 17.4%, 17% and 17.5% EDA of total lipids; they were designated as strains Y4001, Y4002 and Y4003, respectively.

Generation of Strain Y4001U (Leu-, Ura-) to Produce 17% EDA of Total Lipids

Strain Y4001U was created via temporary expression of the Cre recombinase enzyme in plasmid pY116 (FIG. 5B) within strain Y4001 to produce a Leu- and Ura-phenotype. Construct pY116 contained the following components:

TABLE 9

| Description of Plasmid pY116 (SEQ ID NO: 180) | |
|---|---|
| RE Sites And Nucleotides Within SEQ ID NO: 180 | Description Of Fragment And Chimeric Gene Components |
| 1328-448 | ColE1 plasmid origin of replication |
| 2258-1398 | Ampicillin-resistance gene ($Amp^R$) |
| 3157-4461 | *Yarrowia* autonomous replication sequence (ARS18; GenBank Accession No. A17608) |
| PacI/SawI 6667-4504 | *Yarrowia* Leu2 gene (GenBank Accession No. AF260230) |
| 6667-180 | GPAT::Cre::XPR2, comprising: GPAT: *Yarrowia lipolytica* GPAT promoter (WO 2006/031937) Cre: Enterobacteria phage P1 Cre gene for recombinase protein (GenBank Accession No. X03453) XPR2: ~100 bp of the 3' region of the *Yarrowia* Xpr gene (GenBank Accession No. M17741) |

Plasmid pY116 was used for transformation of freshly grown Y4001 cells according to the General Methods. The transformant cells were plated onto MMU plates containing 280 μg/mL sulfonylurea and maintained at 30° C. for 3 to 4 days. Four colonies were picked, inoculated into 3 mL liquid YPD media at 30° C. and shaken at 250 rpm/min for 1 day. The cultures were diluted to 1:50,000 with liquid MMU media, and 100 μL was plated onto new YPD plates and maintained at 30° C. for 2 days. Colonies were picked and streaked onto MMLeu and MMLeu+Ura selection plates. The colonies that could grow on MMLeu+Ura plates but not on MMLeu plates were selected and analyzed by GC to confirm the presence of C20:2 (EDA). One strain, having a Leu- and Ura-phenotype, produced about 17% EDA of total lipids and was designated as Y4001U.

Example 4

Generation of Auto-Replicating Plasmid pFmD8S

Figure 6A:
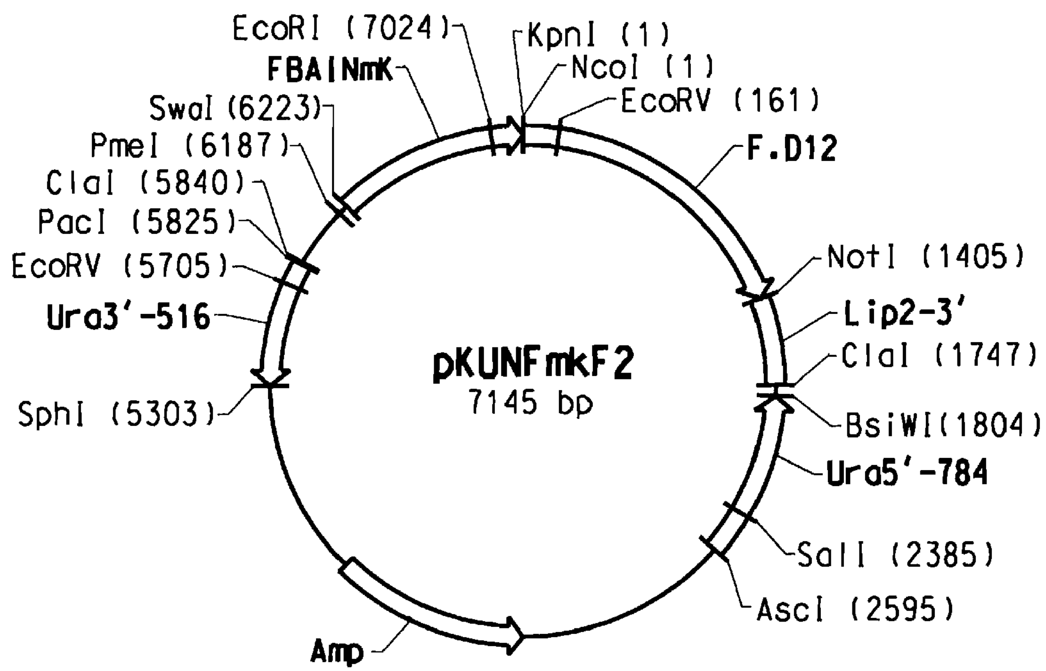
Figure 6B:
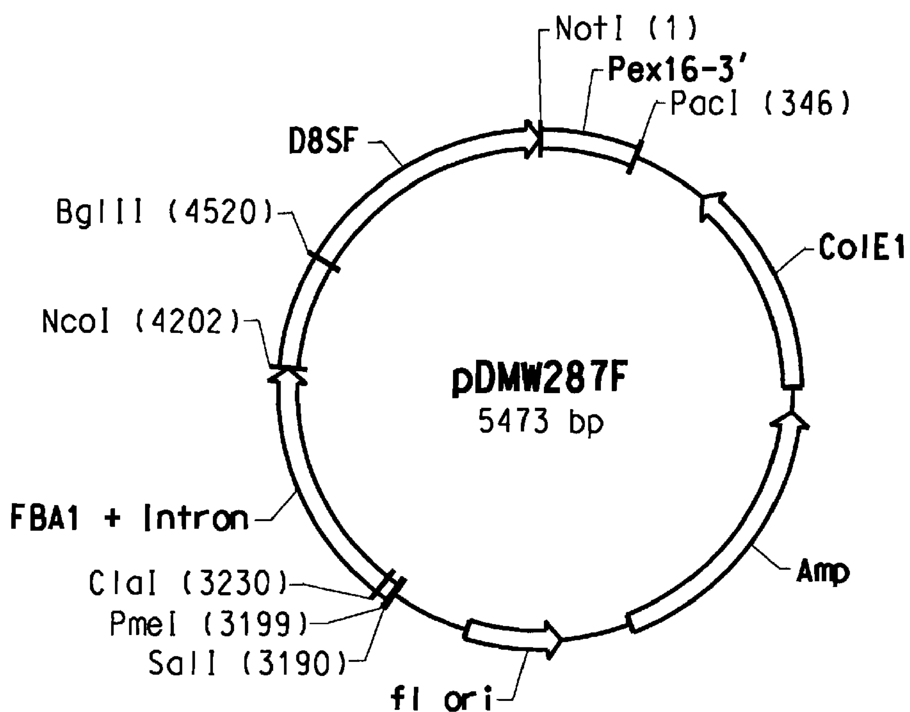
Figure 6C:
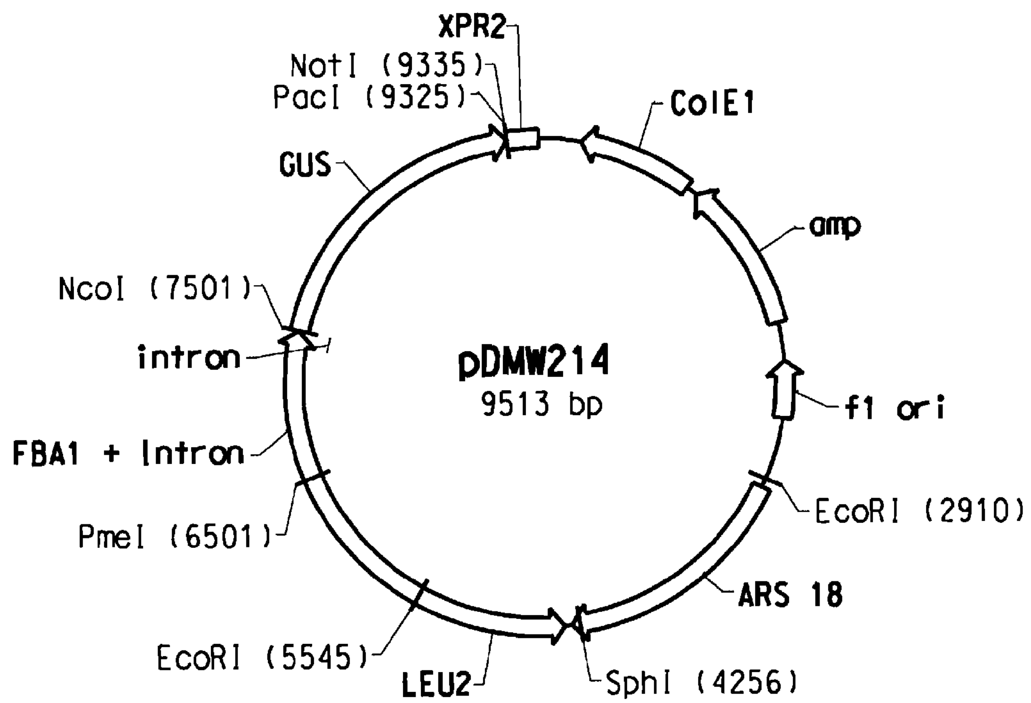
Figure 6D:
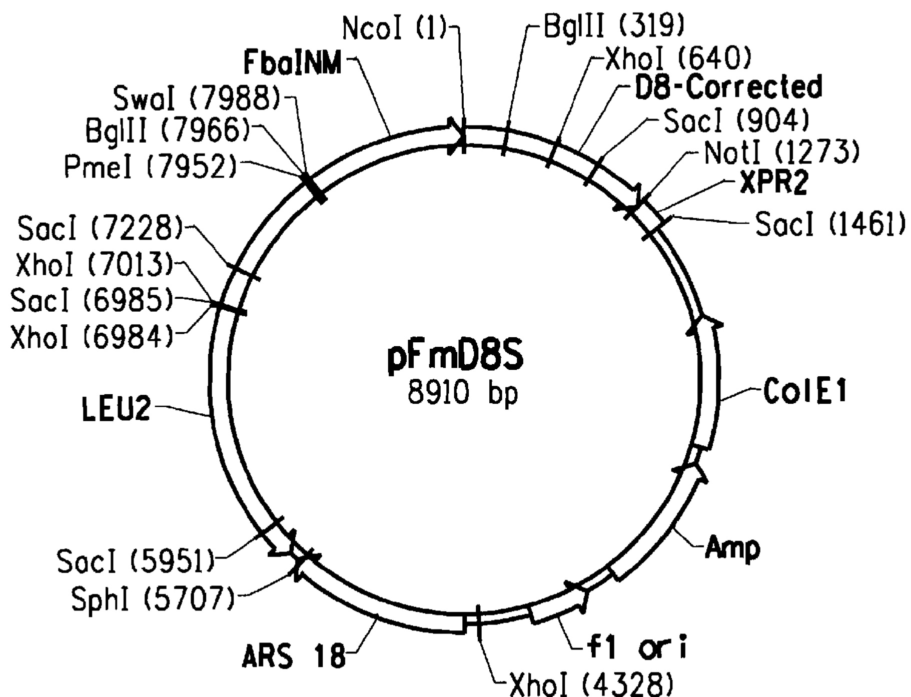

The present Example describes the construction of plasmid pFmD8S comprising a chimeric FBAINm::EgD8S::XPR gene. Plasmid pFmD8S (SEQ ID NO:20; FIG. 6D) was constructed by three-way ligation using fragments from plasmids pKUNFmkF2, pDMW287F and pDMW214. Plasmid pFmD8S, an auto-replicating plasmid that will reside in *Yarrowia* in 1-3 copies, was utilized to test functional expression of EgD8S (and mutations thereof), as described in Examples 5-10, infra.

Plasmid pKUNFmkF2 pKUNFmkF2 (SEQ ID NO:21; FIG. 6A; WO 2006/012326) is a construct comprising a chimeric FBAINm::F.D12::Lip2 gene (wherein "FBAINmK" is the *Yarrowia lipolytica* FBAINm promoter [WO 2005/049805], "F.D12" is the *Fusarium moniliforme* delta-12 desaturase [WO 2005/047485], and "Lip2" is the *Yarrowia lipolytica* Lip2 terminator sequence (GenBank Accession No. AJ012632)).

Plasmid pDMW287F pDMW287F (SEQ ID NO:22; FIG. 6B; WO 2006/012326) is a construct comprising the synthetic delta-8 desaturase, derived from wildtype *Euglena gracilis*, and codon-optimized for expression in *Yarrowia lipolytica* (wherein EgD8S is identified as "D8SF" in the figure). The desaturase gene is flanked by a *Yarrowia lipolytica* FBAIN promoter (WO 2005/049805; identified as "FBA1+intron" in the figure) and a Pex16 terminator sequence of the *Yarrowia* Pex16 gene (GenBank Accession No. U75433).

Plasmid pDMW214 pDMW214 (SEQ ID NO:23; FIG. 6C; WO 2005/049805) is a shuttle plasmid that could replicate both in *E. coli* and *Yarrowia lipolytica*. It contained the following components:

TABLE 10

| Description Of Plasmid pDMW214 (SEQ ID NO: 23) | |
|---|---|
| RE Sites And Nucleotides Within SEQ ID NO: 23 | Description Of Fragment And Chimeric Gene Components |
| 1150-270 | ColE1 plasmid origin of replication |
| 2080-1220 | Ampicillin-resistance gene ($Amp^R$) |
| 2979-4256 | *Yarrowia* autonomous replication sequence (ARS18; GenBank Accession No. A17608) |
| PmeI/SphI 6501-4256 | *Yarrowia* Leu2 gene (GenBank Accession No. AF260230) |
| 6501-1 | FBA1 + intron::GUS::XPR2, comprising: FBA1 + intron: *Yarrowia lipolytica* FBAIN promoter (WO 2005/049805) GUS: *E. coli* gene encoding β-glucuronidase (Jefferson, R. A. Nature. 342: 837-838 (1989) XPR2: ~100 bp of the 3' region of the *Yarrowia* Xpr gene (GenBank Accession No. M17741) |

Final Construction of Plasmid pFmD8S

The PmeI/NcoI fragment of plasmid pKUNFmkF2 (FIG. 6A; comprising the FBAINm promoter) and the NcoI/NotI fragment of plasmid pDMW287F (FIG. 6B; comprising the synthetic delta-8 desaturase gene EgD8S) were used directionally to replace the PmeI/Not I fragment of pDMW214 (FIG. 6C). This resulted in generation of pFmD8S (SEQ ID NO:20; FIG. 6D), comprising a chimeric FBAINm::EgD8S::XPR2 gene. Thus, the components of pFmD8S are as described in Table 11 below.

TABLE 11

| Components Of Plasmid pFmD8S (SEQ ID NO: 20) | |
|---|---|
| RE Sites And Nucleotides Within SEQ ID NO: 20 | Description Of Fragment And Chimeric Gene Components |
| Swa I/Sac II (7988-1461) | FBAINm::EgD8S::XPR2, comprising: FBAINm: *Yarrowia lipolytica* FBAINm promoter (WO 2005/049805) EgD8S: codon-optimized delta-8 desaturase gene (SEQ ID NO: 9, identified as "D8-corrected" in FIG. 6D), derived from *Euglena gracilis* (SEQ ID NO: 11) XPR2: ~100 bp of the 3' region of the *Yarrowia* Xpr gene (GenBank Accession No. M17741) |
| 2601-1721 | ColE1 plasmid origin of replication |
| 3531-2671 | Ampicillin-resistance gene ($Amp^R$) for selection in *E. coli* |
| 4430-5734 | *Yarrowia* autonomous replication sequence (ARS18; GenBank Accession No. A17608) |
| 7942-5741 | *Yarrowia* Leu2 gene (GenBank Accession No. AF260230) |

Example 5

Development of A Quick Screen to Functionally Analyze Delta-8 Desaturase Activity in *Yarrowia lipolytica*

A set of 40 mutations was created using pFmD8S (Example 4) as template and 40 pairs of oligonucleotide primers to individually mutate targeted amino acid residues within EgD8S (SEQ ID NO:10) by site-directed mutagenesis (QuikChange® Kit, Stratagene, La Jolla, Calif.). Specific mutations were selected from those set forth in Table 7 of Example 2 and primer pairs were selected from the oligonucleotides set forth in SEQ ID NOs:24-164, such that creation of the M1 mutation (i.e., 4S to A, 5K to S within SEQ ID NO:10) required primers 1A and 1B (SEQ ID NOs:24 and 25, respectively), etc. Plasmids from each mutation were transformed into *E. coli* XL2Blue cells (Stratagene). Four colonies from each of the 40 transformations were picked and grown individually in liquid media at 37° C. overnight. Plasmids (i.e., 160 total) were isolated from these cultures and sequenced individually to confirm the mutations.

Plasmid pFmD8S and the isolated mutant plasmids were transformed into strain Y4001 (Example 3) individually, as described in the General Methods. The transformants were selected on MM plates. After 2 days growth at 30° C., transformants were scraped from each plate, lipids were extracted, and fatty acid methyl esters were prepared by trans-esterification, and subsequently analyzed with a Hewlett-Packard 6890 GC.

GC analyses showed that there were about 7% DGLA and 12% EDA of total lipids produced by the transformants with plasmid pFmD8S; the average conversion efficiency whereby EgD8S converted EDA to DGLA in the transformants was 36.8%. The conversion efficiency for delta-8 desaturase (also referred to as the delta-8 desaturase activity) was measured according to the following formula: ([product]/[substrate+product])*100, where 'product' includes the immediate product and all products in the pathway derived from it.

GC analyses of transformants carrying mutations within EgD8S showed that 30 of the 40 mutations did not affect the delta-8 desaturase activity (when compared to the synthetic codon-optimized EgD8S delta-8 desaturase activity in transformants carrying plasmid pFmD8S). These results suggested that the screening procedure described herein (i.e., with pFmD8S as parent plasmid and strain Y4001 as a host) could be used to quickly screen the EgD8S mutants and identify which mutations negatively affected delta-8 desaturase activity.

Based on these results, the remaining 30 mutations set forth in Table 7 of Example 2 were synthesized (although some mutations were introduced in combination for efficiency), using the methodology described above. Table 12 describes the delta-8 desaturase relative activity attributed to each mutation site (i.e., M1 to M70), as a percent of the delta-8 desaturase activity resulting in each mutant EgD8S with respect to the delta-8 desaturase activity of the synthetic codon-optimized EgD8S (SEQ ID NO:10). As seen in Table 12, delta-8 desaturase relative activity ranged from 0% up to 125%.

TABLE 12

Mutant Delta-8 Desaturase Activities

| Mutations | Primers Used | Relative Activity % |
|---|---|---|
| M1 | 1A, 1B (SEQ ID NOs: 24 and 25) | 115% |
| M2 | 2A, 2B (SEQ ID NOs: 26 and 27) | 110% |
| M3 | 3A, 3B (SEQ ID NOs: 28 and 29) | 100% |
| M4 | 4A, 4B (SEQ ID NOs: 30 and 31) | N/A |
| M5 | 5A, 5B (SEQ ID NOs: 32 and 33) | N/A |
| M6 | 6A, 6B (SEQ ID NOs: 34 and 35) | 110% |
| M7 | 7A, 7B (SEQ ID NOs: 36 and 37) | 30% |
| M8 | 8A, 8B (SEQ ID NOs: 38 and 39) | 100% |
| M9 | 9A, 9B (SEQ ID NOs: 40 and 41) | N/A |
| M10 | 10A, 10B (SEQ ID NOs: 42 and 43) | N/A |
| M11 | 11A, 11B (SEQ ID NOs: 44 and 45) | 20% |
| M12 | 12A, 12B (SEQ ID NOs: 46 and 47) | 100% |
| M13 | 13A, 13B (SEQ ID NOs: 48 and 49) | N/A |
| M14 | 14A, 14B (SEQ ID NOs: 50 and 51) | 100% |
| M15 | 15A, 15B (SEQ ID NOs: 52 and 53) | 125% |
| M16 | 16A, 16B (SEQ ID NOs: 54 and 55) | 100% |
| M17 | 17A, 17B (SEQ ID NOs: 56 and 57) | 50% |
| M18 | 18A, 18B (SEQ ID NOs: 58 and 59) | N/A |
| M19 | 19A, 19B (SEQ ID NOs: 60 and 61) | 100% |
| M20 | 20A, 20B (SEQ ID NOs: 62 and 63) | 80% |
| M21 | 21A, 21B (SEQ ID NOs: 64 and 65) | 120% |
| M22 | 22A, 22B (SEQ ID NOs: 66 and 67) | 110% |
| M23 | 23A, 23B (SEQ ID NOs: 68 and 69) | 80% |
| M24 | 24A, 24B (SEQ ID NOs: 70 and 71) | N/A |
| M25 | 25A, 25B (SEQ ID NOs: 72 and 73) | N/A |
| M26 | 26A, 26B (SEQ ID NOs: 74 and 75) | 110% |
| M27 | 27A, 27B (SEQ ID NOs: 76 and 77) | 80% |
| M28 | 28A, 28B (SEQ ID NOs: 78 and 79) | 90% |
| M29 | 29A, 29B (SEQ ID NOs: 80 and 81) | N/A |
| M30 | 30A, 30B (SEQ ID NOs: 82 and 83) | 85% |
| M31 | 31A, 31B (SEQ ID NOs: 84 and 85) | 85% |
| M32 | 32A, 32B (SEQ ID NOs: 86 and 87) | N/A |
| M33 | 33A, 33B (SEQ ID NOs: 88 and 89) | N/A |
| M34 | 34A, 34B (SEQ ID NOs: 90 and 91) | N/A |
| M35 | 35A, 35B (SEQ ID NOs: 92 and 93) | 0% |
| M36 | 36A, 36B (SEQ ID NOs: 94 and 95) | 80% |
| M37 | 37A, 37B (SEQ ID NOs: 96 and 97) | 90% |
| M38 | 38A, 38B (SEQ ID NOs: 98 and 99) | 100% |
| M39 | 39A, 39B (SEQ ID NOs: 100 and 101) | 100% |
| M40 | 40A, 40B (SEQ ID NOs: 102 and 103) | 100% |
| M41 | 41A, 41B (SEQ ID NOs: 104 and 105) | 100% |
| M42 | 42A, 42B (SEQ ID NOs: 106 and 107) | 0% |

TABLE 12-continued

Mutant Delta-8 Desaturase Activities

| Mutations | Primers Used | Relative Activity % |
|---|---|---|
| M43 | 43A, 43B (SEQ ID NOs: 108 and 109) | 90% |
| M44 | 44A, 44B (SEQ ID NOs: 110 and 111) | N/A |
| M45 | 45A, 45B (SEQ ID NOs: 112 and 113) | 100% |
| M46 | 46A, 46B (SEQ ID NOs: 114 and 115) | 100% |
| M47 | 47A, 47B (SEQ ID NOs: 116 and 117) | 0% |
| M48 | 48A, 48B (SEQ ID NOs: 118 and 119) | N/A |
| M49 | 49A, 49B (SEQ ID NOs: 120 and 121) | 100% |
| M50 | 50A, 50B (SEQ ID NOs: 122 and 123) | 100% |
| M51 | 51A, 51B (SEQ ID NOs: 124 and 125) | 100% |
| M51B | 51A, 51B (SEQ ID NOs: 126 and 125) | 100% |
| M52 | 52A, 52B (SEQ ID NOs: 127 and 128) | 80% |
| M53 | 53A, 53B (SEQ ID NOs: 129 and 130) | 100% |
| M54 | 54A, 54B (SEQ ID NOs: 131 and 132) | 100% |
| M55 | 55A, 55B (SEQ ID NOs: 133 and 134) | 40% |
| M56 | 56A, 56B (SEQ ID NOs: 135 and 136) | 0% |
| M57 | 57A, 57B (SEQ ID NOs: 137 and 138) | N/A |
| M58 | 58A, 58B (SEQ ID NOs: 139 and 140) | 100% |
| M59 | 59A, 59B (SEQ ID NOs: 141 and 142) | 90% |
| M60 | 60A, 60B (SEQ ID NOs: 143 and 144) | 50% |
| M61 | 61A, 61B (SEQ ID NOs: 145 and 146) | 50% |
| M62 | 62A, 62B (SEQ ID NOs: 147 and 148) | 50% |
| M63 | 63A, 63B (SEQ ID NOs: 149 and 150) | 100% |
| M64 | 64A, 64B (SEQ ID NOs: 151 and 152) | 60% |
| M65 | 65A, 65B (SEQ ID NOs: 153 and 154) | 0% |
| M66 | 66A, 66B (SEQ ID NOs: 155 and 156) | N/A |
| M67 | 67A, 67B (SEQ ID NOs: 157 and 158) | N/A |
| M68 | 68A, 68B (SEQ ID NOs: 159 and 160) | 100% |
| M69 | 69A, 69B (SEQ ID NOs: 161 and 162) | 100% |
| M70 | 70A, 70B (SEQ ID NOs: 163 and 164) | 100% |

*N/A is reported when the desired mutation was not successfully produced of when GC data was lacking.

Example 6

Generation of pFmD8S-1, pFmD8S-001, pFmD8S-2A, pFmD8S-2B, pFmD8S-3A, pFmD8S-3B, pFmD8S-003, pFmD8S-4, pFmD8S-004, pFmD8S-005 and pFmD8S-006 Constructs By Site-Directed Mutagenesis of Eg8S within Construct pFmD8S A series of plasmids were generated by consecutive rounds of continued site-directed mutagenesis to introduce multiple select mutations into EgD8S (SEQ ID NOs:9 and 10). pFmD8S (Example 4), comprising the synthetic codon-optimized EgD8S, was used as the starting template in Tables 13, 14, 16 and 17, while a mutant created thereof (i.e., pFmD8S-M45, comprising 117G to A and 118Y to F mutations with respect to SEQ ID NO:10) was used as the starting template in Table 15. The resulting plasmids comprising mutant EgD8S sequences, as well as details concerning the primers used to produce these mutations, are described in Tables 13, 14, 15, 16 and 17.

The column titled "Mutation Site Introduced" refers to the specific amino acid sites selected for mutation, as listed in Table 7 of Example 2. In the column titled "Total Mutations In Resultant Plasmid With Respect to EgD8S (SEQ ID NO:10)", those amino acid mutations that are highlighted in bold-face text correspond to newly introduced mutations that were not present in the template in the indicated round of site-directed mutagenesis. The number shown in parentheses corresponds with the number of total mutations in the resultant plasmid with respect to EgD8S (SEQ ID NO:10).

TABLE 13

Generation Of pFmD8S-1 And pFmD8S-001 Constructs

| Round - Mutation Site Introduced | Template | Primers | Resultant Plasmid | Total Mutations In Resultant Plasmid With Respect to EgD8S (SEQ ID NO: 10) |
|---|---|---|---|---|
| 1 - M3 | pFmD8S | 3A, 3B (SEQ ID NOs: 28 and 29) | pFmD8S-M3 | **16T to K, 17T to V** (2) |
| 2 - M1 | pFmD8S-M3 | 1A, 1B (SEQ ID NOs: 24 and 25) | pFmD8S-M3, 1 | 16 T to K, 17T to V, **4S to A, 5K to S** (4) |
| 3 - M2 | pFmD8S-M3, 1 | 2A, 2B (SEQ ID NOs: 26 and 27) | pFmD8S-M3, 1, 2 | 16 T to K, 17T to V, 4S to A, 5K to S, **12T to V** (5) |
| 4 - M8 | pFmD8S-M3, 1, 2 | 8A, 8B (SEQ ID NOs: 38 and 39) | pFmD8S-1 | 16 T to K, 17T to V, 4S to A, 5K to S, 12T to V, **66P to Q, 67S to A** (7) |

TABLE 13-continued

| Generation Of pFmD8S-1 And pFmD8S-001 Constructs | | | | |
|---|---|---|---|---|
| Round - Mutation Site Introduced | Template | Primers | Resultant Plasmid | Total Mutations In Resultant Plasmid With Respect to EgD8S (SEQ ID NO: 10) |
| 5 - M38 | pFmD8S-1 | 38A, 38B (SEQ ID NOs: 98 and 99) | pFmD8S-001 | 16 T to K, 17T to V, 4S to A, 5K to S, 12T to V, 65P to Q, 66S to A, **54A to G, 55F to Y** (9) |

TABLE 14

| Generation Of pFmD8S-2A And pFmD8S-003 Constructs | | | | |
|---|---|---|---|---|
| Round - Mutation Site Introduced | Template | Primers | Resultant Plasmid | Total Mutations In Resultant Plasmid With Respect to EgD8S (SEQ ID NO: 10) |
| 1 - M45 | pFmD8S | 45A, 45B (SEQ ID NOs: 112 and 113) | pFmD8S-M45 | **117G to A, 118Y to F** (2) |
| 2 - M21 | pFmD8S-M45 | 21A, 21B (SEQ ID NOs: 64 and 65) | pFmD8S-M45, 21 | 117G to A, 118Y to F, **125Q to H, 126M to L** (4) |
| 3 - M16 | pFmD8S-M45, 21 | 16A, 16B (SEQ ID NOs: 54 and 55) | pFmD8S-M45, 21, 16 | 117G to A, 118Y to F, 125Q to H, 126M to L, **108S to L** (5) |
| 4 - M18 | pFmD8S-M45, 21, 16 | 18A,18B (SEQ ID NOs: 58 and 59) | pFmD8S-2A | 117G to A, 118Y to F, 125Q to H, 126M to L, 108S to L, **120L to M, 121M to L** (7) |
| 5 - M68, M69 | pFmD8S-2A | 68A, 68B (SEQ ID NOs: 159 and 160) 69A, 69B (SEQ ID NOs: 161 and 162) | pFmD8S-003 | 117G to A, 118Y to F, 125Q to H, 126M to L, 108S to L, 120L to M, 121M to L, **162L to V, 163V to L, 170G to A, 171L to V** (11) |

TABLE 15

| Generation Of pFmD8S-2B And pFmD8S-004 Constructs | | | | |
|---|---|---|---|---|
| Round - Mutation Site Introduced | Template | Primers | Resultant Plasmid | Total Mutations In Resultant Plasmid With Respect to EgD8S (SEQ ID NO: 10) |
| 1 - M46 | pFmD8S-M45 | 46A, 46B (SEQ ID NOs: 114 and 115) | pFmD8S-M45, 46 | 117G to A, 118Y to F, **132V to L, 133 L to V** (4) |
| 2 - M16, M21 | pFmD8S-M45, 46 | 16A, 16B (SEQ ID NOs: 54 and 55) 21A, 21B (SEQ ID NOs: 64 and 65) | pFmD8S-M45, 46, 16, 21 | 117G to A, 118Y to F, 132V to L, 133 L to V, **108S to L, 125Q to H, 126M to L** (7) |
| 3 - M18 | pFmD8S-M45, 46, 16, 21 | 18A, 18B (SEQ ID NOs: 58 and 59) | pFmD8S-2B | 117G to A, 118Y to F, 132V to L, 133 L to V, 108S to L, 125Q to H, 126M to L, **120L to M, 121M to L** (9) |

TABLE 15-continued

Generation Of pFmD8S-2B And pFmD8S-004 Constructs

| Round - Mutation Site Introduced | Template | Primers | Resultant Plasmid | Total Mutations In Resultant Plasmid With Respect to EgD8S (SEQ ID NO: 10) |
|---|---|---|---|---|
| 4 - M68, M69 | pFmD8S-2B | 68A, 68B (SEQ ID NOs: 159 and 160) 69A, 69B (SEQ ID NOs: 161 and 162) | pFmD8S-004 | 117G to A, 118Y to F, 132V to L, 133 L to V, 108S to L, 125Q to H, 126M to L, 120L to M, 121M to L, **162L to V, 163V to L, 170G to A, 171L to V** (13) |

TABLE 16

Generation Of pFmD8S-3A, pFmD8S-3B And pFmD8S-005 Constructs

| Round - Mutation Site Introduced | Template | Primers | Resultant Plasmid | Total Mutations In Resultant Plasmid With Respect to EgD8S (SEQ ID NO: 10) |
|---|---|---|---|---|
| 1 - M49 | pFmD8S | 49A, 49B (SEQ ID NOs: 120 and 121) | pFmD8S-M49 | **297F to V, 298V to L** (2) |
| 2 - M26 | pFmD8S-M49 | 26A, 26B (SEQ ID NOs: 74 and 75) | pFmD8S-M49, 26 | 297F to V, 298V to L, **293L to M** (3) |
| 3A - M61 | pFmD8S-M49, 26 | 61A, 61B (SEQ ID NOs: 145 and 146) | pFmD8S-3A | 297F to V, 298V to L, 293L to M, **239F to I, 240I to F** (5) |
| 3B - M62, M63 | pFmD8S-M49, 26 | 62A, 62B (SEQ ID NOs: 147 and 148) 63A, 63B (SEQ ID NOs: 149 and 150) | pFmD8S-3B | 297F to V, 298V to L, 293L to M, **271L to M, 272A to S, 279T to L, 280L to T** (7) |
| 4 - M63 | pFmD8S-3A | 63A, 63B (SEQ ID NOs: 149 and 150) | pFmD8S-005 | 297F to V, 298V to L, 293L to M, 239F to I, 240I to F, **279T to L, 280L to T** (7) |

TABLE 17

Generation Of pFmD8S-4 And pFmD8S-006 Constructs

| Round - Mutation Site Introduced | Template | Primers | Resultant Plasmid | Total Mutations In Resultant Plasmid With Respect to EgD8S (SEQ ID NO: 10) |
|---|---|---|---|---|
| 1 - M51B | pFmD8S | 51A, 51B (SEQ ID NOs: 126 and 125) | pFmD8S-M51 | **346I to V, 347I to L, 348T to S** (3) |
| 2 - M15 | pFmD8S-M51 | 15A, 15B (SEQ ID NOs: 52 and 53) | pFmD8S-M51, 15 | 346I to V, 347I to L, 348T to S, **422L to Q** (4) |
| 3 - M14 | pFmD8S-M51, 15 | 14A, 14B (SEQ ID NOs: 50 and 51) | pFmD8S-M51, 15, 14 | 346I to V, 347I to L, 348T to S, 422L to Q, **416Q to V, 417P to Y** (6) |

TABLE 17-continued

Generation Of pFmD8S-4 And pFmD8S-006 Constructs

| Round - Mutation Site Introduced | Template | Primers | Resultant Plasmid | Total Mutations In Resultant Plasmid With Respect to EgD8S (SEQ ID NO: 10) |
|---|---|---|---|---|
| 4 - M12 | pFmD8S-M51, 15, 14 | 12A, 12B (SEQ ID NOs: 46 and 47) | pFmD8S-4 | 346I to V, 347I to L, 348T to S, 422L to Q, 416Q to V, 417P to Y, **407A to S, 408V to Q** (8) |
| 5 - M70 | pFmD8S-4 | 70, 70B (SEQ ID NOs: 163 and 164) | pFmD8S-006 | 346I to V, 347I to L, 348T to S, 422L to Q, 416Q to V, 417P to Y, 407A to S, 408V to Q, **418A to G, 419G to A** (10) |

After each round of mutagenesis, the mutations in each resulting plasmid was confirmed by DNA sequencing. Additionally, the delta-8 desaturase activity of each mutant EgD8S within each mutant plasmid was compared with the delta-8 desaturase activity of the synthetic codon-optimized EgD8S within pFmD8S by transforming the plasmids into strain Y4001 (Example 3) and assaying activity based on the methodology described in Example 5. Based on these functional analyses, it was demonstrated that the mutations in all 24 of the mutant EgD8S genes within the resultant plasmids generated in Tables 11, 12, 13, 14 and 15 did not affect delta-8 desaturase activity (i.e., pFmD8S-M3; pFmD8S-M3,1; pFmD8S-M3,1,2; pFmD8S-1; pFmD8S-001; pFmD8S-M45; pFmD8S-M45,21; pFmD8S-M45,21,16; pFmD8S-2A; pFmD8S-003; pFmD8S-M45,46; pFmD8S-M45,46,16, 21; pFmD8S-2B; pFmD8S-004; pFmD8S-M49; pFmD8S-M49,26; pFmD8S-3A; pFmD8S-3B; pFmD8S-005; pFmD8S-M51; pFmD8S-M51,15; pFmD8S-M51,15,14; pFmD8S-4; and pFmD8S-006).

Example 7

Generation of Complex Construct pFmD8S-5B By Digestion and Ligation of Multiple Parent Plasmids Plasmid pFmD8S-5B contained 16 mutant amino acids within the first half of EgD8S. This plasmid was generated by 3-way ligation, wherein the 318 bp Nco I/Bgl II fragment from pFmD8S-1 (containing 7 amino acid mutations, corresponding to M1, M2, M3 and M8) and the 954 bp Bgl II/Not I fragment from pFmD8S-2B (containing 9 amino acid mutations, corresponding to M16, M18, M21, M45 and M46) were used to replace the Nco I/Not I fragment of pFmD8S (Example 4; FIG. 6D). DNA sequence confirmed that pFmD8S-5B contained the expected 16 amino acid mutations within EgD8S.

The synthesis of plasmid pFmD8S-5B is schematically diagrammed in FIG. 7 (and a similar format is used in FIG. 8 and FIG. 9). For clarity, the pFmD8S vector backbone in which each mutant EgD8S is contained is not included within the figure; instead, only the 1272 bases corresponding to the mutant EgD8S are shown (wherein the coding sequence for the delta-8 desaturase corresponds to nucleotide bases 2-1270). Thus, the mutant EgD8S fragment labeled as “Mutant EgD8S-1” in FIG. 7 corresponds to the mutant EgD8S found within plasmid pFmD8S-1 and the mutant EgD8S fragment labeled as “Mutant EgD8S-2B” in FIG. 7 corresponds to the mutant EgD8S found within plasmid pFmD8S-2B.

Similarly, the Nco I and Not I restriction enzyme sites that flank each mutant EgD8S gene are not included in the figure. The Nco I nucleotide recognition sequence (“CCATGG”) corresponds to the −2 to +4 region of the mutant EgD8S, wherein the ‘A’ position of the ‘ATG’ translation initiation codon is designated as +1; the first nucleotide recognized as part of the Not I nucleotide recognition sequence is nucleotide+1271 of mutant EgD8S, wherein the ‘TAA’ STOP codon of mutant EgD8S is located at +1269 to +1270.

Mutation sites are labeled on each mutant EgD8S. Those mutation sites shown with an asterisk correspond to a single amino acid mutation (i.e., M2* corresponds to a mutation of 12T to V), while those lacking an asterisk correspond to two individual amino acid mutations (i.e., M1 corresponds to mutations 4S to A and 5K to S); those mutation sites shown with 2 asterisks correspond to a triple amino acid mutation (i.e., M51** corresponds to mutations 346I to V, 347I to L and 348T to S).

The delta-8 desaturase activity of mutant EgD8S-5B within pFmD8S-5B was compared with the delta-8 desaturase activity of the synthetic codon-optimized EgD8S within pFmD8S by transforming each plasmid into strain Y4001 (Example 3) and assaying the activity based on the methodology described in Example 5. Based on this analysis, it was determined that the 16 amino acid mutations within mutant EgD8S-5B (i.e., 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L and 133L to V, corresponding to mutation sites M1, M2, M3, M8, M16, M18, M21, M45 and M46) in pFmD8S-5B did not affect the delta-8 desaturase activity.

Example 8

Generation of pFmD8S-12, pFmD8S-13, pFmD8S-23 and pFmD8S-28 Constructs by Additional Site-Directed Mutagenesis of Mutant EgD8S-5B within Construct pFmD8S-5B An additional series of plasmids were generated by consecutive rounds of continued site-directed mutagenesis to introduce multiple select mutations into mutant EgD8S-5B, using pFmD8S-5B (Example 7) as the starting template. The resulting plasmids comprising mutant EgD8S sequences, as well as details concerning the primers used to produce these mutations, are described below in Table 18. Format and column titles of Table 18 are the same as defined above in Example 6.

TABLE 18

| Generation Of pFmD8S-12, pFmD8S-13, pFmD8S-23 And pFmD8S-28 Constructs | | | | |
|---|---|---|---|---|
| Round - Mutation Site Introduced | Template | Primers | Resultant Plasmid | Total Mutations In Resultant Plasmid With Respect to EgD8S (SEQ ID NO: 10) |
| 1A - M12, M15, M26 | pFmD8S-5B | 12A, 12B (SEQ ID NOs: 46 and 47) 15A, 15B (SEQ ID NOs: 52 and 53) 26A, 26B (SEQ ID NOs: 74 and 75) | pFmD8S-12 | 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L, 133 L to V, **407A to S, 408V to Q, 422L to Q, 293L to M** (20) |
| 1B - M12, M15, M26, M51B | pFmD8S-5B | 12A, 12B (SEQ ID NOs: 46 and 47) 15A, 15B (SEQ ID NOs: 52 and 53) 26A, 26B (SEQ ID NOs: 74 and 75) 51A, 51B (SEQ ID NOs: 126 and 125) | pFmD8S-13 | 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L, 133 L to V, **407A to S, 408V to Q, 422L to Q, 293L to M, 346I to V, 347I to L, 348T to S** (23) |
| 2A - M68, M70 | pFmD8S-12 | 68A, 68B (SEQ ID NOs: 159 and 160) 70A, 70B (SEQ ID NOs: 163 and 164) | pFmD8S-23 | 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L, 133 L to V, 407A to S, 408V to Q, 422L to Q, 293L to M, **162L to V, 163V to L, 418A to G, 419G to A** (24) |
| 2B - M38, M63, M68, M69, M70 | pFmD8S-13 | 38A, 38B (SEQ ID NOs: 98 and 99) 63A, 63B (SEQ ID NOs: 149 and 150) 68A, 68B (SEQ ID NOs: 159 and 160) 69A, 69B (SEQ ID NOs: 161 and 162) 70A, 70B (SEQ ID NOs: 163 and 164) | pFmD8S-28 | 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L, 133 L to V, 407A to S, 408V to Q, 422L to Q, 293L to M, 346I to V, 347I to L, 348T to S, **54A to G, 55F to Y, 279T to L, 280L to T, 162L to V, 163V to L, 170G to A, 171L to V, 418A to G, 419G to A** (33) |

After each round of mutagenesis, the mutations in the resulting plasmid were confirmed by DNA sequencing. Additionally, the delta-8 desaturase activity of each mutant EgD8S within each mutated plasmid was compared with the delta-8 desaturase activity of the synthetic codon-optimized EgD8S within pFmD8S by transforming the plasmids into strain Y4001 (Example 3) and assaying activity based on the methodology described in Example 5. Based on these functional analyses, it was demonstrated that the 20 mutations in mutant EgD8S-12 within pFmD8S-12, the 23 mutations in mutant EgD8S-13 within pFmD8S-13, the 24 mutations in mutant EgD8S-23 within pFmD8S-23 and the 33 mutations in mutant EgD8S-28 within pFmD8S-28 did not affect the delta-8 desaturase activity.

Example 9

Figure 8B:
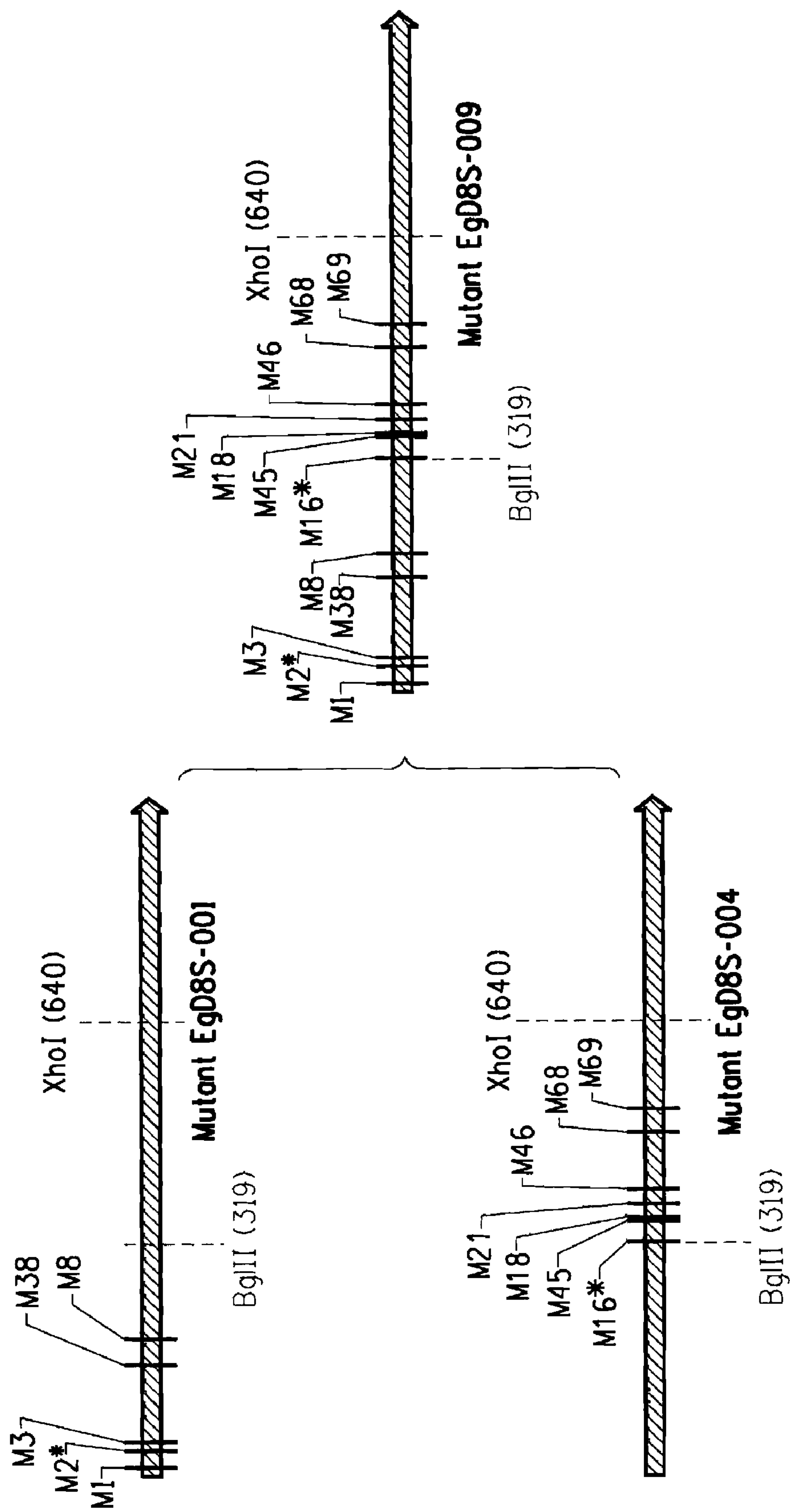

Generation of Complex Constructs pFmD8S-008, pFmD8S-009, pFmD8S-013 and pFmD8S-015 by Digestion and Ligation of Multiple Parent Plasmids Plasmids pFmD8S-008 and pFmD8S-009 contained 20 and 22 mutant amino acids within the first half of EgD8S, respectively. These plasmids were generated by 3-way ligation, as shown in FIGS. 8A and 8B, respectively (figure format is identical to that described for FIG. 7 in Example 7). Specifically, the 318 bp Nco I/Bgl II fragment from pFmD8S-001 (containing 9 amino acid mutations in mutant EgD8S-001 corresponding to M1, M2, M3, M8 and M38) and the 954 bp Bgl II/Not I fragment from either pFmD8S-003 (containing 11 amino acid mutations in mutant EgD8S-003 corresponding to M16, M18, M21, M45, M68 and M69) or pFmD8S-004 (containing 13 amino acid mutations in mutant EgD8S-004, corresponding to M16, M18, M21, M45, M46, M68 and M69) were used to replace the Nco I/Not I fragment of pFmD8S (Example 4; FIG. 6D) to generate mutant EgD8S-008 within pFmD8S-008 and mutant EgD8S-009 within pFmD8S-009, respectively. DNA sequence confirmed that mutant EgD8S-008 contained 20 amino acid mutations and mutant EgD8S-009 contained 22 amino acid mutations, as expected.

Figure 9B:
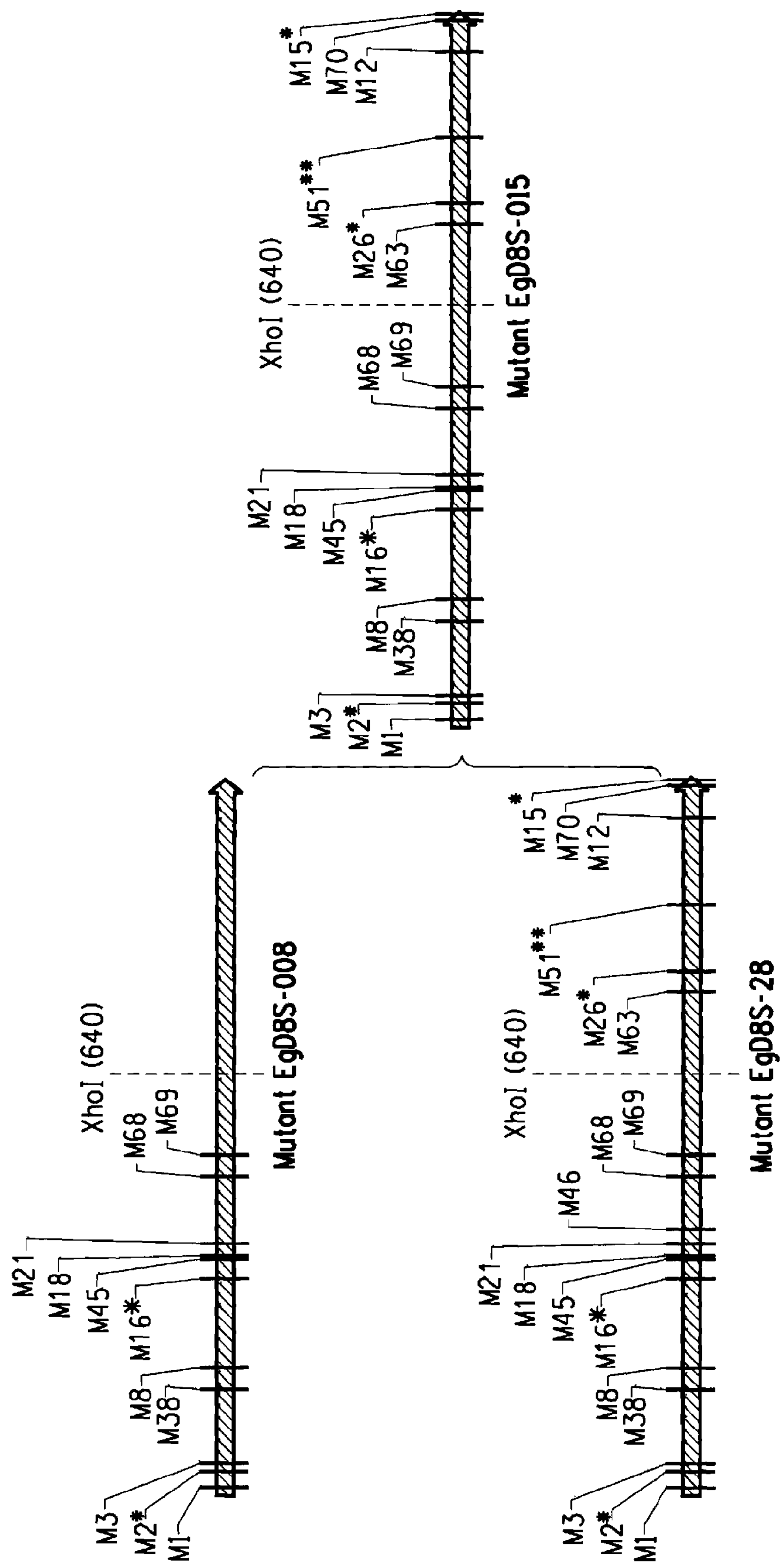

Plasmids pFmD8S-013 and pFmD8S-015, containing 28 and 31 amino acid mutations within mutant EgD8S-013 and mutant EgD8S-015, respectively, were created using a similar 3-way ligation strategy as shown in FIG. 9A and FIG. 9B (figure format is identical to that described for FIG. 7 in Example 7). The 639 bp Nco I/Xho I fragment from either pFmD8S-009 (containing 22 amino acid mutations within mutant EgD8S-009) or pFmD8S-008 (containing 20 amino acid mutations within mutant EgD8S-008) and the 633 bp Xho I/Not I fragment from either pFmD8S-23 (Example 8, containing 6 amino acid mutations within mutant EgD8S-23, corresponding to M12, M15, M26 and M70) or pFmD8S-28 (Example 8, containing 11 amino acid mutations within mutant EgD8S-28, corresponding to M12, M15, M26, M51B, M63 and M70) were used to replace the Nco I/Not I fragment of pFmD8S (Example 4; FIG. 6D) to generate pFmD8S-013 and pFmD8S-015, respectively. DNA sequence confirmed that mutant EgD8S-013 and mutant EgD8S-015 contained 28 amino acid mutations and 31 amino acid mutations, respectively.

The delta-8 desaturase activity of mutant EgD8S-008 within pFmD8S-008, mutant EgD8S-009 within pFmD8S-009, mutant EgD8S-013 within pFmD8S-013 and mutant EgD8S-015 within pFmD8S-015 were compared with the delta-8 desaturase activity of the synthetic codon-optimized EgD8S within pFmD8S by transforming these plasmids into strain Y4001 (Example 3) and assaying activity based on the methodology described in Example 5. Based on these functional analyses, it was demonstrated the delta-8 desaturase activity was not affected by the 20 mutations in mutant EgD8S-008 within pFmD8S-008 (i.e., 4S to A, 5K to S, 12T to V, 16T to K, 17T to V, 66P to Q, 67S to A, 108S to L, 120L to M, 121M to L, 125Q to H, 126M to L, 54A to G, 55F to Y, 117G to A, 118Y to F, 162L to V, 163V to L, 170G to A and 171L to V, corresponding to mutation sites M1, M2, M3, M8, M16, M18, M21, M38, M45, M68 and M69), the 22 mutations in mutant EgD8S-009 within pFmD8S-009 (i.e., 4S to A, 5K to S, 12T to V, 16T to K, 17T to V, 66P to Q, 67S to A, 108S to L, 120L to M, 121M to L, 125Q to H, 126M to L, 54A to G, 55F to Y, 117G to A, 118Y to F, 132V to L, 133L to V, 162L to V, 163V to L, 170G to A and 171L to V, corresponding to mutation sites M1, M2, M3, M8, M16, M18, M21, M38, M45, M46, M68 and M69), the 28 mutations in mutant EgD8S-013 within pFmD8S-013 (i.e., 4S to A, 5K to S, 12T to V, 16T to K, 17T to V, 66P to Q, 67S to A, 407A to S, 408V to Q, 422L to Q, 108S to L, 120L to M, 121M to L, 125Q to H, 126M to L, 293L to M, 54A to G, 55F to Y, 117G to A, 118Y to F, 132V to L, 133L to V, 162L to V, 163V to L, 170G to A, 171L to V, 418A to G and 419G to A, corresponding to mutation sites M1, M2, M3, M8, M12, M15, M16, M18, M21, M26, M38, M45, M46, M68, M69, M70) or the 31 mutations in mutant EgD8S-015 within pFmD8S-015 (i.e., 4S to A, 5K to S, 12T to V, 16T to K, 17T to V, 66P to Q, 67S to A, 407A to S, 408V to Q, 422L to Q, 108S to L, 120L to M, 121M to L, 125Q to H, 126M to L, 293L to M, 54A to G, 55F to Y, 117G to A, 118Y to F, 346I to V, 347I to L, 348T to S, 279T to L, 280L to T, 162L to V, 163V to L, 170G to A, 171L to V, 418A to G and 419G to A, corresponding to mutation sites M1, M2, M3, M8, M12, M15, M16, M18, M21, M26, M38, M45, M51B, M63, M68, M69, M70).

FIG. 10 shows an alignment of EgD8S (SEQ ID NO:10), Mutant EgD8S-23 (SEQ ID NO:4; Example 8), Mutant EgD8S-013 (SEQ ID NO:6; Example 9) and Mutant EgD8S-015 (SEQ ID NO:8; Example 9). The method of alignment used corresponds to the "Clustal W method of alignment".

Example 10

Comparison of Delta-8 Desaturase Activities Among the Synthetic Codon-Optimized EgD8S and its Mutants Upon Integration into the *Yarrowia lipolytica* Genome This Example describes quantitative analyses of the delta-8 desaturase activities of EgD8S and mutants thereof included within pFmD8S-23, pFmD8S-013 and pFmD8S-015. This comparison required each of the chimeric genes comprising EgD8S (or a mutant thereof) to be inserted into the pKO2UFkF2 vector backbone. Specifically, pKO2UFkF2 comprised a 5' and 3' portion of the *Yarrowia lipolytica* delta-12 desaturase gene that was designed to target integration to this locus (although plasmid integration could also occur via random integration into other sites of the genome). Thus, the activities of the chimeric genes containing the synthetic codon-optimized EgD8S, mutant EgD8S-023, mutant EgD8S-013 and mutant EgD8S-015 in the *Yarrowia* genome (i.e., 1 copy) could be more fairly compared upon integration into the *Yarrowia* genome, as opposed to the delta-8 desaturase activity levels that were obtained upon plasmid expression (i.e., via expression in pFmD8S as 1-3 copies) and reported in previous examples.

The components of pKO2UFkF2 are as described in Table 19 below.

TABLE 19

| Components Of Plasmid pKO2UFkF2 (SEQ ID NO: 165) | |
|---|---|
| RE Sites And Nucleotides Within SEQ ID NO: 165 | Description Of Fragment And Chimeric Gene Components |
| SwaI/BsiWI 7638-1722 | FBAINm::F.D12::Pex20, comprising: FBAINm: *Yarrowia lipolytica* FBAINm promoter (WO 2005/049805) F.D12: *Fusarium moniliforme* delta-12 desaturase gene (WO 2005/047485) Pex20: Pex20 terminator sequence of *Yarrowia* Pex20 gene (GenBank Accession No. AF054613) |
| AscI/BsiWI 2459-1722 | 5' portion of *Yarrowia lipolytica* delta-12 desaturase gene (WO 2004/104167) |
| EcoRI/SphI 5723-5167 | 3' portion of *Yarrowia lipolytica* delta-12 desaturase gene (WO 2004/104167) |
| EcoRI/PacI 5723-7240 | *Yarrowia* Ura3 gene (GenBank Accession No. AJ306421) |

Figure 11A:
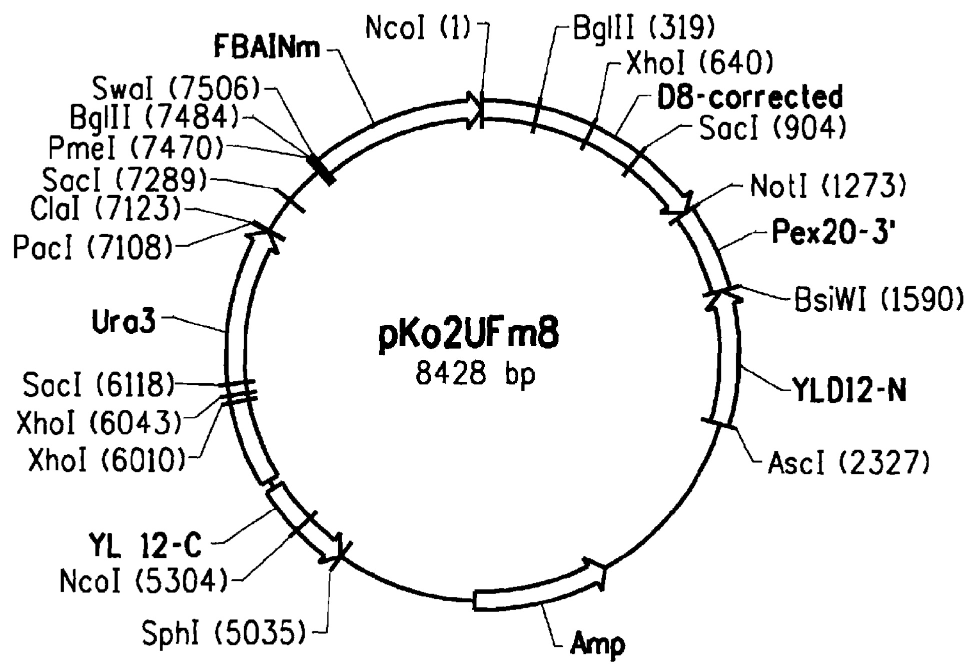

First, the Swa I/Not I fragment from pFmD8S (comprising the chimeric FBAINm::EgD8S gene, wherein EgD8S is identified as "D8-corrected" in FIG. 6D) was used to replace the Swa I/NotI fragment of pKO2UFkF2 (comprising the chimeric FBAINm::F.D12 gene) to generate construct pKO2UFm8 (FIG. 11A). The same methodology was used to replace the SwaI/NotI fragment of pKO2UFkF2 with the Swa I/Not I fragments of pFmD8S-23, pFmD8S-013 and pFmD8S-015, respectively, thereby creating constructs pKO2UFm8-23, pKO2UFm8-013 and pKO2UFm8-015, respectively. As such, the synthetic codon-optimized EgD8S, mutant EgD8S-023, mutant EgD8S-013 and mutant EgD8S-015 were each under the control of the FBAINm promoter and the Pex20 terminator.

Plasmids pKO2UFm8, pKO2UFm8-23, pKO2UFm8-013 and pKO2UFm8-015 were digested with AscI/SphI, and then used for transformation of strain Y4001 individually according to the General Methods. Following transformation, cells were plated onto MM plates and maintained at 30° C. for 2 to 3 days.

A total of 6 transformants from each transformation were picked and re-streaked onto fresh MM plates. Once grown, these strains were individually inoculated into liquid MM at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC. Delta-8 desaturase activity of each delta-8 desaturase are shown below in Table 20; conversion efficiency was calculated as described in Example 5.

TABLE 20

| Delta-8 Desaturase Activity In EgD8S And Its Mutants | | |
|---|---|---|
| Plasmid | Mutations With Respect To EgD8S (SEQ ID NO: 10) | Conversion Efficiency |
| pKO2UFm8 (comprising wildtype EgD8S [SEQ ID NO: 10]) | none | 37.9% (average) |
| pKO2UFm8S-23 (comprising mutant EgD8S-23 [SEQ ID NO: 4]) | 4S to A, 5K to S, 12T to V, 16T to K, 17T to V, 66P to Q, 67S to A, 108S to L, 120L to M, 121M to L, 125Q to H, 126M to L, 117G to A, 118Y to F, 132V to L, 133L to V, 407A to S, 408V to Q, 422L to Q, 293L to M, 162L to V, 163V to L, 418A to G, 419G to A (24) | 35%, 35%, 36.1%, 36.2%, 39.8%, 40% |
| pKO2UFm8S-013 (comprising mutant EgD8S-013 [SEQ ID NO: 6]) | 4S to A, 5K to S, 12T to V, 16T to K, 17T to V, 66P to Q, 67S to A, 407A to S, 408V to Q, 422L to Q, 108S to L, 120L to M, 121M to L, 125Q to H, 126M to L, 293L to M, 54A to G, 55F to Y, 117G to A, 118Y to F, 132V to L, 133L to V, 162L to V, 163V to L, 170G to A, 171L to V, 418A to G and 419G to A (28) | 17.8% 18.4%, 18.6%, 24.4%, 34.4% 39.1% 70.8% |
| pKO2UFm8S-015 (comprising mutant EgD8S-015 [SEQ ID NO: 8]) | 4S to A, 5K to S, 12T to V, 16T to K, 17T to V, 66P to Q, 67S to A, 407A to S, 408V to Q, 422L to Q, 108S to L, 120L to M, 121M to L, 125Q to H, 126M to L, 293L to M, 54A to G, 55F to Y, 117G to A, 118Y to F, 346I to V, 347I to L, 348T to S, 279T to L, 280L to T, 162L to V, 163V to L, 170G to A, 171L to V, 418A to G and 419G to A (31) | 17.3%, 19.8%, 20%, 20.1% 29.2%, 33.5% 38.5% |

The different conversion efficiencies observed for each specific mutant EgD8S may be attributed to a "position effect" based on the respective locations of each gene's integration within the *Yarrowia* genome. In any case, the results demonstrate that several of the transformants comprising mutant EgD8S-23 (SEQ ID NO:4), mutant EgD8S-013 (SEQ ID NO:6) and mutant EgD8S-015 (SEQ ID NO:8) possessed delta-8 desaturase activity that was at least functionally equivalent (or increased) with respect to that of the synthetic codon-optimized EgD8S (SEQ ID NO:10).

Example 11

Generation of *Yarrowia lipolytica* Strains Y4031, Y4032 and Y4033 to Produce about 10-13.6% DGLA of Total Lipids The present Example describes the construction of strains Y4031, Y4032 and Y4033, derived from *Yarrowia lipolytica* Y4001U (Example 3), capable of producing 10-13.6% DGLA (C20:3) relative to the total lipids. These strains were engineered to express the delta-9 elongase/delta-8 desaturase pathway, via expression of a mutant delta-8 desaturase of the present invention and a delta-9 elongase.

Figure 11B:
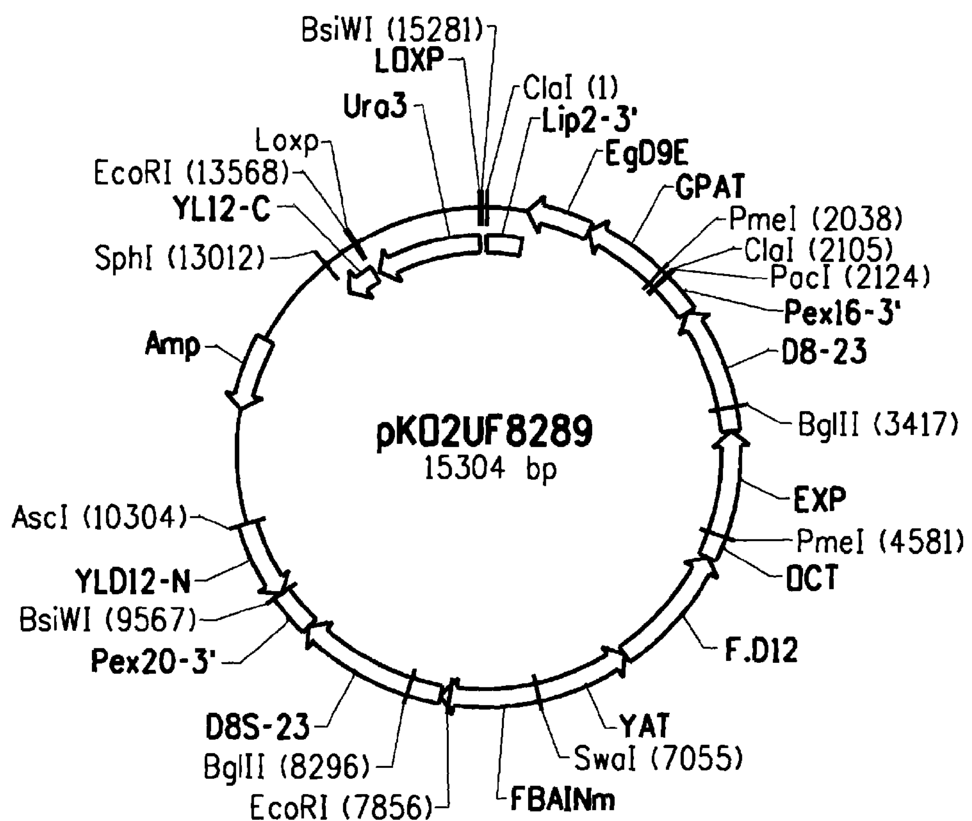

More specifically, construct pKO2UF8289 (FIG. 11B; SEQ ID NO:181) was created to integrate a cluster of four chimeric genes (comprising a delta-12 desaturase, two copies of the mutant EgD8-23 and one delta-9 elongase) into the delta-12 gene locus of *Yarrowia* genome in strain Y4001U. Construct pKO2UF8289 contained the following components:

TABLE 21

| RE Sites And Nucleotides Within SEQ ID NO: 181 | Description Of Fragment And Chimeric Gene Components |
|---|---|
| Description Of Plasmid pKO2UF8289 (SEQ ID NO: 181) | |
| AscI/BsiW I (10304-9567) | 5' portion of *Yarrowia lipolytica* delta-12 desaturase gene (WO 2004/104167) |
| EcoRI/Sph I (13568-13012) | 3' portion of *Yarrowia lipolytica* delta-12 desaturase gene (WO 2004/104167) |
| Cla I/EcoR I (1-13568) | LoxP::Ura3::LoxP, comprising: LoxP sequence (SEQ ID NO: 18) *Yarrowia* Ura3 gene (GenBank Accession No. AJ306421) LoxP sequence (SEQ ID NO: 18) |
| PmeI/ClaI (2038-1) | GPAT::EgD9E::Lip2, comprising: GPAT: *Yarrowia lipolytica* GPAT promoter (WO 2006/031937) EgD9E: codon-optimized delta-9 elongase gene (SEQ ID NO: 177), derived from *Euglena gracilis* (SEQ ID NOs: 175 and 176; U.S. Patent Application No. 60/739989; see also Example 16 herein) Lip2: Lip2 terminator sequence from *Yarrowia* Lip1 gene (GenBank Accession No. AJ012632) |
| PmeI/PacI (4581-2124) | Exp::D8-23::Pex16, comprising: Exp: *Yarrowia lipolytica* export protein (EXP1) promoter (WO 2006/052870 and U.S. Patent Application No. 11/265761) D8-23: mutant EgD8S-23 (Example 8; SEQ ID NO: 4) Pex16: Pex16 terminator sequence of *Yarrowia* Pex 16 gene (GenBank Accession No. U75433) |
| Swa I/Pme I (7055-4581) | YAT::F. D12::Oct, comprising: YAT: *Yarrowia lipolytica* YAT1 promoter (Patent Publication US 2006/0094102-A1) F.D12: *Fusarium moniliforme* delta-12 desaturase gene (WO 2005/047485) OCT: OCT terminator sequence of *Yarrowia* OCT gene (GenBank Accession No. X69988) |
| Swa I/BsiW I (7055-9567) | FBAINm::D8S-23::Pex20, comprising: FBAINm: *Yarrowia lipolytica* FBAINm promoter (WO 2005/049805) D8S-23: mutant EgD8S-23 (Example 8; SEQ ID NO: 4) Pex20: Pex20 terminator sequence of *Yarrowia* Pex20 gene (GenBank Accession No. AF054613) |

Plasmid pKO2UF8289 was digested with Asc I/Sph 1, and then used for transformation of *Y. lipolytica* strain Y4001U (Example 3) according to the General Methods. The transformant cells were plated onto MMLeu media plates and maintained at 30° C. for 2 to 3 days. The colonies were picked and streaked onto MMLeu selection plates at 30° C. for 2 days. These cells were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKO2UF8289, but not in the *Yarrowia* Y4001U control strain. Most of the selected 12 strains produced about 4 to 8% DGLA of total lipids. There were 3 strains (i.e., strains #7, #8 and #12) that produced about 11.3%, 10% and 13.6% DGLA of total lipids; they were designated as strains Y4031, Y4031 and Y4033, respectively.

Example 12

Cloning the *Euglena gracilis* Delta-8 Desaturase Mutant (EgD8S-23) into a Soybean Expression Vector and Co-Expression with the *Isochrysis galbana* Delta-9 Elongase The present Example describes the construction of soybean expression vector pKR1060, suitable for use in the production of DGLA (C20:3). This vector was engineered to enable expression of the delta-9 elongase/delta-8 desaturase pathway, via expression of a mutant delta-8 desaturase of the present invention and a delta-9 elongase.

Through a number of cloning steps, a NotI site was added to the 5' end of the EgD8S-23 gene from pKO2UFm8S-23 (Table 20, Example 10) to produce the sequence set forth in SEQ ID NO:182.

Vector pKR457 (SEQ ID NO:183), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette).

The NotI fragment containing EgD8S-23 described above, was cloned into the NotI site of pKR457 to produce pKR1058 (SEQ ID NO:184).

Plasmid pKR1058 was digested with PstI and the fragment containing EgD8S-23 was cloned into the SbfI site of pKR607 (SEQ ID NO:185), previously described in PCT Publication No. WO 2006/012325 (the contents of which are hereby incorporated by reference) to produce pKR1060 (SEQ ID NO:186). In this way, EgD8S-23 is co-expressed with the *Isochrysis galbana* delta-9 elongase behind strong, seed-specific promoters. A schematic depiction of pKR1060 is shown in FIG. 12.

Example 13

Cloning the *Euglena qracilis* Delta-8 Desaturase Mutant (EgD8S-23) into a Soybean Expression Vector and Co-Expression with the *Euglena gracilis* Delta-9 Elongase The present Example describes the construction of soybean expression vector pKR1059, suitable for use in the production of DGLA (C20:3). This vector was engineered to enable expression of the delta-9 elongase/delta-8 desaturase pathway, via expression of a mutant delta-8 desaturase of the present invention and a delta-9 elongase.

The *Euglena gracilis* delta-9 elongase (SEQ ID NO:175; U.S. Patent Application No. 60/739,989; see also Example 16 herein) was amplified with oligonucleotide primers oEugEL1-1 (SEQ ID NO:187) and oEugEL1-2 (SEQ ID NO:188) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:189).

A starting plasmid pKR72 (ATCC Accession No. PTA-6019; SEQ ID NO:190, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene,* 25:179-188 (1983)), flanked by the T7 promoter and transcription terminator (T7prom/hpt/T7term cassette), and a bacterial origin of replication (ori) for selection and replication in bacteria (e.g., *E. coli*). In addition, pKR72 also contains the hygromycin B phosphotransferase gene, flanked by the 35S promoter (Odell et al., *Nature,* 313:810-812 (1985))

and NOS 3' transcription terminator (Depicker et al., *J. Mol. Appl. Genet.,* 1:561-570 (1982)) (35S/hpt/NOS3' cassette) for selection in plants such as soybean. pKR72 also contains a NotI restriction site, flanked by the promoter for the α' subunit of β-conglycinin (Beachy et al., *EMBO J.,* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site.

The gene for the *Euglena gracilis* delta-9 elongase was released from pKR906 by digestion with NotI and cloned into the NotI site of pKR72 to produce pKR1010 (SEQ ID NO:191). In some instances, pKR1010 is referred to as pKR912 but the two vectors are identical.

Plasmid pKR1058 (from Example 12, SEQ ID NO:184) was digested with PstI and the fragment containing EgD8S-23 was cloned into the SbfI site of pKR1010 (SEQ ID NO:191), to produce pKR1059 (SEQ ID NO:192). In this way, EgD8S-23 is co-expressed with the *Euglena gracilis* delta-9 elongase behind strong, seed-specific promoters. A schematic depiction of pKR1059 is shown in FIG. 13.

Example 14

Co-Expressing Other Promoter/Gene/Terminator Cassette Combinations

In addition to the genes, promoters, terminators and gene cassettes described herein, one skilled in the art can appreciate that other promoter/gene/terminator cassette combinations can be synthesized in a way similar to, but not limited to, that described herein for expression in plants (e.g., soybean). For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 22) and a transcription terminator (such as those listed in, but not limited to, Table 23) is used to clone the desired gene. NotI sites can be added to a gene of interest such as those listed in, but not limited to, Table 24 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 22

Seed-Specific Promoters

| Promoter | Organism | Promoter Reference |
|---|---|---|
| β-conglycinin α'-subunit | soybean | Beachy et al., EMBO J. 4: 3047-3053 (1985) |
| kunitz trypsin inhibitor | soybean | Jofuku et al., Plant Cell 1: 1079-1093 (1989) |
| annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet. 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet. 225: 148-157 (1991) |

TABLE 23

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 24

EPA Biosynthetic Pathway Genes

| Gene | Organism | Reference |
|---|---|---|
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720<br>U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401<br>U.S. Pat. No. 6,677,145 |
| elongase | *Pavlova* sp. | Pereira et al., Biochem. J. 384: 357-366 (2004) |
| delta-4 desaturase | *Schizochytrium aggregatum* | WO 2002/090493 |
| delta-9 elongase | *Isochrysis galbana* | WO 2002/077213 |
| delta-9 elongase | *Euglena gracilis* | U.S. Provisional Application No. 60/739,989 |
| delta-8 desaturase | *Euglena gracilis* | WO 2000/34439<br>U.S. Pat. No. 6,825,017<br>WO 2004/057001<br>WO 2006/012325 |
| delta-8 desaturase | *Acanthamoeba castellanii* | Sayanova et al., FEBS Lett. 580: 1946-1952 (2006) |
| delta-8 desaturase | *Pavlova salina* | WO 2005/103253 |
| delta-8 desaturase | *Pavlova lutheri* | U.S. Provisional Application No. 60/795,810 |

Example 15

Transformation of Somatic Soybean Embryo Cultures with Soybean Expression Vectors Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants were picked 45-55 days after planting. Seeds were removed from the pods and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, and then transferred to SB1 for 2-4 weeks. Plates were wrapped with fiber tape and were maintained at 26° C. with cool white fluorescent lights on 16:8 h day/night photoperiod at light intensity of 60-80 µE/m2/s. After incubation on SB1 medium, secondary embryos were cut and placed into SB196 liquid media for 7 days.

Preparation of DNA for Bombardment:

A DNA fragment from soybean expression plasmid pKR1059 containing the *Euglena gracilis* delta-9 elongase and EgD8S-23, the construction of which is described herein, was obtained by gel isolation of digested plasmids. For this, 100 µg of plasmid DNA was used in 0.5 mL of the specific enzyme mix described below. Plasmid was digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 hr. The resulting DNA fragments were separated by gel electrophoresis on 1% SeaPlaque GTG agarose (BioWhitaker Molecular Applications) and the DNA fragments containing gene cassettes were cut from the agarose gel. DNA was purified from the agarose using the GELase digesting enzyme following the manufacturer's protocol.

A 50 µL aliquot of sterile distilled water containing 1 mg of gold particles was added to 5 µL of a 1 ug/µL DNA solution (DNA fragment prepared as described herein), 50 µL 2.5M $CaCl_2$ and 20 µL of 0.1 M spermidine. The mixture was shaken 3 min on level 3 of a vortex shaker and spun for 10 sec in a bench microfuge. The supernatant was removed, followed by a wash with 400 µL 100% ethanol and another brief centrifugation. The 400 ul ethanol was removed and the pellet was resuspended in 85 µL of 100% ethanol. Five µL of DNA suspension was dispensed to each flying disk of the Biolistic PDS1000/HE instrument disk. Each 5 µL aliquot contained approximately 0.058 mg gold per bombardment (e.g., per disk).

Tissue Preparation and Bombardment with DNA:

Approximately 100-150 mg of seven day old embryogenic suspension cultures was placed in an empty, sterile 60×15 mm petri dish and the dish was covered with plastic mesh. The chamber was evacuated to a vacuum of 27-28 inches of mercury, and tissue was bombarded one or two shots per plate with membrane rupture pressure set at 650 PSI. Tissue was placed approximately 2.5 inches from the retaining/stopping screen.

Selection of Transformed Embryos and Embryo Maturation:

Transformed embryos were selected using hygromycin (hygromycin B phosphotransferase (HPT) gene was used as the selectable marker).

Following bombardment, the tissue was placed into fresh SB196 media and cultured as described above. Six to eight days post-bombardment, the SB196 was exchanged with fresh SB196 containing either 30 mg/L hygromycin. The selection media was refreshed weekly. Four to six weeks post-selection, green, transformed tissue was observed growing from untransformed, necrotic embryogenic clusters.

Transformed embryogenic clusters were removed from SB196 media to 35 mL of SB228 (SHaM liquid media; Schmidt et al., Cell Biology and Morphogenesis 24:393 (2005)) in a 250 mL Erlenmeyer flask for 2-3 weeks. Tissue cultured in SB228 was maintained on a rotary shaker at 130 rpm and 26° C. with cool white fluorescent lights on a 16:8 hr day/night photoperiod at a light intensity of 60-85 µE/m2/s. After maturation in flasks on SB228 media, individual embryos were removed from the clusters, dried and screened for alterations in their fatty acid compositions as described supra.

Media Recipes:

SB 196-FN Lite Liquid Proliferation Medium (per Liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (per Liter)

1 package MS salts (Gibco/BRL-Cat. No. 11117-066)
1 mL B5 vitamins 1000X stock
31.5 g glucose
2 mL 2,4-D (20 mg/L final concentration)
pH 5.7
8 g TC agar SB199 Solid Medium (per Liter)

1 package MS salts (Gibco/BRL-Cat. No. 11117-066)
1 mL B5 vitamins 1000X stock
30 g Sucrose
4 ml 2,4-D (40 mg/L final concentration)
pH 7.0
2 gm Gelrite SB 166 Solid Medium (per Liter)

1 package MS salts (Gibco/BRL-Cat. No. 11117-066)
1 mL B5 vitamins 1000X stock
60 g maltose
750 mg $MgCl_2$ hexahydrate
5 g activated charcoal
pH 5.7
2 g gelrite SB 103 Solid Medium (per Liter)

1 package MS salts (Gibco/BRL-Cat. No. 11117-066)
1 mL B5 vitamins 1000X stock
60 g maltose
750 mg MgCl2 hexahydrate
pH 5.7
2 g gelrite SB 71-4 Solid Medium (per Liter)

1 bottle Gamborg's B5 salts w/sucrose (Gibco/BRL-Cat. No. 21153-036)
pH 5.7
5 g TC agar 2,4-D Stock Obtain premade from Phytotech Cat. No. D 295—concentration 1 mg/mL B5 Vitamins Stock (per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

SB 228-Soybean Histodifferentiation & Maturation (SHaM) (per Liter)

| | |
|---|---|
| DDI $H_2O$ | 600 mL |
| FN-Lite Macro Salts for SHaM 10X | 100 mL |

-continued

| | |
|---|---|
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≦30° C.): | |
| *Glutamine (final concentration 30 mM) 4% | 110 mL |

*Note: Final volume will be 1010 mL after glutamine addition. Since glutamine degrades relatively rapidly, it may be preferable to add immediately prior to using media. Expiration 2 weeks after glutamine is added; base media can be kept longer w/o glutamine.

FN-Lite Macro for SHAM 10X

Stock #1 (per Liter)

| | |
|---|---|
| $(NH_4)2SO_4$ (ammonium sulfate) | 4.63 g |
| $KNO_3$ (potassium nitrate) | 28.3 g |
| $MgSO_4$*$7H_20$ (magnesium sulfate heptahydrate) | 3.7 g |
| $KH_2PO_4$ (potassium phosphate, monobasic) | 1.85 g |
| Bring to volume | |
| Autoclave | |

MS Micro 1000X

Stock #2 (per 1 Liter)

| | |
|---|---|
| $H_3BO_3$ (boric acid) | 6.2 g |
| $MnSO_4$*$H_2O$ (manganese sulfate monohydrate) | 16.9 g |
| $ZnSO_4$*7H20 (zinc sulfate heptahydrate) | 8.6 g |
| $Na_2MoO_4$*2H20 (sodium molybdate dihydrate) | 0.25 g |
| $CuSO_4$*$5H_20$ (copper sulfate pentahydrate) | 0.025 g |
| $CoCl_2$*$6H_20$ (cobalt chloride hexahydrate) | 0.025 g |
| KI (potassium iodide) | 0.8300 g |
| Bring to volume | |
| Autoclave | |

FeEDTA 1100X

Stock #3 (per Liter)

| | |
|---|---|
| $Na_2EDTA$* (sodium EDTA) | 3.73 g |
| $FeSO_4$*$7H_20$ (iron sulfate heptahydrate) | 2.78 g |

*EDTA must be completely dissolved before adding iron.
Bring to Volume
Solution is photosensitive. Bottle(s) should be wrapped in foil to omit light.
Autoclave Ca 100X Stock #4 (per Liter)

| | |
|---|---|
| $CaCl_2$*$2H_20$ (calcium chloride dihydrate) | 44 g |
| Bring to Volume | |
| Autoclave | |

B5 Vitamin 1000X

Stock #5 (per Liter)

| | |
|---|---|
| Thiamine * HCl | 10 g |
| Nicotinic Acid | 1 g |
| Pyridoxine * HCl | 1 g |
| Myo-Inositol | 100 g |
| Bring to Volume | |
| Store frozen | |

4% Glutamine

Stock #6 (per Liter)

| | |
|---|---|
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

Example 16

Identification of a Delta-9 Elongase from *Euglena gracilis*

The present Example, disclosed in U.S. Patent Application No. 60/739,989, describes the isolation of a delta-9 elongase from *Euglena gracilis* (SEQ ID NOs:175 and 176).

*Euglena qracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (U126-01, Difco Laboratories, Detroit, Mich.), 2 g of Bacto® tryptone (0123-17-3, Difco Laboratories), 2 g of Bacto® yeast extract (0127-17-9, Difco Laboratories) in 970 mL of water. After filter sterilizing, 30 mL of soil-water supernatant (15-3790, Carolina Biological Supply Company, Burlington, N.C.) was aseptically added to give the final Eg medium. *Euglena gracilis* cultures were grown at 23° C. with a 16 h light, 8 h dark cycle for 2 weeks with no agitation.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. Cat. No. U-99-A).

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 μg of mRNA was obtained.

*Euglena qracilis* cDNA Synthesis, Library Construction and Sequencing

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 3.2 μg of mRNA (described above) using the Biotin-attB2-Oligo (dT) primer. After synthesis of the first and second strand, the attB1 adapter was added, ligated and the cDNA was size fractionated using column chromatography. DNA from fractions 7 and 8 (size ranging from ~800-1500 bp) were concentrated, recombined into pDONR™222 and transformed into *E. coli* ElectroMAX™ DH10B™ T1 Phage-Resistant cells (Invitrogen Corporation). The *Euglena gracilis* library was named eeg1c.

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 μg/mL Kanamycin (replicated plates). Plasmids then were isolated, using the Templiphi DNA sequencing template amplification kit method (Amersham Biosciences) following the manufacturer's protocol. Briefly, the Templiphi method uses bacteriophage ϕ29 DNA polymerase to amplify circular single-stranded or double-stranded DNA by isothermal rolling circle amplification (Dean et al., *Genome Res.,* 11:1095-1099 (2001); Nelson et al., *Biotechniques,* 32:S44-S47 (2002)). After growing 20 h at 37° C., cells from the replicated plate were added to 5 μL of dilution buffer and denatured at 95° C. for 3 min to partially lyse cells and release the denatured template. Templiphi premix (5 μL) was then added to each sample and the resulting reaction mixture was incubated at 30° C. for 16 h, then at 65° C. for 10 min to inactivate the ϕ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:193), and the ABI BigDye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Identification of Long-Chain Polyunsaturated Fatty Acid Elongation

Enzyme Homologs From *Euglena gracilis* cDNA Library eeg1c cDNA clones encoding long-chain polyunsaturated fatty acid elongation enzyme homologs (LC-PUFA ELO homologs or delta-9 elongases) were identified by conducting BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The *Euglena gracilis* cDNA sequences obtained above were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.,* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequences from clone eeg1c.pk001.n5.f revealed similarity of the protein encoded by the cDNA to the long-chain PUFA elongation enzyme from *Isochrysis galbana* (SEQ ID NO:173) (GenBank Accession No. AAL37626 (GI 17226123), locus AAL37626, CDS AF390174; Qi et al., *FEBS Lett.* 510(3): 159-165 (2002)). The sequence of a portion of the cDNA insert from clone eeg1c.pk001.n5.f is shown in SEQ ID NO:194 (5' end of cDNA insert). Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones.

The 3' end sequence is shown in SEQ ID NO:195. Both the 5' and 3' sequences were aligned using Sequencher™ (Version 4.2, Gene Codes Corporation, Ann Arbor, Mich.) and the resulting sequence for the cDNA is shown in SEQ ID NO:196 (1201 bp). Sequence for the coding sequence from the cDNA in eeg1c.pk001.n5.f and the corresponding deduced amino acid sequence is shown in SEQ ID NO:175 (777 bp) and SEQ ID NO:176 (258 amino acids), respectively.

The amino acid sequence set forth in SEQ ID NO:176 was evaluated by BLASTP, yielding a pLog value of 38.70 (E value of 2e-39) versus the *Isochrysis galbana* sequence (SEQ ID NO:173). The *Euglena gracilis* delta-9 elongase is 39.4% identical to the *Isochrysis galbana* delta-9 elongase sequence using the Jotun Hein method. Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Euglena gracilis* delta-9 elongase is 31.8% identical to the *Isochrysis galbana* delta-9 elongase sequence using the Clustal V method. Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the nucleic acid fragment described herein as SEQ ID NO:175 encodes an entire *Euglena gracilis* delta-9 elongase.

Example 17

Functional Analysis of EgD8S-23 and the *Euglena gracilis* Delta-9 Elongase in Somatic Soybean Embryos Transformed with Soybean Expression Vector pKR1059

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Fatty Acid Analysis of Transgenic Somatic Soybean Embryos Expressing pKR1059

Individual single, matured, somatic soybean embryos that had been transformed with pKR1059 (as described in Example 15 transformants were matured on SHaM liquid media) were picked into glass GC vials and fatty acid methyl esters were prepared by transesterification. For transesterification, 50 μL of trimethylsulfonium hydroxide (TMSH) and 0.5 mL of hexane were added to the embryos in glass vials and incubated for 30 min at room temperature while shaking. Fatty acid methyl esters (5 μL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). Routinely, 6 embryos per event were analyzed by GC, using the methodology described above.

Embryo fatty acid profiles for 31 individual events (6 embryos each) containing pKR1059 were obtained and of these, 23 events contained at least 1 embryo with greater than 1% EDA. The lipid profiles of somatic soybean embryos expressing EgD8S-23 and the *Euglena gracilis* delta-9 elongase for the top 5 events are shown in FIG. 14. Fatty acids are identified as 16:0 (palmitate), 18:0 (stearic acid), 18:1 (oleic acid), LA, GLA, ALA, EDA, DGLA, ERA and ETA; and, fatty acid compositions listed in FIG. 4 are expressed as a weight percent (wt. %) of total fatty acids. The delta-8 desaturase activity of EgD8S-23 is expressed as percent desaturation (% desat), calculated according to the following formula: ([product]/[substrate+product])*100.

More specifically, the combined percent desaturation for EDA and ERA is shown as "C20% delta-8 desat", determined as: ([DGLA+ETA]/[DGLA+ETA+EDA+ERA])*100. This is also referred to as the overall % desaturation. The individual omega-6 delta-8 desaturation ("EDA % delta-8 desat.") was calculated as: ([DGLA]/[DGLA+EDA])*100. Similarly, the individual omega-3 delta-8 desaturation ("ERA % delta-8 desat.") was calculated as: ([ETA]/[ETA+ERA])*100. The ratio of delta-8 desaturation for omega-6 versus omega-3 substrates ("ratio [EDA/ERA] % desat.") was obtained by dividing the EDA % delta-8 desaturation by the ERA % delta-8 desaturation.

In summary of FIG. 14, EgD8S-23 worked in soybean to convert both EDA and ERA to DGLA and ETA, respectively. The line with the highest average DGLA content (i.e., 2063-1-4) had embryos with an average DGLA content of 13.2% and an average ETA content of 4.2%. The highest DGLA and ETA content for an individual embryo from this line was 13.5% and 4.3%, respectively. The highest average overall % desaturation was 68.6% with the highest overall % desaturation for an individual embryo being 69.7%. When broken down into % desaturation for the omega-6 and omega-3 substrates, the highest average % desaturation was 65.4% and 81.3% for EDA and ERA, respectively. The highest % desaturation for an individual embryo was 66.6% and 84.1% for EDA and ERA, respectively. In this example, the D8S-23 had a preference for ERA over EDA, with the average desaturation ratio ranging from 0.7 to 0.8. No significant levels of GLA was found to accumulate in the embryos.

What is claimed is:

1. A method for producing at least one polyunsaturated fatty acid in a soybean seed comprising:

(a) transforming a soybean cell with a first recombinant construct and at least one additional recombinant construct, said first recombinant construct comprising at least one regulatory sequence operably linked to a polynucleotide encoding at least one delta-8 desaturase polypeptide as set forth in SEQ ID NO:2, wherein SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to SEQ ID NO:10, said at least one additional recombinant construct comprising at least one regulatory sequence operably linked to a polynucleotide encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating a soybean plant from the transformed soybean cell of step (a); and (c) selecting seeds obtained from the plants of step (b) having an altered level of polyunsaturated fatty acids when compared to the level in seeds obtained from a nontransformed soybean plant.

2. An oilseed plant comprising:

(a) a first recombinant construct, said first recombinant construct comprising at least one regulatory sequence operably linked to a polynucleotide encoding at least one delta-8 desaturase polypeptide as set forth in SEQ ID NO:2, wherein SEQ ID NO:2 comprises at least one mutation selected from the group consisting of: 4S to A, 5K to S, 12T to V, 16T to K, 17T to V, 54A to G, 55F to Y, 66P to Q, 67S to A, 108S to L, 117G to A, 118Y to F, 120L to M, 121M to L, 125Q to H, 126M to L, 132V to L, 133L to V, 162L to V, 163V to L, 170G to A, 171L to V, 279T to L, 280L to T, 293L to M, 346I to V, 347I to L, 348T to S, 407A to S, 408V to Q, 418A to G, 419G to A and 422L to Q, wherein the mutations are defined with respect to SEQ ID NO:10; and (b) at least one additional recombinant construct comprising at least one regulatory sequence operably linked to a polynucleotide encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, $C_{14/16}$ elongase, a $C_{16/18}$ elongase, a $C_{18/20}$ elongase and a $C_{20/22}$ elongase.

3. The oilseed plant of claim 2, wherein the oilseed plant is selected from the group consisting of soybean, *Brassica* species, sunflower, maize, cotton, flax and safflower.

4. A transgenic seed obtained from the oilseed plant of claim 2.

5. Food or feed comprising the seed of claim 4.

6. Progeny plants obtained from the transgenic seed of claim 4.

* * * * *

SEQUENCE LISTING

```
<160> NUMBER OF SEQ ID NOS: 198

<210> SEQ ID NO 1
<211> LENGTH: 1272
<212> TYPE: DNA
<213> ORGANISM: Artificial Sequence
<220> FEATURE:
<223> OTHER INFORMATION: mutant EgD8S consensus, optionally comprising
      M1, M2, M3, M8, M12, M15, M16, M18, M21, M26, M38, M45, M46, M51,
      M63, M68, M69 and M70 mutation sites
<220> FEATURE:
<221> NAME/KEY: misc_feature
<222> LOCATION: (2)..(1270)
<223> OTHER INFORMATION: mutant delta-8 desaturase CDS

<400> SEQUENCE: 1

catggtgaag nnnnnncgac aggctctgcc cctcnnnatc gacggannnn nntacgacgt     60

ctccgcttgg gtgaacttcc accctggtgg agctgaaatc attgagaact accagggacg    120

agatgctact gacgccttca tggttatgca ctctcaggaa nnnnnngaca agctcaagcg    180

aatgcccaag atcaacnnnn nntccgagct gcctccccag gctgccgtca acgaagctca    240

ggaggatttc cgaaagctcc gagaagagct gatcgccact ggcatgtttg acgcctctcc    300

cctctggtac tcgtacaaga tcnnnaccac cctgggtctt ggcgtgcttn nnnnnttcnn    360

nnnngtccag tacnnnnnnt acttcattgg tgctnnnnnn ctcggtatgc actaccagca    420

aatgggatgg ctgtctcatg acatctgcca ccaccagacc ttcaagaacc gaaactggaa    480

taacnnnnnn ggtctggtct ttggcaacnn nnnncagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagnnnnn    840
```

```
nttccacctc ttctttatgc cctccatcct gacctcgnnn ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcnnnn nnnnngactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgn nnnnnttcgc tcgaatggcc gagaagcagc ccnnnnnnaa   1260

ggctnnntaa gc                                                       1272


<210> SEQ ID NO 2
<211> LENGTH: 422
<212> TYPE: PRT
<213> ORGANISM: Artificial Sequence
<220> FEATURE:
<223> OTHER INFORMATION: mutant EgD8S consensus, optionally comprising
      M1, M2, M3, M8, M12, M15, M16, M18, M21, M26, M38, M45, M46, M51,
      M63, M68, M69 and M70 mutation sites
<220> FEATURE:
<221> NAME/KEY: MISC_FEATURE
<222> LOCATION: (4)..(4)
<223> OTHER INFORMATION: X = S (synthetic codon-optimized) or A (mutant)
<220> FEATURE:
<221> NAME/KEY: MISC_FEATURE
<222> LOCATION: (5)..(5)
<223> OTHER INFORMATION: X = K (synthetic codon-optimized) or S (mutant)
<220> FEATURE:
<221> NAME/KEY: MISC_FEATURE
<222> LOCATION: (12)..(12)
<223> OTHER INFORMATION: X = T (synthetic codon-optimized) or V (mutant)
<220> FEATURE:
<221> NAME/KEY: MISC_FEATURE
<222> LOCATION: (16)..(16)
<223> OTHER INFORMATION: X = T (synthetic codon-optimized) or K (mutant)
<220> FEATURE:
<221> NAME/KEY: MISC_FEATURE
<222> LOCATION: (17)..(17)
<223> OTHER INFORMATION: X = T (synthetic codon-optimized) or V (mutant)
<220> FEATURE:
<221> NAME/KEY: MISC_FEATURE
<222> LOCATION: (54)..(54)
<223> OTHER INFORMATION: X = A (synthetic codon-optimized) or G (mutant)
<220> FEATURE:
<221> NAME/KEY: MISC_FEATURE
<222> LOCATION: (55)..(55)
<223> OTHER INFORMATION: X = F (synthetic codon-optimized) or Y (mutant)
<220> FEATURE:
<221> NAME/KEY: MISC_FEATURE
<222> LOCATION: (66)..(66)
<223> OTHER INFORMATION: X = P (synthetic codon-optimized) or Q (mutant)
<220> FEATURE:
<221> NAME/KEY: MISC_FEATURE
<222> LOCATION: (67)..(67)
<223> OTHER INFORMATION: X = S (synthetic codon-optimized) or A (mutant)
<220> FEATURE:
<221> NAME/KEY: MISC_FEATURE
<222> LOCATION: (108)..(108)
<223> OTHER INFORMATION: X = S (synthetic codon-optimized) or L (mutant)
<220> FEATURE:
<221> NAME/KEY: MISC_FEATURE
<222> LOCATION: (117)..(117)
<223> OTHER INFORMATION: X = G (synthetic codon-optimized) or A (mutant)
<220> FEATURE:
<221> NAME/KEY: MISC_FEATURE
<222> LOCATION: (118)..(118)
<223> OTHER INFORMATION: X = Y (synthetic codon-optimized) or F (mutant)
<220> FEATURE:
<221> NAME/KEY: MISC_FEATURE
<222> LOCATION: (120)..(120)
<223> OTHER INFORMATION: X = L (synthetic codon-optimized) or M (mutant)
```

<220> FEATURE:
<221> NAME/KEY: MISC_FEATURE
<222> LOCATION: (121)..(121)
<223> OTHER INFORMATION: X = M (synthetic codon-optimized) or L (mutant)
<220> FEATURE:
<221> NAME/KEY: MISC_FEATURE
<222> LOCATION: (125)..(125)
<223> OTHER INFORMATION: X = Q (synthetic codon-optimized) or H (mutant)
<220> FEATURE:
<221> NAME/KEY: MISC_FEATURE
<222> LOCATION: (126)..(126)
<223> OTHER INFORMATION: X = M (synthetic codon-optimized) or L (mutant)
<220> FEATURE:
<221> NAME/KEY: MISC_FEATURE
<222> LOCATION: (132)..(132)
<223> OTHER INFORMATION: X = V (synthetic codon-optimized) or L (mutant)
<220> FEATURE:
<221> NAME/KEY: MISC_FEATURE
<222> LOCATION: (133)..(133)
<223> OTHER INFORMATION: X = L (synthetic codon-optimized) or V (mutant)
<220> FEATURE:
<221> NAME/KEY: MISC_FEATURE
<222> LOCATION: (162)..(162)
<223> OTHER INFORMATION: X = L (synthetic codon-optimized) or V (mutant)
<220> FEATURE:
<221> NAME/KEY: MISC_FEATURE
<222> LOCATION: (163)..(163)
<223> OTHER INFORMATION: X = V (synthetic codon-optimized) or L (mutant)
<220> FEATURE:
<221> NAME/KEY: MISC_FEATURE
<222> LOCATION: (170)..(170)
<223> OTHER INFORMATION: X = G (synthetic codon-optimized) or A (mutant)
<220> FEATURE:
<221> NAME/KEY: MISC_FEATURE
<222> LOCATION: (171)..(171)
<223> OTHER INFORMATION: X = L (synthetic codon-optimized) or V (mutant)
<220> FEATURE:
<221> NAME/KEY: MISC_FEATURE
<222> LOCATION: (279)..(279)
<223> OTHER INFORMATION: X = T (synthetic codon-optimized) or L (mutant)
<220> FEATURE:
<221> NAME/KEY: MISC_FEATURE
<222> LOCATION: (280)..(280)
<223> OTHER INFORMATION: X = L (synthetic codon-optimized) or T (mutant)
<220> FEATURE:
<221> NAME/KEY: MISC_FEATURE
<222> LOCATION: (293)..(293)
<223> OTHER INFORMATION: X = L (synthetic codon-optimized) or M (mutant)
<220> FEATURE:
<221> NAME/KEY: MISC_FEATURE
<222> LOCATION: (346)..(346)
<223> OTHER INFORMATION: X = I (synthetic codon-optimized) or V (mutant)
<220> FEATURE:
<221> NAME/KEY: MISC_FEATURE
<222> LOCATION: (347)..(347)
<223> OTHER INFORMATION: X = I (synthetic codon-optimized) or L (mutant)
<220> FEATURE:
<221> NAME/KEY: MISC_FEATURE
<222> LOCATION: (348)..(348)
<223> OTHER INFORMATION: X = T (synthetic codon-optimized) or S (mutant)
<220> FEATURE:
<221> NAME/KEY: MISC_FEATURE
<222> LOCATION: (407)..(407)
<223> OTHER INFORMATION: X = A (synthetic codon-optimized) or S (mutant)
<220> FEATURE:
<221> NAME/KEY: MISC_FEATURE
<222> LOCATION: (408)..(408)
<223> OTHER INFORMATION: X = V (synthetic codon-optimized) or Q (mutant)
<220> FEATURE:
<221> NAME/KEY: MISC_FEATURE
<222> LOCATION: (418)..(418)
<223> OTHER INFORMATION: X = A (synthetic codon-optimized) or G (mutant)
<220> FEATURE:
<221> NAME/KEY: MISC_FEATURE
<222> LOCATION: (419)..(419)
<223> OTHER INFORMATION: X = G (synthetic codon-optimized) or A (mutant)
<220> FEATURE:
<221> NAME/KEY: MISC_FEATURE
<222> LOCATION: (422)..(422)
<223> OTHER INFORMATION: X = L (synthetic codon-optimized) or Q (mutant)

<400> SEQUENCE: 2

```
Met Val Lys Xaa Xaa Arg Gln Ala Leu Pro Leu Xaa Ile Asp Gly Xaa
1               5                   10                  15

Xaa Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Xaa Xaa Asp Lys Leu Lys Arg Met Pro Lys Ile
    50                  55                  60

Asn Xaa Xaa Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Xaa Thr Thr Leu Gly
            100                 105                 110

Leu Gly Val Leu Xaa Xaa Phe Xaa Xaa Val Gln Tyr Xaa Xaa Tyr Phe
        115                 120                 125

Ile Gly Ala Xaa Xaa Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Xaa Xaa Gly Leu Val Phe Gly Asn Xaa Xaa Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Xaa Xaa Phe His Leu Phe Phe Met Pro Ser
        275                 280                 285

Ile Leu Thr Ser Xaa Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Xaa Xaa Xaa Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400
```

```
Ile Leu Leu Arg Tyr Leu Xaa Xaa Phe Ala Arg Met Ala Glu Lys Gln
                405                 410                 415

Pro Xaa Xaa Lys Ala Xaa
            420
```

<210> SEQ ID NO 3
<211> LENGTH: 1272
<212> TYPE: DNA
<213> ORGANISM: Artificial Sequence
<220> FEATURE:
<223> OTHER INFORMATION: mutant EgD8S-23
<220> FEATURE:
<221> NAME/KEY: misc_feature
<222> LOCATION: (2)..(1270)
<223> OTHER INFORMATION: mutant EgD8S-23 delta-8 desaturase CDS

<400> SEQUENCE: 3

```
catggtgaag gcttctcgac aggctctgcc cctcgtcatc gacggaaagg tgtacgacgt     60

ctccgcttgg gtgaacttcc accctggtgg agctgaaatc attgagaact accagggacg    120

agatgctact gacgccttca tggttatgca ctctcaggaa gccttcgaca agctcaagcg    180

aatgcccaag atcaaccagg cttccgagct gcctccccag gctgccgtca acgaagctca    240

ggaggatttc cgaaagctcc gagaagagct gatcgccact ggcatgtttg acgcctctcc    300

cctctggtac tcgtacaaga tcttgaccac cctgggtctt ggcgtgcttg ccttcttcat    360

gctggtccag taccacctgt acttcattgg tgctctcgtg ctcggtatgc actaccagca    420

aatgggatgg ctgtctcatg acatctgcca ccaccagacc ttcaagaacc gaaactggaa    480

taacgtcctg ggtctggtct ttggcaacgg actccagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgatg ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgt cccagttcgc tcgaatggcc gagaagcagc ccggtgccaa   1260

ggctcagtaa gc                                                        1272
```

<210> SEQ ID NO 4
<211> LENGTH: 422
<212> TYPE: PRT
<213> ORGANISM: Artificial Sequence
<220> FEATURE:
<223> OTHER INFORMATION: mutant EgD8S-23, comprising M1, M2, M3, M8, M12, M15, M16, M18, M21, M26, M45, M46, M68 and M70 mutation sites

<400> SEQUENCE: 4

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30
```

```
Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420
```

```
<210> SEQ ID NO 5
<211> LENGTH: 1272
<212> TYPE: DNA
<213> ORGANISM: Artificial Sequence
```

<220> FEATURE:
<223> OTHER INFORMATION: mutant EgD8S-013
<220> FEATURE:
<221> NAME/KEY: misc_feature
<222> LOCATION: (2)..(1270)
<223> OTHER INFORMATION: mutant EgD8S-013 delta-8 desaturase CDS

<400> SEQUENCE: 5

```
catggtgaag gcttctcgac aggctctgcc cctcgtcatc gacggaaagg tgtacgacgt     60

ctccgcttgg gtgaacttcc accctggtgg agctgaaatc attgagaact accagggacg    120

agatgctact gacgccttca tggttatgca ctctcaggaa ggctacgaca agctcaagcg    180

aatgcccaag atcaaccagg cttccgagct gcctccccag gctgccgtca acgaagctca    240

ggaggatttc cgaaagctcc gagaagagct gatcgccact ggcatgtttg acgcctctcc    300

cctctggtac tcgtacaaga tcttgaccac cctgggtctt ggcgtgcttg ccttcttcat    360

gctggtccag taccacctgt acttcattgg tgctctcgtg ctcggtatgc actaccagca    420

aatgggatgg ctgtctcatg acatctgcca ccaccagacc ttcaagaacc gaaactggaa    480

taacgtcctg ggtctggtct ttggcaacgc tgtccagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgatg ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgt cccagttcgc tcgaatggcc gagaagcagc ccggtgccaa   1260

ggctcagtaa gc                                                       1272
```

<210> SEQ ID NO 6
<211> LENGTH: 422
<212> TYPE: PRT
<213> ORGANISM: Artificial Sequence
<220> FEATURE:
<223> OTHER INFORMATION: Mutant EgD8S-013, comprising M1, M2, M3, M8, M12, M15, M16, M18, M21, M26, M38, M45, M46, M68, M69 and M70 mutation sites

<400> SEQUENCE: 6

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Gly Tyr Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80
```

```
Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Ala Val Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420
```

<210> SEQ ID NO 7
<211> LENGTH: 1272
<212> TYPE: DNA
<213> ORGANISM: Artificial Sequence
<220> FEATURE:
<223> OTHER INFORMATION: mutant EgD8S-015
<220> FEATURE:
<221> NAME/KEY: misc_feature
<222> LOCATION: (2)..(1270)
<223> OTHER INFORMATION: mutant EgD8S-015 delta-8 desaturase CDS

<400> SEQUENCE: 7

```
catggtgaag gcttctcgac aggctctgcc cctcgtcatc gacggaaagg tgtacgacgt     60
ctccgcttgg gtgaacttcc accctggtgg agctgaaatc attgagaact accagggacg    120
agatgctact gacgccttca tggttatgca ctctcaggaa ggctacgaca agctcaagcg    180
aatgcccaag atcaaccagg cttccgagct gcctccccag gctgccgtca acgaagctca    240
ggaggatttc cgaaagctcc gagaagagct gatcgccact ggcatgtttg acgcctctcc    300
cctctggtac tcgtacaaga tcttgaccac cctgggtctt ggcgtgcttg ccttcttcat    360
gctggtccag taccacctgt acttcattgg tgctgtgctg ctcggtatgc actaccagca    420
aatgggatgg ctgtctcatg acatctgcca ccaccagacc ttcaagaacc gaaactggaa    480
taacgtcctg ggtctggtct ttggcaacgc tgtccagggc ttctccgtga cctggtggaa    540
ggacagacac aacgcccatc attctgctac caacgttcag ggtcacgatc ccgacattga    600
taacctgcct ctgctcgcct ggtccgagga cgatgtcact cgagcttctc ccatctcccg    660
aaagctcatt cagttccaac agtactattt cctggtcatc tgtattctcc tgcgattcat    720
ctggtgtttc cagtctgtgc tgaccgttcg atccctcaag gaccgagaca accagttcta    780
ccgatctcag tacaagaaag aggccattgg actcgctctg cactggactc tcaagctgac    840
cttccacctc ttctttatgc cctccatcct gacctcgatg ctggtgttct ttgtttccga    900
gctcgtcggt ggcttcggaa ttgccatcgt ggtcttcatg aaccactacc ctctggagaa    960
gatcggtgat tccgtctggg acggacatgg cttctctgtg ggtcagatcc atgagaccat   1020
gaacattcga cgaggcgtcc tctctgactg gttctttgga ggcctgaact accagatcga   1080
gcaccatctc tggcccaccc tgcctcgaca caacctcact gccgtttcct accaggtgga   1140
acagctgtgc cagaagcaca acctccccta ccgaaaccct ctgccccatg aaggtctcgt   1200
catcctgctc cgatacctgt cccagttcgc tcgaatggcc gagaagcagc ccggtgccaa   1260
ggctcagtaa gc                                                       1272
```

<210> SEQ ID NO 8
<211> LENGTH: 422
<212> TYPE: PRT
<213> ORGANISM: Artificial Sequence
<220> FEATURE:
<223> OTHER INFORMATION: mutant EgD8S-015 comprising M1, M2, M3, M8, M12, M15, M16, M18, M21, M26, M38, M45, M51, M63, M68, M69 and M70 mutation sites

<400> SEQUENCE: 8

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Gly Tyr Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110
```

```
Leu Gly Val Leu Ala Phe Phe Met Leu Val Gln Tyr His Leu Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Ala Val Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Leu Thr Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Val Leu Ser Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420
```

<210> SEQ ID NO 9
<211> LENGTH: 1272
<212> TYPE: DNA
<213> ORGANISM: Euglena gracilis
<220> FEATURE:
<221> NAME/KEY: misc_feature
<222> LOCATION: (2)..(1270)
<223> OTHER INFORMATION: synthetic delta-8 desaturase CDS, codon-optimized for Yarrowia lipolytica ("D8SF" or "EgD8S")
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(1272)

<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(1272)

<400> SEQUENCE: 9

```
catggtgaag tccaagcgac aggctctgcc cctcaccatc gacggaacta cctacgacgt     60

ctccgcttgg gtgaacttcc accctggtgg agctgaaatc attgagaact accagggacg    120

agatgctact gacgccttca tggttatgca ctctcaggaa gccttcgaca agctcaagcg    180

aatgcccaag atcaacccct cctccgagct gcctccccag gctgccgtca acgaagctca    240

ggaggatttc cgaaagctcc gagaagagct gatcgccact ggcatgtttg acgcctctcc    300

cctctggtac tcgtacaaga tctccaccac cctgggtctt ggcgtgcttg gatacttcct    360

gatggtccag taccagatgt acttcattgg tgctgtgctg ctcggtatgc actaccagca    420

aatgggatgg ctgtctcatg acatctgcca ccaccagacc ttcaagaacc gaaactggaa    480

taacctcgtg ggtctggtct ttggcaacgg actccagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgctc ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgg ccgtgttcgc tcgaatggcc gagaagcagc ccgctggcaa   1260

ggctctctaa gc                                                       1272
```

<210> SEQ ID NO 10
<211> LENGTH: 422
<212> TYPE: PRT
<213> ORGANISM: Euglena gracilis
<220> FEATURE:
<221> NAME/KEY: MISC_FEATURE
<223> OTHER INFORMATION: synthetic delta-8 desaturase codon-optimized for Yarrowia lipolytica ("D8SF" or "EgD8S")
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(422)
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(422)

<400> SEQUENCE: 10

```
Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Leu Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400
```

```
Ile Leu Leu Arg Tyr Leu Ala Val Phe Ala Arg Met Ala Glu Lys Gln
                405                 410                 415

Pro Ala Gly Lys Ala Leu
            420


<210> SEQ ID NO 11
<211> LENGTH: 1271
<212> TYPE: DNA
<213> ORGANISM: Euglena gracilis
<220> FEATURE:
<221> NAME/KEY: misc_feature
<222> LOCATION: (4)..(1269)
<223> OTHER INFORMATION: delta-8 desaturase ("Eg5" or "EgD8") CDS
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(1271)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(1271)

<400> SEQUENCE: 11

gaaatgaagt caaagcgcca agcgcttccc cttacaattg atggaacaac atatgatgtg      60

tctgcctggg tcaatttcca ccctggtggt gcggaaatta tagagaatta ccaaggaagg     120

gatgccactg atgccttcat ggttatgcac tctcaagaag ccttcgacaa gctcaagcgc     180

atgcccaaaa tcaatcccag ttctgagttg ccaccccagg ctgcagtgaa tgaagctcaa     240

gaggatttcc ggaagctccg agaagagttg atcgcaactg gcatgtttga tgcctccccc     300

ctctggtact catacaaaat cagcaccaca ctgggccttg gagtgctggg ttatttcctg     360

atggttcagt atcagatgta tttcattggg gcagtgttgc ttgggatgca ctatcaacag     420

atgggctggc tttctcatga catttgccac caccagactt tcaagaaccg gaactggaac     480

aacctcgtgg gactggtatt tggcaatggt ctgcaaggtt tttccgtgac atggtggaag     540

gacagacaca atgcacatca ttcggcaacc aatgttcaag ggcacgaccc tgatattgac     600

aacctccccc tcttagcctg gtctgaggat gacgtcacac gggcgtcacc gatttcccgc     660

aagctcattc agttccagca gtactatttc ttggtcatct gtatcttgtt gcggttcatt     720

tggtgtttcc agagcgtgtt gaccgtgcgc agtttgaagg acagagataa ccaattctat     780

cgctctcagt ataagaagga ggccattggc ctcgccctgc actggacctt gaagaccctg     840

ttccacttat tctttatgcc cagcatcctc acatcgctgt tggtgttttt cgtttcggag     900

ctggttggcg gcttcggcat tgcgatcgtg gtgttcatga accactaccc actggagaag     960

atcggggact cagtctggga tggccatgga ttctcggttg gccagatcca tgagaccatg    1020

aacattcggc gagggattat cacagattgg tttttcggag gcttgaatta ccagattgag    1080

caccatttgt ggccgaccct ccctcgccac aacctgacag cggttagcta ccaggtggaa    1140

cagctgtgcc agaagcacaa cctgccgtat cggaacccgc tgccccatga agggttggtc    1200

atcctgctgc gctatctggc ggtgttcgcc cggatggcgg agaagcaacc cgcggggaag    1260

gctctataag g                                                          1271
```

<210> SEQ ID NO 12
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase ("Eg5" or "EgD8")
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(421)
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: US_2005-0287652-A1
<311> PATENT FILING DATE: 2005-06-24
<312> PUBLICATION DATE: 2005-12-29
<313> RELEVANT RESIDUES IN SEQ ID NO: (1)..(421)

<400> SEQUENCE: 12

```
Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300
```

```
Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420


<210> SEQ ID NO 13
<211> LENGTH: 467
<212> TYPE: PRT
<213> ORGANISM: Amylomyces rouxii (GenBank Accession No. AAR27297)

<400> SEQUENCE: 13

Met Ser Ser Asp Val Gly Ala Thr Val Pro His Phe Tyr Thr Arg Ala
1               5                   10                  15

Glu Leu Ala Asp Ile His Gln Asp Val Leu Asp Lys Lys Pro Glu Ala
            20                  25                  30

Arg Lys Leu Ile Val Val Glu Asn Lys Val Tyr Asp Ile Thr Asp Phe
        35                  40                  45

Val Phe Asp His Pro Gly Gly Glu Arg Val Leu Leu Thr Gln Glu Gly
    50                  55                  60

Arg Asp Ala Thr Asp Val Phe His Glu Met His Pro Pro Ser Ala Tyr
65                  70                  75                  80

Glu Leu Leu Ala Asn Cys Tyr Val Gly Asp Cys Glu Pro Lys Leu Pro
                85                  90                  95

Ile Asp Ser Thr Asp Lys Lys Ala Leu Asn Ser Ala Ala Phe Ala Gln
            100                 105                 110

Glu Ile Arg Asp Leu Arg Asp Lys Leu Glu Lys Gln Gly Tyr Phe Asp
        115                 120                 125

Ala Ser Thr Gly Phe Tyr Ile Tyr Lys Val Ser Thr Thr Leu Leu Val
    130                 135                 140

Cys Ile Val Gly Leu Ala Ile Leu Lys Ala Trp Gly Arg Glu Ser Thr
145                 150                 155                 160

Leu Ala Val Phe Ile Ala Ala Ser Leu Val Gly Leu Phe Trp Gln Gln
                165                 170                 175

Cys Gly Trp Leu Ala His Asp Tyr Ala His Tyr Gln Val Ile Lys Asp
            180                 185                 190

Pro Asn Val Asn Asn Leu Phe Leu Val Thr Phe Gly Asn Leu Val Gln
        195                 200                 205

Gly Phe Ser Leu Ser Trp Trp Lys Asn Lys His Asn Thr His His Ala
    210                 215                 220

Ser Thr Asn Val Ser Gly Glu Asp Pro Asp Ile Asp Thr Ala Pro Ile
225                 230                 235                 240

Leu Leu Trp Asp Glu Phe Ala Val Ala Asn Phe Tyr Gly Ser Leu Lys
                245                 250                 255
```

```
Asp Asn Ala Ser Gly Phe Asp Arg Phe Ile Ala Glu His Ile Leu Pro
            260                 265                 270

Tyr Gln Thr Arg Tyr Tyr Phe Phe Ile Leu Gly Phe Ala Arg Thr Ser
        275                 280                 285

Trp Ala Ile Gln Ser Ile Ile Tyr Ser Phe Lys Asn Glu Thr Leu Asn
    290                 295                 300

Lys Ser Lys Leu Leu Ser Trp Cys Glu Arg Ile Phe Leu Ile Val His
305                 310                 315                 320

Trp Val Phe Phe Thr Tyr Cys Thr Ile Ala Trp Ile Ser Ser Ile Arg
                325                 330                 335

Asn Ile Ala Met Phe Phe Val Val Ser Gln Ile Thr Thr Gly Tyr Leu
            340                 345                 350

Leu Ala Ile Val Phe Ala Met Asn His Asn Gly Met Pro Val Tyr Ser
        355                 360                 365

Pro Glu Glu Ala Asn His Thr Glu Phe Tyr Glu Leu Gln Cys Ile Thr
    370                 375                 380

Gly Arg Asp Val Asn Cys Thr Val Phe Gly Asp Trp Leu Met Gly Gly
385                 390                 395                 400

Leu Asn Tyr Gln Ile Glu His His Leu Phe Pro Glu Met Pro Arg His
                405                 410                 415

His Leu Ser Lys Val Lys Ser Met Val Lys Pro Ile Ala Gln Lys Tyr
            420                 425                 430

Asn Ile Pro Tyr His Asp Thr Thr Val Ile Gly Gly Thr Ile Glu Val
        435                 440                 445

Leu Gln Thr Leu Asp Phe Val Gln Lys Ile Ser Gln Lys Phe Ser Lys
    450                 455                 460

Lys Met Leu
465


<210> SEQ ID NO 14
<211> LENGTH: 445
<212> TYPE: PRT
<213> ORGANISM: Rhizopus oryzae (GenBank Accession No. AAS93682)

<400> SEQUENCE: 14

Met Ser Thr Ser Asp Arg Gln Ser Val Phe Thr Leu Lys Glu Leu Glu
1               5                   10                  15

Leu Ile Asn Gln Lys His Arg Asp Gly Asp Lys Ser Ala Met Lys Phe
            20                  25                  30

Ile Ile Ile Asp Arg Lys Val Tyr Asp Val Thr Glu Phe Leu Glu Asp
        35                  40                  45

His Gly Gly Ala Gln Val Leu Leu Thr His Val Gly Lys Asp Ala Ser
    50                  55                  60

Asp Val Phe His Ala Met His Glu Ser Ala Tyr Glu Ile Leu Asn Asn
65                  70                  75                  80

Tyr Phe Val Gly Asp Val Lys Asp Ala His Val Lys Glu Thr Ser Ala
                85                  90                  95

Gln Phe Ala Ser Glu Met Arg Gln Leu Arg Asp Gln Leu Lys Lys Glu
            100                 105                 110

Gly Tyr Phe His Ser Ser Lys Ala Tyr Tyr Val Tyr Lys Val Leu Ser
        115                 120                 125

Thr Leu Ala Leu Cys Ala Ala Gly Leu Thr Leu Leu Tyr Ala Tyr Gly
    130                 135                 140

His Thr Ser Thr Leu Ala Val Val Ala Ser Ala Ile Ile Val Gly Ile
145                 150                 155                 160
```

```
Phe Trp Gln Gln Cys Gly Trp Leu Ala His Asp Phe Gly His His Gln
                165                 170                 175

Cys Phe Glu Asp Arg Ser Trp Asn Asp Val Leu Val Val Phe Leu Gly
            180                 185                 190

Asn Phe Cys Gln Gly Phe Ser Leu Ser Trp Trp Lys Asn Lys His Asn
        195                 200                 205

Thr His His Ala Ser Thr Asn Val His Gly His Asp Asp Ile Asp Thr
    210                 215                 220

Ala Val Leu Leu Trp Asp Glu Tyr Ala Ser Ala Ala Tyr Tyr Ala Ser
225                 230                 235                 240

Leu Asp Glu Glu Thr Met Ile Ser Arg Phe Leu Ala Glu Ser Val Leu
                245                 250                 255

His Gln Thr Arg Tyr Tyr Phe Phe Val Leu Gly Phe Ala Arg Leu Ser
            260                 265                 270

Trp Ala Ile Gln Ser Leu Leu Tyr Ser Phe Lys Gln Gly Ala Ile Asn
        275                 280                 285

Lys Ser His Gln Leu Asn Leu Phe Glu Arg Phe Cys Leu Val Ser His
    290                 295                 300

Trp Thr Leu Phe Thr Tyr Cys Thr Leu Ala Trp Cys Ser Asn Val Tyr
305                 310                 315                 320

His Met Ile Leu Phe Phe Leu Val Ser Gln Ala Thr Thr Gly Tyr Thr
                325                 330                 335

Leu Ala Leu Val Phe Ala Leu Asn His Asn Gly Met Val Ile Thr Glu
            340                 345                 350

Glu Lys Ala Glu Ser Met Glu Phe Phe Glu Ile Gln Val Ile Thr Gly
        355                 360                 365

Arg Asp Val Thr Leu Ser Leu Gly Asp Trp Phe Met Gly Gly Leu Asn
    370                 375                 380

Tyr Gln Ile Glu His His Val Phe Asn Met Arg His Asn Leu Lys Val
385                 390                 395                 400

Lys Met Val Lys Ser Leu Cys Lys Lys Tyr Asp Ile Asn Tyr His Asp
                405                 410                 415

Thr Gly Phe Leu Lys Gly Thr Leu Glu Val Leu Lys Thr Leu Asp Ile
            420                 425                 430

Thr Ser Lys Leu Ser Leu Gln Leu Ser Lys Lys Ser Phe
        435                 440                 445


<210> SEQ ID NO 15
<211> LENGTH: 382
<212> TYPE: PRT
<213> ORGANISM: Leishmania major (GenBank Accession No. CAJ09677)

<400> SEQUENCE: 15

Met Val Phe Glu Leu Thr Tyr Lys Tyr His Ser Ser Leu Lys Cys Val
1               5                   10                  15

Ile Arg Ile Asp Asp Asn Trp Tyr Asp Cys Thr Ser Trp Arg Asn Ser
            20                  25                  30

His Gly Gly Ala Gln Met Cys Asp Glu Phe His Gly Lys Asp Ala Thr
        35                  40                  45

Asp Ala Phe Tyr Ser Leu His Ser Lys Glu Ala Ile Gln Lys Leu Lys
    50                  55                  60

Arg Met Lys Ala Leu Leu Lys Glu Gly Asp Glu Arg Asp Gln Val Ser
65                  70                  75                  80

Leu Asn Phe Glu Lys Leu Leu Gln Gln Leu Arg Ser Glu Gly Trp Phe
                85                  90                  95
```

```
Glu Arg Arg Trp Ile Ile Asp Phe Ala Arg Asn Ile Met Val Ile Val
            100                 105                 110

Leu Cys Val Val Gly Thr Tyr Leu Ser Tyr Ser Arg Phe Leu Ala Thr
        115                 120                 125

Ile Leu Ile Gly Leu Gly Met Gln Gln Gly Gly Trp Leu Ala His Asp
    130                 135                 140

Phe Thr His Ala Arg Gly Lys Phe Ala Arg Phe Leu Ala Asn Ala Cys
145                 150                 155                 160

Gly Gly Met Ile Asn Ala Phe Ser Val Glu Trp Trp Ser Asn Lys His
                165                 170                 175

Asn Ser His His Ile Phe Val Asn Arg Lys Gly Met Asp Ala Asp Ile
            180                 185                 190

His Asn Glu Ala Leu Phe Leu Trp Val Asp Val Ser Glu Asp Thr Ala
        195                 200                 205

Cys Arg Arg Tyr Gln Tyr Thr Phe Tyr Leu Ala Ala Tyr Ala Leu Leu
    210                 215                 220

Tyr Val Ser Trp Arg Ile Gln Ser Leu Arg Phe Ala Leu Gly Ser Gly
225                 230                 235                 240

Asn Arg Leu Glu Leu Ser Leu Met Ala Leu Asn Tyr Leu Trp Leu Ala
                245                 250                 255

Leu Leu Trp Arg Val Ser Leu Gly Ser Val Leu Leu Gly Gly Phe Phe
            260                 265                 270

Val Ala Val Val Val Thr Val Asn His Gln Thr Glu Glu Met Ile Glu
        275                 280                 285

His Asp Glu Tyr Asn Tyr Val Val Asp Gln His Arg Ala Thr Arg Gly
    290                 295                 300

Val His Cys Ser Asp Phe Phe Glu Trp Phe Phe Gly Gly Met Gln Tyr
305                 310                 315                 320

Gln Leu Glu His His Leu Leu Met Val Arg Tyr Arg Tyr Glu Val Arg
                325                 330                 335

Arg Leu Leu Arg Lys Phe Ser Glu Asp Asn Gly Leu Phe His Val Glu
            340                 345                 350

Gly Val Trp Lys Ile Thr Lys Met Asn Phe Asp Ile Leu Tyr Ser Ile
        355                 360                 365

Ser Thr Thr Ala Leu Asn Ser Ala Glu Ala Lys Ser Gly Lys
    370                 375                 380


<210> SEQ ID NO 16
<211> LENGTH: 439
<212> TYPE: PRT
<213> ORGANISM: Mortierella isabellina (GenBank Accession No. AAG38104)

<400> SEQUENCE: 16

Met Ala Ala Ala Ser Val Arg Thr Phe Thr Arg Ala Glu Ile Leu Asn
1               5                   10                  15

Ala Glu Ala Leu Asn Glu Gly Lys Lys Asp Ala Glu Ala Phe Leu Met
            20                  25                  30

Ile Ile Asp Asn Lys Val Tyr Asp Val Arg Glu Phe Val Asp His Gly
        35                  40                  45

Gly Ser Val Ile Leu Thr His Val Gly Lys Asp Gly Thr Asp Val Phe
    50                  55                  60

Asp Thr Phe His Glu Ala Ala Trp Glu Thr Leu Ala Asn Phe Tyr Val
65                  70                  75                  80

Gly Asp Ile Asp Glu Ser Asp Arg Ala Ile Lys Asn Asp Asp Phe Ala
                85                  90                  95
```

-continued

```
Ala Glu Val Arg Lys Leu Arg Thr Leu Phe Gln Ser Leu Gly Tyr Tyr
            100                 105                 110

Asp Ser Ser Lys Ala Tyr Tyr Ala Phe Lys Val Ser Phe Asn Leu Cys
        115                 120                 125

Ile Trp Gly Leu Ser Thr Phe Ile Val Ala Lys Trp Gly Gln Thr Ser
    130                 135                 140

Thr Leu Ala Asn Val Leu Ser Ala Ala Leu Leu Gly Leu Phe Trp Gln
145                 150                 155                 160

Gln Cys Gly Trp Leu Ala His Asp Phe Leu His His Gln Val Phe Gln
                165                 170                 175

Asp Arg Phe Trp Gly Asp Leu Phe Gly Ala Phe Leu Gly Gly Val Cys
            180                 185                 190

Gln Gly Phe Ser Ser Ser Trp Trp Lys Asp Lys His Asn Thr His His
        195                 200                 205

Ala Ala Asn Val His Gly Glu Asp Asp Ile Asp Thr His Leu Leu Thr
    210                 215                 220

Trp Ser Glu His Ala Leu Glu Met Phe Ser Asp Val Asp Glu Glu Leu
225                 230                 235                 240

Thr Arg Met Trp Ser Arg Phe Met Val Leu Asn Gln Thr Trp Phe Tyr
                245                 250                 255

Phe Ile Leu Ser Phe Ala Arg Leu Ser Trp Cys Leu Gln Ser Ile Leu
            260                 265                 270

Leu Val Leu Asn Gly Gln Ala His Lys Ser Gly Ala Arg Val Ser Ile
        275                 280                 285

Ser Leu Val Glu Gln Leu Ser Leu Ala Met His Trp Thr Trp Tyr Leu
    290                 295                 300

Ala Thr Met Phe Leu Phe Ile Lys Asp Val Asn Met Met Val Tyr Phe
305                 310                 315                 320

Leu Val Ser Gln Ala Val Cys Gly Asn Leu Leu Ala Ile Val Phe Ser
                325                 330                 335

Leu Asn His Asn Gly Met Val Ile Ser Lys Glu Glu Ala Val Asp Met
            340                 345                 350

Asp Phe Phe Thr Lys Gln Ile Ile Thr Gly Arg Asp Val His Gly Leu
        355                 360                 365

Phe Ala Asn Trp Phe Thr Gly Gly Leu Asn Tyr Gln Ile Glu His His
    370                 375                 380

Leu Phe Ser Met Arg His Asn Phe Ser Lys Ile Gln Ala Val Glu Thr
385                 390                 395                 400

Leu Cys Lys Lys Tyr Gly Val Arg Tyr His Thr Thr Gly Met Ile Glu
                405                 410                 415

Gly Thr Ala Glu Val Phe Ser Arg Leu Asn Glu Val Ser Lys Ala Ala
            420                 425                 430

Ser Lys Met Gly Lys Ala Gln
        435


<210> SEQ ID NO 17
<211> LENGTH: 14655
<212> TYPE: DNA
<213> ORGANISM: Artificial Sequence
<220> FEATURE:
<223> OTHER INFORMATION: Plasmid pZKLeuN-29E3
<220> FEATURE:
<221> NAME/KEY: misc_feature
<222> LOCATION: (8822)..(8822)
<223> OTHER INFORMATION: n is a, c, g, or t
```

<220> FEATURE:
<221> NAME/KEY: misc_feature
<222> LOCATION: (8827)..(8830)
<223> OTHER INFORMATION: n is a, c, g, or t

<400> SEQUENCE: 17

```
cgattgttgt ctactaacta tcgtacgata acttcgtata gcatacatta tacgaagtta     60

tcgcgtcgac gagtatctgt ctgactcgtc attgccgcct ttggagtacg actccaacta    120

tgagtgtgct tggatcactt tgacgataca ttcttcgttg gaggctgtgg gtctgacagc    180

tgcgttttcg gcgcggttgg ccgacaacaa tatcagctgc aacgtcattg ctggctttca    240

tcatgatcac atttttgtcg gcaaaggcga cgcccagaga gccattgacg ttctttctaa    300

tttggaccga tagccgtata gtccagtcta tctataagtt caactaactc gtaactatta    360

ccataacata tacttcactg ccccagataa ggttccgata aaaagttctg cagactaaat    420

ttatttcagt ctcctcttca ccaccaaaat gccctcctac gaagctcgag ctaacgtcca    480

caagtccgcc tttgccgctc gagtgctcaa gctcgtggca gccaagaaaa ccaacctgtg    540

tgcttctctg gatgttacca ccaccaagga gctcattgag cttgccgata aggtcggacc    600

ttatgtgtgc atgatcaaaa cccatatcga catcattgac gacttcacct acgccggcac    660

tgtgctcccc ctcaaggaac ttgctcttaa gcacggtttc ttcctgttcg aggacagaaa    720

gttcgcagat attggcaaca ctgtcaagca ccagtaccgg tgtcaccgaa tcgccgagtg    780

gtccgatatc accaacgccc acggtgtacc cggaaccgga atcattgctg gcctgcgagc    840

tggtgccgag gaaactgtct ctgaacagaa gaaggaggac gtctctgact acgagaactc    900

ccagtacaag gagttcctag tcccctctcc caacgagaag ctggccagag gtctgctcat    960

gctggccgag ctgtcttgca agggctctct ggccactggc gagtactcca agcagaccat   1020

tgagcttgcc cgatccgacc ccgagtttgt ggttggcttc attgcccaga accgacctaa   1080

gggcgactct gaggactggc ttattctgac cccgggggtg ggtcttgacg acaagggaga   1140

cgctctcgga cagcagtacc gaactgttga ggatgtcatg tctaccggaa cggatatcat   1200

aattgtcggc cgaggtctgt acggccagaa ccgagatcct attgaggagg ccaagcgata   1260

ccagaaggct ggctgggagg cttaccagaa gattaactgt tagaggttag actatggata   1320

tgtaatttaa ctgtgtatat agagagcgtg caagtatgga gcgcttgttc agcttgtatg   1380

atggtcagac gacctgtctg atcgagtatg tatgatactg cacaacctgt gtatccgcat   1440

gatctgtcca atggggcatg ttgttgtgtt tctcgatacg gagatgctgg gtacagtgct   1500

aatacgttga actacttata cttatatgag gctcgaagaa agctgacttg tgtatgactt   1560

attctcaact acatccccag tcacaatacc accactgcac taccactaca ccaaaaccat   1620

gatcaaacca cccatggact tcctggaggc agaagaactt gttatggaaa agctcaagag   1680

agagatcata acttcgtata gcatacatta tacgaagtta tcctgcaggt aaaggaattc   1740

tggagtttct gagagaaaaa ggcaagatac gtatgtaaca aagcgacgca tggtacaata   1800

ataccggagg catgtatcat agagagttag tggttcgatg atggcactgg tgcctggtat   1860

gactttatac ggctgactac atatttgtcc tcagacatac aattacagtc aagcacttac   1920

ccttggacat ctgtaggtac cccccggcca agacgatctc agcgtgtcgt atgtcggatt   1980

ggcgtagctc cctcgctcgt caattggctc ccatctactt tcttctgctt ggctacaccc   2040

agcatgtctg ctatggctcg ttttcgtgcc ttatctatcc tcccagtatt accaactcta   2100

aatgacatga tgtgattggg tctacacttt catatcagag ataaggagta gcacagttgc   2160

ataaaaagcc caactctaat cagcttcttc ctttcttgta attagtacaa aggtgattag   2220
```

-continued

```
cgaaatctgg aagcttagtt ggccctaaaa aaatcaaaaa aagcaaaaaa cgaaaaacga   2280

aaaaccacag ttttgagaac agggaggtaa cgaaggatcg tatatatata tatatatata   2340

tatacccacg gatcccgaga ccggcctttg attcttccct acaaccaacc attctcacca   2400

ccctaattca caaccatgga gtctggaccc atgcctgctg gcattccctt ccctgagtac   2460

tatgacttct ttatggactg gaagactccc ctggccatcg ctgccaccta cactgctgcc   2520

gtcggtctct tcaaccccaa ggttggcaag gtctcccgag tggttgccaa gtcggctaac   2580

gcaaagcctg ccgagcgaac ccagtccgga gctgccatga ctgccttcgt ctttgtgcac   2640

aacctcattc tgtgtgtcta ctctggcatc accttctact acatgtttcc tgctatggtc   2700

aagaacttcc gaacccacac actgcacgaa gcctactgcg acacggatca gtccctctgg   2760

aacaacgcac ttggctactg ggggttacctc ttctacctgt ccaagttcta cgaggtcatt   2820

gacaccatca tcatcatcct gaagggacga cggtcctcgc tgcttcagac ctaccaccat   2880

gctggagcca tgattaccat gtggtctggc atcaactacc aagccactcc catttggatc   2940

tttgtggtct tcaactcctt cattcacacc atcatgtact gttactatgc cttcacctct   3000

atcggattcc atcctcctgg caaaaagtac ctgacttcga tgcagattac tcagtttctg   3060

gtcggtatca ccattgccgt gtcctacctc ttcgttcctg gctgcatccg aacacccggt   3120

gctcagatgg ctgtctggat caacgtcggc tacctgtttc ccttgaccta tctgttcgtg   3180

gactttgcca agcgaaccta ctccaagcga tctgccattg ccgctcagaa aaaggctcag   3240

taagcggccg cattgatgat tggaaacaca cacatgggtt atatctaggt gagagttagt   3300

tggacagtta tatattaaat cagctatgcc aacggtaact tcattcatgt caacgaggaa   3360

ccagtgactg caagtaatat agaatttgac caccttgcca ttctcttgca ctcctttact   3420

atatctcatt tatttcttat atacaaatca cttcttcttc ccagcatcga gctcggaaac   3480

ctcatgagca ataacatcgt ggatctcgtc aatagagggc tttttggact ccttgctgtt   3540

ggccaccttg tccttgctgt ctggctcatt ctgtttcaac gccttttaat taacggagta   3600

ggtctcggtg tcggaagcga cgccagatcc gtcatcctcc tttcgctctc caaagtagat   3660

acctccgacg agctctcgga caatgatgaa gtcggtgccc tcaacgtttc ggatggggga   3720

gagatcggcg agcttgggcg acagcagctg gcagggtcgc aggttggcgt acaggttcag   3780

gtcctttcgc agcttgagga gaccctgctc gggtcgcacg tcggttcgtc cgtcgggagt   3840

ggtccatacg gtgttggcag cgcctccgac agcaccgagc ataatagagt cagcctttcg   3900

gcagatgtcg agagtagcgt cggtgatggg ctcgccctcc ttctcaatgg cagctcctcc   3960

aatgagtcgg tcctcaaaca caaactcggt gccggaggcc tcagcaacag acttgagcac   4020

cttgacggcc tcggcaatca cctcggggcc acagaagtcg ccgccgagaa gaacaatctt   4080

cttggagtca gtcttggtct tcttagtttc gggttccatt gtggatgtgt gtggttgtat   4140

gtgtgatgtg gtgtgtggag tgaaaatctg tggctggcaa acgctcttgt atatatacgc   4200

acttttgccc gtgctatgtg gaagactaaa cctccgaaga ttgtgactca ggtagtgcgg   4260

tatcggctag ggacccaaac cttgtcgatg ccgatagcat gcgacgtcgg gcccaattcg   4320

ccctatagtg agtcgtatta caattcactg gccgtcgttt tacaacgtcg tgactgggaa   4380

aaccctggcg ttacccaact taatcgcctt gcagcacatc ccccttcgc cagctggcgt   4440

aatagcgaag aggcccgcac cgatcgccct tcccaacagt tgcgcagcct gaatggcgaa   4500

tggacgcgcc ctgtagcggc gcattaagcg cggcgggtgt ggtggttacg cgcagcgtga   4560

ccgctacact tgccagcgcc ctagcgcccg ctcctttcgc tttcttccct tcctttctcg   4620
```

```
ccacgttcgc cggctttccc cgtcaagctc taaatcgggg gctcccttta gggttccgat   4680

ttagtgcttt acggcacctc gaccccaaaa aacttgatta gggtgatggt tcacgtagtg   4740

ggccatcgcc ctgatagacg gtttttcgcc ctttgacgtt ggagtccacg ttctttaata   4800

gtggactctt gttccaaact ggaacaacac tcaaccctat ctcggtctat tcttttgatt   4860

tataagggat tttgccgatt tcggcctatt ggttaaaaaa tgagctgatt taacaaaaat   4920

ttaacgcgaa ttttaacaaa atattaacgc ttacaatttc ctgatgcggt attttctcct   4980

tacgcatctg tgcggtattt cacaccgcat caggtggcac ttttcgggga aatgtgcgcg   5040

gaacccctat ttgtttattt ttctaaatac attcaaatat gtatccgctc atgagacaat   5100

aaccctgata aatgcttcaa taatattgaa aaaggaagag tatgagtatt caacatttcc   5160

gtgtcgccct tattcccttt tttgcggcat tttgccttcc tgtttttgct cacccagaaa   5220

cgctggtgaa agtaaaagat gctgaagatc agttgggtgc acgagtgggt tacatcgaac   5280

tggatctcaa cagcggtaag atccttgaga gttttcgccc cgaagaacgt tttccaatga   5340

tgagcacttt taaagttctg ctatgtggcg cggtattatc ccgtattgac gccgggcaag   5400

agcaactcgg tcgccgcata cactattctc agaatgactt ggttgagtac tcaccagtca   5460

cagaaaagca tcttacggat ggcatgacag taagagaatt atgcagtgct gccataacca   5520

tgagtgataa cactgcggcc aacttacttc tgacaacgat cggaggaccg aaggagctaa   5580

ccgctttttt gcacaacatg ggggatcatg taactcgcct tgatcgttgg gaaccggagc   5640

tgaatgaagc cataccaaac gacgagcgtg acaccacgat gcctgtagca atggcaacaa   5700

cgttgcgcaa actattaact ggcgaactac ttactctagc ttcccggcaa caattaatag   5760

actggatgga ggcggataaa gttgcaggac cacttctgcg ctcggccctt ccggctggct   5820

ggtttattgc tgataaatct ggagccggtg agcgtgggtc tcgcggtatc attgcagcac   5880

tggggccaga tggtaagccc tcccgtatcg tagttatcta cacgacgggg agtcaggcaa   5940

ctatggatga acgaaataga cagatcgctg agataggtgc ctcactgatt aagcattggt   6000

aactgtcaga ccaagtttac tcatatatac tttagattga tttaaaactt catttttaat   6060

ttaaaaggat ctaggtgaag atcctttttg ataatctcat gaccaaaatc ccttaacgtg   6120

agttttcgtt ccactgagcg tcagaccccg tagaaaagat caaaggatct tcttgagatc   6180

cttttttct gcgcgtaatc tgctgcttgc aaacaaaaaa accaccgcta ccagcggtgg   6240

tttgtttgcc ggatcaagag ctaccaactc tttttccgaa ggtaactggc ttcagcagag   6300

cgcagatacc aaatactgtt cttctagtgt agccgtagtt aggccaccac ttcaagaact   6360

ctgtagcacc gcctacatac ctcgctctgc taatcctgtt accagtggct gctgccagtg   6420

gcgataagtc gtgtcttacc gggttggact caagacgata gttaccggat aaggcgcagc   6480

ggtcgggctg aacggggggt tcgtgcacac agcccagctt ggagcgaacg acctacaccg   6540

aactgagata cctacagcgt gagctatgag aaagcgccac gcttcccgaa gggagaaagg   6600

cggacaggta tccggtaagc ggcagggtcg gaacaggaga gcgcacgagg gagcttccag   6660

ggggaaacgc ctggtatctt tatagtcctg tcgggtttcg ccacctctga cttgagcgtc   6720

gatttttgtg atgctcgtca ggggggcgga gcctatggaa aaacgccagc aacgcggcct   6780

ttttacggtt cctggccttt tgctggcctt ttgctcacat gttctttcct gcgttatccc   6840

ctgattctgt ggataaccgt attaccgcct ttgagtgagc tgataccgct cgccgcagcc   6900

gaacgaccga gcgcagcgag tcagtgagcg aggaagcgga agagcgccca atacgcaaac   6960

cgcctctccc cgcgcgttgg ccgattcatt aatgcagctg gcgcgcccac tgagctcgtc   7020
```

```
taacggactt gatatacaac caattaaaac aaatgaaaag aaatacagtt ctttgtatca   7080
tttgtaacaa ttaccctgta caaactaagg tattgaaatc ccacaatatt cccaaagtcc   7140
accccttcc aaattgtcat gcctacaact catataccaa gcactaacct accaaacacc   7200
actaaaaccc cacaaaatat atcttaccga atatacagta acaagctacc accacactcg   7260
ttgggtgcag tcgccagctt aaagatatct atccacatca gccacaactc ccttccttta   7320
ataaaccgac tacacccttg gctattgagg ttatgagtga atatactgta gacaagacac   7380
tttcaagaag actgtttcca aaacgtacca ctgtcctcca ctacaaacac acccaatctg   7440
cttcttctag tcaaggttgc tacaccggta aattataaat catcatttca ttagcagggc   7500
agggcccttt ttatagagtc ttatacacta gcggaccctg ccggtagacc aacccgcagg   7560
cgcgtcagtt tgctccttcc atcaatgcgt cgtagaaacg acttactcct tcttgagcag   7620
ctccttgacc ttgttggcaa caagtctccg acctcggagg tggaggaaga gcctccgata   7680
tcggcggtag tgataccagc ctcgacggac tccttgacgg cagcctcaac agcgtcaccg   7740
gcgggcttca tgttaagaga gaacttgagc atcatggcgg cagacagaat ggtggcgtac   7800
gcaactaaca tgaatgaata cgatatacat caaagactat gatacgcagt attgcacact   7860
gtacgagtaa gagcactagc cactgcactc aagtgaaacc gttgcccggg tacgagtatg   7920
agtatgtaca gtatgtttag tattgtactt ggacagtgct tgtatcgtac attctcaagt   7980
gtcaaacata aatatccgtt gctatatcct cgcaccacca cgtagctcgc tatatccctg   8040
tgttgaatcc atccatcttg gattgccaat tgtgcacaca gaaccgggca ctcacttccc   8100
catccacact tgcggccgcg cctacttaag caacgggctt gataacagcg gggggggtgc   8160
ccacgttgtt gcggttgcgg aagaacagaa cacccttacc agcaccctcg gcaccagcgc   8220
tgggctcaac ccactggcac atacgcgcac tgcggtacat ggcgcggatg aagccacgag   8280
gaccatcctg gacatcagcc cggtagtgct tgcccatgat gggcttaatg gcctcggtgg   8340
cctcgtccgc gttgtagaag gggatgctgc tgacgtagtg gtggaggaca tgagtctcga   8400
tgatgccgtg gagaaggtgg cggccgatga agcccatctc acggtcaatg gtagcagcgg   8460
caccacggac gaagttccac tcgtcgttgg tgtagtgggg aagggtaggg tcggtgtgct   8520
ggaggaaggt gatggcaacg agccagtggt taacccagag gtagggaaca aagtaccaga   8580
tggccatgtt gtagaaaccg aacttctgaa cgaggaagta cagagcagtg gccatcagac   8640
cgataccaat atcgctgagg acgatgagct tagcgtcact gttctcgtac agagggctgc   8700
ggggatcgaa gtggttaaca ccaccgccga ggccgttatg cttgcccttg ccgcgaccct   8760
cacgctggcg ctcgtggtag ttgtggccgg taacattggt gatgaggtag ttgggccagc   8820
cnacgannnn ctcagtaaga tgagcgagct cgtgggtcat ctttccgaga cgagtagcct   8880
gctgctcgcg ggttcgggga acgaagacca tgtcacgctc catgttgcca gtggccttgt   8940
ggtgctttcg gtgggagatt tgccagctga agtaggggac aaggagggaa gagtgaagaa   9000
cccagccagt aatgtcgttg atgatgcgag aatcggagaa agcaccgtga ccgcactcat   9060
gggcaataac ccagagacca gtaccgaaaa gaccctgaag aacggtgtac acggcccaca   9120
gaccagcgcg ggcgggggtg gaggggatat attcgggggt cacaaagttg taccagatgc   9180
tgaaagtggt agtcaggagg acaatgtcgc ggaggatata accgtatccc ttgagagcgg   9240
agcgcttgaa gcagtgctta gggatggcat tgtagatgtc cttgatggta aagtcgggaa   9300
cctcgaactg gttgccgtag gtgtcgagca tgacaccata ctcggacttg ggcttggcga   9360
tatcaacctc ggacatggac gagagcgatg tggaagaggc cgagtggcgg ggagagtctg   9420
```

```
aaggagagac ggcggcagac tcagaatccg tcacagtagt tgaggtgacg gtgcgtctaa    9480
gcgcagggtt ctgcttgggc agagccgaag tggacgccat ggttgatgtg tgtttaattc    9540
aagaatgaat atagagaaga gaagaagaaa aaagattcaa ttgagccggc gatgcagacc    9600
cttatataaa tgttgccttg gacagacgga gcaagcccgc ccaaacctac gttcggtata    9660
atatgttaag ctttttaaca caaaggtttg gcttggggta acctgatgtg gtgcaaaaga    9720
ccgggcgttg gcgagccatt gcgcgggcga atggggccgt gactcgtctc aaattcgagg    9780
gcgtgcctca attcgtgccc ccgtggcttt ttcccgccgt ttccgccccg tttgcaccac    9840
tgcagccgct tctttggttc ggacaccttg ctgcgagcta ggtgccttgt gctacttaaa    9900
aagtggcctc ccaacaccaa catgacatga gtgcgtgggc caagacacgt tggcggggtc    9960
gcagtcggct caatggcccg gaaaaaacgc tgctggagct ggttcggacg cagtccgccg   10020
cggcgtatgg atatccgcaa ggttccatag cgccattgcc ctccgtcggc gtctatcccg   10080
caacctctaa atagagcggg aatataaccc aagcttcttt tttttccttt aacacgcaca   10140
cccccaacta tcatgttgct gctgctgttt gactctactc tgtggagggg tgctcccacc   10200
caacccaacc tacaggtgga tccggcgctg tgattggctg ataagtctcc tatccggact   10260
aattctgacc aatgggacat gcgcgcagga cccaaatgcc gcaattacgt aaccccaacg   10320
aaatgcctac ccctctttgg agcccagcgg ccccaaatcc ccccaagcag cccggttcta   10380
ccggcttcca tctccaagca caagcagccc ggttctaccg gcttccatct ccaagcaccc   10440
ctttctccac accccacaaa aagacccgtg caggacatcc tactgcgtcg acatcattta   10500
aattccttca cttcaagttc attcttcatc tgcttctgtt ttactttgac aggcaaatga   10560
agacatggta cgacttgatg gaggccaaga acgccatttc accccgagac accgaagtgc   10620
ctgaaatcct ggctgccccc attgataaca tcggaaacta cggtattccg gaaagtgtat   10680
atagaacctt tccccagctt gtgtctgtgg atatggatgg tgtaatcccc tttgagtact   10740
cgtcttggct tctctccgag cagtatgagg ctctctaatc tagcgcattt aatatctcaa   10800
tgtatttata tatttatctt ctcatgcggc cgctcactga atctttttgg ctcccttgtg   10860
cttcctgacg atatacgttt gcacatagaa attcaagaac aaacacaaga ctgtgccaac   10920
ataaaagtaa ttgaagaacc agccaaacat cctcatccca tcttggcgat aacagggaat   10980
gttcctgtac ttccagacaa tgtagaaacc aacattgaat tgaatgatct gcattgatgt   11040
aatcagggat tttggcatgg ggaacttcag cttgatcaat ctggtccaat aataaccgta   11100
catgatccag tggatgaaac cattcaacag cacaaaaatc caaacagctt catttcggta   11160
attatagaac agccacatat ccatcggtgc cccccaaatga tggaagaatt gcaaccaggt   11220
cagaggcttg cccatcagtg gcaaatagaa ggagtcaata tactccagga acttgctcaa   11280
atagaacaac tgcgtggtga tcctgaagac gttgttgtca aaagccttct cgcagttgtc   11340
agacataaca ccgatggtgt acatggcata tgccattgag aggaatgatc ccaacgaata   11400
aatggacatg agaaggttgt aattggtgaa aacaaacttc atacgagact gacctttttgg   11460
accaaggggg ccaagagtga acttcaagat gacaaatgcg atggacaagt aaagcacctc   11520
acagtgactg gcatcactcc agagttgggc ataatcaact ggttgggtaa aacttcctgc   11580
ccaattgaga ctatttcatt caccacctcc atggccattg ctgtagatat gtcttgtgtg   11640
taagggggtt ggggtggttg tttgtgttct tgacttttgt gttagcaagg gaagacgggc   11700
aaaaaagtga gtgtggttgg gagggagaga cgagccttat atataatgct tgtttgtgtt   11760
tgtgcaagtg gacgccgaaa cgggcaggag ccaaactaaa caaggcagac aatgcgagct   11820
```

```
taattggatt gcctgatggg caggggttag ggctcgatca atgggggtgc gaagtgacaa  11880
aattgggaat taggttcgca agcaaggctg acaagacttt ggcccaaaca tttgtacgcg  11940
gtggacaaca ggagccaccc atcgtctgtc acgggctagc cggtcgtgcg tcctgtcagg  12000
ctccacctag gctccatgcc actccataca atcccactag tgtaccgcta ggccgctttt  12060
agctcccatc taagaccccc ccaaaacctc cactgtacag tgcactgtac tgtgtggcga  12120
tcaagggcaa gggaaaaaag gcgcaaacat gcacgcatgg aatgacgtag gtaaggcgtt  12180
actagactga aaagtggcac atttcggcgt gccaaagggt cctaggtgcg tttcgcgagc  12240
tgggcgccag gccaagccgc tccaaaacgc ctctccgact ccctccagcg gcctccatat  12300
ccccatccct ctccacagca atgttgttaa gccttgcaaa cgaaaaaata gaaaggctaa  12360
taagcttcca atattgtggt gtacgctgca taacgcaaca atgagcgcca aacaacacac  12420
acacacagca cacagcagca ttaaccacga tgaacagcat gacattacag gtgggtgtgt  12480
aatcagggcc ctgattgctg gtggtgggag cccccatcat gggcagatct gcgtacactg  12540
tttaaacagt gtacgcagat ctactataga ggaacattta aattgccccg gagaagacgg  12600
ccaggccgcc tagatgacaa attcaacaac tcacagctga ctttctgcca ttgccactag  12660
ggggggcct ttttatatgg ccaagccaag ctctccacgt cggttgggct gcacccaaca  12720
ataaatgggt agggttgcac caacaaaggg atgggatggg gggtagaaga tacgaggata  12780
acggggctca atggcacaaa taagaacgaa tactgccatt aagactcgtg atccagcgac  12840
tgacaccatt gcatcatcta agggcctcaa aactacctcg gaactgctgc gctgatctgg  12900
acaccacaga ggttccgagc actttaggtt gcaccaaatg tcccaccagg tgcaggcaga  12960
aaacgctgga acagcgtgta cagtttgtct taacaaaaag tgagggcgct gaggtcgagc  13020
agggtggtgt gacttgttat agcctttaga gctgcgaaag cgcgtatgga tttggctcat  13080
caggccagat tgagggtctg tggacacatg tcatgttagt gtacttcaat cgccccctgg  13140
atatagcccc gacaataggc cgtggcctca tttttttgcc ttccgcacat ttccattgct  13200
cgatacccac accttgcttc tcctgcactt gccaacctta atactggttt acattgacca  13260
acatcttaca agcgggggc ttgtctaggg tatatataaa cagtggctct cccaatcggt  13320
tgccagtctc ttttttcctt tctttcccca cagattcgaa atctaaacta cacatcacag  13380
aattccgagc cgtgagtatc cacgacaaga tcagtgtcga gacgacgcgt tttgtgtaat  13440
gacacaatcc gaaagtcgct agcaacacac actctctaca caaactaacc cagctctggt  13500
accatggagg tcgtgaacga aatcgtctcc attggccagg aggttcttcc caaggtcgac  13560
tatgctcagc tctggtctga tgcctcgcac tgcgaggtgc tgtacctctc catcgccttc  13620
gtcatcctga agttcaccct tggtcctctc ggacccaagg gtcagtctcg aatgaagttt  13680
gtgttcacca actacaacct gctcatgtcc atctactcgc tgggctcctt cctctctatg  13740
gcctacgcca tgtacaccat tggtgtcatg tccgacaact gcgagaaggc tttcgacaac  13800
aatgtcttcc gaatcaccac tcagctgttc tacctcagca agttcctcga gtacattgac  13860
tccttctatc tgcccctcat gggcaagcct ctgacctggt tgcagttctt tcaccatctc  13920
ggagctccta tggacatgtg gctgttctac aactaccgaa acgaagccgt ttggatcttt  13980
gtgctgctca acggcttcat tcactggatc atgtacggct actattggac ccgactgatc  14040
aagctcaagt tccctatgcc caagtccctg attacttcta tgcagatcat tcagttcaac  14100
gttggcttct acatcgtctg gaagtaccgg aacattccct gctaccgaca agatggaatg  14160
agaatgtttg gctggttttt caactacttc tacgttggta ctgtcctgtg tctgttcctc  14220
```

```
aacttctacg tgcagaccta catcgtccga aagcacaagg gagccaaaaa gattcagtga  14280

gcggccgcat gtacatacaa gattatttat agaaatgaat cgcgatcgaa caaagagtac  14340

gagtgtacga gtaggggatg atgataaaag tggaagaagt tccgcatctt tggatttatc  14400

aacgtgtagg acgatacttc ctgtaaaaat gcaatgtctt taccataggt tctgctgtag  14460

atgttattaa ctaccattaa catgtctact tgtacagttg cagaccagtt ggagtataga  14520

atggtacact taccaaaaag tgttgatggt tgtaactacg atatataaaa ctgttgacgg  14580

gatccccgct gatatgccta aggaacaatc aaagaggaag atattaattc agaatgctag  14640

tatacagtta gggat                                                   14655
```

<210> SEQ ID NO 18
<211> LENGTH: 34
<212> TYPE: DNA
<213> ORGANISM: Escherichia coli

<400> SEQUENCE: 18

```
ataacttcgt ataatgtatg ctatacgaag ttat                                 34
```

<210> SEQ ID NO 19
<211> LENGTH: 828
<212> TYPE: DNA
<213> ORGANISM: Mortierella alpina
<220> FEATURE:
<221> NAME/KEY: misc_feature
<223> OTHER INFORMATION: synthetic C16/18 elongase codon-optimized for Yarrowia lipolytica; U.S. Patent Application No. 11/253882, filed October 19, 2005

<400> SEQUENCE: 19

```
atggagtctg gacccatgcc tgctggcatt cccttccctg agtactatga cttctttatg     60

gactggaaga ctcccctggc catcgctgcc acctacactg ctgccgtcgg tctcttcaac    120

cccaaggttg gcaaggtctc ccgagtggtt gccaagtcgg ctaacgcaaa gcctgccgag    180

cgaacccagt ccggagctgc catgactgcc ttcgtctttg tgcacaacct cattctgtgt    240

gtctactctg gcatcacctt ctactacatg tttcctgcta tggtcaagaa cttccgaacc    300

cacacactgc acgaagccta ctgcgacacg gatcagtccc tctggaacaa cgcacttggc    360

tactggggtt acctcttcta cctgtccaag ttctacgagg tcattgacac catcatcatc    420

atcctgaagg gacgacggtc ctcgctgctt cagacctacc accatgctgg agccatgatt    480

accatgtggt ctggcatcaa ctaccaagcc actcccattt ggatctttgt ggtcttcaac    540

tccttcattc acaccatcat gtactgttac tatgccttca cctctatcgg attccatcct    600

cctggcaaaa agtacctgac ttcgatgcag attactcagt ttctggtcgg tatcaccatt    660

gccgtgtcct acctcttcgt tcctggctgc atccgaacac ccggtgctca gatggctgtc    720

tggatcaacg tcggctacct gtttcccttg acctatctgt tcgtggactt tgccaagcga    780

acctactcca agcgatctgc cattgccgct cagaaaaagg ctcagtaa                 828
```

<210> SEQ ID NO 20
<211> LENGTH: 8910
<212> TYPE: DNA
<213> ORGANISM: Artificial Sequence
<220> FEATURE:
<223> OTHER INFORMATION: Plasmid pFmD8S

<400> SEQUENCE: 20

```
catggtgaag tccaagcgac aggctctgcc cctcaccatc gacggaacta cctacgacgt     60

ctccgcttgg gtgaacttcc accctggtgg agctgaaatc attgagaact accagggacg    120
```

-continued

```
agatgctact gacgccttca tggttatgca ctctcaggaa gccttcgaca agctcaagcg    180
aatgcccaag atcaacccct cctccgagct gcctccccag gctgccgtca acgaagctca    240
ggaggatttc cgaaagctcc gagaagagct gatcgccact ggcatgtttg acgcctctcc    300
cctctggtac tcgtacaaga tctccaccac cctgggtctt ggcgtgcttg gatacttcct    360
gatggtccag taccagatgt acttcattgg tgctgtgctg ctcggtatgc actaccagca    420
aatgggatgg ctgtctcatg acatctgcca ccaccagacc ttcaagaacc gaaactggaa    480
taacctcgtg ggtctggtct ttggcaacgg actccagggc ttctccgtga cctggtggaa    540
ggacagacac aacgcccatc attctgctac caacgttcag ggtcacgatc ccgacattga    600
taacctgcct ctgctcgcct ggtccgagga cgatgtcact cgagcttctc ccatctcccg    660
aaagctcatt cagttccaac agtactattt cctggtcatc tgtattctcc tgcgattcat    720
ctggtgtttc cagtctgtgc tgaccgttcg atccctcaag gaccgagaca accagttcta    780
ccgatctcag tacaagaaag aggccattgg actcgctctg cactggactc tcaagaccct    840
gttccacctc ttctttatgc cctccatcct gacctcgctc ctggtgttct ttgtttccga    900
gctcgtcggt ggcttcggaa ttgccatcgt ggtcttcatg aaccactacc ctctggagaa    960
gatcggtgat tccgtctggg acggacatgg cttctctgtg ggtcagatcc atgagaccat   1020
gaacattcga cgaggcatca ttactgactg gttctttgga ggcctgaact accagatcga   1080
gcaccatctc tggcccaccc tgcctcgaca caacctcact gccgtttcct accaggtgga   1140
acagctgtgc cagaagcaca acctccccta ccgaaaccct ctgccccatg aaggtctcgt   1200
catcctgctc cgatacctgg ccgtgttcgc tcgaatggcc gagaagcagc ccgctggcaa   1260
ggctctctaa gcggccgcca ccgcggcccg agattccggc ctcttcggcc gccaagcgac   1320
ccgggtggac gtctagaggt acctagcaat taacagatag tttgccggtg ataattctct   1380
taacctccca cactcctttg acataacgat ttatgtaacg aaactgaaat ttgaccagat   1440
attgtgtccg cggtggagct ccagcttttg ttccctttag tgagggttaa tttcgagctt   1500
ggcgtaatca tggtcatagc tgtttcctgt gtgaaattgt tatccgctca caattccaca   1560
caacatacga gccggaagca taaagtgtaa agcctggggt gcctaatgag tgagctaact   1620
cacattaatt gcgttgcgct cactgcccgc tttccagtcg ggaaacctgt cgtgccagct   1680
gcattaatga atcggccaac gcgcggggag aggcggtttg cgtattgggc gctcttccgc   1740
ttcctcgctc actgactcgc tgcgctcggt cgttcggctg cggcgagcgg tatcagctca   1800
ctcaaaggcg gtaatacggt tatccacaga atcaggggat aacgcaggaa agaacatgtg   1860
agcaaaaggc cagcaaaagg ccaggaaccg taaaaaggcc gcgttgctgg cgtttttcca   1920
taggctccgc ccccctgacg agcatcacaa aaatcgacgc tcaagtcaga ggtggcgaaa   1980
cccgacagga ctataaagat accaggcgtt tccccctgga agctccctcg tgcgctctcc   2040
tgttccgacc ctgccgctta ccggatacct gtccgccttt ctcccttcgg gaagcgtggc   2100
gctttctcat agctcacgct gtaggtatct cagttcggtg taggtcgttc gctccaagct   2160
gggctgtgtg cacgaacccc ccgttcagcc cgaccgctgc gccttatccg gtaactatcg   2220
tcttgagtcc aacccggtaa gacacgactt atcgccactg gcagcagcca ctggtaacag   2280
gattagcaga gcgaggtatg taggcggtgc tacagagttc ttgaagtggt ggcctaacta   2340
cggctacact agaaggacag tatttggtat ctgcgctctg ctgaagccag ttaccttcgg   2400
aaaaagagtt ggtagctctt gatccggcaa acaaaccacc gctggtagcg gtggtttttt   2460
tgtttgcaag cagcagatta cgcgcagaaa aaaaggatct caagaagatc ctttgatctt   2520
```

```
ttctacgggg tctgacgctc agtggaacga aaactcacgt taagggattt tggtcatgag   2580
attatcaaaa aggatcttca cctagatcct tttaaattaa aaatgaagtt ttaaatcaat   2640
ctaaagtata tatgagtaaa cttggtctga cagttaccaa tgcttaatca gtgaggcacc   2700
tatctcagcg atctgtctat ttcgttcatc catagttgcc tgactccccg tcgtgtagat   2760
aactacgata cgggagggct taccatctgg ccccagtgct gcaatgatac cgcgagaccc   2820
acgctcaccg gctccagatt tatcagcaat aaaccagcca gccggaaggg ccgagcgcag   2880
aagtggtcct gcaactttat ccgcctccat ccagtctatt aattgttgcc gggaagctag   2940
agtaagtagt tcgccagtta atagtttgcg caacgttgtt gccattgcta caggcatcgt   3000
ggtgtcacgc tcgtcgtttg gtatggcttc attcagctcc ggttcccaac gatcaaggcg   3060
agttacatga tcccccatgt tgtgcaaaaa agcggttagc tccttcggtc ctccgatcgt   3120
tgtcagaagt aagttggccg cagtgttatc actcatggtt atggcagcac tgcataattc   3180
tcttactgtc atgccatccg taagatgctt ttctgtgact ggtgagtact caaccaagtc   3240
attctgagaa tagtgtatgc ggcgaccgag ttgctcttgc ccggcgtcaa tacgggataa   3300
taccgcgcca catagcagaa ctttaaaagt gctcatcatt ggaaaacgtt cttcggggcg   3360
aaaactctca aggatcttac cgctgttgag atccagttcg atgtaaccca ctcgtgcacc   3420
caactgatct tcagcatctt ttactttcac cagcgtttct gggtgagcaa aaacaggaag   3480
gcaaaatgcc gcaaaaaagg gaataagggc gacacggaaa tgttgaatac tcatactctt   3540
cctttttcaa tattattgaa gcatttatca gggttattgt ctcatgagcg gatacatatt   3600
tgaatgtatt tagaaaaata aacaaatagg ggttccgcgc acatttcccc gaaaagtgcc   3660
acctgacgcg ccctgtagcg gcgcattaag cgcggcgggt gtggtggtta cgcgcagcgt   3720
gaccgctaca cttgccagcg ccctagcgcc cgctcctttc gctttcttcc cttcctttct   3780
cgccacgttc gccggctttc cccgtcaagc tctaaatcgg gggctccctt tagggttccg   3840
atttagtgct ttacggcacc tcgaccccaa aaaacttgat tagggtgatg gttcacgtag   3900
tgggccatcg ccctgataga cggtttttcg ccctttgacg ttggagtcca cgttctttaa   3960
tagtggactc ttgttccaaa ctggaacaac actcaaccct atctcggtct attcttttga   4020
tttataaggg attttgccga tttcggccta ttggttaaaa aatgagctga tttaacaaaa   4080
atttaacgcg aattttaaca aaatattaac gcttacaatt tccattcgcc attcaggctg   4140
cgcaactgtt gggaagggcg atcggtgcgg gcctcttcgc tattacgcca gctggcgaaa   4200
gggggatgtg ctgcaaggcg attaagttgg gtaacgccag ggttttccca gtcacgacgt   4260
tgtaaaacga cggccagtga attgtaatac gactcactat agggcgaatt gggtaccggg   4320
ccccccctcg aggtcgatgg tgtcgataag cttgatatcg aattcatgtc acacaaaccg   4380
atcttcgcct caaggaaacc taattctaca tccgagagac tgccgagatc cagtctacac   4440
tgattaattt tcgggccaat aatttaaaaa aatcgtgtta tataatatta tatgtattat   4500
atatatacat catgatgata ctgacagtca tgtcccattg ctaaatagac agactccatc   4560
tgccgcctcc aactgatgtt ctcaatattt aaggggtcat ctcgcattgt ttaataataa   4620
acagactcca tctaccgcct ccaaatgatg ttctcaaaat atattgtatg aacttatttt   4680
tattacttag tattattaga caacttactt gctttatgaa aaacacttcc tatttaggaa   4740
acaatttata atggcagttc gttcatttaa caatttatgt agaataaatg ttataaatgc   4800
gtatgggaaa tcttaaatat ggatagcata aatgatatct gcattgccta attcgaaatc   4860
aacagcaacg aaaaaaatcc cttgtacaac ataaatagtc atcgagaaat atcaactatc   4920
```

-continued

```
aaagaacagc tattcacacg ttactattga gattattatt ggacgagaat cacacactca   4980
actgtctttc tctcttctag aaatacaggt acaagtatgt actattctca ttgttcatac   5040
ttctagtcat ttcatcccac atattccttg gatttctctc caatgaatga cattctatct   5100
tgcaaattca acaattataa taagatatac caaagtagcg gtatagtggc aatcaaaaag   5160
cttctctggt gtgcttctcg tatttatttt tattctaatg atccattaaa ggtatatatt   5220
tatttcttgt tatataatcc ttttgtttat tacatgggct ggatacataa aggtattttg   5280
atttaatttt ttgcttaaat tcaatccccc ctcgttcagt gtcaactgta atggtaggaa   5340
attaccatac ttttgaagaa gcaaaaaaaa tgaaagaaaa aaaaaatcgt atttccaggt   5400
tagacgttcc gcagaatcta gaatgcggta tgcggtacat tgttcttcga acgtaaaagt   5460
tgcgctccct gagatattgt acatttttgc ttttacaagt acaagtacat cgtacaacta   5520
tgtactactg ttgatgcatc cacaacagtt tgttttgttt ttttttgttt ttttttttc   5580
taatgattca ttaccgctat gtatacctac ttgtacttgt agtaagccgg gttattggcg   5640
ttcaattaat catagactta tgaatctgca cggtgtgcgc tgcgagttac ttttagctta   5700
tgcatgctac ttgggtgtaa tattgggatc tgttcggaaa tcaacggatg ctcaaccgat   5760
ttcgacagta ataatttgaa tcgaatcgga gcctaaaatg aacccgagta tatctcataa   5820
aattctcggt gagaggtctg tgactgtcag tacaaggtgc cttcattatg ccctcaacct   5880
taccatacct cactgaatgt agtgtacctc taaaaatgaa atacagtgcc aaaagccaag   5940
gcactgagct cgtctaacgg acttgatata caaccaatta aaacaaatga aaagaaatac   6000
agttctttgt atcatttgta acaattaccc tgtacaaact aaggtattga aatcccacaa   6060
tattcccaaa gtccacccct ttccaaattg tcatgcctac aactcatata ccaagcacta   6120
acctaccaaa caccactaaa accccacaaa atatatctta ccgaatatac agtaacaagc   6180
taccaccaca ctcgttgggt gcagtcgcca gcttaaagat atctatccac atcagccaca   6240
actcccttcc tttaataaac cgactacacc cttggctatt gaggttatga gtgaatatac   6300
tgtagacaag acactttcaa gaagactgtt tccaaaacgt accactgtcc tccactacaa   6360
acacacccaa tctgcttctt ctagtcaagg ttgctacacc ggtaaattat aaatcatcat   6420
ttcattagca gggcagggcc ctttttatag agtcttatac actagcggac cctgccggta   6480
gaccaacccg caggcgcgtc agtttgctcc ttccatcaat gcgtcgtaga aacgacttac   6540
tccttcttga gcagctcctt gaccttgttg gcaacaagtc tccgacctcg gaggtggagg   6600
aagagcctcc gatatcggcg gtagtgatac cagcctcgac ggactccttg acggcagcct   6660
caacagcgtc accggcgggc ttcatgttaa gagagaactt gagcatcatg gcggcagaca   6720
gaatggtggc aatggggttg accttctgct tgccgagatc gggggcagat ccgtgacagg   6780
gctcgtacag accgaacgcc tcgttggtgt cgggcagaga agccagagag gcggagggca   6840
gcagacccag agaaccgggg atgacggagg cctcgtcgga gatgatatcg ccaaacatgt   6900
tggtggtgat gatgatacca ttcatcttgg agggctgctt gatgaggatc atggcggccg   6960
agtcgatcag ctggtggttg agctcgagct gggggaattc gtccttgagg actcgagtga   7020
cagtctttcg ccaaagtcga gaggaggcca gcacgttggc cttgtcaaga gaccacacgg   7080
gaagaggggg gttgtgctga agggccagga aggcggccat tcgggcaatt cgctcaacct   7140
caggaacgga gtaggtctcg gtgtcggaag cgacgccaga tccgtcatcc tcctttcgct   7200
ctccaaagta gatacctccg acgagctctc ggacaatgat gaagtcggtg ccctcaacgt   7260
ttcggatggg ggagagatcg gcgagcttgg gcgacagcag ctggcagggt cgcaggttgg   7320
```

```
cgtacaggtt caggtccttt cgcagcttga ggagaccctg ctcgggtcgc acgtcggttc   7380

gtccgtcggg agtggtccat acggtgttgg cagcgcctcc gacagcaccg agcataatag   7440

agtcagcctt tcggcagatg tcgagagtag cgtcggtgat gggctcgccc tccttctcaa   7500

tggcagctcc tccaatgagt cggtcctcaa acacaaactc ggtgccggag gcctcagcaa   7560

cagacttgag caccttgacg gcctcggcaa tcacctcggg gccacagaag tcgccgccga   7620

gaagaacaat cttcttggag tcagtcttgg tcttcttagt ttcgggttcc attgtggatg   7680

tgtgtggttg tatgtgtgat gtggtgtgtg gagtgaaaat ctgtggctgg caaacgctct   7740

tgtatatata cgcacttttg cccgtgctat gtggaagact aaacctccga agattgtgac   7800

tcaggtagtg cggtatcggc tagggaccca aaccttgtcg atgccgatag cgctatcgaa   7860

cgtaccccag ccggccggga gtatgtcgga ggggacatac gagatcgtca agggtttgtg   7920

gccaactggt aaataaatga tgtcgacgtt taaacagtgt acgcagatct actatagagg   7980

aacatttaaa ttgccccgga gaagacggcc aggccgccta gatgacaaat tcaacaactc   8040

acagctgact ttctgccatt gccactaggg gggggccttt ttatatggcc aagccaagct   8100

ctccacgtcg gttgggctgc acccaacaat aaatgggtag ggttgcacca acaaagggat   8160

gggatggggg gtagaagata cgaggataac ggggctcaat ggcacaaata agaacgaata   8220

ctgccattaa gactcgtgat ccagcgactg acaccattgc atcatctaag ggcctcaaaa   8280

ctacctcgga actgctgcgc tgatctggac accacagagg ttccgagcac tttaggttgc   8340

accaaatgtc ccaccaggtg caggcagaaa acgctggaac agcgtgtaca gtttgtctta   8400

acaaaaagtg agggcgctga ggtcgagcag ggtggtgtga cttgttatag cctttagagc   8460

tgcgaaagcg cgtatggatt tggctcatca ggccagattg agggtctgtg gacacatgtc   8520

atgttagtgt acttcaatcg cccccctggat atagccccga caataggccg tggcctcatt   8580

tttttgcctt ccgcacattt ccattgctcg gtacccacac cttgcttctc ctgcacttgc   8640

caaccttaat actggtttac attgaccaac atcttacaag cggggggctt gtctagggta   8700

tatataaaca gtggctctcc caatcggttg ccagtctctt ttttcctttc tttccccaca   8760

gattcgaaat ctaaactaca catcacagaa ttccgagccg tgagtatcca cgacaagatc   8820

agtgtcgaga cgacgcgttt tgtgtaatga cacaatccga aagtcgctag caacacacac   8880

tctctacaca aactaaccca gctctggtac                                    8910
```

```
<210> SEQ ID NO 21
<211> LENGTH: 7145
<212> TYPE: DNA
<213> ORGANISM: Artificial Sequence
<220> FEATURE:
<223> OTHER INFORMATION: Plasmid pKUNFmkF2
<220> FEATURE:
<221> NAME/KEY: misc_feature
<222> LOCATION: (692)..(695)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 21
```

```
catggcgtcc acttcggctc tgcccaagca gaaccctgcg cttagacgca ccgtcacctc     60

aactactgtg acggattctg agtctgccgc cgtctctcct tcagactctc cccgccactc    120

ggcctcttcc acatcgctct cgtccatgtc cgaggttgat atcgccaagc ccaagtccga    180

gtatggtgtc atgctcgaca cctacggcaa ccagttcgag gttcccgact ttaccatcaa    240
```

```
ggacatctac aatgccatcc ctaagcactg cttcaagcgc tccgctctca agggatacgg    300
ttatatcctc cgcgacattg tcctcctgac taccactttc agcatctggt acaactttgt    360
gacccccgaa tatatcccct ccacccccgc ccgcgctggt ctgtgggccg tgtacaccgt    420
tcttcagggt cttttcggta ctggtctctg ggttattgcc catgagtgcg gtcacggtgc    480
tttctccgat tctcgcatca tcaacgacat tactggctgg gttcttcact cttccctcct    540
tgtcccctac ttcagctggc aaatctccca ccgaaagcac cacaaggcca ctggcaacat    600
ggagcgtgac atggtcttcg ttccccgaac ccgcgagcag caggctactc gtctcggaaa    660
gatgacccac gagctcgctc atcttactga gnnnntcgtn ggctggccca actacctcat    720
caccaatgtt accggccaca actaccacga gcgccagcgt gagggtcgcg gcaagggcaa    780
gcataacggc ctcggcggtg gtgttaacca cttcgatccc cgcagccctc tgtacgagaa    840
cagtgacgct aagctcatcg tcctcagcga tattggtatc ggtctgatgg ccactgctct    900
gtacttcctc gttcagaagt tcggtttcta caacatggcc atctggtact ttgttcccta    960
cctctgggtt aaccactggc tcgttgccat caccttcctc cagcacaccg accctaccct   1020
tccccactac accaacgacg agtggaactt cgtccgtggt gccgctgcta ccattgaccg   1080
tgagatgggc ttcatcggcc gccaccttct ccacggcatc atcgagactc atgtcctcca   1140
ccactacgtc agcagcatcc ccttctacaa cgcggacgag gccaccgagg ccattaagcc   1200
catcatgggc aagcactacc gggctgatgt ccaggatggt cctcgtggct tcatccgcgc   1260
catgtaccgc agtgcgcgta tgtgccagtg ggttgagccc agcgctggtg ccgagggtgc   1320
tggtaagggt gttctgttct tccgcaaccg caacaacgtg ggcacccccc ccgctgttat   1380
caagcccgtt gcttaagtag gcgcggccgc tatttatcac tctttacaac ttctacctca   1440
actatctact ttaataaatg aatatcgttt attctctatg attactgtat atgcgttcct   1500
ctaagacaaa tcgaaaccag catgtgatcg aatggcatac aaaagtttct tccgaagttg   1560
atcaatgtcc tgatagtcag gcagcttgag aagattgaca caggtggagg ccgtagggaa   1620
ccgatcaacc tgtctaccag cgttacgaat ggcaaatgac gggttcaaag ccttgaatcc   1680
ttgcaatggt gccttggata ctgatgtcac aaacttaaga agcagccgct tgtcctcttc   1740
ctcgatcgat ggtcatagct gtttcctgtg tgaaattgtt atccgctcac aattccacac   1800
aacgtacgaa gtcgtcaatg atgtcgatat gggttttgat catgcacaca taaggtccga   1860
ccttatcggc aagctcaatg agctccttgg tggtggtaac atccagagaa gcacacaggt   1920
tggttttctt ggctgccacg agcttgagca ctcgagcggc aaaggcggac ttgtggacgt   1980
tagctcgagc ttcgtaggag ggcattttgg tggtgaagag gagactgaaa taaatttagt   2040
ctgcagaact ttttatcgga accttatctg ggcagtgaa gtatatgtta tggtaatagt    2100
tacgagttag ttgaacttat agatagactg gactatacgg ctatcggtcc aaattagaaa   2160
gaacgtcaat ggctctctgg gcgtcgcctt tgccgacaaa aatgtgatca tgatgaaagc   2220
cagcaatgac gttgcagctg atattgttgt cggccaaccg cgccgaaaac gcagctgtca   2280
gacccacagc ctccaacgaa gaatgtatcg tcaaagtgat ccaagcacac tcatagttgg   2340
agtcgtactc caaaggcggc aatgacgagt cagacagata ctcgtcgacc ttttccttgg   2400
gaaccaccac cgtcagccct tctgactcac gtattgtagc caccgacaca ggcaacagtc   2460
cgtggatagc agaatatgtc ttgtcggtcc atttctcacc aactttaggc gtcaagtgaa   2520
tgttgcagaa gaagtatgtg ccttcattga gaatcggtgt tgctgatttc aataaagtct   2580
tgagatcagt ttggcgcgcc agctgcatta atgaatcggc caacgcgcgg ggagaggcgg   2640
```

-continued

```
tttgcgtatt gggcgctctt ccgcttcctc gctcactgac tcgctgcgct cggtcgttcg   2700
gctgcggcga gcggtatcag ctcactcaaa ggcggtaata cggttatcca cagaatcagg   2760
ggataacgca ggaaagaaca tgtgagcaaa aggccagcaa aaggccagga accgtaaaaa   2820
ggccgcgttg ctggcgtttt tccataggct ccgcccccct gacgagcatc acaaaaatcg   2880
acgctcaagt cagaggtggc gaaacccgac aggactataa agataccagg cgtttccccc   2940
tggaagctcc ctcgtgcgct ctcctgttcc gaccctgccg cttaccggat acctgtccgc   3000
ctttctccct tcgggaagcg tggcgctttc tcatagctca cgctgtaggt atctcagttc   3060
ggtgtaggtc gttcgctcca agctgggctg tgtgcacgaa ccccccgttc agcccgaccg   3120
ctgcgcctta tccggtaact atcgtcttga gtccaacccg gtaagacacg acttatcgcc   3180
actggcagca gccactggta acaggattag cagagcgagg tatgtaggcg gtgctacaga   3240
gttcttgaag tggtggccta actacggcta cactagaaga acagtatttg gtatctgcgc   3300
tctgctgaag ccagttacct tcggaaaaag agttggtagc tcttgatccg gcaaacaaac   3360
caccgctggt agcggtggtt tttttgtttg caagcagcag attacgcgca gaaaaaaagg   3420
atctcaagaa gatcctttga tcttttctac ggggtctgac gctcagtgga acgaaaactc   3480
acgttaaggg attttggtca tgagattatc aaaaaggatc ttcacctaga tccttttaaa   3540
ttaaaaatga agttttaaat caatctaaag tatatatgag taaacttggt ctgacagtta   3600
ccaatgctta atcagtgagg cacctatctc agcgatctgt ctatttcgtt catccatagt   3660
tgcctgactc cccgtcgtgt agataactac gatacgggag ggcttaccat ctggccccag   3720
tgctgcaatg ataccgcgag acccacgctc accggctcca gatttatcag caataaacca   3780
gccagccgga agggccgagc gcagaagtgg tcctgcaact ttatccgcct ccatccagtc   3840
tattaattgt tgccgggaag ctagagtaag tagttcgcca gttaatagtt tgcgcaacgt   3900
tgttgccatt gctacaggca tcgtggtgtc acgctcgtcg tttggtatgg cttcattcag   3960
ctccggttcc caacgatcaa ggcgagttac atgatccccc atgttgtgca aaaaagcggt   4020
tagctccttc ggtcctccga tcgttgtcag aagtaagttg gccgcagtgt tatcactcat   4080
ggttatggca gcactgcata attctcttac tgtcatgcca tccgtaagat gcttttctgt   4140
gactggtgag tactcaacca agtcattctg agaatagtgt atgcggcgac cgagttgctc   4200
ttgcccggcg tcaatacggg ataataccgc gccacatagc agaactttaa aagtgctcat   4260
cattggaaaa cgttcttcgg ggcgaaaact ctcaaggatc ttaccgctgt tgagatccag   4320
ttcgatgtaa cccactcgtg cacccaactg atcttcagca tcttttactt tcaccagcgt   4380
ttctgggtga gcaaaaacag gaaggcaaaa tgccgcaaaa aagggaataa gggcgacacg   4440
gaaatgttga atactcatac tcttcctttt tcaatattat tgaagcattt atcagggtta   4500
ttgtctcatg agcggataca tatttgaatg tatttagaaa aataaacaaa taggggttcc   4560
gcgcacattt ccccgaaaag tgccacctga tgcggtgtga aataccgcac agatgcgtaa   4620
ggagaaaata ccgcatcagg aaattgtaag cgttaatatt ttgttaaaat tcgcgttaaa   4680
tttttgttaa atcagctcat tttttaacca ataggccgaa atcggcaaaa tcccttataa   4740
atcaaaagaa tagaccgaga tagggttgag tgttgttcca gtttggaaca agagtccact   4800
attaaagaac gtggactcca acgtcaaagg gcgaaaaacc gtctatcagg gcgatggccc   4860
actacgtgaa ccatcaccct aatcaagttt tttggggtcg aggtgccgta aagcactaaa   4920
tcggaaccct aaagggagcc cccgatttag agcttgacgg ggaaagccgg cgaacgtggc   4980
gagaaaggaa gggaagaaag cgaaaggagc gggcgctagg gcgctggcaa gtgtagcggt   5040
```

```
cacgctgcgc gtaaccacca cacccgccgc gcttaatgcg ccgctacagg gcgcgtccat   5100

tcgccattca ggctgcgcaa ctgttgggaa gggcgatcgg tgcgggcctc ttcgctatta   5160

cgccagctgg cgaaaggggg atgtgctgca aggcgattaa gttgggtaac gccagggttt   5220

tcccagtcac gacgttgtaa aacgacggcc agtgaattgt aatacgactc actatagggc   5280

gaattgggcc cgacgtcgca tgcagtggtg gtattgtgac tggggatgta gttgagaata   5340

agtcatacac aagtcagctt tcttcgagcc tcatataagt ataagtagtt caacgtatta   5400

gcactgtacc cagcatctcc gtatcgagaa acacaacaac atgccccatt ggacagatca   5460

tgcggataca caggttgtgc agtatcatac atactcgatc agacaggtcg tctgaccatc   5520

atacaagctg aacaagcgct ccatacttgc acgctctcta tatacacagt taaattacat   5580

atccatagtc taacctctaa cagttaatct tctggtaagc ctcccagcca gccttctggt   5640

atcgcttggc ctcctcaata ggatctcggt tctggccgta cagacctcgg ccgacaatta   5700

tgatatccgt tccggtagac atgacatcct caacagttcg gtactgctgt ccgagagcgt   5760

ctcccttgtc gtcaagaccc accccggggg tcagaataag ccagtcctca gagtcgccct   5820

taattaattt gaatcgaatc gatgagccta aaatgaaccc gagtatatct cataaaattc   5880

tcggtgagag gtctgtgact gtcagtacaa ggtgccttca ttatgccctc aaccttacca   5940

tacctcactg aatgtagtgt acctctaaaa atgaaataca gtgccaaaag ccaaggcact   6000

gagctcgtct aacggacttg atatacaacc aattaaaaca aatgaaaaga aatacagttc   6060

tttgtatcat ttgtaacaat taccctgtac aaactaaggt attgaaatcc cacaatattc   6120

ccaaagtcca cccctttcca aattgtcatg cctacaactc atataccaag cactaaccta   6180

ccgtttaaac agtgtacgca gatctactat agaggaacat ttaaattgcc ccggagaaga   6240

cggccaggcc gcctagatga caaattcaac aactcacagc tgactttctg ccattgccac   6300

taggggggggg cctttttata tggccaagcc aagctctcca cgtcggttgg gctgcaccca   6360

acaataaatg ggtagggttg caccaacaaa gggatgggat ggggggtaga agatacgagg   6420

ataacggggc tcaatggcac aaataagaac gaatactgcc attaagactc gtgatccagc   6480

gactgacacc attgcatcat ctaagggcct caaaactacc tcggaactgc tgcgctgatc   6540

tggacaccac agaggttccg agcactttag gttgcaccaa atgtcccacc aggtgcaggc   6600

agaaaacgct ggaacagcgt gtacagtttg tcttaacaaa aagtgagggc gctgaggtcg   6660

agcagggtgg tgtgacttgt tatagccttt agagctgcga aagcgcgtat ggatttggct   6720

catcaggcca gattgagggt ctgtggacac atgtcatgtt agtgtacttc aatcgccccc   6780

tggatatagc cccgacaata ggccgtggcc tcattttttt gccttccgca catttccatt   6840

gctcgatacc cacaccttgc ttctcctgca cttgccaacc ttaatactgg tttacattga   6900

ccaacatctt acaagcgggg ggcttgtcta gggtatatat aaacagtggc tctcccaatc   6960

ggttgccagt ctcttttttc ctttctttcc ccacagattc gaaatctaaa ctacacatca   7020

cagaattccg agccgtgagt atccacgaca agatcagtgt cgagacgacg cgttttgtgt   7080

aatgacacaa tccgaaagtc gctagcaaca cacactctct acacaaacta acccagctct   7140

ggtac                                                                7145
```

<210> SEQ ID NO 22
<211> LENGTH: 5473
<212> TYPE: DNA
<213> ORGANISM: Artificial Sequence
<220> FEATURE:
<223> OTHER INFORMATION: Plasmid pDMW287F

<400> SEQUENCE: 22

```
ggccgcattg atgattggaa acacacacat gggttatatc taggtgagag ttagttggac     60
agttatatat taaatcagct atgccaacgg taacttcatt catgtcaacg aggaaccagt    120
gactgcaagt aatatagaat ttgaccacct tgccattctc ttgcactcct ttactatatc    180
tcatttattt cttatataca aatcacttct tcttcccagc atcgagctcg gaaacctcat    240
gagcaataac atcgtggatc tcgtcaatag agggcttttt ggactccttg ctgttggcca    300
ccttgtcctt gctgtctggc tcattctgtt tcaacgcctt ttaattaatc gagcttggcg    360
taatcatggt catagctgtt tcctgtgtga aattgttatc cgctcacaat tccacacaac    420
atacgagccg gaagcataaa gtgtaaagcc tggggtgcct aatgagtgag ctaactcaca    480
ttaattgcgt tgcgctcact gcccgctttc cagtcgggaa acctgtcgtg ccagctgcat    540
taatgaatcg gccaacgcgc ggggagaggc ggtttgcgta ttgggcgctc ttccgcttcc    600
tcgctcactg actcgctgcg ctcggtcgtt cggctgcggc gagcggtatc agctcactca    660
aaggcggtaa tacggttatc cacagaatca ggggataacg caggaaagaa catgtgagca    720
aaaggccagc aaaaggccag gaaccgtaaa aaggccgcgt tgctggcgtt tttccatagg    780
ctccgccccc ctgacgagca tcacaaaaat cgacgctcaa gtcagaggtg gcgaaacccg    840
acaggactat aaagatacca ggcgtttccc cctggaagct ccctcgtgcg ctctcctgtt    900
ccgaccctgc cgcttaccgg atacctgtcc gcctttctcc cttcgggaag cgtggcgctt    960
tctcatagct cacgctgtag gtatctcagt tcggtgtagg tcgttcgctc caagctgggc   1020
tgtgtgcacg aaccccccgt tcagcccgac cgctgcgcct tatccggtaa ctatcgtctt   1080
gagtccaacc cggtaagaca cgacttatcg ccactggcag cagccactgg taacaggatt   1140
agcagagcga ggtatgtagg cggtgctaca gagttcttga agtggtggcc taactacggc   1200
tacactagaa ggacagtatt tggtatctgc gctctgctga agccagttac cttcggaaaa   1260
agagttggta gctcttgatc cggcaaacaa accaccgctg gtagcggtgg tttttttgtt   1320
tgcaagcagc agattacgcg cagaaaaaaa ggatctcaag aagatccttt gatcttttct   1380
acggggtctg acgctcagtg gaacgaaaac tcacgttaag ggattttggt catgagatta   1440
tcaaaaagga tcttcaccta gatcctttta aattaaaaat gaagttttaa atcaatctaa   1500
agtatatatg agtaaacttg gtctgacagt taccaatgct taatcagtga ggcacctatc   1560
tcagcgatct gtctatttcg ttcatccata gttgcctgac tccccgtcgt gtagataact   1620
acgatacggg agggcttacc atctggcccc agtgctgcaa tgataccgcg agacccacgc   1680
tcaccggctc cagatttatc agcaataaac cagccagccg gaagggccga gcgcagaagt   1740
ggtcctgcaa ctttatccgc ctccatccag tctattaatt gttgccggga agctagagta   1800
agtagttcgc cagttaatag tttgcgcaac gttgttgcca ttgctacagg catcgtggtg   1860
tcacgctcgt cgtttggtat ggcttcattc agctccggtt cccaacgatc aaggcgagtt   1920
acatgatccc ccatgttgtg caaaaaagcg gttagctcct tcggtcctcc gatcgttgtc   1980
agaagtaagt tggccgcagt gttatcactc atggttatgg cagcactgca taattctctt   2040
actgtcatgc catccgtaag atgcttttct gtgactggtg agtactcaac caagtcattc   2100
tgagaatagt gtatgcggcg accgagttgc tcttgcccgg cgtcaatacg ggataatacc   2160
gcgccacata gcagaacttt aaaagtgctc atcattggaa aacgttcttc ggggcgaaaa   2220
ctctcaagga tcttaccgct gttgagatcc agttcgatgt aacccactcg tgcacccaac   2280
tgatcttcag catcttttac tttcaccagc gtttctgggt gagcaaaaac aggaaggcaa   2340
```

```
aatgccgcaa aaaagggaat aagggcgaca cggaaatgtt gaatactcat actcttcctt   2400
tttcaatatt attgaagcat ttatcagggt tattgtctca tgagcggata catatttgaa   2460
tgtatttaga aaaataaaca aataggggtt ccgcgcacat ttccccgaaa agtgccacct   2520
gacgcgccct gtagcggcgc attaagcgcg gcgggtgtgg tggttacgcg cagcgtgacc   2580
gctacacttg ccagcgccct agcgcccgct cctttcgctt tcttcccttc ctttctcgcc   2640
acgttcgccg gctttccccg tcaagctcta aatcgggggc tccctttagg gttccgattt   2700
agtgctttac ggcacctcga ccccaaaaaa cttgattagg gtgatggttc acgtagtggg   2760
ccatcgccct gatagacggt ttttcgccct ttgacgttgg agtccacgtt ctttaatagt   2820
ggactcttgt tccaaactgg aacaacactc aaccctatct cggtctattc ttttgattta   2880
taagggattt tgccgatttc ggcctattgg ttaaaaaatg agctgattta acaaaaattt   2940
aacgcgaatt ttaacaaaat attaacgctt acaatttcca ttcgccattc aggctgcgca   3000
actgttggga agggcgatcg gtgcgggcct cttcgctatt acgccagctg gcgaaagggg   3060
gatgtgctgc aaggcgatta agttgggtaa cgccagggtt ttcccagtca cgacgttgta   3120
aaacgacggc cagtgaattg taatacgact cactataggg cgaattgggt accgggcccc   3180
ccctcgaggt cgacgtttaa acagtgtacg cagtactata gaggaacatc gattgccccg   3240
gagaagacgg ccaggccgcc tagatgacaa attcaacaac tcacagctga ctttctgcca   3300
ttgccactag gggggggcct tttatatggc caagccaag ctctccacgt cggttgggct    3360
gcacccaaca ataaatgggt agggttgcac caacaaaggg atgggatggg gggtagaaga   3420
tacgaggata acggggctca atggcacaaa taagaacgaa tactgccatt aagactcgtg   3480
atccagcgac tgacaccatt gcatcatcta agggcctcaa aactacctcg gaactgctgc   3540
gctgatctgg acaccacaga ggttccgagc actttaggtt gcaccaaatg tcccaccagg   3600
tgcaggcaga aaacgctgga acagcgtgta cagtttgtct taacaaaaag tgagggcgct   3660
gaggtcgagc agggtggtgt gacttgttat agcctttaga gctgcgaaag cgcgtatgga   3720
tttggctcat caggccagat tgagggtctg tggacacatg tcatgttagt gtacttcaat   3780
cgccccctgg atatagcccc gacaataggc cgtggcctca tttttttgcc ttccgcacat   3840
ttccattgct cggtacccac accttgcttc tcctgcactt gccaacctta atactggttt   3900
acattgacca acatcttaca agcggggggc ttgtctaggg tatatataaa cagtggctct   3960
cccaatcggt tgccagtctc ttttttcctt tctttcccca cagattcgaa atctaaacta   4020
cacatcacac aatgcctgtt actgacgtcc ttaagcgaaa gtccggtgtc atcgtcggcg   4080
acgatgtccg agccgtgagt atccacgaca agatcagtgt cgagacgacg cgttttgtgt   4140
aatgacacaa tccgaaagtc gctagcaaca cacactctct acacaaacta acccagctct   4200
ccatggtgaa gtccaagcga caggctctgc ccctcaccat cgacggaact acctacgacg   4260
tctccgcttg ggtgaacttc caccctggtg gagctgaaat cattgagaac taccagggac   4320
gagatgctac tgacgccttc atggttatgc actctcagga agccttcgac aagctcaagc   4380
gaatgcccaa gatcaacccc tcctccgagc tgcctcccca ggctgccgtc aacgaagctc   4440
aggaggattt ccgaaagctc cgagaagagc tgatcgccac tggcatgttt gacgcctctc   4500
ccctctggta ctcgtacaag atctccacca ccctgggtct tggcgtgctt ggatacttcc   4560
tgatggtcca gtaccagatg tacttcattg gtgctgtgct gctcggtatg cactaccagc   4620
aaatgggatg gctgtctcat gacatctgcc accaccagac cttcaagaac cgaaactgga   4680
ataacctcgt gggtctggtc tttggcaacg gactccaggg cttctccgtg acctggtgga   4740
```

```
aggacagaca caacgcccat cattctgcta ccaacgttca gggtcacgat cccgacattg   4800

ataacctgcc tctgctcgcc tggtccgagg acgatgtcac tcgagcttct cccatctccc   4860

gaaagctcat tcagttccaa cagtactatt tcctggtcat ctgtattctc ctgcgattca   4920

tctggtgttt ccagtctgtg ctgaccgttc gatccctcaa ggaccgagac aaccagttct   4980

accgatctca gtacaagaaa gaggccattg gactcgctct gcactggact ctcaagaccc   5040

tgttccacct cttctttatg ccctccatcc tgacctcgct cctggtgttc tttgtttccg   5100

agctcgtcgg tggcttcgga attgccatcg tggtcttcat gaaccactac cctctggaga   5160

agatcggtga ttccgtctgg gacggacatg gcttctctgt gggtcagatc catgagacca   5220

tgaacattcg acgaggcatc attactgact ggttctttgg aggcctgaac taccagatcg   5280

agcaccatct ctggcccacc ctgcctcgac acaacctcac tgccgtttcc taccaggtgg   5340

aacagctgtg ccagaagcac aacctcccct accgaaaccc tctgccccat gaaggtctcg   5400

tcatcctgct ccgatacctg gccgtgttcg ctcgaatggc cgagaagcag cccgctggca   5460

aggctctcta agc                                                      5473
```

<210> SEQ ID NO 23
<211> LENGTH: 9513
<212> TYPE: DNA
<213> ORGANISM: Artificial Sequence
<220> FEATURE:
<223> OTHER INFORMATION: Plasmid pDMW214

<400> SEQUENCE: 23

```
ggtggagctc cagcttttgt tccctttagt gagggttaat ttcgagcttg gcgtaatcat     60

ggtcatagct gtttcctgtg tgaaattgtt atccgctcac aattccacac aacatacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200

atgagtaaac ttggtctgac agttaccaat gcttaatcag tgaggcacct atctcagcga   1260

tctgtctatt tcgttcatcc atagttgcct gactccccgt cgtgtagata actacgatac   1320
```

```
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
```

```
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt tttttttct aatgattcat   4140
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg gggggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagagggggg   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
```

-continued

```
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aataaatgat gtcgacgttt aaacagtgta cgcagtacta tagaggaaca attgccccgg   6540
agaagacggc caggccgcct agatgacaaa ttcaacaact cacagctgac tttctgccat   6600
tgccactagg ggggggcctt tttatatggc caagccaagc tctccacgtc ggttgggctg   6660
cacccaacaa taaatgggta gggttgcacc aacaaaggga tgggatgggg ggtagaagat   6720
acgaggataa cggggctcaa tggcacaaat aagaacgaat actgccatta agactcgtga   6780
tccagcgact gacaccattg catcatctaa gggcctcaaa actacctcgg aactgctgcg   6840
ctgatctgga caccacagag gttccgagca ctttaggttg caccaaatgt cccaccaggt   6900
gcaggcagaa aacgctggaa cagcgtgtac agtttgtctt aacaaaaagt gagggcgctg   6960
aggtcgagca gggtggtgtg acttgttata gcctttagag ctgcgaaagc gcgtatggat   7020
ttggctcatc aggccagatt gagggtctgt ggacacatgt catgttagtg tacttcaatc   7080
gccccctgga tatagccccg acaataggcc gtggcctcat ttttttgcct tccgcacatt   7140
tccattgctc ggtacccaca ccttgcttct cctgcacttg ccaaccttaa tactggttta   7200
cattgaccaa catcttacaa gcgggggggct tgtctagggt atatataaac agtggctctc   7260
ccaatcggtt gccagtctct tttttccttt ctttccccac agattcgaaa tctaaactac   7320
acatcacaca atgcctgtta ctgacgtcct taagcgaaag tccggtgtca tcgtcggcga   7380
cgatgtccga gccgtgagta tccacgacaa gatcagtgtc gagacgacgc gttttgtgta   7440
atgacacaat ccgaaagtcg ctagcaacac acactctcta cacaaactaa cccagctctc   7500
catggcatgg atggtacgtc ctgtagaaac cccaacccgt gaaatcaaaa aactcgacgg   7560
cctgtgggca ttcagtctgg atcgcgaaaa ctgtggaatt gatcagcgtt ggtgggaaag   7620
cgcgttacaa gaaagccggg caattgctgt gccaggcagt tttaacgatc agttcgccga   7680
tgcagatatt cgtaattatg cgggcaacgt ctggtatcag cgcgaagtct ttataccgaa   7740
aggttgggca ggccagcgta tcgtgctgcg tttcgatgcg gtcactcatt acggcaaagt   7800
gtgggtcaat aatcaggaag tgatggagca tcagggcggc tatacgccat ttgaagccga   7860
tgtcacgccg tatgttattg ccgggaaaag tgtacgtatc accgtttgtg tgaacaacga   7920
actgaactgg cagactatcc cgccgggaat ggtgattacc gacgaaaacg gcaagaaaaa   7980
gcagtcttac ttccatgatt tctttaacta tgccgggatc catcgcagcg taatgctcta   8040
caccacgccg aacacctggg tggacgatat caccgtggtg acgcatgtcg cgcaagactg   8100
taaccacgcg tctgttgact ggcaggtggt ggccaatggt gatgtcagcg ttgaactgcg   8160
tgatgcggat caacaggtgg ttgcaactgg acaaggcact agcgggactt tgcaagtggt   8220
gaatccgcac ctctggcaac cgggtgaagg ttatctctat gaactgtgcg tcacagccaa   8280
aagccagaca gagtgtgata tctacccgct tcgcgtcggc atccggtcag tggcagtgaa   8340
gggcgaacag ttcctgatta accacaaacc gttctacttt actggctttg gtcgtcatga   8400
agatgcggac ttacgtggca aaggattcga taacgtgctg atggtgcacg accacgcatt   8460
aatggactgg attggggcca actcctaccg tacctcgcat tacccttacg ctgaagagat   8520
```

```
gctcgactgg gcagatgaac atggcatcgt ggtgattgat gaaactgctg ctgtcggctt   8580

taacctctct ttaggcattg gtttcgaagc gggcaacaag ccgaaagaac tgtacagcga   8640

agaggcagtc aacggggaaa ctcagcaagc gcacttacag gcgattaaag agctgatagc   8700

gcgtgacaaa aaccacccaa gcgtggtgat gtggagtatt gccaacgaac cggatacccg   8760

tccgcaagtg cacgggaata tttcgccact ggcggaagca acgcgtaaac tcgacccgac   8820

gcgtccgatc acctgcgtca atgtaatgtt ctgcgacgct cacaccgata ccatcagcga   8880

tctctttgat gtgctgtgcc tgaaccgtta ttacggatgg tatgtccaaa gcggcgattt   8940

ggaaacggca gagaaggtac tggaaaaaga acttctggcc tggcaggaga aactgcatca   9000

gccgattatc atcaccgaat acggcgtgga tacgttagcc gggctgcact caatgtacac   9060

cgacatgtgg agtgaagagt atcagtgtgc atggctggat atgtatcacc gcgtctttga   9120

tcgcgtcagc gccgtcgtcg gtgaacaggt atggaatttc gccgattttg cgacctcgca   9180

aggcatattg cgcgttggcg gtaacaagaa agggatcttc actcgcgacc gcaaaccgaa   9240

gtcggcggct tttctgctgc aaaaacgctg gactggcatg aacttcggtg aaaaaccgca   9300

gcagggaggc aaacaatgat taattaacta gagcggccgc caccgcggcc cgagattccg   9360

gcctcttcgg ccgccaagcg acccgggtgg acgtctagag gtacctagca attaacagat   9420

agtttgccgg tgataattct cttaacctcc cacactcctt tgacataacg atttatgtaa   9480

cgaaactgaa atttgaccag atattgtgtc cgc                                9513
```

<210> SEQ ID NO 24
<211> LENGTH: 39
<212> TYPE: DNA
<213> ORGANISM: Artificial Sequence
<220> FEATURE:
<223> OTHER INFORMATION: Primer 1A

<400> SEQUENCE: 24

```
tggtaccatg gtgaaggctt ctcgacaggc tctgcccct                             39
```

<210> SEQ ID NO 25
<211> LENGTH: 39
<212> TYPE: DNA
<213> ORGANISM: Artificial Sequence
<220> FEATURE:
<223> OTHER INFORMATION: Primer 1B

<400> SEQUENCE: 25

```
aggggcagag cctgtcgaga agccttcacc atggtacca                             39
```

<210> SEQ ID NO 26
<211> LENGTH: 32
<212> TYPE: DNA
<213> ORGANISM: Artificial Sequence
<220> FEATURE:
<223> OTHER INFORMATION: Primer 2A

<400> SEQUENCE: 26

```
caggctctgc ccctcgtcat cgacggaact ac                                    32
```

<210> SEQ ID NO 27
<211> LENGTH: 32
<212> TYPE: DNA
<213> ORGANISM: Artificial Sequence
<220> FEATURE:
<223> OTHER INFORMATION: Primer 2B

<400> SEQUENCE: 27
gtagttccgt cgatgacgag gggcagagcc tg 32

<210> SEQ ID NO 28
<211> LENGTH: 37
<212> TYPE: DNA
<213> ORGANISM: Artificial Sequence
<220> FEATURE:
<223> OTHER INFORMATION: Primer 3A

<400> SEQUENCE: 28
ctcaccatcg acggaaaggt gtacgacgtc tccgctt 37

<210> SEQ ID NO 29
<211> LENGTH: 37
<212> TYPE: DNA
<213> ORGANISM: Artificial Sequence
<220> FEATURE:
<223> OTHER INFORMATION: Primer 3B

<400> SEQUENCE: 29
aagcggagac gtcgtacacc tttccgtcga tggtgag 37

<210> SEQ ID NO 30
<211> LENGTH: 39
<212> TYPE: DNA
<213> ORGANISM: Artificial Sequence
<220> FEATURE:
<223> OTHER INFORMATION: Primer 4A

<400> SEQUENCE: 30
acgtctccgc ttgggtggac gagcaccctg gtggagctg 39

<210> SEQ ID NO 31
<211> LENGTH: 39
<212> TYPE: DNA
<213> ORGANISM: Artificial Sequence
<220> FEATURE:
<223> OTHER INFORMATION: Primer 4B

<400> SEQUENCE: 31
cagctccacc agggtgctcg tccacccaag cggagacgt 39

<210> SEQ ID NO 32
<211> LENGTH: 39
<212> TYPE: DNA
<213> ORGANISM: Artificial Sequence
<220> FEATURE:
<223> OTHER INFORMATION: Primer 5A

<400> SEQUENCE: 32
cttccaccct ggtggagact ctatcattga gaactacca 39

<210> SEQ ID NO 33
<211> LENGTH: 39
<212> TYPE: DNA
<213> ORGANISM: Artificial Sequence
<220> FEATURE:
<223> OTHER INFORMATION: Primer 5B

<400> SEQUENCE: 33
tggtagttct caatgataga gtctccacca gggtggaag 39

<210> SEQ ID NO 34
<211> LENGTH: 34
<212> TYPE: DNA
<213> ORGANISM: Artificial Sequence
<220> FEATURE:
<223> OTHER INFORMATION: Primer 6A

<400> SEQUENCE: 34
agccttcgac aagctcctgc gaatgcccaa gatc 34

<210> SEQ ID NO 35
<211> LENGTH: 34
<212> TYPE: DNA
<213> ORGANISM: Artificial Sequence
<220> FEATURE:
<223> OTHER INFORMATION: Primer 6B

<400> SEQUENCE: 35
gatcttgggc attcgcagga gcttgtcgaa ggct 34

<210> SEQ ID NO 36
<211> LENGTH: 39
<212> TYPE: DNA
<213> ORGANISM: Artificial Sequence
<220> FEATURE:
<223> OTHER INFORMATION: Primer 7A

<400> SEQUENCE: 36
tcgacaagct caagcgagcc gtcaagatca acccctcct 39

<210> SEQ ID NO 37
<211> LENGTH: 39
<212> TYPE: DNA
<213> ORGANISM: Artificial Sequence
<220> FEATURE:
<223> OTHER INFORMATION: Primer 7B

<400> SEQUENCE: 37
aggaggggtt gatcttgacg gctcgcttga gcttgtcga 39

<210> SEQ ID NO 38
<211> LENGTH: 39
<212> TYPE: DNA
<213> ORGANISM: Artificial Sequence
<220> FEATURE:
<223> OTHER INFORMATION: Primer 8A

<400> SEQUENCE: 38
aatgcccaag atcaaccagg cttccgagct gcctcccca 39

<210> SEQ ID NO 39
<211> LENGTH: 39
<212> TYPE: DNA
<213> ORGANISM: Artificial Sequence
<220> FEATURE:
<223> OTHER INFORMATION: Primer 8B

<400> SEQUENCE: 39
tggggaggca gctcggaagc ctggttgatc ttgggcatt 39

<210> SEQ ID NO 40
<211> LENGTH: 37
<212> TYPE: DNA
<213> ORGANISM: Artificial Sequence
<220> FEATURE:
<223> OTHER INFORMATION: Primer 9A

<400> SEQUENCE: 40
tcctccgagc tgcctcagcc tgctgccgtc aacgaag 37

<210> SEQ ID NO 41
<211> LENGTH: 37
<212> TYPE: DNA
<213> ORGANISM: Artificial Sequence
<220> FEATURE:
<223> OTHER INFORMATION: Primer 9B

<400> SEQUENCE: 41
cttcgttgac ggcagcaggc tgaggcagct cggagga 37

<210> SEQ ID NO 42
<211> LENGTH: 40
<212> TYPE: DNA
<213> ORGANISM: Artificial Sequence
<220> FEATURE:
<223> OTHER INFORMATION: Primer 10A

<400> SEQUENCE: 42
aggctgccgt caacgaacag gctgaggatt tccgaaagct 40

<210> SEQ ID NO 43
<211> LENGTH: 40
<212> TYPE: DNA
<213> ORGANISM: Artificial Sequence
<220> FEATURE:
<223> OTHER INFORMATION: Primer 10B

<400> SEQUENCE: 43
agctttcgga aatcctcagc ctgttcgttg acggcagcct 40

<210> SEQ ID NO 44
<211> LENGTH: 40
<212> TYPE: DNA
<213> ORGANISM: Artificial Sequence
<220> FEATURE:
<223> OTHER INFORMATION: Primer 11A

<400> SEQUENCE: 44
aggatttccg aaagctcgcc atcgagctga tcgccactgg 40

<210> SEQ ID NO 45
<211> LENGTH: 40
<212> TYPE: DNA
<213> ORGANISM: Artificial Sequence
<220> FEATURE:
<223> OTHER INFORMATION: Primer 11B

<400> SEQUENCE: 45
ccagtggcga tcagctcgat ggcgagcttt cggaaatcct 40

<210> SEQ ID NO 46
<211> LENGTH: 40
<212> TYPE: DNA
<213> ORGANISM: Artificial Sequence
<220> FEATURE:
<223> OTHER INFORMATION: Primer 12A

<400> SEQUENCE: 46
tcctgctccg atacctgtcc cagttcgctc gaatggccga 40

<210> SEQ ID NO 47
<211> LENGTH: 39
<212> TYPE: DNA
<213> ORGANISM: Artificial Sequence
<220> FEATURE:
<223> OTHER INFORMATION: Primer 12B

<400> SEQUENCE: 47
tcggccattc gagcgaactg ggacaggtat cggagcagg 39

<210> SEQ ID NO 48
<211> LENGTH: 38
<212> TYPE: DNA
<213> ORGANISM: Artificial Sequence
<220> FEATURE:
<223> OTHER INFORMATION: Primer 13A

<400> SEQUENCE: 48
tggccgtgtt cgctcgactg tccgagaagc agcccgct 38

<210> SEQ ID NO 49
<211> LENGTH: 38
<212> TYPE: DNA
<213> ORGANISM: Artificial Sequence
<220> FEATURE:
<223> OTHER INFORMATION: Primer 13B

<400> SEQUENCE: 49
agcgggctgc ttctcggaca gtcgagcgaa cacggcca 38

<210> SEQ ID NO 50
<211> LENGTH: 37
<212> TYPE: DNA
<213> ORGANISM: Artificial Sequence
<220> FEATURE:
<223> OTHER INFORMATION: Primer 14A

<400> SEQUENCE: 50
tcgaatggcc gagaaggtgt acgctggcaa ggctctc 37

<210> SEQ ID NO 51
<211> LENGTH: 37
<212> TYPE: DNA
<213> ORGANISM: Artificial Sequence
<220> FEATURE:
<223> OTHER INFORMATION: Primer 14B

<400> SEQUENCE: 51
gagagccttg ccagcgtaca ccttctcggc cattcga 37

<210> SEQ ID NO 52
<211> LENGTH: 37
<212> TYPE: DNA
<213> ORGANISM: Artificial Sequence
<220> FEATURE:
<223> OTHER INFORMATION: Primer 15A

<400> SEQUENCE: 52
agcccgctgg caaggctcag taagcggccg ccaccgc 37

<210> SEQ ID NO 53
<211> LENGTH: 37
<212> TYPE: DNA
<213> ORGANISM: Artificial Sequence
<220> FEATURE:
<223> OTHER INFORMATION: Primer 15B

<400> SEQUENCE: 53
gcggtggcgg ccgcttactg agccttgcca gcgggct 37

<210> SEQ ID NO 54
<211> LENGTH: 33
<212> TYPE: DNA
<213> ORGANISM: Artificial Sequence
<220> FEATURE:
<223> OTHER INFORMATION: Primer 16A

<400> SEQUENCE: 54
gtactcgtac aagatcgtca ccaccctggg tct 33

<210> SEQ ID NO 55
<211> LENGTH: 33
<212> TYPE: DNA
<213> ORGANISM: Artificial Sequence
<220> FEATURE:
<223> OTHER INFORMATION: Primer 16B

<400> SEQUENCE: 55
agacccaggg tggtgacgat cttgtacgag tac 33

<210> SEQ ID NO 56
<211> LENGTH: 40
<212> TYPE: DNA
<213> ORGANISM: Artificial Sequence
<220> FEATURE:
<223> OTHER INFORMATION: Primer 17A

<400> SEQUENCE: 56
actcgtacaa gatctccttc gctctgggtc ttggcgtgct 40

<210> SEQ ID NO 57
<211> LENGTH: 40
<212> TYPE: DNA
<213> ORGANISM: Artificial Sequence
<220> FEATURE:
<223> OTHER INFORMATION: Primer 17B

<400> SEQUENCE: 57
agcacgccaa gacccagagc gaaggagatc ttgtacgagt 40

<210> SEQ ID NO 58
<211> LENGTH: 38
<212> TYPE: DNA
<213> ORGANISM: Artificial Sequence
<220> FEATURE:
<223> OTHER INFORMATION: Primer 18A

<400> SEQUENCE: 58
gcgtgcttgg atacttcatg ctggtccagt accagatg 38

<210> SEQ ID NO 59
<211> LENGTH: 38
<212> TYPE: DNA
<213> ORGANISM: Artificial Sequence
<220> FEATURE:
<223> OTHER INFORMATION: Primer 18B

<400> SEQUENCE: 59
catctggtac tggaccagca tgaagtatcc aagcacgc 38

<210> SEQ ID NO 60
<211> LENGTH: 34
<212> TYPE: DNA
<213> ORGANISM: Artificial Sequence
<220> FEATURE:
<223> OTHER INFORMATION: Primer 19A

<400> SEQUENCE: 60
tggatacttc ctgatgtccc agtaccagat gtac 34

<210> SEQ ID NO 61
<211> LENGTH: 34
<212> TYPE: DNA
<213> ORGANISM: Artificial Sequence
<220> FEATURE:
<223> OTHER INFORMATION: Primer 19B

<400> SEQUENCE: 61
gtacatctgg tactgggaca tcaggaagta tcca 34

<210> SEQ ID NO 62
<211> LENGTH: 40
<212> TYPE: DNA
<213> ORGANISM: Artificial Sequence
<220> FEATURE:
<223> OTHER INFORMATION: Primer 20A

<400> SEQUENCE: 62
gatacttcct gatggtctac cagcagatgt acttcattgg 40

<210> SEQ ID NO 63
<211> LENGTH: 40
<212> TYPE: DNA
<213> ORGANISM: Artificial Sequence
<220> FEATURE:
<223> OTHER INFORMATION: Primer 20B

<400> SEQUENCE: 63
ccaatgaagt acatctgctg gtagaccatc aggaagtatc 40

<210> SEQ ID NO 64
<211> LENGTH: 34
<212> TYPE: DNA
<213> ORGANISM: Artificial Sequence
<220> FEATURE:
<223> OTHER INFORMATION: Primer 21A

<400> SEQUENCE: 64
tgatggtcca gtaccacctg tacttcattg gtgc 34

<210> SEQ ID NO 65
<211> LENGTH: 34
<212> TYPE: DNA
<213> ORGANISM: Artificial Sequence
<220> FEATURE:
<223> OTHER INFORMATION: Primer 21B

<400> SEQUENCE: 65
gcaccaatga agtacaggtg gtactggacc atca 34

<210> SEQ ID NO 66
<211> LENGTH: 37
<212> TYPE: DNA
<213> ORGANISM: Artificial Sequence
<220> FEATURE:
<223> OTHER INFORMATION: Primer 22A

<400> SEQUENCE: 66
tggtccagta ccagatgcag ttcattggtg ctgtgct 37

<210> SEQ ID NO 67
<211> LENGTH: 37
<212> TYPE: DNA
<213> ORGANISM: Artificial Sequence
<220> FEATURE:
<223> OTHER INFORMATION: Primer 22B

<400> SEQUENCE: 67
agcacagcac caatgaactg catctggtac tggacca 37

<210> SEQ ID NO 68
<211> LENGTH: 34
<212> TYPE: DNA
<213> ORGANISM: Artificial Sequence
<220> FEATURE:
<223> OTHER INFORMATION: Primer 23A

<400> SEQUENCE: 68
cctcttcttt atgcccaaca tcctgacctc gctc 34

<210> SEQ ID NO 69
<211> LENGTH: 34
<212> TYPE: DNA
<213> ORGANISM: Artificial Sequence
<220> FEATURE:
<223> OTHER INFORMATION: Primer 23B

<400> SEQUENCE: 69
gagcgaggtc aggatgttgg gcataaagaa gagg 34

<210> SEQ ID NO 70
<211> LENGTH: 38
<212> TYPE: DNA
<213> ORGANISM: Artificial Sequence
<220> FEATURE:
<223> OTHER INFORMATION: Primer 24A

<400> SEQUENCE: 70
tcttctttat gccctcccct atgacctcgc tcctggtg 38

<210> SEQ ID NO 71
<211> LENGTH: 38
<212> TYPE: DNA
<213> ORGANISM: Artificial Sequence
<220> FEATURE:
<223> OTHER INFORMATION: Primer 24B

<400> SEQUENCE: 71
caccaggagc gaggtcatag gggagggcat aaagaaga 38

<210> SEQ ID NO 72
<211> LENGTH: 39
<212> TYPE: DNA
<213> ORGANISM: Artificial Sequence
<220> FEATURE:
<223> OTHER INFORMATION: Primer 25A

<400> SEQUENCE: 72
ttatgccctc catcctggtc gtgctcctgg tgttctttg 39

<210> SEQ ID NO 73
<211> LENGTH: 39
<212> TYPE: DNA
<213> ORGANISM: Artificial Sequence
<220> FEATURE:
<223> OTHER INFORMATION: Primer 25B

<400> SEQUENCE: 73
caaagaacac caggagcacg accaggatgg agggcataa 39

<210> SEQ ID NO 74
<211> LENGTH: 37
<212> TYPE: DNA
<213> ORGANISM: Artificial Sequence
<220> FEATURE:
<223> OTHER INFORMATION: Primer 26A

<400> SEQUENCE: 74
cctccatcct gacctcgatg ctggtgttct ttgtttc 37

<210> SEQ ID NO 75
<211> LENGTH: 37
<212> TYPE: DNA
<213> ORGANISM: Artificial Sequence
<220> FEATURE:
<223> OTHER INFORMATION: Primer 26B

<400> SEQUENCE: 75
gaaacaaaga acaccagcat cgaggtcagg atggagg 37

<210> SEQ ID NO 76
<211> LENGTH: 34
<212> TYPE: DNA
<213> ORGANISM: Artificial Sequence
<220> FEATURE:
<223> OTHER INFORMATION: Primer 27A

<400> SEQUENCE: 76
gacctcgctc ctggtgacct ttgtttccga gctc 34

<210> SEQ ID NO 77
<211> LENGTH: 34
<212> TYPE: DNA
<213> ORGANISM: Artificial Sequence
<220> FEATURE:
<223> OTHER INFORMATION: Primer 27B

<400> SEQUENCE: 77
gagctcggaa acaaaggtca ccaggagcga ggtc 34

<210> SEQ ID NO 78
<211> LENGTH: 34
<212> TYPE: DNA
<213> ORGANISM: Artificial Sequence
<220> FEATURE:
<223> OTHER INFORMATION: Primer 28A

<400> SEQUENCE: 78
gctcctggtg ttcttttctt ccgagctcgt cggt 34

<210> SEQ ID NO 79
<211> LENGTH: 34
<212> TYPE: DNA
<213> ORGANISM: Artificial Sequence
<220> FEATURE:
<223> OTHER INFORMATION: Primer 28B

<400> SEQUENCE: 79
accgacgagc tcggaagaaa agaacaccag gagc 34

<210> SEQ ID NO 80
<211> LENGTH: 38
<212> TYPE: DNA
<213> ORGANISM: Artificial Sequence
<220> FEATURE:
<223> OTHER INFORMATION: Primer 29A

<400> SEQUENCE: 80
acaacctccc ctaccgaacc actctgcccc atgaaggt 38

<210> SEQ ID NO 81
<211> LENGTH: 38
<212> TYPE: DNA
<213> ORGANISM: Artificial Sequence
<220> FEATURE:
<223> OTHER INFORMATION: Primer 29B

<400> SEQUENCE: 81
accttcatgg ggcagagtgg ttcggtaggg gaggttgt 38

<210> SEQ ID NO 82
<211> LENGTH: 40
<212> TYPE: DNA
<213> ORGANISM: Artificial Sequence
<220> FEATURE:
<223> OTHER INFORMATION: Primer 30A

<400> SEQUENCE: 82
tcccctaccg aaaccctggc atgcatgaag gtctcgtcat 40

<210> SEQ ID NO 83
<211> LENGTH: 40
<212> TYPE: DNA
<213> ORGANISM: Artificial Sequence
<220> FEATURE:
<223> OTHER INFORMATION: Primer 30B

<400> SEQUENCE: 83
atgacgagac cttcatgcat gccagggttt cggtagggga 40

<210> SEQ ID NO 84
<211> LENGTH: 36
<212> TYPE: DNA
<213> ORGANISM: Artificial Sequence
<220> FEATURE:
<223> OTHER INFORMATION: Primer 31A

<400> SEQUENCE: 84
gtgaagtcca agcgactgtc tctgcccctc accatc 36

<210> SEQ ID NO 85
<211> LENGTH: 36
<212> TYPE: DNA
<213> ORGANISM: Artificial Sequence
<220> FEATURE:
<223> OTHER INFORMATION: Primer 31B

<400> SEQUENCE: 85
gatggtgagg ggcagagaca gtcgcttgga cttcac 36

<210> SEQ ID NO 86
<211> LENGTH: 40
<212> TYPE: DNA
<213> ORGANISM: Artificial Sequence
<220> FEATURE:
<223> OTHER INFORMATION: Primer 32A

<400> SEQUENCE: 86
ccaagcgaca ggctctgtgg cagaccatcg acggaactac 40

<210> SEQ ID NO 87
<211> LENGTH: 40
<212> TYPE: DNA
<213> ORGANISM: Artificial Sequence
<220> FEATURE:
<223> OTHER INFORMATION: Primer 32B

<400> SEQUENCE: 87
gtagttccgt cgatggtctg ccacagagcc tgtcgcttgg 40

<210> SEQ ID NO 88
<211> LENGTH: 37
<212> TYPE: DNA
<213> ORGANISM: Artificial Sequence
<220> FEATURE:
<223> OTHER INFORMATION: Primer 33A

<400> SEQUENCE: 88
aactacctac gacgtcttct cttgggtgaa cttccac 37

<210> SEQ ID NO 89
<211> LENGTH: 37
<212> TYPE: DNA
<213> ORGANISM: Artificial Sequence
<220> FEATURE:
<223> OTHER INFORMATION: Primer 33B

<400> SEQUENCE: 89
gtggaagttc acccaagaga agacgtcgta ggtagtt 37

<210> SEQ ID NO 90
<211> LENGTH: 37
<212> TYPE: DNA
<213> ORGANISM: Artificial Sequence
<220> FEATURE:
<223> OTHER INFORMATION: Primer 34A

<400> SEQUENCE: 90
agatgctact gacgcctccc tggttatgca ctctcag 37

<210> SEQ ID NO 91
<211> LENGTH: 37
<212> TYPE: DNA
<213> ORGANISM: Artificial Sequence
<220> FEATURE:
<223> OTHER INFORMATION: Primer 34B

<400> SEQUENCE: 91
ctgagagtgc ataaccaggg aggcgtcagt agcatct 37

<210> SEQ ID NO 92
<211> LENGTH: 38
<212> TYPE: DNA
<213> ORGANISM: Artificial Sequence
<220> FEATURE:
<223> OTHER INFORMATION: Primer 35A

<400> SEQUENCE: 92
ctactgacgc cttcatgttc ctgcactctc aggaagcc 38

<210> SEQ ID NO 93
<211> LENGTH: 38
<212> TYPE: DNA
<213> ORGANISM: Artificial Sequence
<220> FEATURE:
<223> OTHER INFORMATION: Primer 35B

<400> SEQUENCE: 93
ggcttcctga gagtgcagga acatgaaggc gtcagtag 38

<210> SEQ ID NO 94
<211> LENGTH: 39
<212> TYPE: DNA
<213> ORGANISM: Artificial Sequence
<220> FEATURE:
<223> OTHER INFORMATION: Primer 36A

<400> SEQUENCE: 94
tgaaatcatt gagaacttca acggacgaga tgctactga 39

<210> SEQ ID NO 95
<211> LENGTH: 39
<212> TYPE: DNA
<213> ORGANISM: Artificial Sequence
<220> FEATURE:
<223> OTHER INFORMATION: Primer 36B

<400> SEQUENCE: 95
tcagtagcat ctcgtccgtt gaagttctca atgatttca 39

<210> SEQ ID NO 96
<211> LENGTH: 40
<212> TYPE: DNA
<213> ORGANISM: Artificial Sequence
<220> FEATURE:
<223> OTHER INFORMATION: Primer 37A

<400> SEQUENCE: 96
ccttcatggt tatgcacacc aacgaagcct tcgacaagct 40

<210> SEQ ID NO 97
<211> LENGTH: 40
<212> TYPE: DNA
<213> ORGANISM: Artificial Sequence
<220> FEATURE:
<223> OTHER INFORMATION: Primer 37B

<400> SEQUENCE: 97
agcttgtcga aggcttcgtt ggtgtgcata accatgaagg 40

<210> SEQ ID NO 98
<211> LENGTH: 36
<212> TYPE: DNA
<213> ORGANISM: Artificial Sequence
<220> FEATURE:
<223> OTHER INFORMATION: Primer 38A

<400> SEQUENCE: 98
atgcactctc aggaaggcta cgacaagctc aagcga 36

<210> SEQ ID NO 99
<211> LENGTH: 36
<212> TYPE: DNA
<213> ORGANISM: Artificial Sequence
<220> FEATURE:
<223> OTHER INFORMATION: Primer 38B

<400> SEQUENCE: 99
tcgcttgagc ttgtcgtagc cttcctgaga gtgcat 36

<210> SEQ ID NO 100
<211> LENGTH: 38
<212> TYPE: DNA
<213> ORGANISM: Artificial Sequence
<220> FEATURE:
<223> OTHER INFORMATION: Primer 39A

<400> SEQUENCE: 100
ctcaagcgaa tgcccaagct tgatccctcc tttgagct 38

<210> SEQ ID NO 101
<211> LENGTH: 38
<212> TYPE: DNA
<213> ORGANISM: Artificial Sequence
<220> FEATURE:
<223> OTHER INFORMATION: Primer 39B

<400> SEQUENCE: 101
agctcaaagg agggatcaag cttgggcatt cgcttgag 38

<210> SEQ ID NO 102
<211> LENGTH: 33
<212> TYPE: DNA
<213> ORGANISM: Artificial Sequence
<220> FEATURE:
<223> OTHER INFORMATION: Primer 40A

<400> SEQUENCE: 102
tcaacccctc ctttgatgtg cctccccagg ctg 33

<210> SEQ ID NO 103
<211> LENGTH: 33
<212> TYPE: DNA
<213> ORGANISM: Artificial Sequence
<220> FEATURE:
<223> OTHER INFORMATION: Primer 40B

<400> SEQUENCE: 103
cagcctgggg aggcacatca aaggaggggt tga 33

<210> SEQ ID NO 104
<211> LENGTH: 33
<212> TYPE: DNA
<213> ORGANISM: Artificial Sequence
<220> FEATURE:
<223> OTHER INFORMATION: Primer 41A

<400> SEQUENCE: 104
tgcctcccca ggctggactc aacgaagctc agg 33

<210> SEQ ID NO 105
<211> LENGTH: 33
<212> TYPE: DNA
<213> ORGANISM: Artificial Sequence
<220> FEATURE:
<223> OTHER INFORMATION: Primer 41B

<400> SEQUENCE: 105
cctgagcttc gttgagtcca gcctggggag gca 33

<210> SEQ ID NO 106
<211> LENGTH: 36
<212> TYPE: DNA
<213> ORGANISM: Artificial Sequence
<220> FEATURE:
<223> OTHER INFORMATION: Primer 42A

<400> SEQUENCE: 106
gaaagctccg agaagacatc atcgccactg gcatgt 36

<210> SEQ ID NO 107
<211> LENGTH: 36
<212> TYPE: DNA
<213> ORGANISM: Artificial Sequence
<220> FEATURE:
<223> OTHER INFORMATION: Primer 42B

<400> SEQUENCE: 107
acatgccagt ggcgatgatg tcttctcgga gctttc 36

<210> SEQ ID NO 108
<211> LENGTH: 35
<212> TYPE: DNA
<213> ORGANISM: Artificial Sequence
<220> FEATURE:
<223> OTHER INFORMATION: Primer 43A

<400> SEQUENCE: 108
ccactggcat gtttgaggtc tctcccctct ggtac 35

<210> SEQ ID NO 109
<211> LENGTH: 35
<212> TYPE: DNA
<213> ORGANISM: Artificial Sequence
<220> FEATURE:
<223> OTHER INFORMATION: Primer 43B

<400> SEQUENCE: 109
gtaccagagg ggagagacct caaacatgcc agtgg 35

<210> SEQ ID NO 110
<211> LENGTH: 36
<212> TYPE: DNA
<213> ORGANISM: Artificial Sequence
<220> FEATURE:
<223> OTHER INFORMATION: Primer 44A

<400> SEQUENCE: 110
gtacaagatc tccacctcgg tgggtcttgg cgtgct 36

<210> SEQ ID NO 111
<211> LENGTH: 36
<212> TYPE: DNA
<213> ORGANISM: Artificial Sequence
<220> FEATURE:
<223> OTHER INFORMATION: Primer 44B

<400> SEQUENCE: 111
agcacgccaa gacccaccga ggtggagatc ttgtac 36

<210> SEQ ID NO 112
<211> LENGTH: 36
<212> TYPE: DNA
<213> ORGANISM: Artificial Sequence
<220> FEATURE:
<223> OTHER INFORMATION: Primer 45A

<400> SEQUENCE: 112
ggtcttggcg tgcttgcctt cttcctgatg gtccag 36

<210> SEQ ID NO 113
<211> LENGTH: 36
<212> TYPE: DNA
<213> ORGANISM: Artificial Sequence
<220> FEATURE:
<223> OTHER INFORMATION: Primer 45B

<400> SEQUENCE: 113
ctggaccatc aggaagaagg caagcacgcc aagacc 36

<210> SEQ ID NO 114
<211> LENGTH: 36
<212> TYPE: DNA
<213> ORGANISM: Artificial Sequence
<220> FEATURE:
<223> OTHER INFORMATION: Primer 46A

<400> SEQUENCE: 114
gtacttcatt ggtgctctcg tgctcggtat gcacta 36

<210> SEQ ID NO 115
<211> LENGTH: 36
<212> TYPE: DNA
<213> ORGANISM: Artificial Sequence
<220> FEATURE:
<223> OTHER INFORMATION: Primer 46B

<400> SEQUENCE: 115
tagtgcatac cgagcacgag agcaccaatg aagtac 36

<210> SEQ ID NO 116
<211> LENGTH: 34
<212> TYPE: DNA
<213> ORGANISM: Artificial Sequence
<220> FEATURE:
<223> OTHER INFORMATION: Primer 47A

<400> SEQUENCE: 116
agggtcacga tcccgagctt gataacctgc ctct 34

<210> SEQ ID NO 117
<211> LENGTH: 34
<212> TYPE: DNA
<213> ORGANISM: Artificial Sequence
<220> FEATURE:
<223> OTHER INFORMATION: Primer 47B

<400> SEQUENCE: 117
agaggcaggt tatcaagctc gggatcgtga ccct 34

<210> SEQ ID NO 118
<211> LENGTH: 36
<212> TYPE: DNA
<213> ORGANISM: Artificial Sequence
<220> FEATURE:
<223> OTHER INFORMATION: Primer 48A

<400> SEQUENCE: 118
ccaacagtac tatttcgtcc tcatctgtat tctcct 36

<210> SEQ ID NO 119
<211> LENGTH: 36
<212> TYPE: DNA
<213> ORGANISM: Artificial Sequence
<220> FEATURE:
<223> OTHER INFORMATION: Primer 48B

<400> SEQUENCE: 119
aggagaatac agatgaggac gaaatagtac tgttgg 36

<210> SEQ ID NO 120
<211> LENGTH: 37
<212> TYPE: DNA
<213> ORGANISM: Artificial Sequence
<220> FEATURE:
<223> OTHER INFORMATION: Primer 49A

<400> SEQUENCE: 120
ctcgctcctg gtgttcgttc tttccgagct cgtcggt 37

<210> SEQ ID NO 121
<211> LENGTH: 37
<212> TYPE: DNA
<213> ORGANISM: Artificial Sequence
<220> FEATURE:
<223> OTHER INFORMATION: Primer 49B

<400> SEQUENCE: 121
accgacgagc tcggaaagaa cgaacaccag gagcgag 37

<210> SEQ ID NO 122
<211> LENGTH: 40
<212> TYPE: DNA
<213> ORGANISM: Artificial Sequence
<220> FEATURE:
<223> OTHER INFORMATION: Primer 50A

<400> SEQUENCE: 122
gtggcttcgg aattgccgtg atcgtcttca tgaaccacta 40

<210> SEQ ID NO 123
<211> LENGTH: 40
<212> TYPE: DNA
<213> ORGANISM: Artificial Sequence
<220> FEATURE:
<223> OTHER INFORMATION: Primer 50B

<400> SEQUENCE: 123
tagtggttca tgaagacgat cacggcaatt ccgaagccac 40

<210> SEQ ID NO 124
<211> LENGTH: 36
<212> TYPE: DNA
<213> ORGANISM: Artificial Sequence
<220> FEATURE:
<223> OTHER INFORMATION: Primer 51A (for 347I to L and 348T to S mutations)

<400> SEQUENCE: 124
cattcgacga ggcatcctct ctgactggtt ctttgg 36

<210> SEQ ID NO 125
<211> LENGTH: 36
<212> TYPE: DNA
<213> ORGANISM: Artificial Sequence
<220> FEATURE:
<223> OTHER INFORMATION: Primer 51B

<400> SEQUENCE: 125
ccaaagaacc agtcagagag gatgcctcgt cgaatg 36

<210> SEQ ID NO 126
<211> LENGTH: 39
<212> TYPE: DNA
<213> ORGANISM: Artificial Sequence
<220> FEATURE:
<223> OTHER INFORMATION: Primer 51A (for 346I to V, 347I to L and 348T to S mutations)

<400> SEQUENCE: 126
gaacattcga cgaggcgtcc tctctgactg gttctttgg 39

<210> SEQ ID NO 127
<211> LENGTH: 37
<212> TYPE: DNA
<213> ORGANISM: Artificial Sequence
<220> FEATURE:
<223> OTHER INFORMATION: Primer 52A

<400> SEQUENCE: 127
tgccccatga aggtctcatc gtcctgctcc gatacct 37

<210> SEQ ID NO 128
<211> LENGTH: 37
<212> TYPE: DNA
<213> ORGANISM: Artificial Sequence
<220> FEATURE:
<223> OTHER INFORMATION: Primer 52B

<400> SEQUENCE: 128
aggtatcgga gcaggacgat gagaccttca tggggca 37

<210> SEQ ID NO 129
<211> LENGTH: 35
<212> TYPE: DNA
<213> ORGANISM: Artificial Sequence
<220> FEATURE:
<223> OTHER INFORMATION: Primer 53A

<400> SEQUENCE: 129
gtccaagcga caggctgttc ccctcaccat cgacg 35

<210> SEQ ID NO 130
<211> LENGTH: 35
<212> TYPE: DNA
<213> ORGANISM: Artificial Sequence
<220> FEATURE:
<223> OTHER INFORMATION: Primer 53B

<400> SEQUENCE: 130
cgtcgatggt gaggggaaca gcctgtcgct tggac 35

<210> SEQ ID NO 131
<211> LENGTH: 36
<212> TYPE: DNA
<213> ORGANISM: Artificial Sequence
<220> FEATURE:
<223> OTHER INFORMATION: Primer 54A

<400> SEQUENCE: 131
gacggaacta cctacgagat ctccgcttgg gtgaac 36

<210> SEQ ID NO 132
<211> LENGTH: 36
<212> TYPE: DNA
<213> ORGANISM: Artificial Sequence
<220> FEATURE:
<223> OTHER INFORMATION: Primer 54B

<400> SEQUENCE: 132
gttcacccaa gcggagatct cgtaggtagt tccgtc 36

<210> SEQ ID NO 133
<211> LENGTH: 36
<212> TYPE: DNA
<213> ORGANISM: Artificial Sequence
<220> FEATURE:
<223> OTHER INFORMATION: Primer 55A

<400> SEQUENCE: 133
accctggtgg agctgaactg attgagaact accagg 36

<210> SEQ ID NO 134
<211> LENGTH: 36
<212> TYPE: DNA
<213> ORGANISM: Artificial Sequence
<220> FEATURE:
<223> OTHER INFORMATION: Primer 55B

<400> SEQUENCE: 134
cctggtagtt ctcaatcagt tcagctccac cagggt 36

<210> SEQ ID NO 135
<211> LENGTH: 38
<212> TYPE: DNA
<213> ORGANISM: Artificial Sequence
<220> FEATURE:
<223> OTHER INFORMATION: Primer 56A

<400> SEQUENCE: 135
acgagatgct actgacggct acatggttat gcactctc 38

<210> SEQ ID NO 136
<211> LENGTH: 38
<212> TYPE: DNA
<213> ORGANISM: Artificial Sequence
<220> FEATURE:
<223> OTHER INFORMATION: Primer 56B

<400> SEQUENCE: 136
gagagtgcat aaccatgtag ccgtcagtag catctcgt 38

<210> SEQ ID NO 137
<211> LENGTH: 38
<212> TYPE: DNA
<213> ORGANISM: Artificial Sequence
<220> FEATURE:
<223> OTHER INFORMATION: Primer 57A

<400> SEQUENCE: 137
ctcaggaagc cttcgaccga atcaagcgaa tgcccaag 38

<210> SEQ ID NO 138
<211> LENGTH: 38
<212> TYPE: DNA
<213> ORGANISM: Artificial Sequence
<220> FEATURE:
<223> OTHER INFORMATION: Primer 57B

<400> SEQUENCE: 138
cttgggcatt cgcttgattc ggtcgaaggc ttcctgag 38

<210> SEQ ID NO 139
<211> LENGTH: 35
<212> TYPE: DNA
<213> ORGANISM: Artificial Sequence
<220> FEATURE:
<223> OTHER INFORMATION: Primer 58A

<400> SEQUENCE: 139
gcgaatgccc aagatccaac cctcctccga gctgc 35

<210> SEQ ID NO 140
<211> LENGTH: 35
<212> TYPE: DNA
<213> ORGANISM: Artificial Sequence
<220> FEATURE:
<223> OTHER INFORMATION: Primer 58B

<400> SEQUENCE: 140
gcagctcgga ggagggttgg atcttgggca ttcgc 35

<210> SEQ ID NO 141
<211> LENGTH: 39
<212> TYPE: DNA
<213> ORGANISM: Artificial Sequence
<220> FEATURE:
<223> OTHER INFORMATION: Primer 59A

<400> SEQUENCE: 141
cctccgagct gcctcccaac ggtgccgtca acgaagctc 39

<210> SEQ ID NO 142
<211> LENGTH: 39
<212> TYPE: DNA
<213> ORGANISM: Artificial Sequence
<220> FEATURE:
<223> OTHER INFORMATION: Primer 59B

<400> SEQUENCE: 142
gagcttcgtt gacggcaccg ttgggaggca gctcggagg 39

<210> SEQ ID NO 143
<211> LENGTH: 36
<212> TYPE: DNA
<213> ORGANISM: Artificial Sequence
<220> FEATURE:
<223> OTHER INFORMATION: Primer 60A

<400> SEQUENCE: 143
gatcgccact ggcatgtacg acgcctctcc cctctg 36

<210> SEQ ID NO 144
<211> LENGTH: 36
<212> TYPE: DNA
<213> ORGANISM: Artificial Sequence
<220> FEATURE:
<223> OTHER INFORMATION: Primer 60B

<400> SEQUENCE: 144
cagaggggag aggcgtcgta catgccagtg gcgatc 36

<210> SEQ ID NO 145
<211> LENGTH: 36
<212> TYPE: DNA
<213> ORGANISM: Artificial Sequence
<220> FEATURE:
<223> OTHER INFORMATION: Primer 61A

<400> SEQUENCE: 145
ctgtattctc ctgcgaatct tctggtgttt ccagtc 36

<210> SEQ ID NO 146
<211> LENGTH: 36
<212> TYPE: DNA
<213> ORGANISM: Artificial Sequence
<220> FEATURE:
<223> OTHER INFORMATION: Primer 61B

<400> SEQUENCE: 146
gactggaaac accagaagat tcgcaggaga atacag 36

<210> SEQ ID NO 147
<211> LENGTH: 36
<212> TYPE: DNA
<213> ORGANISM: Artificial Sequence
<220> FEATURE:
<223> OTHER INFORMATION: Primer 62A

<400> SEQUENCE: 147
gaaagaggcc attggaatgt ctctgcactg gactct 36

<210> SEQ ID NO 148
<211> LENGTH: 36
<212> TYPE: DNA
<213> ORGANISM: Artificial Sequence
<220> FEATURE:
<223> OTHER INFORMATION: Primer 62B

<400> SEQUENCE: 148
agagtccagt gcagagacat tccaatggcc tctttc 36

<210> SEQ ID NO 149
<211> LENGTH: 40
<212> TYPE: DNA
<213> ORGANISM: Artificial Sequence
<220> FEATURE:
<223> OTHER INFORMATION: Primer 63A

<400> SEQUENCE: 149
tgcactggac tctcaagctg accttccacc tcttctttat 40

<210> SEQ ID NO 150
<211> LENGTH: 40
<212> TYPE: DNA
<213> ORGANISM: Artificial Sequence
<220> FEATURE:
<223> OTHER INFORMATION: Primer 63B

<400> SEQUENCE: 150
ataaagaaga ggtggaaggt cagcttgaga gtccagtgca 40

<210> SEQ ID NO 151
<211> LENGTH: 36
<212> TYPE: DNA
<213> ORGANISM: Artificial Sequence
<220> FEATURE:
<223> OTHER INFORMATION: Primer 64A

<400> SEQUENCE: 151
cacctgtact tcattgctgg tctcgtgctc ggtatg 36

<210> SEQ ID NO 152
<211> LENGTH: 36
<212> TYPE: DNA
<213> ORGANISM: Artificial Sequence
<220> FEATURE:
<223> OTHER INFORMATION: Primer 64B

<400> SEQUENCE: 152
cataccgagc acgagaccag caatgaagta caggtg 36

<210> SEQ ID NO 153
<211> LENGTH: 37
<212> TYPE: DNA
<213> ORGANISM: Artificial Sequence
<220> FEATURE:
<223> OTHER INFORMATION: Primer 65A

<400> SEQUENCE: 153
ttccgagctc gtcggtttcg gcggaattgc catcgtg 37

<210> SEQ ID NO 154
<211> LENGTH: 37
<212> TYPE: DNA
<213> ORGANISM: Artificial Sequence
<220> FEATURE:
<223> OTHER INFORMATION: Primer 65B

<400> SEQUENCE: 154
cacgatggca attccgccga aaccgacgag ctcggaa 37

<210> SEQ ID NO 155
<211> LENGTH: 36
<212> TYPE: DNA
<213> ORGANISM: Artificial Sequence
<220> FEATURE:
<223> OTHER INFORMATION: Primer 66A

<400> SEQUENCE: 155
agttccaaca gtacttctat ctggtcatct gtattc 36

<210> SEQ ID NO 156
<211> LENGTH: 36
<212> TYPE: DNA
<213> ORGANISM: Artificial Sequence
<220> FEATURE:
<223> OTHER INFORMATION: Primer 66B

<400> SEQUENCE: 156
gaatacagat gaccagatag aagtactgtt ggaact 36

<210> SEQ ID NO 157
<211> LENGTH: 36
<212> TYPE: DNA
<213> ORGANISM: Artificial Sequence
<220> FEATURE:
<223> OTHER INFORMATION: Primer 67A

<400> SEQUENCE: 157
atgccctcca tcctgagcct gatgttcgtg ttcgtt 36

<210> SEQ ID NO 158
<211> LENGTH: 36
<212> TYPE: DNA
<213> ORGANISM: Artificial Sequence
<220> FEATURE:
<223> OTHER INFORMATION: Primer 67B

<400> SEQUENCE: 158
aacgaacacg aacatcaggc tcaggatgga gggcat 36

<210> SEQ ID NO 159
<211> LENGTH: 34
<212> TYPE: DNA
<213> ORGANISM: Artificial Sequence
<220> FEATURE:
<223> OTHER INFORMATION: Primer 68A

<400> SEQUENCE: 159
cgaaactgga ataacgtcct gggtctggtc tttg 34

<210> SEQ ID NO 160
<211> LENGTH: 34
<212> TYPE: DNA
<213> ORGANISM: Artificial Sequence
<220> FEATURE:
<223> OTHER INFORMATION: Primer 68B

<400> SEQUENCE: 160
caaagaccag acccaggacg ttattccagt ttcg 34

<210> SEQ ID NO 161
<211> LENGTH: 33
<212> TYPE: DNA
<213> ORGANISM: Artificial Sequence
<220> FEATURE:
<223> OTHER INFORMATION: Primer 69A

<400> SEQUENCE: 161
tggtctttgg caacgctgtc cagggcttct ccg 33

<210> SEQ ID NO 162
<211> LENGTH: 33
<212> TYPE: DNA
<213> ORGANISM: Artificial Sequence
<220> FEATURE:
<223> OTHER INFORMATION: Primer 69B

<400> SEQUENCE: 162
cggagaagcc ctggacagcg ttgccaaaga cca 33

<210> SEQ ID NO 163
<211> LENGTH: 36
<212> TYPE: DNA
<213> ORGANISM: Artificial Sequence
<220> FEATURE:
<223> OTHER INFORMATION: Primer 70A

<400> SEQUENCE: 163
gccgagaagg tgtacggtgc caaggctcag taagcg 36

<210> SEQ ID NO 164
<211> LENGTH: 36
<212> TYPE: DNA
<213> ORGANISM: Artificial Sequence
<220> FEATURE:
<223> OTHER INFORMATION: Primer 70B

<400> SEQUENCE: 164
cgcttactga gccttggcac cgtacacctt ctcggc 36

<210> SEQ ID NO 165
<211> LENGTH: 8560
<212> TYPE: DNA
<213> ORGANISM: Artificial Sequence
<220> FEATURE:
<223> OTHER INFORMATION: Plasmid pKO2UFkF2
<220> FEATURE:
<221> NAME/KEY: misc_feature
<222> LOCATION: (692)..(695)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 165
catggcgtcc acttcggctc tgcccaagca gaaccctgcg cttagacgca ccgtcacctc 60
aactactgtg acggattctg agtctgccgc cgtctctcct tcagactctc cccgccactc 120
ggcctcttcc acatcgctct cgtccatgtc cgaggttgat atcgccaagc ccaagtccga 180
gtatggtgtc atgctcgaca cctacggcaa ccagttcgag gttcccgact ttaccatcaa 240
ggacatctac aatgccatcc ctaagcactg cttcaagcgc tccgctctca agggatacgg 300
ttatatcctc cgcgacattg tcctcctgac taccactttc agcatctggt acaactttgt 360
gacccccgaa tatatcccct ccacccccgc ccgcgctggt ctgtgggccg tgtacaccgt 420
tcttcagggt cttttcggta ctggtctctg ggttattgcc catgagtgcg gtcacggtgc 480
tttctccgat tctcgcatca tcaacgacat tactggctgg gttcttcact cttccctcct 540
tgtcccctac ttcagctggc aaatctccca ccgaaagcac cacaaggcca ctggcaacat 600
ggagcgtgac atggtcttcg ttccccgaac ccgcgagcag caggctactc gtctcggaaa 660
gatgacccac gagctcgctc atcttactga gnnnntcgtn ggctggccca actacctcat 720
caccaatgtt accggccaca actaccacga gcgccagcgt gagggtcgcg gcaagggcaa 780
gcataacggc ctcggcggtg gtgttaacca cttcgatccc cgcagccctc tgtacgagaa 840
cagtgacgct aagctcatcg tcctcagcga tattggtatc ggtctgatgg ccactgctct 900
gtacttcctc gttcagaagt tcggtttcta caacatggcc atctggtact ttgttcccta 960
cctctgggtt aaccactggc tcgttgccat caccttcctc cagcacaccg accctaccct 1020
tccccactac accaacgacg agtggaactt cgtccgtggt gccgctgcta ccattgaccg 1080
tgagatgggc ttcatcggcc gccaccttct ccacggcatc atcgagactc atgtcctcca 1140
ccactacgtc agcagcatcc ccttctacaa cgcggacgag gccaccgagg ccattaagcc 1200
catcatgggc aagcactacc gggctgatgt ccaggatggt cctcgtggct tcatccgcgc 1260
catgtaccgc agtgcgcgta tgtgccagtg ggttgagccc agcgctggtg ccgagggtgc 1320
tggtaagggt gttctgttct tccgcaaccg caacaacgtg ggcacccccc ccgctgttat 1380
caagcccgtt gcttaagtag gcgcggccgc aagtgtggat ggggaagtga gtgcccggtt 1440
ctgtgtgcac aattggcaat ccaagatgga tggattcaac acagggatat agcgagctac 1500
gtggtggtgc gaggatatag caacggatat ttatgtttga cacttgagaa tgtacgatac 1560

-continued

```
aagcactgtc caagtacaat actaaacata ctgtacatac tcatactcgt acccgggcaa   1620
cggtttcact tgagtgcagt ggctagtgct cttactcgta cagtgtgcaa tactgcgtat   1680
catagtcttt gatgtatatc gtattcattc atgttagttg cgtacgggtg aagcttccac   1740
tggtcggcgt ggtagtgggg cagagtgggg tcggtgtgct gcaggtaggt gatggccacg   1800
agccagtggt tgacccacag gtaggggatc aggtagtaga gggtgacgga agccaggccc   1860
catcggttga tggagtatgc gatgacggac atggtgatac caataccgac gttagagatc   1920
cagatgttga accagtcctt cttctcaaac agcggggcgt tggggttgaa gtggttgaca   1980
gcccatttgt tgagcttggg gtacttctgt ccggtaacgt aagacagcag atacagaggc   2040
catccaaaca cctgctgggt gatgaggccg tagagggtca tgaggggagc gtcctcagca   2100
agctcagacc agtcatgggc gcctcggttc tccataaact cctttcggtc cttgggcaca   2160
aacaccatat cacgggtgag gtgaccagtg gacttgtggt gcatggagtg ggtcagcttc   2220
caggcgtagt aagggaccag catggaggag tgcagaaccc atccggtgac gttgttgacg   2280
gtgttagagt cggagaaagc agagtggcca cactcgtggg caagaaccca cagaccggtg   2340
ccaaacagac cctggacaat ggagtacatg gcccaggcca cagctcggcc ggaagccgag   2400
ggaataagag gcaggtacgc gtaggccatg taggcaaaaa cggcgataaa gaagcaggcg   2460
cgccagctgc attaatgaat cggccaacgc gcggggagag gcggtttgcg tattgggcgc   2520
tcttccgctt cctcgctcac tgactcgctg cgctcggtcg ttcggctgcg gcgagcggta   2580
tcagctcact caaaggcggt aatacggtta tccacagaat caggggataa cgcaggaaag   2640
aacatgtgag caaaaggcca gcaaaaggcc aggaaccgta aaaaggccgc gttgctggcg   2700
tttttccata ggctccgccc ccctgacgag catcacaaaa atcgacgctc aagtcagagg   2760
tggcgaaacc cgacaggact ataaagatac caggcgtttc cccctggaag ctccctcgtg   2820
cgctctcctg ttccgaccct gccgcttacc ggatacctgt ccgcctttct cccttcggga   2880
agcgtggcgc tttctcatag ctcacgctgt aggtatctca gttcggtgta ggtcgttcgc   2940
tccaagctgg gctgtgtgca cgaacccccc gttcagcccg accgctgcgc cttatccggt   3000
aactatcgtc ttgagtccaa cccggtaaga cacgacttat cgccactggc agcagccact   3060
ggtaacagga ttagcagagc gaggtatgta ggcggtgcta cagagttctt gaagtggtgg   3120
cctaactacg gctacactag aagaacagta tttggtatct gcgctctgct gaagccagtt   3180
accttcggaa aaagagttgg tagctcttga tccggcaaac aaaccaccgc tggtagcggt   3240
ggtttttttg tttgcaagca gcagattacg cgcagaaaaa aaggatctca agaagatcct   3300
ttgatctttt ctacggggtc tgacgctcag tggaacgaaa actcacgtta agggattttg   3360
gtcatgagat tatcaaaaag gatcttcacc tagatccttt taaattaaaa atgaagtttt   3420
aaatcaatct aaagtatata tgagtaaact tggtctgaca gttaccaatg cttaatcagt   3480
gaggcaccta tctcagcgat ctgtctattt cgttcatcca tagttgcctg actccccgtc   3540
gtgtagataa ctacgatacg ggagggctta ccatctggcc ccagtgctgc aatgataccg   3600
cgagacccac gctcaccggc tccagattta tcagcaataa accagccagc cggaagggcc   3660
gagcgcagaa gtggtcctgc aactttatcc gcctccatcc agtctattaa ttgttgccgg   3720
gaagctagag taagtagttc gccagttaat agtttgcgca acgttgttgc cattgctaca   3780
ggcatcgtgg tgtcacgctc gtcgtttggt atggcttcat tcagctccgg ttcccaacga   3840
tcaaggcgag ttacatgatc ccccatgttg tgcaaaaaag cggttagctc cttcggtcct   3900
ccgatcgttg tcagaagtaa gttggccgca gtgttatcac tcatggttat ggcagcactg   3960
```

```
cataattctc ttactgtcat gccatccgta agatgctttt ctgtgactgg tgagtactca   4020
accaagtcat tctgagaata gtgtatgcgg cgaccgagtt gctcttgccc ggcgtcaata   4080
cgggataata ccgcgccaca tagcagaact ttaaaagtgc tcatcattgg aaaacgttct   4140
tcggggcgaa aactctcaag gatcttaccg ctgttgagat ccagttcgat gtaacccact   4200
cgtgcaccca actgatcttc agcatctttt actttcacca gcgtttctgg gtgagcaaaa   4260
acaggaaggc aaaatgccgc aaaaaaggga ataagggcga cacggaaatg ttgaatactc   4320
atactcttcc tttttcaata ttattgaagc atttatcagg gttattgtct catgagcgga   4380
tacatatttg aatgtattta gaaaaataaa caaatagggg ttccgcgcac atttccccga   4440
aaagtgccac ctgatgcggt gtgaaatacc gcacagatgc gtaaggagaa aataccgcat   4500
caggaaattg taagcgttaa tattttgtta aaattcgcgt taaatttttg ttaaatcagc   4560
tcatttttta accaataggc cgaaatcggc aaaatccctt ataaatcaaa agaatagacc   4620
gagatagggt tgagtgttgt tccagtttgg aacaagagtc cactattaaa gaacgtggac   4680
tccaacgtca aagggcgaaa aaccgtctat cagggcgatg gcccactacg tgaaccatca   4740
ccctaatcaa gttttttggg gtcgaggtgc cgtaaagcac taaatcggaa ccctaaaggg   4800
agcccccgat ttagagcttg acggggaaag ccggcgaacg tggcgagaaa ggaagggaag   4860
aaagcgaaag gagcgggcgc tagggcgctg gcaagtgtag cggtcacgct gcgcgtaacc   4920
accacacccg ccgcgcttaa tgcgccgcta cagggcgcgt ccattcgcca ttcaggctgc   4980
gcaactgttg ggaagggcga tcggtgcggg cctcttcgct attacgccag ctggcgaaag   5040
ggggatgtgc tgcaaggcga ttaagttggg taacgccagg gttttcccag tcacgacgtt   5100
gtaaaacgac ggccagtgaa ttgtaatacg actcactata gggcgaattg ggcccgacgt   5160
cgcatgcttg aatctacaag taggagggtt ggagtgatta agtgaaactt ctttaacggc   5220
tctatgccag ttctattgat atccgaaaca tcagtatgaa ggtctgataa gggtgacttc   5280
ttcccacaga ttcgtatcag tacgagtacg agaccggtac ttgtaacagt attgatacta   5340
aagggaaact acaacggttg tcagcgtaat gtgacttcgc ccatgaacgc agacacgcag   5400
tgccgagtgc ggtgatatcg cctactcgtt acgtccatgg actacacaac ccctcggctt   5460
cgcttggctt agcctcgggc tcggtgctgt tcagttaaaa cacaatcaaa taacatttct   5520
actttttaga aggcaggccg tcaggagcaa ctccgactcc attgacgttt ctaaacatct   5580
gaatgccttc cttaccttca acaaactggc aggttcgggc gacagtgtaa agagacttga   5640
tgaagttggt gtcgtcgtgt cggtagtgct tgcccatgac cttcttgatc ttctcagtgg   5700
cgattcgggc gttgtagaag ggaattccgt cgtcgcctga gtcgacgagt atctgtctga   5760
ctcgtcattg ccgcctttgg agtacgactc caactatgag tgtgcttgga tcactttgac   5820
gatacattct tcgttggagg ctgtgggtct gacagctgcg ttttcggcgc ggttggccga   5880
caacaatatc agctgcaacg tcattgctgg ctttcatcat gatcacattt ttgtcggcaa   5940
aggcgacgcc cagagagcca ttgacgttct ttctaatttg gaccgatagc cgtatagtcc   6000
agtctatcta taagttcaac taactcgtaa ctattaccat aacatatact tcactgcccc   6060
agataaggtt ccgataaaaa gttctgcaga ctaaatttat ttcagtctcc tcttcaccac   6120
caaaatgccc tcctacgaag ctcgagctaa cgtccacaag tccgcctttg ccgctcgagt   6180
gctcaagctc gtggcagcca agaaaaccaa cctgtgtgct tctctggatg ttaccaccac   6240
caaggagctc attgagcttg ccgataaggt cggaccttat gtgtgcatga tcaaaaccca   6300
tatcgacatc attgacgact tcacctacgc cggcactgtg ctccccctca aggaacttgc   6360
```

-continued

```
tcttaagcac ggtttcttcc tgttcgagga cagaaagttc gcagatattg gcaacactgt   6420
caagcaccag taccggtgtc accgaatcgc cgagtggtcc gatatcacca acgcccacgg   6480
tgtacccgga accggaatca ttgctggcct gcgagctggt gccgaggaaa ctgtctctga   6540
acagaagaag gaggacgtct ctgactacga gaactcccag tacaaggagt tcctagtccc   6600
ctctcccaac gagaagctgg ccagaggtct gctcatgctg gccgagctgt cttgcaaggg   6660
ctctctggcc actggcgagt actccaagca gaccattgag cttgcccgat ccgaccccga   6720
gtttgtggtt ggcttcattg cccagaaccg acctaagggc gactctgagg actggcttat   6780
tctgaccccc ggggtgggtc ttgacgacaa gggagacgct ctcggacagc agtaccgaac   6840
tgttgaggat gtcatgtcta ccggaacgga tatcataatt gtcggccgag gtctgtacgg   6900
ccagaaccga gatcctattg aggaggccaa gcgataccag aaggctggct gggaggctta   6960
ccagaagatt aactgttaga ggttagacta tggatatgta atttaactgt gtatatagag   7020
agcgtgcaag tatggagcgc ttgttcagct tgtatgatgg tcagacgacc tgtctgatcg   7080
agtatgtatg atactgcaca acctgtgtat ccgcatgatc tgtccaatgg ggcatgttgt   7140
tgtgtttctc gatacggaga tgctgggtac agtgctaata cgttgaacta cttatactta   7200
tatgaggctc gaagaaagct gacttgtgta tgacttaatt aatttgaatc gaatcgatga   7260
gcctaaaatg aacccgagta tatctcataa aattctcggt gagaggtctg tgactgtcag   7320
tacaaggtgc cttcattatg ccctcaacct taccatacct cactgaatgt agtgtacctc   7380
taaaaatgaa atacagtgcc aaaagccaag gcactgagct cgtctaacgg acttgatata   7440
caaccaatta aaacaaatga aaagaaatac agttctttgt atcatttgta acaattaccc   7500
tgtacaaact aaggtattga aatcccacaa tattcccaaa gtccacccct ttccaaattg   7560
tcatgcctac aactcatata ccaagcacta acctaccgtt taaacagtgt acgcagatct   7620
actatagagg aacatttaaa ttgccccgga gaagacggcc aggccgccta gatgacaaat   7680
tcaacaactc acagctgact ttctgccatt gccactaggg gggggccttt ttatatggcc   7740
aagccaagct ctccacgtcg gttgggctgc acccaacaat aaatgggtag ggttgcacca   7800
acaaagggat gggatggggg gtagaagata cgaggataac ggggctcaat ggcacaaata   7860
agaacgaata ctgccattaa gactcgtgat ccagcgactg acaccattgc atcatctaag   7920
ggcctcaaaa ctacctcgga actgctgcgc tgatctggac accacagagg ttccgagcac   7980
tttaggttgc accaaatgtc ccaccaggtg caggcagaaa acgctggaac agcgtgtaca   8040
gtttgtctta acaaaaagtg agggcgctga ggtcgagcag ggtggtgtga cttgttatag   8100
cctttagagc tgcgaaagcg cgtatggatt tggctcatca ggccagattg agggtctgtg   8160
gacacatgtc atgttagtgt acttcaatcg ccccctggat atagccccga caataggccg   8220
tggcctcatt tttttgcctt ccgcacattt ccattgctcg atacccacac cttgcttctc   8280
ctgcacttgc caaccttaat actggtttac attgaccaac atcttacaag cggggggctt   8340
gtctagggta tatataaaca gtggctctcc caatcggttg ccagtctctt ttttcctttc   8400
tttccccaca gattcgaaat ctaaactaca catcacagaa ttccgagccg tgagtatcca   8460
cgacaagatc agtgtcgaga cgacgcgttt tgtgtaatga cacaatccga aagtcgctag   8520
caacacacac tctctacaca aactaaccca gctctggtac                        8560
```

<210> SEQ ID NO 166
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 166

His Xaa Xaa Xaa His
1               5

<210> SEQ ID NO 167
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 167

His Xaa Xaa Xaa Xaa His
1               5

<210> SEQ ID NO 168
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 168

His Xaa Xaa His His
1               5

<210> SEQ ID NO 169
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 169

His Xaa Xaa Xaa His His
1               5

<210> SEQ ID NO 170
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: X = His (H) or Gln (Q)
<220> FEATURE:
<221> NAME/KEY: misc_feature
<222> LOCATION: (2)..(3)
<223> OTHER INFORMATION: Xaa can be any naturally occurring amino acid

```
<400> SEQUENCE: 170

Xaa Xaa Xaa His His
1               5


<210> SEQ ID NO 171
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: X = His (H) or Gln (Q)
<220> FEATURE:
<221> NAME/KEY: misc_feature
<222> LOCATION: (2)..(4)
<223> OTHER INFORMATION: Xaa can be any naturally occurring amino acid

<400> SEQUENCE: 171

Xaa Xaa Xaa Xaa His His
1               5


<210> SEQ ID NO 172
<211> LENGTH: 1064
<212> TYPE: DNA
<213> ORGANISM: Isochrysis galbana (GenBank Accession No. AF390174)
<220> FEATURE:
<221> NAME/KEY: CDS
<222> LOCATION: (2)..(793)
<223> OTHER INFORMATION: delta-9 elongase

<400> SEQUENCE: 172

g atg gcc ctc gca aac gac gcg gga gag cgc atc tgg gcg gct gtg acc      49
  Met Ala Leu Ala Asn Asp Ala Gly Glu Arg Ile Trp Ala Ala Val Thr
  1               5                   10                  15

gac ccg gaa atc ctc att ggc acc ttc tcg tac ttg cta ctc aaa ccg       97
Asp Pro Glu Ile Leu Ile Gly Thr Phe Ser Tyr Leu Leu Leu Lys Pro
            20                  25                  30

ctg ctc cgc aat tcc ggg ctg gtg gat gag aag aag ggc gca tac agg      145
Leu Leu Arg Asn Ser Gly Leu Val Asp Glu Lys Lys Gly Ala Tyr Arg
        35                  40                  45

acg tcc atg atc tgg tac aac gtt ctg ctg gcg ctc ttc tct gcg ctg      193
Thr Ser Met Ile Trp Tyr Asn Val Leu Leu Ala Leu Phe Ser Ala Leu
    50                  55                  60

agc ttc tac gtg acg gcg acc gcc ctc ggc tgg gac tat ggt acg ggc      241
Ser Phe Tyr Val Thr Ala Thr Ala Leu Gly Trp Asp Tyr Gly Thr Gly
65                  70                  75                  80

gcg tgg ctg cgc agg caa acc ggc gac aca ccg cag ccg ctc ttc cag      289
Ala Trp Leu Arg Arg Gln Thr Gly Asp Thr Pro Gln Pro Leu Phe Gln
                85                  90                  95

tgc ccg tcc ccg gtt tgg gac tcg aag ctc ttc aca tgg acc gcc aag      337
Cys Pro Ser Pro Val Trp Asp Ser Lys Leu Phe Thr Trp Thr Ala Lys
            100                 105                 110

gca ttc tat tac tcc aag tac gtg gag tac ctc gac acg gcc tgg ctg      385
Ala Phe Tyr Tyr Ser Lys Tyr Val Glu Tyr Leu Asp Thr Ala Trp Leu
        115                 120                 125

gtg ctc aag ggc aag agg gtc tcc ttt ctc cag gcc ttc cac cac ttt      433
Val Leu Lys Gly Lys Arg Val Ser Phe Leu Gln Ala Phe His His Phe
    130                 135                 140

ggc gcg ccg tgg gat gtg tac ctc ggc att cgg ctg cac aac gag ggc      481
Gly Ala Pro Trp Asp Val Tyr Leu Gly Ile Arg Leu His Asn Glu Gly
145                 150                 155                 160
```

```
gta tgg atc ttc atg ttt ttc aac tcg ttc att cac acc atc atg tac      529
Val Trp Ile Phe Met Phe Phe Asn Ser Phe Ile His Thr Ile Met Tyr
                165                 170                 175

acc tac tac ggc ctc acc gcc gcc ggg tat aag ttc aag gcc aag ccg      577
Thr Tyr Tyr Gly Leu Thr Ala Ala Gly Tyr Lys Phe Lys Ala Lys Pro
            180                 185                 190

ctc atc acc gcg atg cag atc tgc cag ttc gtg ggc ggc ttc ctg ttg      625
Leu Ile Thr Ala Met Gln Ile Cys Gln Phe Val Gly Gly Phe Leu Leu
        195                 200                 205

gtc tgg gac tac atc aac gtc ccc tgc ttc aac tcg gac aaa ggg aag      673
Val Trp Asp Tyr Ile Asn Val Pro Cys Phe Asn Ser Asp Lys Gly Lys
    210                 215                 220

ttg ttc agc tgg gct ttc aac tat gca tac gtc ggc tcg gtc ttc ttg      721
Leu Phe Ser Trp Ala Phe Asn Tyr Ala Tyr Val Gly Ser Val Phe Leu
225                 230                 235                 240

ctc ttc tgc cac ttt ttc tac cag gac aac ttg gca acg aag aaa tcg      769
Leu Phe Cys His Phe Phe Tyr Gln Asp Asn Leu Ala Thr Lys Lys Ser
                245                 250                 255

gcc aag gcg ggc aag cag ctc tag gcctcgagcc ggctcgcggg ttcaaggagg     823
Ala Lys Ala Gly Lys Gln Leu
            260

gcgacacggg ggtgggacgt ttgcatggag atggattgtg gatgtcctta cgccttactc    883

atcaatgtcc tcccatctct cccctctaga ccttctacta gccatctaga agggcagctc    943

agagacggat accgttcccc ctccccttcc ttttcgtctt tgctttgcca ttgtttgttt   1003

gtctctattt tttaaactat tgacgctaac gcgttacgct cgcaaaaaaa aaaaaaaaaa   1063

a                                                                   1064


<210> SEQ ID NO 173
<211> LENGTH: 263
<212> TYPE: PRT
<213> ORGANISM: Isochrysis galbana (GenBank Accession No. AF390174)

<400> SEQUENCE: 173

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175
```

```
Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260


<210> SEQ ID NO 174
<211> LENGTH: 792
<212> TYPE: DNA
<213> ORGANISM: Artificial Sequence
<220> FEATURE:
<223> OTHER INFORMATION: IgD9e: synthetic delta-9 elongase
      (codon-optimized for Yarrowia lipolytica)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(792)

<400> SEQUENCE: 174

atggctctgg ccaacgacgc tggcgagcga atctgggctg ccgtcaccga tcccgaaatc     60

ctcattggca ccttctccta cctgctcctg aagcctctcc tgcgaaactc tggtctcgtg    120

gacgagaaga aaggagccta ccgaacctcc atgatctggt acaacgtcct cctggctctc    180

ttctctgccc tgtccttcta cgtgactgcc accgctctcg gctgggacta cggtactgga    240

gcctggctgc gaagacagac cggtgatact ccccagcctc tctttcagtg tccctctcct    300

gtctgggact ccaagctgtt cacctggact gccaaggcct tctactattc taagtacgtg    360

gagtacctcg acaccgcttg gctggtcctc aagggcaagc gagtgtcctt tctgcaggcc    420

ttccatcact ttggagctcc ctgggacgtc tacctcggca ttcgactgca caacgagggt    480

gtgtggatct tcatgttctt taactcgttc attcacacca tcatgtacac ctactatgga    540

ctgactgccg ctggctacaa gttcaaggcc aagcctctga tcactgccat gcagatttgc    600

cagttcgtcg gtggctttct cctggtctgg gactacatca acgttccctg cttcaactct    660

gacaagggca agctgttctc ctgggctttc aactacgcct acgtcggatc tgtctttctc    720

ctgttctgtc acttctttta ccaggacaac ctggccacca agaaatccgc taaggctggt    780

aagcagcttt ag                                                        792


<210> SEQ ID NO 175
<211> LENGTH: 777
<212> TYPE: DNA
<213> ORGANISM: Euglena gracilis
<220> FEATURE:
<221> NAME/KEY: misc_feature
<222> LOCATION: (1)..(777)
<223> OTHER INFORMATION: delta-9 elongase; U.S. Patent Application No.
      60/739989, filed 11/23/2005

<400> SEQUENCE: 175

atggaggtgg tgaatgaaat agtctcaatt gggcaggaag ttttacccaa agttgattat     60

gcccaactct ggagtgatgc cagtcactgt gaggtgcttt acttgtccat cgcatttgtc    120
```

```
atcttgaagt tcactcttgg ccccttggt ccaaaaggtc agtctcgtat gaagtttgtt    180

ttcaccaatt acaaccttct catgtccatt tattcgttgg gatcattcct ctcaatggca    240

tatgccatgt acaccatcgg tgttatgtct gacaactgcg agaaggcttt tgacaacaac    300

gtcttcagga tcaccacgca gttgttctat ttgagcaagt tcctggagta tattgactcc    360

ttctatttgc cactgatggg caagcctctg acctggttgc aattcttcca tcatttgggg    420

gcaccgatgg atatgtggct gttctataat taccgaaatg aagctgtttg gatttttgtg    480

ctgttgaatg gtttcatcca ctggatcatg tacggttatt attggaccag attgatcaag    540

ctgaagttcc ccatgccaaa atccctgatt acatcaatgc agatcattca attcaatgtt    600

ggtttctaca ttgtctggaa gtacaggaac attccctgtt atcgccaaga tgggatgagg    660

atgtttggct ggttcttcaa ttacttttat gttggcacag tcttgtgttt gttcttgaat    720

ttctatgtgc aaacgtatat cgtcaggaag cacaagggag ccaaaaagat tcagtga       777
```

<210> SEQ ID NO 176
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: delta-9 elongase; U.S. Patent Application No. 60/739989, filed 11/23/2005

<400> SEQUENCE: 176

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240
```

```
Phe Tyr Val Gln Thr Tyr Ile Val Arg Lys His Lys Gly Ala Lys Lys
                245                 250                 255

Ile Gln


<210> SEQ ID NO 177
<211> LENGTH: 777
<212> TYPE: DNA
<213> ORGANISM: Euglena gracilis
<220> FEATURE:
<221> NAME/KEY: misc_feature
<222> LOCATION: (1)..(777)
<223> OTHER INFORMATION: synthetic delta-9 elongase codon-optimized for
      Yarrowia lipolytica; U.S. Patent Application No. 60/739989, filed
      11/23/2005

<400> SEQUENCE: 177

atggaggtcg tgaacgaaat cgtctccatt ggccaggagg ttcttcccaa ggtcgactat      60

gctcagctct ggtctgatgc ctcgcactgc gaggtgctgt acctctccat cgccttcgtc     120

atcctgaagt tcacccttgg tcctctcgga cccaagggtc agtctcgaat gaagtttgtg     180

ttcaccaact acaacctgct catgtccatc tactcgctgg gctccttcct ctctatggcc     240

tacgccatgt acaccattgg tgtcatgtcc gacaactgcg agaaggcttt cgacaacaat     300

gtcttccgaa tcaccactca gctgttctac ctcagcaagt tcctcgagta cattgactcc     360

ttctatctgc ccctcatggg caagcctctg acctggttgc agttctttca ccatctcgga     420

gctcctatgg acatgtggct gttctacaac taccgaaacg aagccgtttg gatctttgtg     480

ctgctcaacg gcttcattca ctggatcatg tacggctact attggacccg actgatcaag     540

ctcaagttcc ctatgcccaa gtccctgatt acttctatgc agatcattca gttcaacgtt     600

ggcttctaca tcgtctggaa gtaccggaac attccctgct accgacaaga tggaatgaga     660

atgtttggct ggtttttcaa ctacttctac gttggtactg tcctgtgtct gttcctcaac     720

ttctacgtgc agacctacat cgtccgaaag cacaagggag ccaaaaagat tcagtga        777


<210> SEQ ID NO 178
<211> LENGTH: 120
<212> TYPE: PRT
<213> ORGANISM: Saccharomyces cerevisiae (GenBank Accession No. P40312)

<400> SEQUENCE: 178

Met Pro Lys Val Tyr Ser Tyr Gln Glu Val Ala Glu His Asn Gly Pro
1               5                   10                  15

Glu Asn Phe Trp Ile Ile Ile Asp Asp Lys Val Tyr Asp Val Ser Gln
            20                  25                  30

Phe Lys Asp Glu His Pro Gly Gly Asp Glu Ile Ile Met Asp Leu Gly
        35                  40                  45

Gly Gln Asp Ala Thr Glu Ser Phe Val Asp Ile Gly His Ser Asp Glu
    50                  55                  60

Ala Leu Arg Leu Leu Lys Gly Leu Tyr Ile Gly Asp Val Asp Lys Thr
65                  70                  75                  80

Ser Glu Arg Val Ser Val Glu Lys Val Ser Thr Ser Glu Asn Gln Ser
                85                  90                  95

Lys Gly Ser Gly Thr Leu Val Val Ile Leu Ala Ile Leu Met Leu Gly
            100                 105                 110

Val Ala Tyr Tyr Leu Leu Asn Glu
        115                 120
```

<210> SEQ ID NO 179
<211> LENGTH: 124
<212> TYPE: PRT
<213> ORGANISM: Schizosaccharomyces pombe (GenBank Accession No. O94391)

<400> SEQUENCE: 179

```
Met Ser Val Lys Tyr Phe Glu Pro Glu Glu Ile Val Glu His Asn Asn
1               5                   10                  15

Ser Lys Asp Met Tyr Met Val Ile Asn Gly Lys Val Tyr Asp Val Ser
            20                  25                  30

Asn Phe Ala Asp Asp His Pro Gly Gly Leu Asp Ile Met Leu Asp Tyr
        35                  40                  45

Ala Gly Gln Asp Ala Thr Lys Ala Tyr Gln Asp Ile Gly His Ser Ile
    50                  55                  60

Ala Ala Asp Glu Leu Leu Glu Glu Met Tyr Ile Gly Asp Leu Lys Pro
65                  70                  75                  80

Gly Thr Glu Glu Arg Leu Lys Glu Leu Lys Lys Pro Arg Ser Phe Asp
                85                  90                  95

Asn Asp Thr Pro Pro Leu Pro Leu Leu Ile Ala Leu Ile Val Leu Pro
            100                 105                 110

Ala Ile Ala Val Ile Val Phe Val Lys Leu Asn Lys
        115                 120
```

<210> SEQ ID NO 180
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 180

```
ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggtttaaa cgagcttggc gtaatcatgg    240

tcatagctgt ttcctgtgtg aaattgttat ccgctcacaa ttccacacaa cgtacgagcc    300

ggaagcataa agtgtaaagc ctggggtgcc taatgagtga gctaactcac attaattgcg    360

ttgcgctcac tgcccgcttt ccagtcggga aacctgtcgt gccagctgca ttaatgaatc    420

ggccaacgcg cggggagagg cggtttgcgt attgggcgct cttccgcttc ctcgctcact    480

gactcgctgc gctcggtcgt tcggctgcgg cgagcggtat cagctcactc aaaggcggta    540

atacggttat ccacagaatc aggggataac gcaggaaaga acatgtgagc aaaaggccag    600

caaaaggcca ggaaccgtaa aaaggccgcg ttgctggcgt ttttccatag gctccgcccc    660

cctgacgagc atcacaaaaa tcgacgctca agtcagaggt ggcgaaaccc gacaggacta    720

taaagatacc aggcgtttcc ccctggaagc tccctcgtgc gctctcctgt tccgaccctg    780

ccgcttaccg gatacctgtc cgcctttctc ccttcgggaa gcgtggcgct ttctcatagc    840

tcacgctgta ggtatctcag ttcggtgtag gtcgttcgct ccaagctggg ctgtgtgcac    900

gaaccccccg ttcagcccga ccgctgcgcc ttatccggta actatcgtct tgagtccaac    960

ccggtaagac acgacttatc gccactggca gcagccactg gtaacaggat tagcagagcg   1020

aggtatgtag gcggtgctac agagttcttg aagtggtggc ctaactacgg ctacactaga   1080

aggacagtat ttggtatctg cgctctgctg aagccagtta ccttcggaaa aagagttggt   1140

agctcttgat ccggcaaaca aaccaccgct ggtagcggtg gtttttttgt ttgcaagcag   1200
```

-continued

```
cagattacgc gcagaaaaaa aggatctcaa gaagatcctt tgatcttttc tacggggtct   1260
gacgctcagt ggaacgaaaa ctcacgttaa gggattttgg tcatgagatt atcaaaaagg   1320
atcttcacct agatcctttt aaattaaaaa tgaagtttta aatcaatcta aagtatatat   1380
gagtaaactt ggtctgacag ttaccaatgc ttaatcagtg aggcacctat ctcagcgatc   1440
tgtctatttc gttcatccat agttgcctga ctccccgtcg tgtagataac tacgatacgg   1500
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag ggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
```

```
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taattttttg   4020
cttaaattca atccccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaatttg aatcgaatcg gagcctaaaa tgaacccgag tatatctcat aaaattctcg   4560
gtgagaggtc tgtgactgtc agtacaaggt gccttcatta tgccctcaac cttaccatac   4620
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
aatctgcttc ttctagtcaa ggttgctaca ccggtaaatt ataaatcatc atttcattag   5160
cagggcaggg cccttttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcgggggcag atccgtgaca gggctcgtac   5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
```

```
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
agccggccgg gagtatgtcg gaggggacat acgagatcgt caagggtttg tggccaactg   6660
gtatttaaat gtagctaacg gtagcaggcg aactactggt acatacctcc cccggaatat   6720
gtacaggcat aatgcgtatc tgtgggacat gtggtcgttg cgccattatg taagcagcgt   6780
gtactcctct gactgtccat atggtttgct ccatctcacc ctcatcgttt tcattgttca   6840
caggcggcca caaaaaaact gtcttctctc cttctctctt cgccttagtc tactcggacc   6900
agttttagtt tagcttggcg ccactggata aatgagacct caggccttgt gatgaggagg   6960
tcacttatga agcatgttag gaggtgcttg tatggataga gaagcaccca aaataataag   7020
aataataata aaacaggggg cgttgtcatt tcatatcgtg ttttcaccat caatacacct   7080
ccaaacaatg cccttcatgt ggccagcccc aatattgtcc tgtagttcaa ctctatgcag   7140
ctcgtatctt attgagcaag taaaactctg tcagccgata ttgcccgacc cgcgacaagg   7200
gtcaacaagg tggtgtaagg ccttcgcaga agtcaaaact gtgccaaaca aacatctaga   7260
gtctctttgg tgtttctcgc atatatttwa tcggctgtct tacgtatttg cgcctcggta   7320
ccggactaat ttcggatcat ccccaatacg ctttttcttc gcagctgtca acagtgtcca   7380
tgatctatcc acctaaatgg gtcatatgag gcgtataatt tcgtggtgct gataataatt   7440
cccatatatt tgacacaaaa cttccccccc tagacataca tctcacaatc tcacttcttg   7500
tgcttctgtc acacatctcc tccagctgac ttcaactcac acctctgccc cagttggtct   7560
acagcggtat aaggtttctc cgcatagagg tgcaccactc ctcccgatac ttgtttgtgt   7620
gacttgtggg tcacgacata tatatctaca cacattgcgc caccctttgg ttcttccagc   7680
acaacaaaaa cacgacacgc taaccatggc caatttactg accgtacacc aaaatttgcc   7740
tgcattaccg gtcgatgcaa cgagtgatga ggttcgcaag aacctgatgg acatgttcag   7800
ggatcgccag gcgttttctg agcatacctg gaaaatgctt ctgtccgttt gccggtcgtg   7860
ggcggcatgg tgcaagttga ataaccggaa atggtttccc gcagaacctg aagatgttcg   7920
cgattatctt ctatatcttc aggcgcgcgg tctggcagta aaaactatcc agcaacattt   7980
gggccagcta aacatgcttc atcgtcggtc cgggctgcca cgaccaagtg acagcaatgc   8040
tgtttcactg gttatgcggc ggatccgaaa agaaaacgtt gatgccggtg aacgtgcaaa   8100
acaggctcta gcgttcgaac gcactgattt cgaccaggtt cgttcactca tggaaaatag   8160
cgatcgctgc caggatatac gtaatctggc atttctgggg attgcttata acaccctgtt   8220
acgtatagcc gaaattgcca ggatcagggt taaagatatc tcacgtactg acggtgggag   8280
aatgttaatc catattggca gaacgaaaac gctggttagc accgcaggtg tagagaaggc   8340
acttagcctg gggtaactaa aactggtcga gcgatggatt tccgtctctg gtgtagctga   8400
```

```
tgatccgaat aactacctgt tttgccgggt cagaaaaaat ggtgttgccg cgccatctgc   8460

caccagccag ctatcaactc gcgccctgga agggattttt gaagcaactc atcgattgat   8520

ttacggcgct aaggatgact ctggtcagag atacctggcc tggtctggac acagtgcccg   8580

tgtcggagcc gcgcgagata tggcccgcgc tggagtttca ataccggaga tcatgcaagc   8640

tggtggctgg accaatgtaa atattgtcat gaactatatc cgtaacctgg atagtgaaac   8700

aggggcaatg gtgcgcctgc tggaagatgg cgattaagc                          8739
```

<210> SEQ ID NO 181
<211> LENGTH: 15304
<212> TYPE: DNA
<213> ORGANISM: Artificial Sequence
<220> FEATURE:
<223> OTHER INFORMATION: Plasmid pKO2UF8289
<220> FEATURE:
<221> NAME/KEY: misc_feature
<222> LOCATION: (5601)..(5601)
<223> OTHER INFORMATION: n is a, c, g, or t
<220> FEATURE:
<221> NAME/KEY: misc_feature
<222> LOCATION: (5606)..(5609)
<223> OTHER INFORMATION: n is a, c, g, or t

<400> SEQUENCE: 181

```
cgatcgagga agaggacaag cggctgcttc ttaagtttgt gacatcagta tccaaggcac     60

cattgcaagg attcaaggct ttgaacccgt catttgccat tcgtaacgct ggtagacagg    120

ttgatcggtt ccctacggcc tccacctgtg tcaatcttct caagctgcct gactatcagg    180

acattgatca acttcggaag aaacttttgt atgccattcg atcacatgct ggtttcgatt    240

tgtcttagag gaacgcatat acagtaatca tagagaataa acgatattca tttattaaag    300

tagatagttg aggtagaagt tgtaaagagt gataaatagc ggccgctcac tgaatctttt    360

tggctccctt gtgcttcctg acgatatacg tttgcacata gaaattcaag aacaaacaca    420

agactgtgcc aacataaaag taattgaaga accagccaaa catcctcatc ccatcttggc    480

gataacaggg aatgttcctg tacttccaga caatgtagaa accaacattg aattgaatga    540

tctgcattga tgtaatcagg gattttggca tggggaactt cagcttgatc aatctggtcc    600

aataataacc gtacatgatc cagtggatga aaccattcaa cagcacaaaa atccaaacag    660

cttcatttcg gtaattatag aacagccaca tatccatcgg tgcccccaaa tgatggaaga    720

attgcaacca ggtcagaggc ttgcccatca gtggcaaata gaaggagtca atatactcca    780

ggaacttgct caaatagaac aactgcgtgg tgatcctgaa gacgttgttg tcaaaagcct    840

tctcgcagtt gtcagacata acaccgatgg tgtacatggc atatgccatt gagaggaatg    900

atcccaacga ataaatggac atgagaaggt tgtaattggt gaaaacaaac ttcatacgag    960

actgaccttt tggaccaagg gggccaagag tgaacttcaa gatgacaaat gcgatggaca   1020

agtaaagcac ctcacagtga ctggcatcac tccagagttg ggcataatca actggttggg   1080

taaaacttcc tgcccaattg agactatttc attcaccacc tccatggtta gcgtgtcgtg   1140

tttttgttgt gctggaagaa ccaaagggtg gcgcaatgtg tgtagatata tatgtcgtga   1200

cccacaagtc acacaaacaa gtatcgggag gagtggtgca cctctatgcg gagaaacctt   1260

ataccgctgt agaccaactg ggcagaggt gtgagttgaa gtcagctgga ggagatgtgt   1320

gacagaagca caagaagtga gattgtgaga tgtatgtcta gggggggaag ttttgtgtca   1380

aatatatggg aattattatc agcaccacga aattatacgc ctcatatgac ccatttaggt   1440

ggatagatca tggacactgt tgacagctgc gaagaaaaag cgtattgggg atgatccgaa   1500
```

```
attagtccgg taccgaggcg caaatacgta agacagccga twaaatatat gcgagaaaca   1560
ccaaagagac tctagatgtt tgtttggcac agttttgact tctgcgaagg ccttacacca   1620
ccttgttgac ccttgtcgcg ggtcgggcaa tatcggctga cagagtttta cttgctcaat   1680
aagatacgag ctgcatagag ttgaactaca ggacaatatt ggggctggcc acatgaaggg   1740
cattgtttgg aggtgtattg atggtgaaaa cacgatatga aatgacaacg ccccctgttt   1800
tattattatt cttattattt tgggtgcttc tctatccata caagcacctc ctaacatgct   1860
tcataagtga cctcctcatc acaaggcctg aggtctcatt tatccagtgg cgccaagcta   1920
aactaaaact ggtccgagta gactaaggcg aagagagaag gagagaagac agttttttg    1980
tggccgcctg tgaacaatga aaacgatgag ggtgagatgg agcaaaccat atggtttaaa   2040
cagtcagagg agtacacgct gcttacataa tggcgcaacg accacatgtc ccacagatac   2100
gcatcgattc gattcaaatt aattaaaagg cgttgaaaca gaatgagcca gacagcaagg   2160
acaaggtggc caacagcaag gagtccaaaa agccctctat tgacgagatc cacgatgtta   2220
ttgctcatga ggtttccgag ctcgatgctg ggaagaagaa gtgatttgta tataagaaat   2280
aaatgagata tagtaaagga gtgcaagaga atggcaaggt ggtcaaattc tatattactt   2340
gcagtcactg gttcctcgtt gacatgaatg aagttaccgt tggcatagct gatttaatat   2400
ataactgtcc aactaactct cacctagata taacccatgt gtgtgtttcc aatcatcaat   2460
gcggccgctt actgagcctt ggcaccgggc tgcttctcgg ccattcgagc gaactgggac   2520
aggtatcgga gcaggatgac gagaccttca tggggcagag ggtttcggta ggggaggttg   2580
tgcttctggc acagctgttc cacctggtag gaaacggcag tgaggttgtg tcgaggcagg   2640
gtgggccaga gatggtgctc gatctggtag ttcaggcctc caaagaacca gtcagtaatg   2700
atgcctcgtc gaatgttcat ggtctcatgg atctgaccca cagagaagcc atgtccgtcc   2760
cagacggaat caccgatctt ctccagaggg tagtggttca tgaagaccac gatggcaatt   2820
ccgaagccac cgacgagctc ggaaacaaag aacaccagca tcgaggtcag gatggagggc   2880
ataaagaaga ggtggaacag ggtcttgaga gtccagtgca gagcgagtcc aatggcctct   2940
ttcttgtact gagatcggta gaactggttg tctcggtcct tgagggatcg aacggtcagc   3000
acagactgga aacaccagat gaatcgcagg agaatacaga tgaccaggaa atagtactgt   3060
tggaactgaa tgagctttcg ggagatggga gaagctcgag tgacatcgtc ctcggaccag   3120
gcgagcagag gcaggttatc aatgtcggga tcgtgaccct gaacgttggt agcagaatga   3180
tgggcgttgt gtctgtcctt ccaccaggtc acggagaagc cctggagtcc gttgccaaag   3240
accagaccca ggacgttatt ccagtttcgg ttcttgaagg tctggtggtg gcagatgtca   3300
tgagacagcc atcccatttg ctggtagtgc ataccgagca cgagagcacc aatgaagtac   3360
aggtggtact ggaccagcat gaagaaggca agcacgccaa gacccagggt ggtcaagatc   3420
ttgtacgagt accagagggg agaggcgtca aacatgccag tggcgatcag ctcttctcgg   3480
agctttcgga aatcctcctg agcttcgttg acggcagcct ggggaggcag ctcggaagcc   3540
tggttgatct tgggcattcg cttgagcttg tcgaaggctt cctgagagtg cataaccatg   3600
aaggcgtcag tagcatctcg tccctggtag ttctcaatga tttcagctcc accagggtgg   3660
aagttcaccc aagcggagac gtcgtacacc tttccgtcga tgacgagggg cagagcctgt   3720
cgagaagcct tcaccatggc cattgctgta gatatgtctt gtgtgtaagg gggttggggt   3780
ggttgtttgt gttcttgact tttgtgttag caagggaaga cgggcaaaaa agtgagtgtg   3840
gttgggaggg agagacgagc cttatatata atgcttgttt gtgtttgtgc aagtggacgc   3900
```

```
cgaaacgggc aggagccaaa ctaaacaagg cagacaatgc gagcttaatt ggattgcctg   3960
atgggcaggg gttagggctc gatcaatggg ggtgcgaagt gacaaaattg ggaattaggt   4020
tcgcaagcaa ggctgacaag actttggccc aaacatttgt acgcggtgga caacaggagc   4080
cacccatcgt ctgtcacggg ctagccggtc gtgcgtcctg tcaggctcca cctaggctcc   4140
atgccactcc atacaatccc actagtgtac cgctaggccg cttttagctc ccatctaaga   4200
ccccccccaaa acctccactg tacagtgcac tgtactgtgt ggcgatcaag ggcaagggaa   4260
aaaaggcgca aacatgcacg catggaatga cgtaggtaag gcgttactag actgaaaagt   4320
ggcacatttc ggcgtgccaa agggtcctag gtgcgtttcg cgagctgggc gccaggccaa   4380
gccgctccaa aacgcctctc cgactccctc cagcggcctc catatcccca tccctctcca   4440
cagcaatgtt gttaagcctt gcaaacgaaa aaatagaaag gctaataagc ttccaatatt   4500
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgcgc ctacttaagc aacgggcttg   4920
ataacagcgg ggggggtgcc cacgttgttg cggttgcgga agaacagaac acccttacca   4980
gcaccctcgg caccagcgct gggctcaacc cactggcaca tacgcgcact gcggtacatg   5040
gcgcggatga agccacgagg accatcctgg acatcagccc ggtagtgctt gcccatgatg   5100
ggcttaatgg cctcggtggc ctcgtccgcg ttgtagaagg ggatgctgct gacgtagtgg   5160
tggaggacat gagtctcgat gatgccgtgg agaaggtggc ggccgatgaa gcccatctca   5220
cggtcaatgg tagcagcggc accacggacg aagttccact cgtcgttggt gtagtgggga   5280
agggtagggt cggtgtgctg gaggaaggtg atggcaacga gccagtggtt aacccagagg   5340
tagggaacaa agtaccagat ggccatgttg tagaaaccga acttctgaac gaggaagtac   5400
agagcagtgg ccatcagacc gataccaata tcgctgagga cgatgagctt agcgtcactg   5460
ttctcgtaca gagggctgcg gggatcgaag tggttaacac caccgccgag gccgttatgc   5520
ttgcccttgc cgcgaccctc acgctggcgc tcgtggtagt tgtggccggt aacattggtg   5580
atgaggtagt tgggccagcc nacgannnnc tcagtaagat gagcgagctc gtgggtcatc   5640
tttccgagac gagtagcctg ctgctcgcgg gttcggggaa cgaagaccat gtcacgctcc   5700
atgttgccag tggccttgtg gtgctttcgg tgggagattt gccagctgaa gtaggggaca   5760
aggagggaag agtgaagaac ccagccagta atgtcgttga tgatgcgaga atcggagaaa   5820
gcaccgtgac cgcactcatg ggcaataacc cagagaccag taccgaaaag accctgaaga   5880
acggtgtaca cggcccacag accagcgcgg gcgggggtgg aggggatata ttcgggggtc   5940
acaaagttgt accagatgct gaaagtggta gtcaggagga caatgtcgcg gaggatataa   6000
ccgtatccct tgagagcgga gcgcttgaag cagtgcttag ggatggcatt gtagatgtcc   6060
ttgatggtaa agtcgggaac ctcgaactgg ttgccgtagg tgtcgagcat gacaccatac   6120
tcggacttgg gcttggcgat atcaacctcg gacatggacg agagcgatgt ggaagaggcc   6180
gagtggcggg gagagtctga aggagagacg gcggcagact cagaatccgt cacagtagtt   6240
gaggtgacgg tgcgtctaag cgcagggttc tgcttgggca gagccgaagt ggacgccatg   6300
```

```
gttgtgaatt agggtggtga gaatggttgg ttgtagggaa gaatcaaagg ccggtctcgg   6360
gatccgtggg tatatatata tatatatata tatacgatcc ttcgttacct ccctgttctc   6420
aaaactgtgg tttttcgttt ttcgtttttt gcttttttg atttttttag ggccaactaa   6480
gcttccagat ttcgctaatc acctttgtac taattacaag aaaggaagaa gctgattaga   6540
gttgggcttt ttatgcaact gtgctactcc ttatctctga tatgaaagtg tagacccaat   6600
cacatcatgt catttagagt tggtaatact gggaggatag ataaggcacg aaaacgagcc   6660
atagcagaca tgctgggtgt agccaagcag aagaaagtag atgggagcca attgacgagc   6720
gagggagcta cgccaatccg acatacgaca cgctgagatc gtcttggccg gggggtacct   6780
acagatgtcc aagggtaagt gcttgactgt aattgtatgt ctgaggacaa atatgtagtc   6840
agccgtataa agtcatacca ggcaccagtg ccatcatcga accactaact ctctatgata   6900
catgcctccg gtattattgt accatgcgtc gctttgttac atacgtatct tgccttttc    6960
tctcagaaac tccagacttt ggctattggt cgagataagc ccggaccata gtgagtcttt   7020
cacactctac atttctccct tgctccaact atttaaattg ccccggagaa gacggccagg   7080
ccgcctagat gacaaattca acaactcaca gctgactttc tgccattgcc actagggggg   7140
ggccttttta tatggccaag ccaagctctc cacgtcggtt gggctgcacc caacaataaa   7200
tgggtagggt tgcaccaaca aagggatggg atgggggta gaagatacga ggataacggg    7260
gctcaatggc acaaataaga acgaatactg ccattaagac tcgtgatcca gcgactgaca   7320
ccattgcatc atctaagggc ctcaaaacta cctcggaact gctgcgctga tctggacacc   7380
acagaggttc cgagcacttt aggttgcacc aaatgtccca ccaggtgcag gcagaaaacg   7440
ctggaacagc gtgtacagtt tgtcttaaca aaaagtgagg gcgctgaggt cgagcagggt   7500
ggtgtgactt gttatagcct ttagagctgc gaaagcgcgt atggatttgg ctcatcaggc   7560
cagattgagg gtctgtggac acatgtcatg ttagtgtact tcaatcgccc cctggatata   7620
gccccgacaa taggccgtgg cctcattttt ttgccttccg cacatttcca ttgctcggta   7680
cccacacctt gcttctcctg cacttgccaa ccttaatact ggtttacatt gaccaacatc   7740
ttacaagcgg ggggcttgtc tagggtatat ataaacagtg gctctcccaa tcggttgcca   7800
gtctcttttt tcctttcttt ccccacagat tcgaaatcta aactacacat cacagaattc   7860
cgagccgtga gtatccacga caagatcagt gtcgagacga cgcgttttgt gtaatgacac   7920
aatccgaaag tcgctagcaa cacacactct ctacacaaac taacccagct ctggtaccat   7980
ggtgaaggct tctcgacagg ctctgcccct cgtcatcgac ggaaaggtgt acgacgtctc   8040
cgcttgggtg aacttccacc ctggtggagc tgaaatcatt gagaactacc agggacgaga   8100
tgctactgac gccttcatgg ttatgcactc tcaggaagcc ttcgacaagc tcaagcgaat   8160
gcccaagatc aaccaggctt ccgagctgcc tccccaggct gccgtcaacg aagctcagga   8220
ggatttccga aagctccgag aagagctgat cgccactggc atgtttgacg cctctcccct   8280
ctggtactcg tacaagatct tgaccaccct gggtcttggc gtgcttgcct tcttcatgct   8340
ggtccagtac cacctgtact tcattggtgc tctcgtgctc ggtatgcact accagcaaat   8400
gggatggctg tctcatgaca tctgccacca ccagaccttc aagaaccgaa actggaataa   8460
cgtcctgggt ctggtctttg gcaacggact ccagggcttc tccgtgacct ggtggaagga   8520
cagacacaac gcccatcatt ctgctaccaa cgttcagggt cacgatcccg acattgataa   8580
cctgcctctg ctcgcctggt ccgaggacga tgtcactcga gcttctccca tctcccgaaa   8640
gctcattcag ttccaacagt actatttcct ggtcatctgt attctcctgc gattcatctg   8700
```

-continued

```
gtgtttccag tctgtgctga ccgttcgatc cctcaaggac cgagacaacc agttctaccg   8760
atctcagtac aagaaagagg ccattggact cgctctgcac tggactctca agaccctgtt   8820
ccacctcttc tttatgccct ccatcctgac ctcgatgctg gtgttctttg tttccgagct   8880
cgtcggtggc ttcggaattg ccatcgtggt cttcatgaac cactaccctc tggagaagat   8940
cggtgattcc gtctgggacg gacatggctt ctctgtgggt cagatccatg agaccatgaa   9000
cattcgacga ggcatcatta ctgactggtt ctttggaggc ctgaactacc agatcgagca   9060
ccatctctgg cccaccctgc ctcgacacaa cctcactgcc gtttcctacc aggtggaaca   9120
gctgtgccag aagcacaacc tcccctaccg aaaccctctg ccccatgaag gtctcgtcat   9180
cctgctccga tacctgtccc agttcgctcg aatggccgag aagcagcccg gtgccaaggc   9240
tcagtaagcg gccgcaagtg tggatgggga agtgagtgcc cggttctgtg tgcacaattg   9300
gcaatccaag atggatggat tcaacacagg gatatagcga gctacgtggt ggtgcgagga   9360
tatagcaacg gatatttatg tttgacactt gagaatgtac gatacaagca ctgtccaagt   9420
acaatactaa acatactgta catactcata ctcgtacccg ggcaacggtt tcacttgagt   9480
gcagtggcta gtgctcttac tcgtacagtg tgcaatactg cgtatcatag tctttgatgt   9540
atatcgtatt cattcatgtt agttgcgtac gggtgaagct tccactggtc ggcgtggtag   9600
tggggcagag tggggtcggt gtgctgcagg taggtgatgg ccacgagcca gtggttgacc   9660
cacaggtagg ggatcaggta gtagagggtg acggaagcca ggccccatcg gttgatggag   9720
tatgcgatga cggacatggt gataccaata ccgacgttag agatccagat gttgaaccag   9780
tccttcttct caaacagcgg ggcgttgggg ttgaagtggt tgacagccca tttgttgagc   9840
ttggggtact tctgtccggt aacgtaagac agcagataca gaggccatcc aaacacctgc   9900
tgggtgatga ggccgtagag ggtcatgagg ggagcgtcct cagcaagctc agaccagtca   9960
tgggcgcctc ggttctccat aaactccttt cggtccttgg gcacaaacac catatcacgg  10020
gtgaggtgac cagtggactt gtggtgcatg gagtgggtca gcttccaggc gtagtaaggg  10080
accagcatgg aggagtgcag aacccatccg gtgacgttgt tgacggtgtt agagtcggag  10140
aaagcagagt ggccacactc gtgggcaaga acccacagac cggtgccaaa cagaccctgg  10200
acaatggagt acatggccca ggccacagct cggccggaag ccgagggaat aagaggcagg  10260
tacgcgtagg ccatgtaggc aaaaacggcg ataaagaagc aggcgcgcca gctgcattaa  10320
tgaatcggcc aacgcgcggg gagaggcggt ttgcgtattg ggcgctcttc cgcttcctcg  10380
ctcactgact cgctgcgctc ggtcgttcgg ctgcggcgag cggtatcagc tcactcaaag  10440
gcggtaatac ggttatccac agaatcaggg gataacgcag gaaagaacat gtgagcaaaa  10500
ggccagcaaa aggccaggaa ccgtaaaaag gccgcgttgc tggcgttttt ccataggctc  10560
cgcccccctg acgagcatca caaaaatcga cgctcaagtc agaggtggcg aaacccgaca  10620
ggactataaa gataccaggc gtttccccct ggaagctccc tcgtgcgctc tcctgttccg  10680
accctgccgc ttaccggata cctgtccgcc tttctccctt cgggaagcgt ggcgctttct  10740
catagctcac gctgtaggta tctcagttcg gtgtaggtcg ttcgctccaa gctgggctgt  10800
gtgcacgaac cccccgttca gcccgaccgc tgcgccttat ccggtaacta tcgtcttgag  10860
tccaacccgg taagacacga cttatcgcca ctggcagcag ccactggtaa caggattagc  10920
agagcgaggt atgtaggcgg tgctacagag ttcttgaagt ggtggcctaa ctacggctac  10980
actagaagaa cagtatttgg tatctgcgct ctgctgaagc cagttacctt cggaaaaaga  11040
gttggtagct cttgatccgg caaacaaacc accgctggta gcggtggttt ttttgtttgc  11100
```

```
aagcagcaga ttacgcgcag aaaaaaagga tctcaagaag atcctttgat cttttctacg  11160
gggtctgacg ctcagtggaa cgaaaactca cgttaaggga ttttggtcat gagattatca  11220
aaaaggatct tcacctagat ccttttaaat taaaaatgaa gttttaaatc aatctaaagt  11280
atatatgagt aaacttggtc tgacagttac caatgcttaa tcagtgaggc acctatctca  11340
gcgatctgtc tatttcgttc atccatagtt gcctgactcc ccgtcgtgta gataactacg  11400
atacgggagg gcttaccatc tggccccagt gctgcaatga taccgcgaga cccacgctca  11460
ccggctccag atttatcagc aataaaccag ccagccggaa gggccgagcg cagaagtggt  11520
cctgcaactt tatccgcctc catccagtct attaattgtt gccgggaagc tagagtaagt  11580
agttcgccag ttaatagttt gcgcaacgtt gttgccattg ctacaggcat cgtggtgtca  11640
cgctcgtcgt ttggtatggc ttcattcagc tccggttccc aacgatcaag gcgagttaca  11700
tgatccccca tgttgtgcaa aaaagcggtt agctccttcg gtcctccgat cgttgtcaga  11760
agtaagttgg ccgcagtgtt atcactcatg gttatggcag cactgcataa ttctcttact  11820
gtcatgccat ccgtaagatg cttttctgtg actggtgagt actcaaccaa gtcattctga  11880
gaatagtgta tgcggcgacc gagttgctct tgcccggcgt caatacggga taataccgcg  11940
ccacatagca gaactttaaa agtgctcatc attggaaaac gttcttcggg gcgaaaactc  12000
tcaaggatct taccgctgtt gagatccagt tcgatgtaac ccactcgtgc acccaactga  12060
tcttcagcat cttttacttt caccagcgtt tctgggtgag caaaaacagg aaggcaaaat  12120
gccgcaaaaa agggaataag ggcgacacgg aaatgttgaa tactcatact cttccttttt  12180
caatattatt gaagcattta tcagggttat tgtctcatga gcggatacat atttgaatgt  12240
atttagaaaa ataaacaaat aggggttccg cgcacatttc cccgaaaagt gccacctgat  12300
gcggtgtgaa ataccgcaca gatgcgtaag gagaaaatac cgcatcagga aattgtaagc  12360
gttaatattt tgttaaaatt cgcgttaaat ttttgttaaa tcagctcatt ttttaaccaa  12420
taggccgaaa tcggcaaaat cccttataaa tcaaaagaat agaccgagat agggttgagt  12480
gttgttccag tttggaacaa gagtccacta ttaaagaacg tggactccaa cgtcaaaggg  12540
cgaaaaaccg tctatcaggg cgatggccca ctacgtgaac catcacccta atcaagtttt  12600
ttggggtcga ggtgccgtaa agcactaaat cggaacccta aagggagccc ccgatttaga  12660
gcttgacggg gaaagccggc gaacgtggcg agaaaggaag ggaagaaagc gaaaggagcg  12720
ggcgctaggg cgctggcaag tgtagcggtc acgctgcgcg taaccaccac acccgccgcg  12780
cttaatgcgc cgctacaggg cgcgtccatt cgccattcag gctgcgcaac tgttgggaag  12840
ggcgatcggt gcgggcctct tcgctattac gccagctggc gaaaggggga tgtgctgcaa  12900
ggcgattaag ttgggtaacg ccagggtttt cccagtcacg acgttgtaaa acgacggcca  12960
gtgaattgta atacgactca ctatagggcg aattgggccc gacgtcgcat gcttgaatct  13020
acaagtagga gggttggagt gattaagtga aacttcttta acggctctat gccagttcta  13080
ttgatatccg aaacatcagt atgaaggtct gataagggtg acttcttccc acagattcgt  13140
atcagtacga gtacgagacc ggtacttgta acagtattga tactaaaggg aaactacaac  13200
ggttgtcagc gtaatgtgac ttcgcccatg aacgcagaca cgcagtgccg agtgcggtga  13260
tatcgcctac tcgttacgtc catggactac acaacccctc ggcttcgctt ggcttagcct  13320
cgggctcggt gctgttcagt taaaacacaa tcaaataaca tttctacttt ttagaaggca  13380
ggccgtcagg agcaactccg actccattga cgtttctaaa catctgaatg ccttccttac  13440
cttcaacaaa ctggcaggtt cgggcgacag tgtaaagaga cttgatgaag ttggtgtcgt  13500
```

```
cgtgtcggta gtgcttgccc atgaccttct tgatcttctc agtggcgatt cgggcgttgt  13560

agaagggaat tcctttacct gcaggataac ttcgtataat gtatgctata cgaagttatg  13620

atctctctct tgagcttttc cataacaagt tcttctgcct ccaggaagtc catgggtggt  13680

ttgatcatgg ttttggtgta gtggtagtgc agtggtggta ttgtgactgg ggatgtagtt  13740

gagaataagt catacacaag tcagctttct tcgagcctca tataagtata agtagttcaa  13800

cgtattagca ctgtacccag catctccgta tcgagaaaca caacaacatg ccccattgga  13860

cagatcatgc ggatacacag gttgtgcagt atcatacata ctcgatcaga caggtcgtct  13920

gaccatcata caagctgaac aagcgctcca tacttgcacg ctctctatat acacagttaa  13980

attacatatc catagtctaa cctctaacag ttaatcttct ggtaagcctc ccagccagcc  14040

ttctggtatc gcttggcctc ctcaatagga tctcggttct ggccgtacag acctcggccg  14100

acaattatga tatccgttcc ggtagacatg acatcctcaa cagttcggta ctgctgtccg  14160

agagcgtctc ccttgtcgtc aagacccacc ccgggggtca gaataagcca gtcctcagag  14220

tcgcccttag gtcggttctg ggcaatgaag ccaaccacaa actcggggtc ggatcgggca  14280

agctcaatgg tctgcttgga gtactcgcca gtggccagag agcccttgca agacagctcg  14340

gccagcatga gcagacctct ggccagcttc tcgttgggag aggggactag gaactccttg  14400

tactgggagt tctcgtagtc agagacgtcc tccttcttct gttcagagac agtttcctcg  14460

gcaccagctc gcaggccagc aatgattccg gttccgggta caccgtgggc gttggtgata  14520

tcggaccact cggcgattcg gtgacaccgg tactggtgct tgacagtgtt gccaatatct  14580

gcgaactttc tgtcctcgaa caggaagaaa ccgtgcttaa gagcaagttc cttgaggggg  14640

agcacagtgc cggcgtaggt gaagtcgtca atgatgtcga tatgggtttt gatcatgcac  14700

acataaggtc cgaccttatc ggcaagctca atgagctcct tggtggtggt aacatccaga  14760

gaagcacaca ggttggtttt cttggctgcc acgagcttga gcactcgagc ggcaaaggcg  14820

gacttgtgga cgttagctcg agcttcgtag gagggcattt tggtggtgaa gaggagactg  14880

aaataaattt agtctgcaga actttttatc ggaaccttat ctggggcagt gaagtatatg  14940

ttatggtaat agttacgagt tagttgaact tatagataga ctggactata cggctatcgg  15000

tccaaattag aaagaacgtc aatggctctc tgggcgtcgc ctttgccgac aaaaatgtga  15060

tcatgatgaa agccagcaat gacgttgcag ctgatattgt tgtcggccaa ccgcgccgaa  15120

aacgcagctg tcagacccac agcctccaac gaagaatgta tcgtcaaagt gatccaagca  15180

cactcatagt tggagtcgta ctccaaaggc ggcaatgacg agtcagacag atactcgtcg  15240

acgcgataac ttcgtataat gtatgctata cgaagttatc gtacgatagt tagtagacaa  15300

caat                                                              15304
```

<210> SEQ ID NO 182
<211> LENGTH: 1288
<212> TYPE: DNA
<213> ORGANISM: Artificial Sequence
<220> FEATURE:
<223> OTHER INFORMATION: modified mutant EgD8S-23, comprising a 5' Not1 site

<400> SEQUENCE: 182

```
gcggccgcac catggtgaag gcttctcgac aggctctgcc cctcgtcatc gacggaaagg     60

tgtacgacgt ctccgcttgg gtgaacttcc accctggtgg agctgaaatc attgagaact    120

accagggacg agatgctact gacgccttca tggttatgca ctctcaggaa gccttcgaca    180

agctcaagcg aatgcccaag atcaaccagg cttccgagct gcctccccag gctgccgtca    240
```

```
acgaagctca ggaggatttc cgaaagctcc gagaagagct gatcgccact ggcatgtttg    300

acgcctctcc cctctggtac tcgtacaaga tcttgaccac cctgggtctt ggcgtgcttg    360

ccttcttcat gctggtccag taccacctgt acttcattgg tgctctcgtg ctcggtatgc    420

actaccagca aatgggatgg ctgtctcatg acatctgcca ccaccagacc ttcaagaacc    480

gaaactggaa taacgtcctg ggtctggtct ttggcaacgg actccagggc ttctccgtga    540

cctggtggaa ggacagacac aacgcccatc attctgctac caacgttcag ggtcacgatc    600

ccgacattga taacctgcct ctgctcgcct ggtccgagga cgatgtcact cgagcttctc    660

ccatctcccg aaagctcatt cagttccaac agtactattt cctggtcatc tgtattctcc    720

tgcgattcat ctggtgtttc cagtctgtgc tgaccgttcg atccctcaag gaccgagaca    780

accagttcta ccgatctcag tacaagaaag aggccattgg actcgctctg cactggactc    840

tcaagaccct gttccacctc ttctttatgc cctccatcct gacctcgatg ctggtgttct    900

ttgtttccga gctcgtcggt ggcttcggaa ttgccatcgt ggtcttcatg aaccactacc    960

ctctggagaa gatcggtgat tccgtctggg acggacatgg cttctctgtg ggtcagatcc   1020

atgagaccat gaacattcga cgaggcatca ttactgactg gttctttgga ggcctgaact   1080

accagatcga gcaccatctc tggcccaccc tgcctcgaca caacctcact gccgtttcct   1140

accaggtgga acagctgtgc cagaagcaca acctccccta ccgaaaccct ctgccccatg   1200

aaggtctcgt catcctgctc cgatacctgt cccagttcgc tcgaatggcc gagaagcagc   1260

ccggtgccaa ggctcagtaa gcggccgc                                     1288
```

<210> SEQ ID NO 183
<211> LENGTH: 5252
<212> TYPE: DNA
<213> ORGANISM: Artificial Sequence
<220> FEATURE:
<223> OTHER INFORMATION: Plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 183

```
gtacgtgggc ggatccccog ggctgcagga attcactggc cgtcgtttta caacgtcgtg     60

actgggaaaa ccctggcgtt acccaactta atcgccttgc agcacatccc cctttcgcca    120

gctggcgtaa tagcgaagag gcccgcaccg atcgcccttc ccaacagttg cgcagcctga    180

atggcgaatg gcgcctgatg cggtattttc tccttacgca tctgtgcggt atttcacacc    240

gcatatggtg cactctcagt acaatctgct ctgatgccgc atagttaagc cagccccgac    300

acccgccaac acccgctgac gcgccctgac gggcttgtct gctcccggca tccgcttaca    360

gacaagctgt gaccgtctcc gggagctgca tgtgtcagag gttttcaccg tcatcaccga    420

aacgcgcgag acgaaagggc ctcgtgatac gcctattttt ataggttaat gtcatgataa    480

taatggtttc ttagacgtca ggtggcactt ttcggggaaa tgtgcgcgga acccctattt    540

gtttattttt ctaaatacat tcaaatatgt atccgctcat gagacaataa ccctgataaa    600

tgcttcaata atattgaaaa aggaagagta tgagtattca acatttccgt gtcgccctta    660

ttcccttttt tgcggcattt tgccttcctg tttttgctca cccagaaacg ctggtgaaag    720

taaaagatgc tgaagatcag ttgggtgcac gagtgggtta catcgaactg gatctcaaca    780

gcggtaagat ccttgagagt tttcgccccg aagaacgttt tccaatgatg agcactttta    840

aagttctgct atgtggcgcg gtattatccc gtattgacgc cgggcaagag caactcggtc    900
```

-continued

```
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
taccaaacga cgagcgtgac accacgatgc ctgtagcaat ggcaacaacg ttgcgcaaac   1200
tattaactgg cgaactactt actctagctt cccggcaaca attaatagac tggatggagg   1260
cggataaagt tgcaggacca cttctgcgct cggcccttcc ggctggctgg tttattgctg   1320
ataaatctgg agccggtgag cgtgggtctc gcggtatcat tgcagcactg gggccagatg   1380
gtaagccctc ccgtatcgta gttatctaca cgacggggag tcaggcaact atggatgaac   1440
gaaatagaca gatcgctgag ataggtgcct cactgattaa gcattggtaa ctgtcagacc   1500
aagtttactc atatatactt tagattgatt taaaacttca tttttaattt aaaaggatct   1560
aggtgaagat cctttttgat aatctcatga ccaaaatccc ttaacgtgag ttttcgttcc   1620
actgagcgtc agaccccgta gaaaagatca aaggatcttc ttgagatcct ttttttctgc   1680
gcgtaatctg ctgcttgcaa acaaaaaaac caccgctacc agcggtggtt tgtttgccgg   1740
atcaagagct accaactctt tttccgaagg taactggctt cagcagagcg cagataccaa   1800
atactgtcct tctagtgtag ccgtagttag gccaccactt caagaactct gtagcaccgc   1860
ctacatacct cgctctgcta atcctgttac cagtggctgc tgccagtggc gataagtcgt   1920
gtcttaccgg gttggactca agacgatagt taccggataa ggcgcagcgg tcgggctgaa   1980
cggggggttc gtgcacacag cccagcttgg agcgaacgac ctacaccgaa ctgagatacc   2040
tacagcgtga gctatgagaa agcgccacgc ttcccgaagg gagaaaggcg gacaggtatc   2100
cggtaagcgg cagggtcgga acaggagagc gcacgaggga gcttccaggg ggaaacgcct   2160
ggtatcttta tagtcctgtc gggtttcgcc acctctgact tgagcgtcga tttttgtgat   2220
gctcgtcagg ggggcggagc ctatggaaaa acgccagcaa cgcggccttt ttacggttcc   2280
tggccttttg ctggcctttt gctcacatgt tctttcctgc gttatcccct gattctgtgg   2340
ataaccgtat taccgccttt gagtgagctg ataccgctcg ccgcagccga acgaccgagc   2400
gcagcgagtc agtgagcgag gaagcggaag agcgcccaat acgcaaaccg cctctccccg   2460
cgcgttggcc gattcattaa tgcagctggc acgacaggtt tcccgactgg aaagcgggca   2520
gtgagcgcaa cgcaattaat gtgagttagc tcactcatta ggcaccccag gctttacact   2580
ttatgcttcc ggctcgtatg ttgtgtggaa ttgtgagcgg ataacaattt cacacaggaa   2640
acagctatga ccatgattac gccaagcttg catgcctgca ggtcgactcg acgtacgtcc   2700
tcgaagagaa gggttaataa cacatttttt aacattttta acacaaattt tagttattta   2760
aaaatttatt aaaaaattta aaataagaag aggaactctt taaataaatc taacttacaa   2820
aatttatgat tttaataag ttttcaccaa taaaaaatgt cataaaaata tgttaaaaag   2880
tatattatca atattctctt tatgataaat aaaaagaaaa aaaaaataaa agttaagtga   2940
aaatgagatt gaagtgactt taggtgtgta taaatatatc aaccccgcca acaatttatt   3000
taatccaaat atattgaagt atattattcc atagccttta tttatttata tatttattat   3060
ataaaagctt tatttgttct aggttgttca tgaaatattt ttttggtttt atctccgttg   3120
taagaaaatc atgtgctttg tgtcgccact cactattgca gctttttcat gcattggtca   3180
gattgacggt tgattgtatt tttgtttttt atggttttgt gttatgactt aagtcttcat   3240
ctctttatct cttcatcagg tttgatggtt acctaatatg gtccatgggt acatgcatgg   3300
```

-continued

```
ttaaattagg tggccaactt tgttgtgaac gatagaattt tttttatatt aagtaaacta   3360

tttttatatt atgaaataat aataaaaaaa atattttatc attattaaca aaatcatatt   3420

agttaatttg ttaactctat aataaaagaa atactgtaac attcacatta catggtaaca   3480

tctttccacc ctttcatttg ttttttgttt gatgactttt tttcttgttt aaatttattt   3540

cccttctttt aaatttggaa tacattatca tcatatataa actaaaatac taaaaacagg   3600

attacacaaa tgataaataa taacacaaat atttataaat ctagctgcaa tatatttaaa   3660

ctagctatat cgatattgta aaataaaact agctgcattg atactgataa aaaaatatca   3720

tgtgctttct ggactgatga tgcagtatac ttttgacatt gcctttattt tatttttcag   3780

aaaagctttc ttagttctgg gttcttcatt atttgtttcc catctccatt gtgaattgaa   3840

tcatttgctt cgtgtcacaa atacaattta gntaggtaca tgcattggtc agattcacgg   3900

tttattatgt catgacttaa gttcatggta gtacattacc tgccacgcat gcattatatt   3960

ggttagattt gataggcaaa tttggttgtc aacaatataa atataaataa tgtttttata   4020

ttacgaaata acagtgatca aaacaaacag ttttatcttt attaacaaga ttttgttttt   4080

gtttgatgac gtttttttaat gtttacgctt tccccttct tttgaattta gaacacttta   4140

tcatcataaa atcaaatact aaaaaaatta catatttcat aaataataac acaaatattt   4200

ttaaaaaatc tgaaataata atgaacaata ttacatatta tcacgaaaat tcattaataa   4260

aaatattata taaataaaat gtaatagtag ttatatgtag gaaaaaagta ctgcacgcat   4320

aatatataca aaaagattaa aatgaactat tataaataat aacactaaat taatggtgaa   4380

tcatatcaaa ataatgaaaa agtaaataaa atttgtaatt aacttctata tgtattacac   4440

acacaaataa taaataatag taaaaaaaat tatgataaat atttaccatc tcataagata   4500

tttaaaataa tgataaaaat atagattatt ttttatgcaa ctagctagcc aaaaagagaa   4560

cacgggtata tataaaaaga gtacctttaa attctactgt acttccttta ttcctgacgt   4620

ttttatatca agtggacata cgtgaagatt ttaattatca gtctaaatat ttcattagca   4680

cttaatactt ttctgtttta ttcctatcct ataagtagtc ccgattctcc caacattgct   4740

tattcacaca actaactaag aaagtcttcc atagcccccc aagcggccgc gacacaagtg   4800

tgagagtact aaataaatgc tttggttgta cgaaatcatt acactaaata aaataatcaa   4860

agcttatata tgccttccgc taaggccgaa tgcaaagaaa ttggttcttt ctcgttatct   4920

tttgccactt ttactagtac gtattaatta ctacttaatc atctttgttt acggctcatt   4980

atatccggtc tagaggatcc aaggccgcga agttaaaagc aatgttgtca cttgtcgtac   5040

taacacatga tgtgatagtt tatgctagct agctataaca taagctgtct ctgagtgtgt   5100

tgtatattaa taaagatcat cactggtgaa tggtgatcgt gtacgtaccc tacttagtag   5160

gcaatggaag cacttagagt gtgctttgtg catggccttg cctctgtttt gagacttttg   5220

taatgttttc gagtttaaat ctttgccttt gc                                 5252
```

```
<210> SEQ ID NO 184
<211> LENGTH: 6532
<212> TYPE: DNA
<213> ORGANISM: Artificial Sequence
<220> FEATURE:
<223> OTHER INFORMATION: Plasmid pKR1058
<220> FEATURE:
<221> NAME/KEY: misc_feature
<222> LOCATION: (4340)..(4340)
<223> OTHER INFORMATION: n is a, c, g, or t
```

<400> SEQUENCE: 184

```
ggccgcgaca caagtgtgag agtactaaat aaatgctttg gttgtacgaa atcattacac     60
taaataaaat aatcaaagct tatatatgcc ttccgctaag gccgaatgca aagaaattgg    120
ttctttctcg ttatcttttg ccacttttac tagtacgtat taattactac ttaatcatct    180
ttgtttacgg ctcattatat ccggtctaga ggatccaagg ccgcgaagtt aaaagcaatg    240
ttgtcacttg tcgtactaac acatgatgtg atagtttatg ctagctagct ataacataag    300
ctgtctctga gtgtgttgta tattaataaa gatcatcact ggtgaatggt gatcgtgtac    360
gtaccctact tagtaggcaa tggaagcact tagagtgtgc tttgtgcatg gccttgcctc    420
tgttttgaga cttttgtaat gttttcgagt ttaaatcttt gcctttgcgt acgtgggcgg    480
atcccccggg ctgcaggaat tcactggccg tcgttttaca acgtcgtgac tgggaaaacc    540
ctggcgttac ccaacttaat cgccttgcag cacatccccc tttcgccagc tggcgtaata    600
gcgaagaggc ccgcaccgat cgcccttccc aacagttgcg cagcctgaat ggcgaatggc    660
gcctgatgcg gtattttctc cttacgcatc tgtgcggtat ttcacaccgc atatggtgca    720
ctctcagtac aatctgctct gatgccgcat agttaagcca gccccgacac ccgccaacac    780
ccgctgacgc gccctgacgg gcttgtctgc tcccggcatc cgcttacaga caagctgtga    840
ccgtctccgg gagctgcatg tgtcagaggt tttcaccgtc atcaccgaaa cgcgcgagac    900
gaaagggcct cgtgatacgc ctatttttat aggttaatgt catgataata atggtttctt    960
agacgtcagg tggcactttt cggggaaatg tgcgcggaac ccctatttgt ttatttttct   1020
aaatacattc aaatatgtat ccgctcatga gacaataacc ctgataaatg cttcaataat   1080
attgaaaaag gaagagtatg agtattcaac atttccgtgt cgcccttatt cccttttttg   1140
cggcattttg ccttcctgtt tttgctcacc cagaaacgct ggtgaaagta aaagatgctg   1200
aagatcagtt gggtgcacga gtgggttaca tcgaactgga tctcaacagc ggtaagatcc   1260
ttgagagttt tcgccccgaa gaacgttttc caatgatgag cacttttaaa gttctgctat   1320
gtggcgcggt attatcccgt attgacgccg ggcaagagca actcggtcgc cgcatacact   1380
attctcagaa tgacttggtt gagtactcac cagtcacaga aaagcatctt acggatggca   1440
tgacagtaag agaattatgc agtgctgcca taaccatgag tgataacact gcggccaact   1500
tacttctgac aacgatcgga ggaccgaagg agctaaccgc ttttttgcac aacatggggg   1560
atcatgtaac tcgccttgat cgttgggaac cggagctgaa tgaagccata ccaaacgacg   1620
agcgtgacac cacgatgcct gtagcaatgg caacaacgtt gcgcaaacta ttaactggcg   1680
aactacttac tctagcttcc cggcaacaat taatagactg gatggaggcg gataaagttg   1740
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
caactctttt tccgaaggta actggcttca gcagagcgca gataccaaat actgtccttc   2280
tagtgtagcc gtagttaggc caccacttca agaactctgt agcaccgcct acatacctcg   2340
```

-continued

```
ctctgctaat cctgttacca gtggctgctg ccagtggcga taagtcgtgt cttaccgggt   2400
tggactcaag acgatagtta ccggataagg cgcagcggtc gggctgaacg gggggttcgt   2460
gcacacagcc cagcttggag cgaacgacct acaccgaact gagataccta cagcgtgagc   2520
tatgagaaag cgccacgctt cccgaaggga gaaaggcgga caggtatccg gtaagcggca   2580
gggtcggaac aggagagcgc acgagggagc ttccaggggg aaacgcctgg tatctttata   2640
gtcctgtcgg gtttcgccac ctctgacttg agcgtcgatt tttgtgatgc tcgtcagggg   2700
ggcggagcct atggaaaaac gccagcaacg cggccttttt acggttcctg gccttttgct   2760
ggccttttgc tcacatgttc tttcctgcgt tatcccctga ttctgtggat aaccgtatta   2820
ccgcctttga gtgagctgat accgctcgcc gcagccgaac gaccgagcgc agcgagtcag   2880
tgagcgagga agcggaagag cgcccaatac gcaaaccgcc tctccccgcg cgttggccga   2940
ttcattaatg cagctggcac gacaggtttc ccgactggaa agcgggcagt gagcgcaacg   3000
caattaatgt gagttagctc actcattagg caccccaggc tttacacttt atgcttccgg   3060
ctcgtatgtt gtgtggaatt gtgagcggat aacaatttca cacaggaaac agctatgacc   3120
atgattacgc caagcttgca tgcctgcagg tcgactcgac gtacgtcctc gaagagaagg   3180
gttaataaca cattttttaa catttttaac acaaatttta gttatttaaa aatttattaa   3240
aaaatttaaa ataagaagag gaactcttta aataaatcta acttacaaaa tttatgattt   3300
ttaataagtt ttcaccaata aaaaatgtca taaaaaatatg ttaaaaagta tattatcaat   3360
attctcttta tgataaataa aaagaaaaaa aaaataaaag ttaagtgaaa atgagattga   3420
agtgacttta ggtgtgtata aatatatcaa ccccgccaac aatttattta atccaaatat   3480
attgaagtat attattccat agcctttatt tatttatata tttattatat aaaagcttta   3540
tttgttctag gttgttcatg aaatattttt ttggttttat ctccgttgta agaaaatcat   3600
gtgctttgtg tcgccactca ctattgcagc tttttcatgc attggtcaga ttgacggttg   3660
attgtatttt tgttttttat ggttttgtgt tatgacttaa gtcttcatct ctttatctct   3720
tcatcaggtt tgatggttac ctaatatggt ccatgggtac atgcatggtt aaattaggtg   3780
gccaactttg ttgtgaacga tagaattttt tttatattaa gtaaactatt tttatattat   3840
gaaataataa taaaaaaaat attttatcat tattaacaaa atcatattag ttaatttgtt   3900
aactctataa taaaagaaat actgtaacat tcacattaca tggtaacatc tttccaccct   3960
ttcatttgtt ttttgtttga tgactttttt tcttgtttaa atttatttcc cttcttttaa   4020
atttggaata cattatcatc atatataaac taaaatacta aaaacaggat tacacaaatg   4080
ataaataata acacaaatat ttataaatct agctgcaata tatttaaact agctatatcg   4140
atattgtaaa ataaaactag ctgcattgat actgataaaa aaatatcatg tgctttctgg   4200
actgatgatg cagtatactt ttgacattgc ctttatttta tttttcagaa aagctttctt   4260
agttctgggt tcttcattat ttgtttccca tctccattgt gaattgaatc atttgcttcg   4320
tgtcacaaat acaatttagn taggtacatg cattggtcag attcacggtt tattatgtca   4380
tgacttaagt tcatggtagt acattacctg ccacgcatgc attatattgg ttagatttga   4440
taggcaaatt tggttgtcaa caatataaat ataaataatg tttttatatt acgaaataac   4500
agtgatcaaa acaaacagtt ttatctttat taacaagatt ttgtttttgt ttgatgacgt   4560
tttttaatgt ttacgctttc ccccttcttt tgaatttaga acactttatc atcataaaat   4620
caaatactaa aaaaattaca tatttcataa ataataacac aaatattttt aaaaaatctg   4680
aaataataat gaacaatatt acatattatc acgaaaattc attaataaaa atattatata   4740
```

```
aataaaatgt aatagtagtt atatgtagga aaaaagtact gcacgcataa tatatacaaa   4800

aagattaaaa tgaactatta taaataataa cactaaatta atggtgaatc atatcaaaat   4860

aatgaaaaag taaataaaat ttgtaattaa cttctatatg tattacacac acaaataata   4920

aataatagta aaaaaaatta tgataaatat ttaccatctc ataagatatt taaaataatg   4980

ataaaaatat agattatttt ttatgcaact agctagccaa aaagagaaca cgggtatata   5040

taaaaagagt acctttaaat tctactgtac ttcctttatt cctgacgttt ttatatcaag   5100

tggacatacg tgaagatttt aattatcagt ctaaatattt cattagcact taatactttt   5160

ctgttttatt cctatcctat aagtagtccc gattctccca acattgctta ttcacacaac   5220

taactaagaa agtcttccat agccccccaa gcggccgcac catggtgaag gcttctcgac   5280

aggctctgcc cctcgtcatc gacggaaagg tgtacgacgt ctccgcttgg gtgaacttcc   5340

accctggtgg agctgaaatc attgagaact accagggacg agatgctact gacgccttca   5400

tggttatgca ctctcaggaa gccttcgaca agctcaagcg aatgcccaag atcaaccagg   5460

cttccgagct gcctccccag gctgccgtca acgaagctca ggaggatttc cgaaagctcc   5520

gagaagagct gatcgccact ggcatgtttg acgcctctcc cctctggtac tcgtacaaga   5580

tcttgaccac cctgggtctt ggcgtgcttg ccttcttcat gctggtccag taccacctgt   5640

acttcattgg tgctctcgtg ctcggtatgc actaccagca aatgggatgg ctgtctcatg   5700

acatctgcca ccaccagacc ttcaagaacc gaaactggaa taacgtcctg ggtctggtct   5760

ttggcaacgg actccagggc ttctccgtga cctggtggaa ggacagacac aacgcccatc   5820

attctgctac caacgttcag ggtcacgatc ccgacattga taacctgcct ctgctcgcct   5880

ggtccgagga cgatgtcact cgagcttctc ccatctcccg aaagctcatt cagttccaac   5940

agtactattt cctggtcatc tgtattctcc tgcgattcat ctggtgtttc cagtctgtgc   6000

tgaccgttcg atccctcaag gaccgagaca accagttcta ccgatctcag tacaagaaag   6060

aggccattgg actcgctctg cactggactc tcaagaccct gttccacctc ttctttatgc   6120

cctccatcct gacctcgatg ctggtgttct ttgtttccga gctcgtcggt ggcttcggaa   6180

ttgccatcgt ggtcttcatg aaccactacc ctctggagaa gatcggtgat tccgtctggg   6240

acggacatgg cttctctgtg ggtcagatcc atgagaccat gaacattcga cgaggcatca   6300

ttactgactg gttctttgga ggcctgaact accagatcga gcaccatctc tggcccaccc   6360

tgcctcgaca caacctcact gccgtttcct accaggtgga acagctgtgc cagaagcaca   6420

acctccccta ccgaaaccct ctgccccatg aaggtctcgt catcctgctc cgatacctgt   6480

cccagttcgc tcgaatggcc gagaagcagc ccggtgccaa ggctcagtaa gc           6532
```

<210> SEQ ID NO 185
<211> LENGTH: 7887
<212> TYPE: DNA
<213> ORGANISM: Artificial Sequence
<220> FEATURE:
<223> OTHER INFORMATION: Plasmid pKR607

<400> SEQUENCE: 185

```
ggccgcagta tatcttaaat tctttaatac ggtgtactag gatattgaac tggttcttga     60

tgatgaaaac ctgggccgag attgcagcta tttatagtca taggtcttgt taacatgcat    120

ggacatttgg ccacggggtg gcatgcagtt tgacgggtgt tgaaataaac aaaaatgagg    180

tggcggaaga gaatacgagt ttgaggttgg gttagaaaca acaaatgtga gggctcatga    240

tgggttgagt tggtgaatgt tttgggctgc tcgattgaca cctttgtgag tacgtgttgt    300
```

-continued

```
tgtgcatggc ttttggggtc cagttttttt ttcttgacgc ggcgatcctg atcagctagt    360
ggataagtga tgtccactgt gtgtgattgc gtttttgttt gaattttatg aacttagaca    420
ttgctatgca aaggatactc tcattgtgtt ttgtcttctt ttgttccttg gctttttctt    480
atgatccaag agactagtca gtgttgtggc attcgagact accaagatta attatgatgg    540
gggaaggata agtaactgat tagtacggac tgttaccaaa ttaattaata agcggcaaat    600
gaagggcatg gatcaaaagc ttggatctcc tgcaggatct ggccggccgg atctcgtacg    660
gatccgtcga cggcgcgccc gatcatccgg atatagttcc tcctttcagc aaaaaacccc    720
tcaagacccg tttagaggcc ccaaggggtt atgctagtta ttgctcagcg gtggcagcag    780
ccaactcagc ttcctttcgg gctttgttag cagccggatc gatccaagct gtacctcact    840
attcctttgc cctcggacga gtgctggggc gtcggtttcc actatcggcg agtacttcta    900
cacagccatc ggtccagacg gccgcgcttc tgcgggcgat ttgtgtacgc ccgacagtcc    960
cggctccgga tcggacgatt gcgtcgcatc gaccctgcgc ccaagctgca tcatcgaaat   1020
tgccgtcaac caagctctga tagagttggt caagaccaat gcggagcata tacgcccgga   1080
gccgcggcga tcctgcaagc tccggatgcc tccgctcgaa gtagcgcgtc tgctgctcca   1140
tacaagccaa ccacggcctc cagaagaaga tgttggcgac ctcgtattgg gaatccccga   1200
acatcgcctc gctccagtca atgaccgctg ttatgcggcc attgtccgtc aggacattgt   1260
tggagccgaa atccgcgtgc acgaggtgcc ggacttcggg gcagtcctcg gcccaaagca   1320
tcagctcatc gagagcctgc gcgacggacg cactgacggt gtcgtccatc acagtttgcc   1380
agtgatacac atggggatca gcaatcgcgc atatgaaatc acgccatgta gtgtattgac   1440
cgattccttg cggtccgaat gggccgaacc cgctcgtctg gctaagatcg gccgcagcga   1500
tcgcatccat agcctccgcg accggctgca gaacagcggg cagttcggtt tcaggcaggt   1560
cttgcaacgt gacaccctgt gcacggcggg agatgcaata ggtcaggctc tcgctgaatt   1620
ccccaatgtc aagcacttcc ggaatcggga gcgcggccga tgcaaagtgc cgataaacat   1680
aacgatcttt gtagaaacca tcggcgcagc tatttacccg caggacatat ccacgccctc   1740
ctacatcgaa gctgaaagca cgagattctt cgccctccga gagctgcatc aggtcggaga   1800
cgctgtcgaa cttttcgatc agaaacttct cgacagacgt cgcggtgagt tcaggctttt   1860
ccatgggtat atctccttct taaagttaaa caaaattatt tctagaggga aaccgttgtg   1920
gtctccctat agtgagtcgt attaatttcg cgggatcgag atcgatccaa ttccaatccc   1980
acaaaaatct gagcttaaca gcacagttgc tcctctcaga gcagaatcgg gtattcaaca   2040
ccctcatatc aactactacg ttgtgtataa cggtccacat gccggtatat acgatgactg   2100
gggttgtaca aaggcggcaa caaacggcgt tcccggagtt gcacacaaga aatttgccac   2160
tattacagag gcaagagcag cagctgacgc gtacacaaca agtcagcaaa cagacaggtt   2220
gaacttcatc cccaaaggag aagctcaact caagcccaag agctttgcta aggccctaac   2280
aagcccacca aagcaaaaag cccactggct cacgctagga accaaaaggc ccagcagtga   2340
tccagcccca aaagagatct cctttgcccc ggagattaca atggacgatt tcctctatct   2400
ttacgatcta ggaaggaagt tcgaaggtga aggtgacgac actatgttca ccactgataa   2460
tgagaaggtt agcctcttca atttcagaaa gaatgctgac ccacagatgg ttagagaggc   2520
ctacgcagca ggtctcatca agacgatcta cccgagtaac aatctccagg agatcaaata   2580
ccttcccaag aaggttaaag atgcagtcaa aagattcagg actaattgca tcaagaacac   2640
agagaaagac atatttctca agatcagaag tactattcca gtatggacga ttcaaggctt   2700
```

-continued

```
gcttcataaa ccaaggcaag taatagagat tggagtctct aaaaaggtag ttcctactga   2760
atctaaggcc atgcatggag tctaagattc aaatcgagga tctaacagaa ctcgccgtga   2820
agactggcga acagttcata cagagtcttt tacgactcaa tgacaagaag aaaatcttcg   2880
tcaacatggt ggagcacgac actctggtct actccaaaaa tgtcaaagat acagtctcag   2940
aagaccaaag ggctattgag acttttcaac aaaggataat ttcgggaaac ctcctcggat   3000
tccattgccc agctatctgt cacttcatcg aaaggacagt agaaaaggaa ggtggctcct   3060
acaaatgcca tcattgcgat aaaggaaagg ctatcattca agatgcctct gccgacagtg   3120
gtcccaaaga tggaccccca cccacgagga gcatcgtgga aaaagaagac gttccaacca   3180
cgtcttcaaa gcaagtggat tgatgtgaca tctccactga cgtaagggat gacgcacaat   3240
cccactatcc ttcgcaagac ccttcctcta tataaggaag ttcatttcat ttggagagga   3300
cacgctcgag ctcatttctc tattacttca gccataacaa aagaactctt ttctcttctt   3360
attaaaccat gaaaaagcct gaactcaccg cgacgtctgt cgagaagttt ctgatcgaaa   3420
agttcgacag cgtctccgac ctgatgcagc tctcggaggg cgaagaatct cgtgctttca   3480
gcttcgatgt aggagggcgt ggatatgtcc tgcgggtaaa tagctgcgcc gatggtttct   3540
acaaagatcg ttatgtttat cggcactttg catcggccgc gctcccgatt ccggaagtgc   3600
ttgacattgg ggaattcagc gagagcctga cctattgcat ctcccgccgt gcacagggtg   3660
tcacgttgca agacctgcct gaaaccgaac tgcccgctgt tctgcagccg gtcgcggagg   3720
ccatggatgc gatcgctgcg gccgatctta gccagacgag cgggttcggc ccattcggac   3780
cgcaaggaat cggtcaatac actacatggc gtgatttcat atgcgcgatt gctgatcccc   3840
atgtgtatca ctggcaaact gtgatggacg acaccgtcag tgcgtccgtc gcgcaggctc   3900
tcgatgagct gatgctttgg gccgaggact gccccgaagt ccggcacctc gtgcacgcgg   3960
atttcggctc caacaatgtc ctgacggaca atggccgcat aacagcggtc attgactgga   4020
gcgaggcgat gttcggggat tcccaatacg aggtcgccaa catcttcttc tggaggccgt   4080
ggttggcttg tatggagcag cagacgcgct acttcgagcg gaggcatccg gagcttgcag   4140
gatcgccgcg gctccgggcg tatatgctcc gcattggtct tgaccaactc tatcagagct   4200
tggttgacgg caatttcgat gatgcagctt gggcgcaggg tcgatgcgac gcaatcgtcc   4260
gatccggagc cgggactgtc gggcgtacac aaatcgcccg cagaagcgcg gccgtctgga   4320
ccgatggctg tgtagaagta ctcgccgata gtggaaaccg acgccccagc actcgtccga   4380
gggcaaagga atagtgaggt acctaaagaa ggagtgcgtc gaagcagatc gttcaaacat   4440
ttggcaataa agtttcttaa gattgaatcc tgttgccggt cttgcgatga ttatcatata   4500
atttctgttg aattacgtta agcatgtaat aattaacatg taatgcatga cgttatttat   4560
gagatgggtt tttatgatta gagtcccgca attatacatt taatacgcga tagaaaacaa   4620
aatatagcgc gcaaactagg ataaattatc gcgcgcggtg tcatctatgt tactagatcg   4680
atgtcgaatc gatcaacctg cattaatgaa tcggccaacg cgcggggaga ggcggtttgc   4740
gtattgggcg ctcttccgct tcctcgctca ctgactcgct gcgctcggtc gttcggctgc   4800
ggcgagcggt atcagctcac tcaaaggcgg taatacggtt atccacagaa tcaggggata   4860
acgcaggaaa gaacatgtga gcaaaaggcc agcaaaaggc caggaaccgt aaaaaggccg   4920
cgttgctggc gtttttccat aggctccgcc cccctgacga gcatcacaaa aatcgacgct   4980
caagtcagag gtggcgaaac ccgacaggac tataaagata ccaggcgttt ccccctggaa   5040
gctccctcgt gcgctctcct gttccgaccc tgccgcttac cggatacctg tccgcctttc   5100
```

```
tcccttcggg aagcgtggcg ctttctcaat gctcacgctg taggtatctc agttcggtgt   5160
aggtcgttcg ctccaagctg ggctgtgtgc acgaaccccc cgttcagccc gaccgctgcg   5220
ccttatccgg taactatcgt cttgagtcca acccggtaag acacgactta tcgccactgg   5280
cagcagccac tggtaacagg attagcagag cgaggtatgt aggcggtgct acagagttct   5340
tgaagtggtg gcctaactac ggctacacta gaaggacagt atttggtatc tgcgctctgc   5400
tgaagccagt taccttcgga aaaagagttg gtagctcttg atccggcaaa caaaccaccg   5460
ctggtagcgg tggttttttt gtttgcaagc agcagattac gcgcagaaaa aaaggatctc   5520
aagaagatcc tttgatcttt tctacggggt ctgacgctca gtggaacgaa aactcacgtt   5580
aagggatttt ggtcatgaca ttaacctata aaaataggcg tatcacgagg ccctttcgtc   5640
tcgcgcgttt cggtgatgac ggtgaaaacc tctgacacat gcagctcccg gagacggtca   5700
cagcttgtct gtaagcggat gccgggagca gacaagcccg tcagggcgcg tcagcgggtg   5760
ttggcgggtg tcggggctgg cttaactatg cggcatcaga gcagattgta ctgagagtgc   5820
accatatgga catattgtcg ttagaacgcg gctacaatta atacataacc ttatgtatca   5880
tacacatacg atttaggtga cactatagaa cggcgcgcca agcttgttga aacatccctg   5940
aagtgtctca ttttatttta tttattcttt gctgataaaa aaataaaata aaagaagcta   6000
agcacacggt caaccattgc tctactgcta aaagggttat gtgtagtgtt ttactgcata   6060
aattatgcag caaacaagac aactcaaatt aaaaaatttc ctttgcttgt ttttttgttg   6120
tctctgactt gactttcttg tggaagttgg ttgtataagg attgggacac cattgtcctt   6180
cttaatttaa ttttattctt tgctgataaa aaaaaaaatt tcatatagtg ttaaataata   6240
atttgttaaa taaccaaaaa gtcaaatatg tttactctcg tttaaataat tgagattcgt   6300
ccagcaaggc taaacgattg tatagattta tgacaatatt tacttttttta tagataaatg   6360
ttatattata ataaatttat atacatatat tatatgttat ttattattat tttaaatcct   6420
tcaatatttt atcaaaccaa ctcataattt tttttttatc tgtaagaagc aataaaatta   6480
aatagaccca ctttaaggat gatccaacct ttatacagag taagagagtt caaatagtac   6540
cctttcatat acatatcaac taaaatatta gaaatatcat ggatcaaacc ttataaagac   6600
attaaataag tggataagta taatatataa atgggtagta tataatatat aaatggatac   6660
aaacttctct ctttataatt gttatgtctc cttaacatcc taatataata cataagtggg   6720
taatatataa tatataaatg gagacaaact tcttccatta taattgttat gtcttcttaa   6780
cacttatgtc tcgttcacaa tgctaaggtt agaattgttt agaaagtctt atagtacaca   6840
tttgtttttg tactatttga agcattccat aagccgtcac gattcagatg atttataata   6900
ataagaggaa atttatcata gaacaataag gtgcatagat agagtgttaa tatatcataa   6960
catcctttgt ttattcatag aagaagtgag atggagctca gttattatac tgttacatgg   7020
tcggatacaa tattccatgc tctccatgag ctcttacacc tacatgcatt ttagttcata   7080
cttgcggccg ctaaagctgc ttaccagcct tagcggattt cttggtggcc aggttgtcct   7140
ggtaaaagaa gtgacagaac aggagaaaga cagatccgac gtaggcgtag ttgaaagccc   7200
aggagaacag cttgcccttg tcagagttga agcagggaac gttgatgtag tcccagacca   7260
ggagaaagcc accgacgaac tggcaaatct gcatggcagt gatcagaggc ttggccttga   7320
acttgtagcc agcggcagtc agtccatagt aggtgtacat gatggtgtga atgaacgagt   7380
taaagaacat gaagatccac acaccctcgt tgtgcagtcg aatgccgagg tagacgtccc   7440
agggagctcc aaagtgatgg aaggcctgca gaaaggacac tcgcttgccc ttgaggacca   7500
```

```
gccaagcggt gtcgaggtac tccacgtact tagaatagta gaaggccttg gcagtccagg   7560

tgaacagctt ggagtcccag acaggagagg gacactgaaa gagaggctgg ggagtatcac   7620

cggtctgtct tcgcagccag gctccagtac cgtagtccca gccgagagcg gtggcagtca   7680

cgtagaagga cagggcagag aagagagcca ggaggacgtt gtaccagatc atggaggttc   7740

ggtaggctcc tttcttctcg tccacgagac cagagtttcg caggagaggc ttcaggagca   7800

ggtaggagaa ggtgccaatg aggatttcgg gatcggtgac ggcagcccag attcgctcgc   7860

cagcgtcgtt ggccagagcc atggtgc                                       7887
```

<210> SEQ ID NO 186
<211> LENGTH: 11766
<212> TYPE: DNA
<213> ORGANISM: Artificial Sequence
<220> FEATURE:
<223> OTHER INFORMATION: Plasmid pKR1060
<220> FEATURE:
<221> NAME/KEY: misc_feature
<222> LOCATION: (10571)..(10571)
<223> OTHER INFORMATION: n is a, c, g, or t

<400> SEQUENCE: 186

```
ggagatccaa gcttttgatc catgcccttc atttgccgct tattaattaa tttggtaaca     60

gtccgtacta atcagttact tatccttccc ccatcataat taatcttggt agtctcgaat    120

gccacaacac tgactagtct cttggatcat aagaaaaagc caaggaacaa aagaagacaa    180

aacacaatga gagtatcctt tgcatagcaa tgtctaagtt cataaaattc aaacaaaaac    240

gcaatcacac acagtggaca tcacttatcc actagctgat caggatcgcc gcgtcaagaa    300

aaaaaaactg gaccccaaaa gccatgcaca acaacacgta ctcacaaagg tgtcaatcga    360

gcagcccaaa acattcacca actcaaccca tcatgagccc tcacatttgt tgtttctaac    420

ccaacctcaa actcgtattc tcttccgcca cctcattttt gtttatttca acacccgtca    480

aactgcatgc caccccgtgg ccaaatgtcc atgcatgtta acaagaccta tgactataaa    540

tagctgcaat ctcggcccag gttttcatca tcaagaacca gttcaatatc ctagtacacc    600

gtattaaaga atttaagata tactgcggcc gcaccatggc tctggccaac gacgctggcg    660

agcgaatctg ggctgccgtc accgatcccg aaatcctcat tggcaccttc tcctacctgc    720

tcctgaagcc tctcctgcga aactctggtc tcgtggacga gaagaaagga gcctaccgaa    780

cctccatgat ctggtacaac gtcctcctgg ctctcttctc tgccctgtcc ttctacgtga    840

ctgccaccgc tctcggctgg gactacggta ctggagcctg gctgcgaaga cagaccggtg    900

atactcccca gcctctcttt cagtgtccct ctcctgtctg ggactccaag ctgttcacct    960

ggactgccaa ggccttctac tattctaagt acgtggagta cctcgacacc gcttggctgg   1020

tcctcaaggg caagcgagtg tcctttctgc aggccttcca tcactttgga gctccctggg   1080

acgtctacct cggcattcga ctgcacaacg agggtgtgtg gatcttcatg ttctttaact   1140

cgttcattca caccatcatg tacacctact atggactgac tgccgctggc tacaagttca   1200

aggccaagcc tctgatcact gccatgcaga tttgccagtt cgtcggtggc tttctcctgg   1260

tctgggacta catcaacgtt ccctgcttca actctgacaa gggcaagctg ttctcctggg   1320

ctttcaacta cgcctacgtc ggatctgtct ttctcctgtt ctgtcacttc ttttaccagg   1380

acaacctggc caccaagaaa tccgctaagg ctggtaagca gctttagcgg ccgcaagtat   1440

gaactaaaat gcatgtaggt gtaagagctc atggagagca tggaatattg tatccgacca   1500

tgtaacagta taataactga gctccatctc acttcttcta tgaataaaca aaggatgtta   1560
```

```
tgatatatta acactctatc tatgcacctt attgttctat gataaatttc ctcttattat   1620
tataaatcat ctgaatcgtg acggcttatg gaatgcttca aatagtacaa aaacaaatgt   1680
gtactataag actttctaaa caattctaac cttagcattg tgaacgagac ataagtgtta   1740
agaagacata acaattataa tggaagaagt ttgtctccat ttatatatta tatattaccc   1800
acttatgtat tatattagga tgttaaggag acataacaat tataaagaga gaagtttgta   1860
tccatttata tattatatac tacccattta tatattatac ttatccactt atttaatgtc   1920
tttataaggt ttgatccatg atatttctaa tattttagtt gatatgtata tgaaagggta   1980
ctatttgaac tctcttactc tgtataaagg ttggatcatc cttaaagtgg gtctatttaa   2040
ttttattgct tcttacagat aaaaaaaaaa ttatgagttg gtttgataaa atattgaagg   2100
atttaaaata ataataaata acatataata tatgtatata aatttattat aatataacat   2160
ttatctataa aaaagtaaat attgtcataa atctatacaa tcgtttagcc ttgctggacg   2220
aatctcaatt atttaaacga gagtaaacat atttgacttt ttggttattt aacaaattat   2280
tatttaacac tatatgaaat ttttttttt atcagcaaag aataaaatta aattaagaag   2340
gacaatggtg tcccaatcct tatacaacca acttccacaa gaaagtcaag tcagagacaa   2400
caaaaaaaca agcaaaggaa attttttaat ttgagttgtc ttgtttgctg cataatttat   2460
gcagtaaaac actacacata acccttttag cagtagagca atggttgacc gtgtgcttag   2520
cttcttttat tttattttt tatcagcaaa gaataaataa aataaaatga gacacttcag   2580
ggatgtttca acaagcttgg cgcgccgttc tatagtgtca cctaaatcgt atgtgtatga   2640
tacataaggt tatgtattaa ttgtagccgc gttctaacga caatatgtcc atatggtgca   2700
ctctcagtac aatctgctct gatgccgcat agttaagcca gccccgacac ccgccaacac   2760
ccgctgacgc gccctgacgg gcttgtctgc tcccggcatc cgcttacaga caagctgtga   2820
ccgtctccgg gagctgcatg tgtcagaggt tttcaccgtc atcaccgaaa cgcgcgagac   2880
gaaagggcct cgtgatacgc ctatttttat aggttaatgt catgaccaaa atcccttaac   2940
gtgagttttc gttccactga gcgtcagacc ccgtagaaaa gatcaaagga tcttcttgag   3000
atcctttttt tctgcgcgta atctgctgct tgcaaacaaa aaaaccaccg ctaccagcgg   3060
tggtttgttt gccggatcaa gagctaccaa ctcttttcc gaaggtaact ggcttcagca   3120
gagcgcagat accaaatact gtccttctag tgtagccgta gttaggccac cacttcaaga   3180
actctgtagc accgcctaca tacctcgctc tgctaatcct gttaccagtg gctgctgcca   3240
gtggcgataa gtcgtgtctt accgggttgg actcaagacg atagttaccg gataaggcgc   3300
agcggtcggg ctgaacgggg ggttcgtgca cacagcccag cttggagcga acgacctaca   3360
ccgaactgag atacctacag cgtgagcatt gagaaagcgc cacgcttccc gaagggagaa   3420
aggcggacag gtatccggta agcggcaggg tcggaacagg agagcgcacg agggagcttc   3480
caggggggaaa cgcctggtat ctttatagtc ctgtcgggtt tcgccacctc tgacttgagc   3540
gtcgattttt gtgatgctcg tcaggggggc ggagcctatg gaaaaacgcc agcaacgcgg   3600
cctttttacg gttcctggcc ttttgctggc cttttgctca catgttcttt cctgcgttat   3660
cccctgattc tgtggataac cgtattaccg cctttgagtg agctgatacc gctcgccgca   3720
gccgaacgac cgagcgcagc gagtcagtga gcgaggaagc ggaagagcgc ccaatacgca   3780
aaccgcctct ccccgcgcgt tggccgattc attaatgcag gttgatcgat tcgacatcga   3840
tctagtaaca tagatgacac cgcgcgcgat aatttatcct agtttgcgcg ctatattttg   3900
ttttctatcg cgtattaaat gtataattgc gggactctaa tcataaaaac ccatctcata   3960
```

```
aataacgtca tgcattacat gttaattatt acatgcttaa cgtaattcaa cagaaattat   4020
atgataatca tcgcaagacc ggcaacagga ttcaatctta agaaacttta ttgccaaatg   4080
tttgaacgat ctgcttcgac gcactccttc tttaggtacc tcactattcc tttgccctcg   4140
gacgagtgct ggggcgtcgg tttccactat cggcgagtac ttctacacag ccatcggtcc   4200
agacggccgc gcttctgcgg gcgatttgtg tacgcccgac agtcccggct ccggatcgga   4260
cgattgcgtc gcatcgaccc tgcgcccaag ctgcatcatc gaaattgccg tcaaccaagc   4320
tctgatagag ttggtcaaga ccaatgcgga gcatatacgc ccggagccgc ggcgatcctg   4380
caagctccgg atgcctccgc tcgaagtagc gcgtctgctg ctccatacaa gccaaccacg   4440
gcctccagaa gaagatgttg gcgacctcgt attgggaatc cccgaacatc gcctcgctcc   4500
agtcaatgac cgctgttatg cggccattgt ccgtcaggac attgttggag ccgaaatccg   4560
cgtgcacgag gtgccggact tcggggcagt cctcggccca aagcatcagc tcatcgagag   4620
cctgcgcgac ggacgcactg acggtgtcgt ccatcacagt ttgccagtga tacacatggg   4680
gatcagcaat cgcgcatatg aaatcacgcc atgtagtgta ttgaccgatt ccttgcggtc   4740
cgaatgggcc gaacccgctc gtctggctaa gatcggccgc agcgatcgca tccatggcct   4800
ccgcgaccgg ctgcagaaca gcgggcagtt cggtttcagg caggtcttgc aacgtgacac   4860
cctgtgcacg gcgggagatg caataggtca ggctctcgct gaattcccca atgtcaagca   4920
cttccggaat cgggagcgcg gccgatgcaa agtgccgata aacataacga tctttgtaga   4980
aaccatcggc gcagctattt acccgcagga catatccacg ccctcctaca tcgaagctga   5040
aagcacgaga ttcttcgccc tccgagagct gcatcaggtc ggagacgctg tcgaactttt   5100
cgatcagaaa cttctcgaca gacgtcgcgg tgagttcagg ctttttcatg gtttaataag   5160
aagagaaaag agttcttttg ttatggctga agtaatagag aaatgagctc gagcgtgtcc   5220
tctccaaatg aaatgaactt ccttatatag aggaagggtc ttgcgaagga tagtgggatt   5280
gtgcgtcatc ccttacgtca gtggagatgt cacatcaatc cacttgcttt gaagacgtgg   5340
ttggaacgtc ttcttttttcc acgatgctcc tcgtgggtgg gggtccatct ttgggaccac   5400
tgtcggcaga ggcatcttga atgatagcct ttcctttatc gcaatgatgg catttgtagg   5460
agccaccttc cttttctact gtcctttcga tgaagtgaca gatagctggg caatggaatc   5520
cgaggaggtt tcccgaaatt atcctttgtt gaaaagtctc aatagccctt tggtcttctg   5580
agactgtatc tttgacattt ttggagtaga ccagagtgtc gtgctccacc atgttgacga   5640
agattttctt cttgtcattg agtcgtaaaa gactctgtat gaactgttcg ccagtcttca   5700
cggcgagttc tgttagatcc tcgatttgaa tcttagactc catgcatggc cttagattca   5760
gtaggaacta cctttttaga gactccaatc tctattactt gccttggttt atgaagcaag   5820
ccttgaatcg tccatactgg aatagtactt ctgatcttga gaaatatgtc tttctctgtg   5880
ttcttgatgc aattagtcct gaatcttttg actgcatctt taaccttctt gggaaggtat   5940
ttgatctcct ggagattgtt actcgggtag atcgtcttga tgagacctgc tgcgtaggcc   6000
tctctaacca tctgtgggtc agcattcttt ctgaaattga agaggctaac cttctcatta   6060
tcagtggtga acatagtgtc gtcaccttca ccttcgaact tccttcctag atcgtaaaga   6120
tagaggaaat cgtccattgt aatctccggg gcaaaggaga tctcttttgg ggctggatca   6180
ctgctgggcc ttttggttcc tagcgtgagc cagtgggctt tttgctttgg tgggcttgtt   6240
agggccttag caaagctctt gggcttgagt tgagcttctc ctttggggat gaagttcaac   6300
ctgtctgttt gctgacttgt tgtgtacgcg tcagctgctg ctcttgcctc tgtaatagtg   6360
```

-continued

```
gcaaatttct tgtgtgcaac tccgggaacg ccgtttgttg ccgcctttgt acaaccccag   6420
tcatcgtata taccggcatg tggaccgtta tacacaacgt agtagttgat atgagggtgt   6480
tgaataccg attctgctct gagaggagca actgtgctgt taagctcaga tttttgtggg   6540
attggaattg gatcgatctc gatcccgcga aattaatacg actcactata gggagaccac   6600
aacggtttcc ctctagaaat aattttgttt aactttaaga aggagatata cccatggaaa   6660
agcctgaact caccgcgacg tctgtcgaga agtttctgat cgaaaagttc gacagcgtct   6720
ccgacctgat gcagctctcg gagggcgaag aatctcgtgc tttcagcttc gatgtaggag   6780
ggcgtggata tgtcctgcgg gtaaatagct gcgccgatgg tttctacaaa gatcgttatg   6840
tttatcggca ctttgcatcg gccgcgctcc cgattccgga agtgcttgac attggggaat   6900
tcagcgagag cctgacctat tgcatctccc gccgtgcaca gggtgtcacg ttgcaagacc   6960
tgcctgaaac cgaactgccc gctgttctgc agccggtcgc ggaggctatg gatgcgatcg   7020
ctgcggccga tcttagccag acgagcgggt tcggcccatt cggaccgcaa ggaatcggtc   7080
aatacactac atggcgtgat ttcatatgcg cgattgctga tccccatgtg tatcactggc   7140
aaactgtgat ggacgacacc gtcagtgcgt ccgtcgcgca ggctctcgat gagctgatgc   7200
tttgggccga ggactgcccc gaagtccggc acctcgtgca cgcggatttc ggctccaaca   7260
atgtcctgac ggacaatggc cgcataacag cggtcattga ctggagcgag gcgatgttcg   7320
gggattccca atacgaggtc gccaacatct tcttctggag gccgtggttg gcttgtatgg   7380
agcagcagac gcgctacttc gagcggaggc atccggagct tgcaggatcg ccgcggctcc   7440
gggcgtatat gctccgcatt ggtcttgacc aactctatca gagcttggtt gacggcaatt   7500
tcgatgatgc agcttgggcg cagggtcgat gcgacgcaat cgtccgatcc ggagccggga   7560
ctgtcgggcg tacacaaatc gcccgcagaa gcgcggccgt ctggaccgat ggctgtgtag   7620
aagtactcgc cgatagtgga aaccgacgcc ccagcactcg tccgagggca aaggaatagt   7680
gaggtacagc ttggatcgat ccggctgcta acaaagcccg aaaggaagct gagttggctg   7740
ctgccaccgc tgagcaataa ctagcataac cccttggggc ctctaaacgg gtcttgaggg   7800
gttttttgct gaaaggagga actatatccg gatgatcggg cgcgccgtcg acggatccgt   7860
acgagatccg gccggccaga tcctgcagcc cgggggatcc gcccacgtac gcaaaggcaa   7920
agatttaaac tcgaaaacat tacaaaagtc tcaaaacaga ggcaaggcca tgcacaaagc   7980
acactctaag tgcttccatt gcctactaag tagggtacgt acacgatcac cattcaccag   8040
tgatgatctt tattaatata caacacactc agagacagct tatgttatag ctagctagca   8100
taaactatca catcatgtgt tagtacgaca agtgacaaca ttgcttttaa cttcgcggcc   8160
ttggatcctc tagaccggat ataatgagcc gtaaacaaag atgattaagt agtaattaat   8220
acgtactagt aaaagtggca aaagataacg agaaagaacc aatttctttg cattcggcct   8280
tagcggaagg catatataag ctttgattat tttatttagt gtaatgattt cgtacaacca   8340
aagcatttat ttagtactct cacacttgtg tcgcggccgc ttactgagcc ttggcaccgg   8400
gctgcttctc ggccattcga gcgaactggg acaggtatcg gagcaggatg acgagacctt   8460
catggggcag agggtttcgg taggggaggt tgtgcttctg gcacagctgt tccacctggt   8520
aggaaacggc agtgaggttg tgtcgaggca gggtgggcca gagatggtgc tcgatctggt   8580
agttcaggcc tccaaagaac cagtcagtaa tgatgcctcg tcgaatgttc atggtctcat   8640
ggatctgacc cacagagaag ccatgtccgt cccagacgga atcaccgatc ttctccagag   8700
ggtagtggtt catgaagacc acgatggcaa ttccgaagcc accgacgagc tcggaaacaa   8760
```

```
agaacaccag catcgaggtc aggatggagg gcataaagaa gaggtggaac agggtcttga   8820
gagtccagtg cagagcgagt ccaatggcct ctttcttgta ctgagatcgg tagaactggt   8880
tgtctcggtc cttgagggat cgaacggtca gcacagactg gaaacaccag atgaatcgca   8940
ggagaataca gatgaccagg aaatagtact gttggaactg aatgagcttt cgggagatgg   9000
gagaagctcg agtgacatcg tcctcggacc aggcgagcag aggcaggtta tcaatgtcgg   9060
gatcgtgacc ctgaacgttg gtagcagaat gatgggcgtt gtgtctgtcc ttccaccagg   9120
tcacggagaa gccctggagt ccgttgccaa agaccagacc caggacgtta ttccagtttc   9180
ggttcttgaa ggtctggtgg tggcagatgt catgagacag ccatcccatt tgctggtagt   9240
gcataccgag cacgagagca ccaatgaagt acaggtggta ctggaccagc atgaagaagg   9300
caagcacgcc aagacccagg gtggtcaaga tcttgtacga gtaccagagg ggagaggcgt   9360
caaacatgcc agtggcgatc agctcttctc ggagctttcg gaaatcctcc tgagcttcgt   9420
tgacggcagc ctggggaggc agctcggaag cctggttgat cttgggcatt cgcttgagct   9480
tgtcgaaggc ttcctgagag tgcataacca tgaaggcgtc agtagcatct cgtccctggt   9540
agttctcaat gatttcagct ccaccagggt ggaagttcac ccaagcggag acgtcgtaca   9600
cctttccgtc gatgacgagg ggcagagcct gtcgagaagc cttcaccatg gtgcggccgc   9660
ttgggggggct atggaagact ttcttagtta gttgtgtgaa taagcaatgt tgggagaatc   9720
gggactactt ataggatagg aataaaacag aaaagtatta agtgctaatg aaatatttag   9780
actgataatt aaaatcttca cgtatgtcca cttgatataa aaacgtcagg aataaaggaa   9840
gtacagtaga atttaaaggt actcttttta tatatacccg tgttctcttt ttggctagct   9900
agttgcataa aaaataatct atatttttat cattatttta aatatcttat gagatggtaa   9960
atatttatca taattttttt tactattatt tattatttgt gtgtgtaata catatagaag  10020
ttaattacaa attttattta ctttttcatt attttgatat gattcaccat taatttagtg  10080
ttattattta taatagttca ttttaatctt tttgtatata ttatgcgtgc agtacttttt  10140
tcctacatat aactactatt acattttatt tatataatat ttttattaat gaattttcgt  10200
gataatatgt aatattgttc attattattt cagatttttt aaaaatattt gtgttattat  10260
ttatgaaata tgtaattttt ttagtatttg attttatgat gataaagtgt tctaaattca  10320
aaagaagggg gaaagcgtaa acattaaaaa acgtcatcaa acaaaaacaa aatcttgtta  10380
ataaagataa aactgtttgt tttgatcact gttatttcgt aatataaaaa cattatttat  10440
atttatattg ttgacaacca aatttgccta tcaaatctaa ccaatataat gcatgcgtgg  10500
caggtaatgt actaccatga acttaagtca tgacataata aaccgtgaat ctgaccaatg  10560
catgtaccta nctaaattgt atttgtgaca cgaagcaaat gattcaattc acaatggaga  10620
tgggaaacaa ataatgaaga acccagaact aagaaagctt ttctgaaaaa taaaataaag  10680
gcaatgtcaa aagtatactg catcatcagt ccagaaagca catgatattt ttttatcagt  10740
atcaatgcag ctagttttat tttacaatat cgatatagct agtttaaata tattgcagct  10800
agatttataa atatttgtgt tattatttat catttgtgta atcctgtttt tagtatttta  10860
gtttatatat gatgataatg tattccaaat ttaaaagaag ggaaataaat ttaaacaaga  10920
aaaaaagtca tcaaacaaaa aacaaatgaa agggtggaaa gatgttacca tgtaatgtga  10980
atgttacagt atttctttta ttatagagtt aacaaattaa ctaatatgat tttgttaata  11040
atgataaaat attttttta ttattatttc ataatataaa aatagtttac ttaatataaa  11100
aaaaattcta tcgttcacaa caaagttggc cacctaattt aaccatgcat gtacccatgg  11160
```

```
accatattag gtaaccatca aacctgatga agagataaag agatgaagac ttaagtcata  11220

acacaaaacc ataaaaaaca aaaatacaat caaccgtcaa tctgaccaat gcatgaaaaa  11280

gctgcaatag tgagtggcga cacaaagcac atgatttttct tacaacggag ataaaaccaa  11340

aaaaatattt catgaacaac ctagaacaaa taaagctttt atataataaa tatataaata  11400

aataaaggct atggaataat atacttcaat atatttggat taaataaatt gttggcgggg  11460

ttgatatatt tatacacacc taaagtcact tcaatctcat tttcacttaa cttttatttt  11520

tttttctttt ttatttatca taaagagaat attgataata tactttttaa catattttta  11580

tgacattttt tattggtgaa aacttattaa aaatcataaa ttttgtaagt tagatttatt  11640

taaagagttc ctcttcttat tttaaatttt ttaataaatt tttaaataac taaaatttgt  11700

gttaaaaatg ttaaaaaatg tgttattaac ccttctcttc gaggacgtac gtcgagtcga  11760

cctgca                                                             11766
```

<210> SEQ ID NO 187
<211> LENGTH: 30
<212> TYPE: DNA
<213> ORGANISM: Artificial Sequence
<220> FEATURE:
<223> OTHER INFORMATION: Primer oEugEL1-1

<400> SEQUENCE: 187

```
agcggccgca ccatggaggt ggtgaatgaa                                      30
```

<210> SEQ ID NO 188
<211> LENGTH: 30
<212> TYPE: DNA
<213> ORGANISM: Artificial Sequence
<220> FEATURE:
<223> OTHER INFORMATION: Primer oEugEL1-2

<400> SEQUENCE: 188

```
tgcggccgct cactgaatct ttttggctcc                                      30
```

<210> SEQ ID NO 189
<211> LENGTH: 4311
<212> TYPE: DNA
<213> ORGANISM: Artificial Sequence
<220> FEATURE:
<223> OTHER INFORMATION: Plasmid pKR906

<400> SEQUENCE: 189

```
agcggccgca ccatggaggt ggtgaatgaa atagtctcaa ttgggcagga agttttaccc     60

aaagttgatt atgcccaact ctggagtgat gccagtcact gtgaggtgct ttacttgtcc    120

atcgcatttg tcatcttgaa gttcactctt ggcccccttg gtccaaaagg tcagtctcgt    180

atgaagtttg ttttcaccaa ttacaacctt ctcatgtcca tttattcgtt gggatcattc    240

ctctcaatgg catatgccat gtacaccatc ggtgttatgt ctgacaactg cgagaaggct    300

tttgacaaca acgtcttcag gatcaccacg cagttgttct atttgagcaa gttcctggag    360

tatattgact ccttctattt gccactgatg ggcaagcctc tgacctggtt gcaattcttc    420

catcatttgg gggcaccgat ggatatgtgg ctgttctata attaccgaaa tgaagctgtt    480

tggatttttg tgctgttgaa tggtttcatc cactggatca tgtacggtta ttattggacc    540

agattgatca agctgaagtt ccccatgcca aaatccctga ttacatcaat gcagatcatt    600

caattcaatg ttggtttcta cattgtctgg aagtacagga acattccctg ttatcgccaa    660

gatgggatga ggatgtttgg ctggttcttc aattactttt atgttggcac agtcttgtgt    720
```

```
ttgttcttga atttctatgt gcaaacgtat atcgtcagga agcacaaggg agccaaaaag    780
attcagtgag cggccgcacc tgaattccag cacactggcg gccgttacta gtggatccga    840
gctcggtacc aagcttgatg catagcttga gtattctaac gcgtcaccta aatagcttgg    900
cgtaatcatg gtcatagctg tttcctgtgt gaaattgtta tccgctcaca attccacaca    960
acatacgagc cggaagcata aagtgtaaag cctggggtgc ctaatgagtg agctaactca   1020
cattaattgc gttgcgctca ctgcccgctt tccagtcggg aaacctgtcg tgccagctgc   1080
attaatgaat cggccaacgc gcggggagag gcggtttgcg tattgggcgc tcttccgctt   1140
cctcgctcac tgactcgctg cgctcggtcg ttcggctgcg gcgagcggta tcagctcact   1200
caaaggcggt aatacggtta tccacagaat caggggataa cgcaggaaag aacatgtgag   1260
caaaaggcca gcaaaagccc aggaaccgta aaaaggccgc gttgctggcg tttttccata   1320
ggctccgccc ccctgacgag catcacaaaa atcgacgctc aagtcagagg tggcgaaacc   1380
cgacaggact ataaagatac caggcgtttc cccctggaag ctccctcgtg cgctctcctg   1440
ttccgaccct gccgcttacc ggatacctgt ccgcctttct cccttcggga agcgtggcgc   1500
tttctcatag ctcacgctgt aggtatctca gttcggtgta ggtcgttcgc tccaagctgg   1560
gctgtgtgca cgaacccccc gttcagcccg accgctgcgc cttatccggt aactatcgtc   1620
ttgagtccaa cccggtaaga cacgacttat cgccactggc agcagccact ggtaacagga   1680
ttagcagagc gaggtatgta ggcggtgcta cagagttctt gaagtggtgg cctaactacg   1740
gctacactag aaggacagta tttggtatct gcgctctgct gaagccagtt accttcggaa   1800
aaagagttgg tagctcttga tccggcaaac aaaccaccgc tggtagcggt ggtttttttg   1860
tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacgc agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac cacaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaatattt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agcccctgat gctcttcgtc   2940
cagatcatcc tgatcgacaa gaccggcttc catccgagta cgtgctcgct cgatgcgatg   3000
tttcgcttgg tggtcgaatg ggcaggtagc cggatcaagc gtatgcagcc gccgcattgc   3060
atcagccatg atggatactt tctcggcagg agcaaggtga gatgacagga gatcctgccc   3120
```

```
cggcacttcg cccaatagca gccagtccct tcccgcttca gtgacaacgt cgagcacagc   3180

tgcgcaagga acgcccgtcg tggccagcca cgatagccgc gctgcctcgt cttgcagttc   3240

attcagggca ccggacaggt cggtcttgac aaaaagaacc gggcgcccct gcgctgacag   3300

ccggaacacg gcggcatcag agcagccgat tgtctgttgt gcccagtcat agccgaatag   3360

cctctccacc caagcggccg gagaacctgc gtgcaatcca tcttgttcaa tcatgcgaaa   3420

cgatcctcat cctgtctctt gatcagagct tgatcccctg cgccatcaga tccttggcgg   3480

cgagaaagcc atccagttta ctttgcaggg cttcccaacc ttaccagagg gcgccccagc   3540

tggcaattcc ggttcgcttg ctgtccataa aaccgcccag tctagctatc gccatgtaag   3600

cccactgcaa gctacctgct ttctctttgc gcttgcgttt tcccttgtcc agatagccca   3660

gtagctgaca ttcatccggg gtcagcaccg tttctgcgga ctggctttct acgtgaaaag   3720

gatctaggtg aagatccttt ttgataatct catgcctgac atttatattc cccagaacat   3780

caggttaatg gcgtttttga tgtcattttc gcggtggctg agatcagcca cttcttcccc   3840

gataacggag accggcacac tggccatatc ggtggtcatc atgcgccagc tttcatcccc   3900

gatatgcacc accgggtaaa gttcacggga gactttatct gacagcagac gtgcactggc   3960

caggggggatc accatccgtc gccccggcgt gtcaataata tcactctgta catccacaaa   4020

cagacgataa cggctctctc ttttataggt gtaaacctta aactgccgta cgtataggct   4080

gcgcaactgt tgggaagggc gatcggtgcg ggcctcttcg ctattacgcc agctggcgaa   4140

aggggggatgt gctgcaaggc gattaagttg ggtaacgcca gggttttccc agtcacgacg   4200

ttgtaaaacg acggccagtg aattgtaata cgactcacta tagggcgaat tgggccctct   4260

agatgcatgc tcgagcggcc gccagtgtga tggatatctg cagaattcag g            4311
```

<210> SEQ ID NO 190
<211> LENGTH: 7085
<212> TYPE: DNA
<213> ORGANISM: Artificial Sequence
<220> FEATURE:
<223> OTHER INFORMATION: Plasmid pKR72

<400> SEQUENCE: 190

```
gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180

tcactattcc tttgccctcg gacgagtgct ggggcgtcgg tttccactat cggcgagtac    240

ttctacacag ccatcggtcc agacggccgc gcttctgcgg gcgatttgtg tacgcccgac    300

agtcccggct ccggatcgga cgattgcgtc gcatcgaccc tgcgcccaag ctgcatcatc    360

gaaattgccg tcaaccaagc tctgatagag ttggtcaaga ccaatgcgga gcatatacgc    420

ccggagccgc ggcgatcctg caagctccgg atgcctccgc tcgaagtagc gcgtctgctg    480

ctccatacaa gccaaccacg gcctccagaa gaagatgttg gcgacctcgt attgggaatc    540

cccgaacatc gcctcgctcc agtcaatgac cgctgttatg cggccattgt ccgtcaggac    600

attgttggag ccgaaatccg cgtgcacgag gtgccggact tcggggcagt cctcggccca    660

aagcatcagc tcatcgagag cctgcgcgac ggacgcactg acggtgtcgt ccatcacagt    720

ttgccagtga tacacatggg gatcagcaat cgcgcatatg aaatcacgcc atgtagtgta    780

ttgaccgatt ccttgcggtc cgaatgggcc gaacccgctc gtctggctaa gatcggccgc    840

agcgatcgca tccatagcct ccgcgaccgg ctgcagaaca gcgggcagtt cggtttcagg    900
```

-continued

```
caggtcttgc aacgtgacac cctgtgcacg gcgggagatg caataggtca ggctctcgct    960
gaattcccca atgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga aagcacgaga ttcttcgccc tccgagagct gcatcaggtc   1140
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatcga tccaattcca   1320
atcccacaaa aatctgagct taacagcaca gttgctcctc tcagagcaga atcgggtatt   1380
caacaccctc atatcaacta ctacgttgtg tataacggtc cacatgccgg tatatacgat   1440
gactggggtt gtacaaaggc ggcaacaaac ggcgttcccg gagttgcaca caagaaattt   1500
gccactatta cagaggcaag agcagcagct gacgcgtaca caacaagtca gcaaacagac   1560
aggttgaact tcatccccaa aggagaagct caactcaagc ccaagagctt tgctaaggcc   1620
ctaacaagcc caccaaagca aaaagcccac tggctcacgc taggaaccaa aaggcccagc   1680
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
```

```
cgcggatttc ggctccaaca atgtcctgac ggacaatggc cgcataacag cggtcattga   3360

ctggagcgag gcgatgttcg gggattccca atacgaggtc gccaacatct tcttctggag   3420

gccgtggttg gcttgtatgg agcagcagac gcgctacttc gagcggaggc atccggagct   3480

tgcaggatcg ccgcggctcc gggcgtatat gctccgcatt ggtcttgacc aactctatca   3540

gagcttggtt gacggcaatt tcgatgatgc agcttgggcg cagggtcgat gcgacgcaat   3600

cgtccgatcc ggagccggga ctgtcgggcg tacacaaatc gcccgcagaa gcgcggccgt   3660

ctggaccgat ggctgtgtag aagtactcgc cgatagtgga aaccgacgcc ccagcactcg   3720

tccgagggca aaggaatagt gaggtaccta aagaaggagt gcgtcgaagc agatcgttca   3780

aacatttggc aataaagttt cttaagattg aatcctgttg ccggtcttgc gatgattatc   3840

atataatttc tgttgaatta cgttaagcat gtaataatta acatgtaatg catgacgtta   3900

tttatgagat gggtttttat gattagagtc ccgcaattat acatttaata cgcgatagaa   3960

aacaaaatat agcgcgcaaa ctaggataaa ttatcgcgcg cggtgtcatc tatgttacta   4020

gatcgatgtc gaatcgatca acctgcatta atgaatcggc caacgcgcgg ggagaggcgg   4080

tttgcgtatt gggcgctctt ccgcttcctc gctcactgac tcgctgcgct cggtcgttcg   4140

gctgcggcga gcggtatcag ctcactcaaa ggcggtaata cggttatcca cagaatcagg   4200

ggataacgca ggaaagaaca tgtgagcaaa aggccagcaa aaggccagga accgtaaaaa   4260

ggccgcgttg ctggcgtttt tccataggct ccgcccccct gacgagcatc acaaaaatcg   4320

acgctcaagt cagaggtggc gaaacccgac aggactataa agataccagg cgtttccccc   4380

tggaagctcc ctcgtgcgct ctcctgttcc gaccctgccg cttaccggat acctgtccgc   4440

ctttctccct tcgggaagcg tggcgctttc tcaatgctca cgctgtaggt atctcagttc   4500

ggtgtaggtc gttcgctcca agctgggctg tgtgcacgaa ccccccgttc agcccgaccg   4560

ctgcgcctta tccggtaact atcgtcttga gtccaacccg gtaagacacg acttatcgcc   4620

actggcagca gccactggta acaggattag cagagcgagg tatgtaggcg gtgctacaga   4680

gttcttgaag tggtggccta actacggcta cactagaagg acagtatttg gtatctgcgc   4740

tctgctgaag ccagttacct tcggaaaaag agttggtagc tcttgatccg gcaaacaaac   4800

caccgctggt agcggtggtt tttttgtttg caagcagcag attacgcgca gaaaaaaagg   4860

atctcaagaa gatcctttga tcttttctac ggggtctgac gctcagtgga acgaaaactc   4920

acgttaaggg attttggtca tgacattaac ctataaaaat aggcgtatca cgaggccctt   4980

tcgtctcgcg cgtttcggtg atgacggtga aaacctctga cacatgcagc tcccggagac   5040

ggtcacagct tgtctgtaag cggatgccgg gagcagacaa gcccgtcagg gcgcgtcagc   5100

gggtgttggc gggtgtcggg gctggcttaa ctatgcggca tcagagcaga ttgtactgag   5160

agtgcaccat atggacatat tgtcgttaga acgcggctac aattaataca taaccttatg   5220

tatcatacac atacgattta ggtgacacta tagaacggcg cgccaagctt gttgaaacat   5280

ccctgaagtg tctcatttta ttttatttat tctttgctga taaaaaaata aaataaaaga   5340

agctaagcac acggtcaacc attgctctac tgctaaaagg gttatgtgta gtgttttact   5400

gcataaatta tgcagcaaac aagacaactc aaattaaaaa atttcctttg cttgtttttt   5460

tgttgtctct gacttgactt tcttgtggaa gttggttgta taaggattgg gacaccattg   5520

tccttcttaa tttaatttta ttctttgctg ataaaaaaaa aaatttcata tagtgttaaa   5580

taataatttg ttaaataacc aaaaagtcaa atatgtttac tctcgtttaa ataattgaga   5640

ttcgtccagc aaggctaaac gattgtatag atttatgaca atatttactt ttttatagat   5700
```

```
aaatgttata ttataataaa tttatataca tatattatat gttatttatt attattttaa   5760

atccttcaat attttatcaa accaactcat aatttttttt ttatctgtaa gaagcaataa   5820

aattaaatag acccacttta aggatgatcc aacctttata cagagtaaga gagttcaaat   5880

agtacccttt catatacata tcaactaaaa tattagaaat atcatggatc aaaccttata   5940

aagacattaa ataagtggat aagtataata tataaatggg tagtatataa tatataaatg   6000

gatacaaact tctctcttta taattgttat gtctccttaa catcctaata taatacataa   6060

gtgggtaata tataatatat aaatggagac aaacttcttc cattataatt gttatgtctt   6120

cttaacactt atgtctcgtt cacaatgcta aggttagaat tgtttagaaa gtcttatagt   6180

acacatttgt ttttgtacta tttgaagcat tccataagcc gtcacgattc agatgattta   6240

taataataag aggaaattta tcatagaaca ataaggtgca tagatagagt gttaatatat   6300

cataacatcc tttgtttatt catagaagaa gtgagatgga gctcagttat tatactgtta   6360

catggtcgga tacaatattc catgctctcc atgagctctt acacctacat gcattttagt   6420

tcatacttgc ggccgcagta tatcttaaat tctttaatac ggtgtactag gatattgaac   6480

tggttcttga tgatgaaaac ctgggccgag attgcagcta tttatagtca taggtcttgt   6540

taacatgcat ggacatttgg ccacggggtg gcatgcagtt tgacgggtgt tgaaataaac   6600

aaaaatgagg tggcggaaga gaatacgagt ttgaggttgg gttagaaaca acaaatgtga   6660

gggctcatga tgggttgagt tggtgaatgt tttgggctgc tcgattgaca cctttgtgag   6720

tacgtgttgt tgtgcatggc ttttggggtc cagttttttt ttcttgacgc ggcgatcctg   6780

atcagctagt ggataagtga tgtccactgt gtgtgattgc gtttttgttt gaattttatg   6840

aacttagaca ttgctatgca aaggatactc tcattgtgtt ttgtcttctt ttgttccttg   6900

gctttttctt atgatccaag agactagtca gtgttgtggc attcgagact accaagatta   6960

attatgatgg gggaaggata agtaactgat tagtacggac tgttaccaaa ttaattaata   7020

agcggcaaat gaagggcatg gatcaaaagc ttggatctcc tgcaggatct ggccggccgg   7080

atctc                                                               7085
```

```
<210> SEQ ID NO 191
<211> LENGTH: 7873
<212> TYPE: DNA
<213> ORGANISM: Artificial Sequence
<220> FEATURE:
<223> OTHER INFORMATION: Plasmid pKR1010

<400> SEQUENCE: 191

cgcgccgttc tatagtgtca cctaaatcgt atgtgtatga tacataaggt tatgtattaa     60

ttgtagccgc gttctaacga caatatgtcc atatggtgca ctctcagtac aatctgctct    120

gatgccgcat agttaagcca gccccgacac ccgccaacac ccgctgacgc gccctgacgg    180

gcttgtctgc tcccggcatc cgcttacaga caagctgtga ccgtctccgg gagctgcatg    240

tgtcagaggt tttcaccgtc atcaccgaaa cgcgcgagac gaaagggcct cgtgatacgc    300

ctatttttat aggttaatgt catgaccaaa atcccttaac gtgagttttc gttccactga    360

gcgtcagacc ccgtagaaaa gatcaaagga tcttcttgag atcctttttt tctgcgcgta    420

atctgctgct tgcaaacaaa aaaaccaccg ctaccagcgg tggtttgttt gccggatcaa    480

gagctaccaa ctctttttcc gaaggtaact ggcttcagca gagcgcagat accaaatact    540

gtccttctag tgtagccgta gttaggccac cacttcaaga actctgtagc accgcctaca    600

tacctcgctc tgctaatcct gttaccagtg gctgctgcca gtggcgataa gtcgtgtctt    660
```

```
accgggttgg actcaagacg atagttaccg gataaggcgc agcggtcggg ctgaacgggg    720
ggttcgtgca cacagcccag cttggagcga acgacctaca ccgaactgag atacctacag    780
cgtgagcatt gagaaagcgc cacgcttccc gaagggagaa aggcggacag gtatccggta    840
agcggcaggg tcggaacagg agagcgcacg agggagcttc caggggggaaa cgcctggtat    900
ctttatagtc ctgtcgggtt tcgccacctc tgacttgagc gtcgattttt gtgatgctcg    960
tcaggggggc ggagcctatg gaaaaacgcc agcaacgcgg cctttttacg gttcctggcc   1020
ttttgctggc cttttgctca catgttcttt cctgcgttat cccctgattc tgtggataac   1080
cgtattaccg cctttgagtg agctgatacc gctcgccgca gccgaacgac cgagcgcagc   1140
gagtcagtga gcgaggaagc ggaagagcgc ccaatacgca aaccgcctct ccccgcgcgt   1200
tggccgattc attaatgcag gttgatcgat tcgacatcga tctagtaaca tagatgacac   1260
cgcgcgcgat aatttatcct agtttgcgcg ctatattttg ttttctatcg cgtattaaat   1320
gtataattgc gggactctaa tcataaaaac ccatctcata aataacgtca tgcattacat   1380
gttaattatt acatgcttaa cgtaattcaa cagaaattat atgataatca tcgcaagacc   1440
ggcaacagga ttcaatctta agaaacttta ttgccaaatg tttgaacgat ctgcttcgac   1500
gcactccttc tttaggtacc tcactattcc tttgccctcg gacgagtgct ggggcgtcgg   1560
tttccactat cggcgagtac ttctacacag ccatcggtcc agacggccgc gcttctgcgg   1620
gcgatttgtg tacgcccgac agtcccggct ccggatcgga cgattgcgtc gcatcgaccc   1680
tgcgcccaag ctgcatcatc gaaattgccg tcaaccaagc tctgatagag ttggtcaaga   1740
ccaatgcgga gcatatacgc ccggagccgc ggcgatcctg caagctccgg atgcctccgc   1800
tcgaagtagc gcgtctgctg ctccatacaa gccaaccacg gcctccagaa gaagatgttg   1860
gcgacctcgt attgggaatc cccgaacatc gcctcgctcc agtcaatgac cgctgttatg   1920
cggccattgt ccgtcaggac attgttggag ccgaaatccg cgtgcacgag gtgccggact   1980
tcggggcagt cctcggccca aagcatcagc tcatcgagag cctgcgcgac ggacgcactg   2040
acggtgtcgt ccatcacagt ttgccagtga tacacatggg gatcagcaat cgcgcatatg   2100
aaatcacgcc atgtagtgta ttgaccgatt ccttgcggtc cgaatgggcc gaacccgctc   2160
gtctggctaa gatcggccgc agcgatcgca tccatggcct ccgcgaccgg ctgcagaaca   2220
gcgggcagtt cggtttcagg caggtcttgc aacgtgacac cctgtgcacg gcgggagatg   2280
caataggtca ggctctcgct gaattcccca atgtcaagca cttccggaat cgggagcgcg   2340
gccgatgcaa agtgccgata aacataacga tctttgtaga aaccatcggc gcagctattt   2400
acccgcagga catatccacg ccctcctaca tcgaagctga aagcacgaga ttcttcgccc   2460
tccgagagct gcatcaggtc ggagacgctg tcgaactttt cgatcagaaa cttctcgaca   2520
gacgtcgcgg tgagttcagg ctttttcatg gtttaataag aagagaaaag agttcttttg   2580
ttatggctga agtaatagag aaatgagctc gagcgtgtcc tctccaaatg aaatgaactt   2640
ccttatatag aggaagggtc ttgcgaagga tagtgggatt gtgcgtcatc ccttacgtca   2700
gtggagatgt cacatcaatc cacttgcttt gaagacgtgg ttggaacgtc ttcttttttcc   2760
acgatgctcc tcgtgggtgg gggtccatct ttgggaccac tgtcggcaga ggcatcttga   2820
atgatagcct ttcctttatc gcaatgatgg catttgtagg agccaccttc cttttctact   2880
gtcctttcga tgaagtgaca gatagctggg caatggaatc cgaggaggtt tcccgaaatt   2940
atcctttgtt gaaaagtctc aatagccctt tggtcttctg agactgtatc tttgacattt   3000
ttggagtaga ccagagtgtc gtgctccacc atgttgacga agattttctt cttgtcattg   3060
```

```
agtcgtaaaa gactctgtat gaactgttcg ccagtcttca cggcgagttc tgttagatcc   3120
tcgatttgaa tcttagactc catgcatggc cttagattca gtaggaacta ccttttaga    3180
gactccaatc tctattactt gccttggttt atgaagcaag ccttgaatcg tccatactgg   3240
aatagtactt ctgatcttga gaaatatgtc tttctctgtg ttcttgatgc aattagtcct   3300
gaatcttttg actgcatctt taaccttctt gggaaggtat ttgatctcct ggagattgtt   3360
actcgggtag atcgtcttga tgagacctgc tgcgtaggcc tctctaacca tctgtgggtc   3420
agcattcttt ctgaaattga agaggctaac cttctcatta tcagtggtga acatagtgtc   3480
gtcaccttca ccttcgaact tccttcctag atcgtaaaga tagaggaaat cgtccattgt   3540
aatctccggg gcaaaggaga tctcttttgg ggctggatca ctgctgggcc ttttggttcc   3600
tagcgtgagc cagtgggctt tttgctttgg tgggcttgtt agggccttag caaagctctt   3660
gggcttgagt tgagcttctc ctttggggat gaagttcaac ctgtctgttt gctgacttgt   3720
tgtgtacgcg tcagctgctg ctcttgcctc tgtaatagtg gcaaatttct tgtgtgcaac   3780
tccgggaacg ccgtttgttg ccgcctttgt acaaccccag tcatcgtata taccggcatg   3840
tggaccgtta tacacaacgt agtagttgat atgagggtgt tgaatacccg attctgctct   3900
gagaggagca actgtgctgt taagctcaga tttttgtggg attggaattg gatcgatctc   3960
gatcccgcga aattaatacg actcactata gggagaccac aacggtttcc ctctagaaat   4020
aattttgttt aactttaaga aggagatata cccatggaaa agcctgaact caccgcgacg   4080
tctgtcgaga agtttctgat cgaaaagttc gacagcgtct ccgacctgat gcagctctcg   4140
gagggcgaag aatctcgtgc tttcagcttc gatgtaggag ggcgtggata tgtcctgcgg   4200
gtaaatagct gcgccgatgg tttctacaaa gatcgttatg tttatcggca ctttgcatcg   4260
gccgcgctcc cgattccgga agtgcttgac attggggaat tcagcgagag cctgacctat   4320
tgcatctccc gccgtgcaca gggtgtcacg ttgcaagacc tgcctgaaac cgaactgccc   4380
gctgttctgc agccggtcgc ggaggctatg gatgcgatcg ctgcggccga tcttagccag   4440
acgagcgggt tcggcccatt cggaccgcaa ggaatcggtc aatacactac atggcgtgat   4500
ttcatatgcg cgattgctga tccccatgtg tatcactggc aaactgtgat ggacgacacc   4560
gtcagtgcgt ccgtcgcgca ggctctcgat gagctgatgc tttgggccga ggactgcccc   4620
gaagtccggc acctcgtgca cgcggatttc ggctccaaca atgtcctgac ggacaatggc   4680
cgcataacag cggtcattga ctggagcgag gcgatgttcg gggattccca atacgaggtc   4740
gccaacatct tcttctggag gccgtggttg gcttgtatgg agcagcagac gcgctacttc   4800
gagcggaggc atccggagct tgcaggatcg ccgcggctcc gggcgtatat gctccgcatt   4860
ggtcttgacc aactctatca gagcttggtt gacggcaatt tcgatgatgc agcttgggcg   4920
cagggtcgat gcgacgcaat cgtccgatcc ggagccggga ctgtcgggcg tacacaaatc   4980
gcccgcagaa gcgcggccgt ctggaccgat ggctgtgtag aagtactcgc cgatagtgga   5040
aaccgacgcc ccagcactcg tccgagggca aaggaatagt gaggtacagc ttggatcgat   5100
ccggctgcta acaaagcccg aaaggaagct gagttggctg ctgccaccgc tgagcaataa   5160
ctagcataac cccttggggc ctctaaacgg gtcttgaggg gttttttgct gaaaggagga   5220
actatatccg gatgatcggg cgcgccgtcg acggatccgt acgagatccg gccggccaga   5280
tcctgcagga gatccaagct tttgatccat gcccttcatt tgccgcttat taattaattt   5340
ggtaacagtc cgtactaatc agttacttat ccttccccca tcataattaa tcttggtagt   5400
ctcgaatgcc acaacactga ctagtctctt ggatcataag aaaaagccaa ggaacaaaag   5460
```

-continued

```
aagacaaaac acaatgagag tatcctttgc atagcaatgt ctaagttcat aaaattcaaa   5520
caaaaacgca atcacacaca gtggacatca cttatccact agctgatcag gatcgccgcg   5580
tcaagaaaaa aaaactggac cccaaaagcc atgcacaaca acacgtactc acaaaggtgt   5640
caatcgagca gcccaaaaca ttcaccaact caacccatca tgagccctca catttgttgt   5700
ttctaaccca acctcaaact cgtattctct tccgccacct catttttgtt tatttcaaca   5760
cccgtcaaac tgcatgccac cccgtggcca aatgtccatg catgttaaca agacctatga   5820
ctataaatag ctgcaatctc ggcccaggtt ttcatcatca agaaccagtt caatatccta   5880
gtacaccgta ttaaagaatt taagatatac tgcggccgca ccatggaggt ggtgaatgaa   5940
atagtctcaa ttgggcagga agttttaccc aaagttgatt atgcccaact ctggagtgat   6000
gccagtcact gtgaggtgct ttacttgtcc atcgcatttg tcatcttgaa gttcactctt   6060
ggcccccttg gtccaaaagg tcagtctcgt atgaagtttg ttttcaccaa ttacaacctt   6120
ctcatgtcca tttattcgtt gggatcattc ctctcaatgg catatgccat gtacaccatc   6180
ggtgttatgt ctgacaactg cgagaaggct tttgacaaca acgtcttcag gatcaccacg   6240
cagttgttct atttgagcaa gttcctggag tatattgact ccttctattt gccactgatg   6300
ggcaagcctc tgacctggtt gcaattcttc catcatttgg gggcaccgat ggatatgtgg   6360
ctgttctata attaccgaaa tgaagctgtt tggatttttg tgctgttgaa tggtttcatc   6420
cactggatca tgtacggtta ttattggacc agattgatca agctgaagtt ccccatgcca   6480
aaatccctga ttacatcaat gcagatcatt caattcaatg ttggtttcta cattgtctgg   6540
aagtacagga acattccctg ttatcgccaa gatgggatga ggatgtttgg ctggttcttc   6600
aattactttt atgttggcac agtcttgtgt ttgttcttga atttctatgt gcaaacgtat   6660
atcgtcagga agcacaaggg agccaaaaag attcagtgag cggccgcaag tatgaactaa   6720
aatgcatgta ggtgtaagag ctcatggaga gcatggaata ttgtatccga ccatgtaaca   6780
gtataataac tgagctccat ctcacttctt ctatgaataa acaaaggatg ttatgatata   6840
ttaacactct atctatgcac cttattgttc tatgataaat ttcctcttat tattataaat   6900
catctgaatc gtgacggctt atggaatgct tcaaatagta caaaaacaaa tgtgtactat   6960
aagactttct aaacaattct aaccttagca ttgtgaacga gacataagtg ttaagaagac   7020
ataacaatta taatggaaga agtttgtctc catttatata ttatatatta cccacttatg   7080
tattatatta ggatgttaag gagacataac aattataaag agagaagttt gtatccattt   7140
atatattata tactacccat ttatatatta tacttatcca cttatttaat gtctttataa   7200
ggtttgatcc atgatatttc taatatttta gttgatatgt atatgaaagg gtactatttg   7260
aactctctta ctctgtataa aggttggatc atccttaaag tgggtctatt taattttatt   7320
gcttcttaca gataaaaaaa aaattatgag ttggtttgat aaaatattga aggatttaaa   7380
ataataataa ataacatata atatatgtat ataaatttat tataatataa catttatcta   7440
taaaaaagta aatattgtca taaatctata caatcgttta gccttgctgg acgaatctca   7500
attatttaaa cgagagtaaa catatttgac tttttggtta tttaacaaat tattatttaa   7560
cactatatga aatttttttt tttatcagca aagaataaaa ttaaattaag aaggacaatg   7620
gtgtcccaat ccttatacaa ccaacttcca caagaaagtc aagtcagaga caacaaaaaa   7680
acaagcaaag gaaatttttt aatttgagtt gtcttgtttg ctgcataatt tatgcagtaa   7740
aacactacac ataacccttt tagcagtaga gcaatggttg accgtgtgct tagcttcttt   7800
```

tattttattt ttttatcagc aaagaataaa taaaataaaa tgagacactt cagggatgtt 7860
tcaacaagct tgg 7873

<210> SEQ ID NO 192
<211> LENGTH: 11752
<212> TYPE: DNA
<213> ORGANISM: Artificial Sequence
<220> FEATURE:
<223> OTHER INFORMATION: Plasmid pKR1059
<220> FEATURE:
<221> NAME/KEY: misc_feature
<222> LOCATION: (10557)..(10557)
<223> OTHER INFORMATION: n is a, c, g, or t

<400> SEQUENCE: 192
ggagatccaa gcttttgatc catgcccttc atttgccgct tattaattaa tttggtaaca 60
gtccgtacta atcagttact tatccttccc ccatcataat taatcttggt agtctcgaat 120
gccacaacac tgactagtct cttggatcat aagaaaaagc caaggaacaa aagaagacaa 180
aacacaatga gagtatcctt tgcatagcaa tgtctaagtt cataaaattc aaacaaaaac 240
gcaatcacac acagtggaca tcacttatcc actagctgat caggatcgcc gcgtcaagaa 300
aaaaaaactg gaccccaaaa gccatgcaca acaacacgta ctcacaaagg tgtcaatcga 360
gcagcccaaa acattcacca actcaaccca tcatgagccc tcacatttgt tgtttctaac 420
ccaacctcaa actcgtattc tcttccgcca cctcattttt gtttatttca acacccgtca 480
aactgcatgc caccccgtgg ccaaatgtcc atgcatgtta acaagaccta tgactataaa 540
tagctgcaat ctcggcccag gttttcatca tcaagaacca gttcaatatc ctagtacacc 600
gtattaaaga atttaagata tactgcggcc gcaccatgga ggtggtgaat gaaatagtct 660
caattgggca ggaagtttta cccaaagttg attatgccca actctggagt gatgccagtc 720
actgtgaggt gctttacttg tccatcgcat ttgtcatctt gaagttcact cttggccccc 780
ttggtccaaa aggtcagtct cgtatgaagt ttgttttcac caattacaac cttctcatgt 840
ccatttattc gttgggatca ttcctctcaa tggcatatgc catgtacacc atcggtgtta 900
tgtctgacaa ctgcgagaag gcttttgaca acaacgtctt caggatcacc acgcagttgt 960
tctatttgag caagttcctg gagtatattg actccttcta tttgccactg atgggcaagc 1020
ctctgacctg gttgcaattc ttccatcatt tgggggcacc gatggatatg tggctgttct 1080
ataattaccg aaatgaagct gtttggattt ttgtgctgtt gaatggtttc atccactgga 1140
tcatgtacgg ttattattgg accagattga tcaagctgaa gttccccatg ccaaaatccc 1200
tgattacatc aatgcagatc attcaattca atgttggttt ctacattgtc tggaagtaca 1260
ggaacattcc ctgttatcgc caagatggga tgaggatgtt tggctggttc ttcaattact 1320
tttatgttgg cacagtcttg tgtttgttct tgaatttcta tgtgcaaacg tatatcgtca 1380
ggaagcacaa gggagccaaa aagattcagt gagcggccgc aagtatgaac taaaatgcat 1440
gtaggtgtaa gagctcatgg agagcatgga atattgtatc cgaccatgta acagtataat 1500
aactgagctc catctcactt cttctatgaa taaacaaagg atgttatgat atattaacac 1560
tctatctatg caccttattg ttctatgata aatttcctct tattattata aatcatctga 1620
atcgtgacgg cttatggaat gcttcaaata gtacaaaaac aaatgtgtac tataagactt 1680
tctaaacaat tctaacctta gcattgtgaa cgagacataa gtgttaagaa gacataacaa 1740
ttataatgga agaagtttgt ctccatttat atattatata ttacccactt atgtattata 1800
ttaggatgtt aaggagacat aacaattata aagagagaag tttgtatcca tttatatatt 1860

```
atatactacc catttatata ttatacttat ccacttattt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaaattat gagttggttt gataaaatat tgaaggattt aaaataataa   2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt tttttatca gcaaagaata aaattaaatt aagaaggaca atggtgtccc   2340
aatccttata caaccaactt ccacaagaaa gtcaagtcag agacaacaaa aaaacaagca   2400
aaggaaattt tttaatttga gttgtcttgt ttgctgcata atttatgcag taaaacacta   2460
cacataaccc ttttagcagt agagcaatgg ttgaccgtgt gcttagcttc ttttatttta   2520
ttttttatc agcaaagaat aaataaaata aaatgagaca cttcagggat gtttcaacaa   2580
gcttggcgcg ccgttctata gtgtcaccta aatcgtatgt gtatgataca taaggttatg   2640
tattaattgt agccgcgttc taacgacaat atgtccatat ggtgcactct cagtacaatc   2700
tgctctgatg ccgcatagtt aagccagccc cgacacccgc caacacccgc tgacgcgccc   2760
tgacgggctt gtctgctccc ggcatccgct tacagacaag ctgtgaccgt ctccgggagc   2820
tgcatgtgtc agaggttttc accgtcatca ccgaaacgcg cgagacgaaa gggcctcgtg   2880
atacgcctat ttttataggt taatgtcatg accaaaatcc cttaacgtga gttttcgttc   2940
cactgagcgt cagaccccgt agaaaagatc aaaggatctt cttgagatcc ttttttctg   3000
cgcgtaatct gctgcttgca aacaaaaaaa ccaccgctac cagcggtggt ttgtttgccg   3060
gatcaagagc taccaactct ttttccgaag gtaactggct tcagcagagc gcagatacca   3120
aatactgtcc ttctagtgta gccgtagtta ggccaccact tcaagaactc tgtagcaccg   3180
cctacatacc tcgctctgct aatcctgtta ccagtggctg ctgccagtgg cgataagtcg   3240
tgtcttaccg ggttggactc aagacgatag ttaccggata aggcgcagcg gtcgggctga   3300
acggggggtt cgtgcacaca gcccagcttg gagcgaacga cctacaccga actgagatac   3360
ctacagcgtg agcattgaga aagcgccacg cttcccgaag ggagaaaggc ggacaggtat   3420
ccggtaagcg gcagggtcgg aacaggagag cgcacgaggg agcttccagg gggaaacgcc   3480
tggtatcttt atagtcctgt cgggtttcgc cacctctgac ttgagcgtcg atttttgtga   3540
tgctcgtcag gggggcggag cctatggaaa aacgccagca acgcggcctt tttacggttc   3600
ctggcctttt gctggccttt tgctcacatg ttctttcctg cgttatcccc tgattctgtg   3660
gataaccgta ttaccgcctt tgagtgagct gataccgctc gccgcagccg aacgaccgag   3720
cgcagcgagt cagtgagcga ggaagcggaa gagcgcccaa tacgcaaacc gcctctcccc   3780
gcgcgttggc cgattcatta atgcaggttg atcgattcga catcgatcta gtaacataga   3840
tgacaccgcg cgcgataatt tatcctagtt tgcgcgctat attttgtttt ctatcgcgta   3900
ttaaatgtat aattgcggga ctctaatcat aaaaacccat ctcataaata acgtcatgca   3960
ttacatgtta attattacat gcttaacgta attcaacaga aattatatga taatcatcgc   4020
aagaccggca acaggattca atcttaagaa actttattgc caaatgtttg aacgatctgc   4080
ttcgacgcac tccttcttta ggtacctcac tattcctttg ccctcggacg agtgctgggg   4140
cgtcggtttc cactatcggc gagtacttct acacagccat cggtccagac ggccgcgctt   4200
ctgcgggcga tttgtgtacg cccgacagtc ccggctccgg atcggacgat tgcgtcgcat   4260
```

-continued

```
cgaccctgcg cccaagctgc atcatcgaaa ttgccgtcaa ccaagctctg atagagttgg   4320
tcaagaccaa tgcggagcat atacgcccgg agccgcggcg atcctgcaag ctccggatgc   4380
ctccgctcga agtagcgcgt ctgctgctcc atacaagcca accacggcct ccagaagaag   4440
atgttggcga cctcgtattg ggaatccccg aacatcgcct cgctccagtc aatgaccgct   4500
gttatgcggc cattgtccgt caggacattg ttggagccga aatccgcgtg cacgaggtgc   4560
cggacttcgg ggcagtcctc ggcccaaagc atcagctcat cgagagcctg cgcgacggac   4620
gcactgacgg tgtcgtccat cacagtttgc cagtgataca catggggatc agcaatcgcg   4680
catatgaaat cacgccatgt agtgtattga ccgattcctt gcggtccgaa tgggccgaac   4740
ccgctcgtct ggctaagatc ggccgcagcg atcgcatcca tggcctccgc gaccggctgc   4800
agaacagcgg gcagttcggt ttcaggcagg tcttgcaacg tgacaccctg tgcacggcgg   4860
gagatgcaat aggtcaggct ctcgctgaat tccccaatgt caagcacttc cggaatcggg   4920
agcgcggccg atgcaaagtg ccgataaaca taacgatctt tgtagaaacc atcggcgcag   4980
ctatttaccc gcaggacata tccacgccct cctacatcga agctgaaagc acgagattct   5040
tcgccctccg agagctgcat caggtcggag acgctgtcga acttttcgat cagaaacttc   5100
tcgacagacg tcgcggtgag ttcaggcttt ttcatggttt aataagaaga gaaaagagtt   5160
cttttgttat ggctgaagta atagagaaat gagctcgagc gtgtcctctc caaatgaaat   5220
gaacttcctt atatagagga agggtcttgc gaaggatagt gggattgtgc gtcatccctt   5280
acgtcagtgg agatgtcaca tcaatccact tgctttgaag acgtggttgg aacgtcttct   5340
ttttccacga tgctcctcgt gggtgggggt ccatctttgg gaccactgtc ggcagaggca   5400
tcttgaatga tagcctttcc tttatcgcaa tgatggcatt tgtaggagcc accttccttt   5460
tctactgtcc tttcgatgaa gtgacagata gctgggcaat ggaatccgag gaggtttccc   5520
gaaattatcc tttgttgaaa agtctcaata gccctttggt cttctgagac tgtatctttg   5580
acatttttgg agtagaccag agtgtcgtgc tccaccatgt tgacgaagat tttcttcttg   5640
tcattgagtc gtaaaagact ctgtatgaac tgttcgccag tcttcacggc gagttctgtt   5700
agatcctcga tttgaatctt agactccatg catggcctta gattcagtag gaactacctt   5760
tttagagact ccaatctcta ttacttgcct tggtttatga agcaagcctt gaatcgtcca   5820
tactggaata gtacttctga tcttgagaaa tatgtctttc tctgtgttct tgatgcaatt   5880
agtcctgaat cttttgactg catctttaac cttcttggga aggtatttga tctcctggag   5940
attgttactc gggtagatcg tcttgatgag acctgctgcg taggcctctc taaccatctg   6000
tgggtcagca ttctttctga aattgaagag gctaaccttc tcattatcag tggtgaacat   6060
agtgtcgtca ccttcacctt cgaacttcct tcctagatcg taaagataga ggaaatcgtc   6120
cattgtaatc tccggggcaa aggagatctc ttttggggct ggatcactgc tgggcctttt   6180
ggttcctagc gtgagccagt gggctttttg ctttggtggg cttgttaggg ccttagcaaa   6240
gctcttgggc ttgagttgag cttctccttt ggggatgaag ttcaacctgt ctgtttgctg   6300
acttgttgtg tacgcgtcag ctgctgctct tgcctctgta atagtggcaa atttcttgtg   6360
tgcaactccg ggaacgccgt ttgttgccgc ctttgtacaa ccccagtcat cgtatatacc   6420
ggcatgtgga ccgttataca caacgtagta gttgatatga gggtgttgaa tacccgattc   6480
tgctctgaga ggagcaactg tgctgttaag ctcagatttt tgtgggattg gaattggatc   6540
gatctcgatc ccgcgaaatt aatacgactc actataggga gaccacaacg gtttccctct   6600
agaaataatt ttgtttaact ttaagaagga gatataccca tggaaaagcc tgaactcacc   6660
```

-continued

```
gcgacgtctg tcgagaagtt tctgatcgaa aagttcgaca gcgtctccga cctgatgcag   6720
ctctcggagg gcgaagaatc tcgtgctttc agcttcgatg taggagggcg tggatatgtc   6780
ctgcgggtaa atagctgcgc cgatggtttc tacaaagatc gttatgttta tcggcacttt   6840
gcatcggccg cgctcccgat tccggaagtg cttgacattg gggaattcag cgagagcctg   6900
acctattgca tctcccgccg tgcacagggt gtcacgttgc aagacctgcc tgaaaccgaa   6960
ctgcccgctg ttctgcagcc ggtcgcggag gctatggatg cgatcgctgc ggccgatctt   7020
agccagacga gcgggttcgg cccattcgga ccgcaaggaa tcggtcaata cactacatgg   7080
cgtgatttca tatgcgcgat tgctgatccc catgtgtatc actggcaaac tgtgatggac   7140
gacaccgtca gtgcgtccgt cgcgcaggct ctcgatgagc tgatgctttg ggccgaggac   7200
tgccccgaag tccggcacct cgtgcacgcg gatttcggct ccaacaatgt cctgacggac   7260
aatggccgca taacagcggt cattgactgg agcgaggcga tgttcgggga ttcccaatac   7320
gaggtcgcca acatcttctt ctggaggccg tggttggctt gtatggagca gcagacgcgc   7380
tacttcgagc ggaggcatcc ggagcttgca ggatcgccgc ggctccgggc gtatatgctc   7440
cgcattggtc ttgaccaact ctatcagagc ttggttgacg gcaatttcga tgatgcagct   7500
tgggcgcagg gtcgatgcga cgcaatcgtc cgatccggag ccgggactgt cgggcgtaca   7560
caaatcgccc gcagaagcgc ggccgtctgg accgatggct gtgtagaagt actcgccgat   7620
agtggaaacc gacgccccag cactcgtccg agggcaaagg aatagtgagg tacagcttgg   7680
atcgatccgg ctgctaacaa agcccgaaag gaagctgagt tggctgctgc caccgctgag   7740
caataactag cataacccct tggggcctct aaacgggtct tgaggggttt tttgctgaaa   7800
ggaggaacta tatccggatg atcgggcgcg ccgtcgacgg atccgtacga gatccggccg   7860
gccagatcct gcagcccggg ggatccgccc acgtacgcaa aggcaaagat ttaaactcga   7920
aaacattaca aaagtctcaa aacagaggca aggccatgca caaagcacac tctaagtgct   7980
tccattgcct actaagtagg gtacgtacac gatcaccatt caccagtgat gatctttatt   8040
aatatacaac acactcagag acagcttatg ttatagctag ctagcataaa ctatcacatc   8100
atgtgttagt acgacaagtg acaacattgc ttttaacttc gcggccttgg atcctctaga   8160
ccggatataa tgagccgtaa acaaagatga ttaagtagta attaatacgt actagtaaaa   8220
gtggcaaaag ataacgagaa agaaccaatt tctttgcatt cggccttagc ggaaggcata   8280
tataagcttt gattatttta tttagtgtaa tgatttcgta caaccaaagc atttatttag   8340
tactctcaca cttgtgtcgc ggccgcttac tgagccttgg caccgggctg cttctcggcc   8400
attcgagcga actgggacag gtatcggagc aggatgacga gaccttcatg ggcagaggg    8460
tttcggtagg ggaggttgtg cttctggcac agctgttcca cctggtagga aacggcagtg   8520
aggttgtgtc gaggcagggt gggccagaga tggtgctcga tctggtagtt caggcctcca   8580
aagaaccagt cagtaatgat gcctcgtcga atgttcatgg tctcatggat ctgacccaca   8640
gagaagccat gtccgtccca gacggaatca ccgatcttct ccagagggta gtggttcatg   8700
aagaccacga tggcaattcc gaagccaccg acgagctcgg aaacaaagaa caccagcatc   8760
gaggtcagga tggagggcat aaagaagagg tggaacaggg tcttgagagt ccagtgcaga   8820
gcgagtccaa tggcctcttt cttgtactga gatcggtaga actggttgtc tcggtccttg   8880
agggatcgaa cggtcagcac agactggaaa caccagatga atcgcaggag aatacagatg   8940
accaggaaat agtactgttg gaactgaatg agctttcggg agatgggaga agctcgagtg   9000
acatcgtcct cggaccaggc gagcagaggc aggttatcaa tgtcgggatc gtgaccctga   9060
```

-continued

```
acgttggtag cagaatgatg ggcgttgtgt ctgtccttcc accaggtcac ggagaagccc   9120
tggagtccgt tgccaaagac cagacccagg acgttattcc agtttcggtt cttgaaggtc   9180
tggtggtggc agatgtcatg agacagccat cccatttgct ggtagtgcat accgagcacg   9240
agagcaccaa tgaagtacag gtggtactgg accagcatga agaaggcaag cacgccaaga   9300
cccagggtgg tcaagatctt gtacgagtac cagaggggag aggcgtcaaa catgccagtg   9360
gcgatcagct cttctcggag ctttcggaaa tcctcctgag cttcgttgac ggcagcctgg   9420
ggaggcagct cggaagcctg gttgatcttg ggcattcgct tgagcttgtc gaaggcttcc   9480
tgagagtgca taaccatgaa ggcgtcagta gcatctcgtc cctggtagtt ctcaatgatt   9540
tcagctccac cagggtggaa gttcacccaa gcggagacgt cgtacacctt tccgtcgatg   9600
acgaggggca gagcctgtcg agaagccttc accatggtgc ggccgcttgg ggggctatgg   9660
aagactttct tagttagttg tgtgaataag caatgttggg agaatcggga ctacttatag   9720
gataggaata aaacagaaaa gtattaagtg ctaatgaaat atttagactg ataattaaaa   9780
tcttcacgta tgtccacttg atataaaaac gtcaggaata aaggaagtac agtagaattt   9840
aaaggtactc tttttatata tacccgtgtt ctctttttgg ctagctagtt gcataaaaaa   9900
taatctatat ttttatcatt attttaaata tcttatgaga tggtaaatat ttatcataat   9960
ttttttact attatttatt atttgtgtgt gtaatacata tagaagttaa ttacaaattt  10020
tatttacttt ttcattattt tgatatgatt caccattaat ttagtgttat tatttataat  10080
agttcatttt aatctttttg tatatattat gcgtgcagta ctttttttcct acatataact  10140
actattacat tttatttata taatattttt attaatgaat tttcgtgata atatgtaata  10200
ttgttcatta ttatttcaga ttttttaaaa atatttgtgt tattatttat gaaatatgta  10260
attttttag tatttgattt tatgatgata aagtgttcta aattcaaaag aagggggaaa  10320
gcgtaaacat taaaaaacgt catcaaacaa aaacaaaatc ttgttaataa agataaaact  10380
gtttgttttg atcactgtta tttcgtaata taaaaacatt atttatattt atattgttga  10440
caaccaaatt tgcctatcaa atctaaccaa tataatgcat gcgtggcagg taatgtacta  10500
ccatgaactt aagtcatgac ataataaacc gtgaatctga ccaatgcatg tacctancta  10560
aattgtattt gtgacacgaa gcaaatgatt caattcacaa tggagatggg aaacaaataa  10620
tgaagaaccc agaactaaga aagcttttct gaaaaataaa ataaaggcaa tgtcaaaagt  10680
atactgcatc atcagtccag aaagcacatg atatttttttt atcagtatca atgcagctag  10740
ttttatttta caatatcgat atagctagtt taaatatatt gcagctagat tttataaatat  10800
ttgtgttatt atttatcatt tgtgtaatcc tgtttttagt attttagttt atatatgatg  10860
ataatgtatt ccaaatttaa aagaagggaa ataaatttaa acaagaaaaa aagtcatcaa  10920
acaaaaaaca aatgaaaggg tggaaagatg ttaccatgta atgtgaatgt tacagtattt  10980
cttttattat agagttaaca aattaactaa tatgattttg ttaataatga taaaatattt  11040
tttttattat tatttcataa tataaaaata gtttacttaa tataaaaaaa attctatcgt  11100
tcacaacaaa gttggccacc taatttaacc atgcatgtac ccatggacca tattaggtaa  11160
ccatcaaacc tgatgaagag ataaagagat gaagacttaa gtcataacac aaaaccataa  11220
aaaacaaaaa tacaatcaac cgtcaatctg accaatgcat gaaaaagctg caatagtgag  11280
tggcgacaca aagcacatga ttttcttaca acggagataa aaccaaaaaa atatttcatg  11340
aacaacctag aacaaataaa gcttttatat aataaatata taaataaata aaggctatgg  11400
aataatatac ttcaatatat ttggattaaa taaattgttg gcggggttga tatatttata  11460
```

```
cacacctaaa gtcacttcaa tctcattttc acttaacttt tatttttttt ttctttttat  11520

ttatcataaa gagaatattg ataatatact ttttaacata tttttatgac atttttttatt  11580

ggtgaaaact tattaaaaat cataaatttt gtaagttaga tttatttaaa gagttcctct  11640

tcttatttta aattttttaa taaattttta aataactaaa atttgtgtta aaaatgttaa  11700

aaaatgtgtt attaaccctt ctcttcgagg acgtacgtcg agtcgacctg ca         11752
```

<210> SEQ ID NO 193
<211> LENGTH: 18
<212> TYPE: DNA
<213> ORGANISM: Artificial Sequence
<220> FEATURE:
<223> OTHER INFORMATION: M13F Universal primer

<400> SEQUENCE: 193

```
tgtaaaacga cggccagt                                                  18
```

<210> SEQ ID NO 194
<211> LENGTH: 757
<212> TYPE: DNA
<213> ORGANISM: Euglena gracilis
<220> FEATURE:
<221> NAME/KEY: misc_feature
<222> LOCATION: (677)..(677)
<223> OTHER INFORMATION: n is a, c, g, or t

<400> SEQUENCE: 194

```
ttttttttcg aacacttaat ggaggtggtg aatgaaatag tctcaattgg gcaggaagtt     60

ttacccaaag ttgattatgc ccaactctgg agtgatgcca gtcactgtga ggtgctttac    120

ttgtccatcg catttgtcat cttgaagttc actcttggcc cccttggtcc aaaaggtcag    180

tctcgtatga agtttgtttt caccaattac aaccttctca tgtccattta ttcgttggga    240

tcattcctct caatggcata tgccatgtac accatcggtg ttatgtctga caactgcgag    300

aaggcttttg acaacaacgt cttcaggatc accacgcagt tgttctattt gagcaagttc    360

ctggagtata ttgactcctt ctatttgcca ctgatgggca agcctctgac ctggttgcaa    420

ttcttccatc atttgggggc accgatggat atgtggctgt tctataatta ccgaaatgaa    480

gctgtttgga tttttgtgct gttgaatggt ttcatccact ggatcatgta cggttattat    540

tggaccagat tgatcaagct gaagttcccc atgccaaaat ccctgattac atcaatgcag    600

atcattcaat tcaatgttgg tttctacatt gtctggaagt acaggaacat tccctgttat    660

cgccaagatg ggatgangat gtttggctgg ttcttcaatt acttttatgt tggcacagtc    720

ttgtgtttgt tcttgaattt ctatgtgcaa acgtata                            757
```

<210> SEQ ID NO 195
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 195

```
tcaggatcac cacgcagttg ttctatttga gcangttcct ggagtatatt gactccttct     60

atttgccant gatgggcaag cntctgacct ggttgcaatt cttccatcat tngggggcac    120

cgatggatat gtggctgttc tataattacc gaaatgaagc tgtttggatt tttgtgctgt    180

tgaatggttt catccactgg atcatgtacg gttattannn gaccagattg atcaagctga    240

agttccccat gccaaaatcc ctgattacat caatgcagat cattcaattc aatgttggtt    300

tctacattgt ctggaagtac aggaacattc cctgttatcg ccaagatggg atgaggatgt    360

ttggctggtt cttcaattac ttttatgttg gcacagtctt gtgtttgttc ttgaatttct    420

atgtgcaaac gtatatcgtc aggaagcaca agggagccaa aaagattcag tgatatttcc    480

tcctctgcgg tggcctcttt tgacctcccc ttgacaccta taatgtggag gtgtcgggct    540

ctctccgtct caccagcact tgactctgca ggtgctcact tttatttttt acccatcttt    600

gcttgttgac cattcacctc tcccacttcc acatagtcca ttctaactgt tgcagactgc    660

ggtccatttt ttccagagct cccaatgacc atacgcgaca ccttgtnnnc ncccagccca    720

ttgtgcacaa ttcatagtgg catcgttttg ccttgatacg tgtgcatcca gcgg          774
```

<210> SEQ ID NO 196
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 196

```
gacatggcaa ctatgatttt attttgactg atagtgacct gttcgttgca acaaattgat     60

gagcaatgct tttttataat gccaactttg tacaaaaaag ttggattttt tttcgaacac    120

ttaatggagg tggtgaatga aatagtctca attgggcagg aagttttacc caaagttgat    180

tatgcccaac tctggagtga tgccagtcac tgtgaggtgc tttacttgtc catcgcattt    240

gtcatcttga agttcactct tggccccctt ggtccaaaag gtcagtctcg tatgaagttt    300

gttttcacca attacaacct tctcatgtcc atttattcgt tgggatcatt cctctcaatg    360

gcatatgcca tgtacaccat cggtgttatg tctgacaact gcgagaaggc ttttgacaac    420

aacgtcttca ggatcaccac gcagttgttc tatttgagca agttcctgga gtatattgac    480

tccttctatt tgccactgat gggcaagcct ctgacctggt tgcaattctt ccatcatttg    540

ggggcaccga tggatatgtg gctgttctat aattaccgaa atgaagctgt ttggattttt    600
```

```
gtgctgttga atggtttcat ccactggatc atgtacggtt attattggac cagattgatc    660

aagctgaagt tccccatgcc aaaatccctg attacatcaa tgcagatcat tcaattcaat    720

gttggtttct acattgtctg gaagtacagg aacattccct gttatcgcca agatgggatg    780

aggatgtttg gctggttctt caattacttt tatgttggca cagtcttgtg tttgttcttg    840

aatttctatg tgcaaacgta tatcgtcagg aagcacaagg gagccaaaaa gattcagtga    900

tatttcctcc tctgcggtgg cctcttttga cctccccttg acacctataa tgtggaggtg    960

tcgggctctc tccgtctcac cagcacttga ctctgcaggt gctcactttt atttttttacc  1020

catctttgct tgttgaccat tcacctctcc cacttccaca tagtccattc taactgttgc   1080

agactgcggt ccatttttttc cagagctccc aatgaccata cgcgacacct tgtnnncncc  1140

cagcccattg tgcacaattc atagtggcat cgttttgcct tgatacgtgt gcatccagcg   1200

g                                                                   1201
```

<210> SEQ ID NO 197
<211> LENGTH: 1272
<212> TYPE: DNA
<213> ORGANISM: Artificial Sequence
<220> FEATURE:
<223> OTHER INFORMATION: mutant EgD8S consensus, optionally comprising M1, M2, M3, M6, M8, M12, M14, M15, M16, M18, M19, M21, M22, M26, M38, M39, M40, M41, M45, M46, M49, M50, M51, M53, M54, M58, M63, M68, M69 and M70 mutation sites
<220> FEATURE:
<221> NAME/KEY: misc_feature
<222> LOCATION: (2)..(1270)
<223> OTHER INFORMATION: mutant delta-8 desaturase CDS

<400> SEQUENCE: 197

```
catggtgaag nnnnnncgac aggctnnncc cctcnnnatc gacggannnn nntacnnnnn     60

ntccgcttgg gtgaacttcc accctggtgg agctgaaatc attgagaact accagggacg    120

agatgctact gacgccttca tggttatgca ctctcaggaa nnnnnngaca agctcnnncg    180

aatgcccaag nnnnnnnnnn nntccnnnnn ncctccccag gctnnnnnna acgaagctca    240

ggaggatttc cgaaagctcc gagaagagct gatcgccact ggcatgtttg acgcctctcc    300

cctctggtac tcgtacaaga tcnnnaccac cctgggtctt ggcgtgcttn nnnnnttcnn    360

nnnnnnncag tacnnnnnnn nnttcattgg tgctnnnnnn ctcggtatgc actaccagca    420

aatgggatgg ctgtctcatg acatctgcca ccaccagacc ttcaagaacc gaaactggaa    480

taacnnnnnn ggtctggtct ttggcaacnn nnnncagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagnnnnn    840

nttccacctc ttctttatgc cctccatcct gacctcgnnn ctggtgttcn nnnnntccga    900

gctcgtcggt ggcttcggaa ttgccnnnnn ngtcttcatg aaccactacc ctctggagaa    960

gatcggtgat tccgtctggg acggacatgg cttctctgtg ggtcagatcc atgagaccat   1020

gaacattcga cgaggcnnnn nnnnngactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200
```

```
catcctgctc cgatacctgn nnnnnttcgc tcgaatggcc gagaagnnnn nnnnnnnnaa   1260

ggctnnntaa gc                                                       1272


<210> SEQ ID NO 198
<211> LENGTH: 422
<212> TYPE: PRT
<213> ORGANISM: Artificial Sequence
<220> FEATURE:
<223> OTHER INFORMATION: mutant EgD8S consensus, optionally comprising
      M1, M2, M3, M6, M8, M12, M14, M15, M16, M18, M19, M21, M22, M26,
      M38, M39, M40, M41, M45, M46, M49, M50, M51, M53, M54, M58, M63,
      M68, M69 and M70 mutation sites
<220> FEATURE:
<221> NAME/KEY: MISC_FEATURE
<222> LOCATION: (4)..(4)
<223> OTHER INFORMATION: X = S (synthetic codon-optimized) or A (mutant)
<220> FEATURE:
<221> NAME/KEY: MISC_FEATURE
<222> LOCATION: (5)..(5)
<223> OTHER INFORMATION: X = K (synthetic codon-optimized) or S (mutant)
<220> FEATURE:
<221> NAME/KEY: MISC_FEATURE
<222> LOCATION: (9)..(9)
<223> OTHER INFORMATION: X = L (synthetic codon-optimized) or V (mutant)
<220> FEATURE:
<221> NAME/KEY: MISC_FEATURE
<222> LOCATION: (12)..(12)
<223> OTHER INFORMATION: X = T (synthetic codon-optimized) or V (mutant)
<220> FEATURE:
<221> NAME/KEY: MISC_FEATURE
<222> LOCATION: (16)..(16)
<223> OTHER INFORMATION: X = T (synthetic codon-optimized) or K (mutant)
<220> FEATURE:
<221> NAME/KEY: MISC_FEATURE
<222> LOCATION: (17)..(17)
<223> OTHER INFORMATION: X = T (synthetic codon-optimized) or V (mutant)
<220> FEATURE:
<221> NAME/KEY: MISC_FEATURE
<222> LOCATION: (19)..(19)
<223> OTHER INFORMATION: X = D (synthetic codon-optimized) or E (mutant)
<220> FEATURE:
<221> NAME/KEY: MISC_FEATURE
<222> LOCATION: (20)..(20)
<223> OTHER INFORMATION: X = V (synthetic codon-optimized) or I (mutant)
<220> FEATURE:
<221> NAME/KEY: MISC_FEATURE
<222> LOCATION: (54)..(54)
<223> OTHER INFORMATION: X = A (synthetic codon-optimized) or G (mutant)
<220> FEATURE:
<221> NAME/KEY: MISC_FEATURE
<222> LOCATION: (55)..(55)
<223> OTHER INFORMATION: X = F (synthetic codon-optimized) or Y (mutant)
<220> FEATURE:
<221> NAME/KEY: MISC_FEATURE
<222> LOCATION: (59)..(59)
<223> OTHER INFORMATION: X = K (synthetic codon-optimized) or L (mutant)
<220> FEATURE:
<221> NAME/KEY: MISC_FEATURE
<222> LOCATION: (64)..(64)
<223> OTHER INFORMATION: X = I (synthetic codon-optimized) or L (mutant)
<220> FEATURE:
<221> NAME/KEY: MISC_FEATURE
<222> LOCATION: (65)..(65)
<223> OTHER INFORMATION: X = N (synthetic codon-optimized) or D (mutant)
      or Q (mutant)
<220> FEATURE:
<221> NAME/KEY: MISC_FEATURE
<222> LOCATION: (66)..(66)
<223> OTHER INFORMATION: X = P (synthetic codon-optimized) or Q (mutant)
<220> FEATURE:
<221> NAME/KEY: MISC_FEATURE
<222> LOCATION: (67)..(67)
<223> OTHER INFORMATION: X = S (synthetic codon-optimized) or A (mutant)
<220> FEATURE:
<221> NAME/KEY: MISC_FEATURE
<222> LOCATION: (69)..(69)
<223> OTHER INFORMATION: X = E (synthetic codon-optimized) or D (mutant)
```

<220> FEATURE:
<221> NAME/KEY: MISC_FEATURE
<222> LOCATION: (70)..(70)
<223> OTHER INFORMATION: X = L (synthetic codon-optimized) or V (mutant)
<220> FEATURE:
<221> NAME/KEY: MISC_FEATURE
<222> LOCATION: (75)..(75)
<223> OTHER INFORMATION: X = A (synthetic codon-optimized) or G (mutant)
<220> FEATURE:
<221> NAME/KEY: MISC_FEATURE
<222> LOCATION: (76)..(76)
<223> OTHER INFORMATION: X = V (synthetic codon-optimized) or L (mutant)
<220> FEATURE:
<221> NAME/KEY: MISC_FEATURE
<222> LOCATION: (108)..(108)
<223> OTHER INFORMATION: X = S (synthetic codon-optimized) or L (mutant)
<220> FEATURE:
<221> NAME/KEY: MISC_FEATURE
<222> LOCATION: (117)..(117)
<223> OTHER INFORMATION: X = G (synthetic codon-optimized) or A (mutant)
<220> FEATURE:
<221> NAME/KEY: MISC_FEATURE
<222> LOCATION: (118)..(118)
<223> OTHER INFORMATION: X = Y (synthetic codon-optimized) or F (mutant)
<220> FEATURE:
<221> NAME/KEY: MISC_FEATURE
<222> LOCATION: (120)..(120)
<223> OTHER INFORMATION: X = L (synthetic codon-optimized) or M (mutant)
<220> FEATURE:
<221> NAME/KEY: MISC_FEATURE
<222> LOCATION: (121)..(121)
<223> OTHER INFORMATION: X = M (synthetic codon-optimized) or L (mutant)
<220> FEATURE:
<221> NAME/KEY: MISC_FEATURE
<222> LOCATION: (122)..(122)
<223> OTHER INFORMATION: X = V (synthetic codon-optimized) or S (mutant)
<220> FEATURE:
<221> NAME/KEY: MISC_FEATURE
<222> LOCATION: (125)..(125)
<223> OTHER INFORMATION: X = Q (synthetic codon-optimized) or H (mutant)
<220> FEATURE:
<221> NAME/KEY: MISC_FEATURE
<222> LOCATION: (126)..(126)
<223> OTHER INFORMATION: X = M (synthetic codon-optimized) or L (mutant)
<220> FEATURE:
<221> NAME/KEY: MISC_FEATURE
<222> LOCATION: (127)..(127)
<223> OTHER INFORMATION: X = Y (synthetic codon-optimized) or Q (mutant)
<220> FEATURE:
<221> NAME/KEY: MISC_FEATURE
<222> LOCATION: (132)..(132)
<223> OTHER INFORMATION: X = V (synthetic codon-optimized) or L (mutant)
<220> FEATURE:
<221> NAME/KEY: MISC_FEATURE
<222> LOCATION: (133)..(133)
<223> OTHER INFORMATION: X = L (synthetic codon-optimized) or V (mutant)
<220> FEATURE:
<221> NAME/KEY: MISC_FEATURE
<222> LOCATION: (162)..(162)
<223> OTHER INFORMATION: X = L (synthetic codon-optimized) or V (mutant)
<220> FEATURE:
<221> NAME/KEY: MISC_FEATURE
<222> LOCATION: (163)..(163)
<223> OTHER INFORMATION: X = V (synthetic codon-optimized) or L (mutant)
<220> FEATURE:
<221> NAME/KEY: MISC_FEATURE
<222> LOCATION: (170)..(170)
<223> OTHER INFORMATION: X = G (synthetic codon-optimized) or A (mutant)
<220> FEATURE:
<221> NAME/KEY: MISC_FEATURE
<222> LOCATION: (171)..(171)
<223> OTHER INFORMATION: X = L (synthetic codon-optimized) or V (mutant)
<220> FEATURE:
<221> NAME/KEY: MISC_FEATURE
<222> LOCATION: (279)..(279)
<223> OTHER INFORMATION: X = T (synthetic codon-optimized) or L (mutant)
<220> FEATURE:
<221> NAME/KEY: MISC_FEATURE
<222> LOCATION: (280)..(280)
<223> OTHER INFORMATION: X = L (synthetic codon-optimized) or T (mutant)

<220> FEATURE:
<221> NAME/KEY: MISC_FEATURE
<222> LOCATION: (293)..(293)
<223> OTHER INFORMATION: X = L (synthetic codon-optimized) or M (mutant)
<220> FEATURE:
<221> NAME/KEY: MISC_FEATURE
<222> LOCATION: (297)..(297)
<223> OTHER INFORMATION: X = F (synthetic codon-optimized) or V (mutant)
<220> FEATURE:
<221> NAME/KEY: MISC_FEATURE
<222> LOCATION: (298)..(298)
<223> OTHER INFORMATION: X = V (synthetic codon-optimized) or L (mutant)
<220> FEATURE:
<221> NAME/KEY: MISC_FEATURE
<222> LOCATION: (309)..(309)
<223> OTHER INFORMATION: X = I (synthetic codon-optimized) or V (mutant)
<220> FEATURE:
<221> NAME/KEY: MISC_FEATURE
<222> LOCATION: (310)..(310)
<223> OTHER INFORMATION: X = V (synthetic codon-optimized) or I (mutant)
<220> FEATURE:
<221> NAME/KEY: MISC_FEATURE
<222> LOCATION: (346)..(346)
<223> OTHER INFORMATION: X = I (synthetic codon-optimized) or V (mutant)
<220> FEATURE:
<221> NAME/KEY: MISC_FEATURE
<222> LOCATION: (347)..(347)
<223> OTHER INFORMATION: X = I (synthetic codon-optimized) or L (mutant)
<220> FEATURE:
<221> NAME/KEY: MISC_FEATURE
<222> LOCATION: (347)..(347)
<223> OTHER INFORMATION: X = I (synthetic codon-optimized) or L (mutant)
<220> FEATURE:
<221> NAME/KEY: MISC_FEATURE
<222> LOCATION: (348)..(348)
<223> OTHER INFORMATION: X = T (synthetic codon-optimized) or S (mutant)
<220> FEATURE:
<221> NAME/KEY: MISC_FEATURE
<222> LOCATION: (348)..(348)
<223> OTHER INFORMATION: X = T (synthetic codon-optimized) or S (mutant)
<220> FEATURE:
<221> NAME/KEY: MISC_FEATURE
<222> LOCATION: (407)..(407)
<223> OTHER INFORMATION: X = A (synthetic codon-optimized) or S (mutant)
<220> FEATURE:
<221> NAME/KEY: MISC_FEATURE
<222> LOCATION: (408)..(408)
<223> OTHER INFORMATION: X = V (synthetic codon-optimized) or Q (mutant)
<220> FEATURE:
<221> NAME/KEY: MISC_FEATURE
<222> LOCATION: (416)..(416)
<223> OTHER INFORMATION: X = Q (synthetic codon-optimized) or V (mutant)
<220> FEATURE:
<221> NAME/KEY: MISC_FEATURE
<222> LOCATION: (417)..(417)
<223> OTHER INFORMATION: X = P (synthetic codon-optimized) or Y (mutant)
<220> FEATURE:
<221> NAME/KEY: MISC_FEATURE
<222> LOCATION: (418)..(418)
<223> OTHER INFORMATION: X = A (synthetic codon-optimized) or G (mutant)
<220> FEATURE:
<221> NAME/KEY: MISC_FEATURE
<222> LOCATION: (419)..(419)
<223> OTHER INFORMATION: X = G (synthetic codon-optimized) or A (mutant)
<220> FEATURE:
<221> NAME/KEY: MISC_FEATURE
<222> LOCATION: (422)..(422)
<223> OTHER INFORMATION: X = L (synthetic codon-optimized) or Q (mutant)

<400> SEQUENCE: 198

```
Met Val Lys Xaa Xaa Arg Gln Ala Xaa Pro Leu Xaa Ile Asp Gly Xaa
1               5                   10                  15

Xaa Tyr Xaa Xaa Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45
```

-continued

```
Met His Ser Gln Glu Xaa Xaa Asp Lys Leu Xaa Arg Met Pro Lys Xaa
    50                  55                  60

Xaa Xaa Xaa Ser Xaa Xaa Pro Pro Gln Ala Xaa Xaa Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Xaa Thr Thr Leu Gly
            100                 105                 110

Leu Gly Val Leu Xaa Xaa Phe Xaa Xaa Xaa Gln Tyr Xaa Xaa Xaa Phe
        115                 120                 125

Ile Gly Ala Xaa Xaa Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Xaa Xaa Gly Leu Val Phe Gly Asn Xaa Xaa Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Xaa Xaa Phe His Leu Phe Phe Met Pro Ser
        275                 280                 285

Ile Leu Thr Ser Xaa Leu Val Phe Xaa Xaa Ser Glu Leu Val Gly Gly
    290                 295                 300

Phe Gly Ile Ala Xaa Xaa Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Xaa Xaa Xaa Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Xaa Xaa Phe Ala Arg Met Ala Glu Lys Xaa
                405                 410                 415

Xaa Xaa Xaa Lys Ala Xaa
            420
```